US006921847B2

(12) United States Patent
Navarro Acevedo et al.

(10) Patent No.: US 6,921,847 B2
(45) Date of Patent: Jul. 26, 2005

(54) LIPOXYGENASE POLYNUCLEOTIDES AND METHODS OF USE

(75) Inventors: Pedro A. Navarro Acevedo, Ames, IA (US); Jonathan P. Duvick, Des Moines, IA (US); Mikhailo V. Kolomiets, College Station, TX (US); Carl R. Simmons, Des Moines, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 197 days.

(21) Appl. No.: 10/132,350

(22) Filed: Apr. 25, 2002

(65) Prior Publication Data

US 2003/0166855 A1 Sep. 4, 2003

Related U.S. Application Data

(60) Provisional application No. 60/286,889, filed on Apr. 27, 2001, and provisional application No. 60/305,366, filed on Jul. 13, 2001.

(51) Int. Cl.$^7$ .................. C12N 15/09; C12N 15/29; C12N 15/82; A01H 5/00; A01H 5/10
(52) U.S. Cl. ............... 800/279; 800/278; 800/298; 800/295; 800/320; 800/317; 435/320.1; 435/468; 435/419; 536/23.2; 536/23.6
(58) Field of Search .................. 800/278, 279, 800/298, 295, 320, 317, 281, 286; 435/320.1, 419, 468; 536/23.2, 23.6, 24.5

(56) References Cited

PUBLICATIONS

Science Journal. 2001, vol. 292, pp. 1486–1487.*
Bork et al. Genome Research. 2000, vol. 10, pp. 398–400.*
Lazar et al. Molecular and Cellular Biology, Mar. 1998, vol. 8, No. 3, pp. 1247–1257.*
Broun et al. Nov. 1998, vol. 282, pp. 131–133.*
Bell, et al., (1991), *Mol Gen Genet*, 230:456–462, "Lipoxygenase gene expression is modulated in plants by water deficit, wounding, and methyl jasmonate".
Ohta, et al., (1991), *Plant Physiol*, 97:94–98, "A Lipoxygenase Pathway Is Activated in Rice after Infection with the Rice Blast Fungus *Magnaporthe grisea*".
Bostock, et al., (1992), *Plant Physiol*, 100:1448–1456, "Rapid Stimulation of 5–Lipoxygenase Activity in Potato by the Fungal Elicitor Arachidonic Acid".
Doderer, et al., (1992), *Biochim Biophys Acta*, 1120:97–104, "Purification and characterization of two lipoxygenase isoenzymes from germinating barley".
Melan, et al., (1993), *Plant Physiol*, 101:441–450, "An *Arabidopsis thaliana* Lipoxygenase Gene Can Be Induced by Pathogens, Abscisic Acid and Methyl Jasmonate".
Bell, et al., (1995), *P Natl A Sci, USA*, 92:8675–8679, "A chloroplast lipoxygenase is required for wound–induced jasmonic acid accumulation in *Arabidopsis*".

Raventós, et al., (1995), *Plant J*, 7(1):147–155, "A 20 bp cis–acting element is both necessary and sufficient to mediate elicitor response of a maize *PRms* gene".
Rushton, et al., (1996), *EMBO J*, 15(20):5690–5700, "Interaction of elicitor–induced DNA–binding proteins with elicitor response elements in the promoters of parsley PR1 genes".
Bohland, et al., (1997), *Plant Physiol.*, 114:679–685, "Differential Induction of Lipoxygenase Isoforms in Wheat upon Treatment with Rust Fungus Elicitor, Chitin Oligosaccharides, Chitosan, and Methyl Jasmonate".
Burow, et al., (1997), *MPMI*, 10(3):380–387, "Seed Lipoxygenase Products Modulate *Aspergillus* Mycotoxin Biosynthesis".
Heitz, et al., (1997), *Plant Physiol*, 114:1085–1093, "A Gene Encoding a Chloroplast–Targeted Lipoxygenase in Tomato Leaves Is Transiently Induced by Wounding, Systemin, and Methyl Jasmonate".
Creelman and Mullet, (1997), *Ann Rev Plant Physio*, 48:355–381, "Biosynthesis and Action of Jasmonates in Plants".
Thomma, et al., (1998), *P Natl A Sci, USA*, 95:15107–15111, "Separate jasmonate–dependent and salicylate–dependent defense–response pathways in *Arabidopsis* are essential for resistance to distinct microbial pathogens".
Vijayan, et al., (1998), *P Natl A Sci, USA*, 95:7209–7214, "A role for jasmonate in pathogen defense of *Arabidopsis*".
Xie, et al., (1998), *Science*, 280:1091–1094, "COI1: An *Arabidopsis* Gene Required for Jasmonate–Regulated Defense and Fertility".
Rancé et al., (1998), *P Natl A Sci, USA*, 95:6554–6559, "The incompatible interaction between *Phytophthora parasitica* var. *nicotianae* race 0 and tobacco is suppressed in transgenic plants expressing antisense lipoxygenase sequences".
Blée, Elizabeth, (1998), *Prog. Lipid Res.*, 37(1):33–72, "Phytooxylipins and Plant Defense Reactions".
Rustérucci, et al., (1999), *J Biol Chem*, 274(51):36446–36455, "Involvement of Lipoxygenase–dependent Production of Fatty Acid Hydroperoxides in the Development of the Hypersensitive Cell Death induced by Cryptogein on Tobacco Leaves".
Eulgem, et al., (1999) *EMBO J*, 18(17):4689–4699, "Early nuclear events in plant defense signalling: rapid gene activation by WRKY transcription factors".
Royo, et al., (1999), *P Natl A Sci, USA*, 96:1146–1151, "Antisense–mediated depletion of a potato lipoxygenase reduces wound induction of proteinase inhibitors and increases weight gain of insect pests".

(Continued)

*Primary Examiner*—Medina A. Ibrahim

(57) ABSTRACT

Methods and nucleotide sequences encoding maize lipoxygenase proteins for modulating defense response are provided. The nucleotide sequences can be used in expression cassettes for modulating plant defense response. Transformed plants, plant cells and seed are also provided.

14 Claims, 2 Drawing Sheets

OTHER PUBLICATIONS

Fischer, et al., (1999), *Plant J*, 19(5): 543–554, "Protein dynamics, activity and cellular localization of soybean lipoxygenases indicate distinct functional roles for individual isoforms".

Kolomiets, et al., (2000), *Plant Physiol*, 124:1121–1130, "A Leaf Lipoxygenase of Potato Induced Specifically by Pathogen Infection".

Chiron, et al., (2000), *Plant Physiol*, 124:865–872, "Gene Induction of Stilbene Biosynthesis in Scots Pine in Response to Ozone Treatment, Wounding, and Fungal Infection".

Ohme–Takagi, et al., (2000), *Plant Cell Physiol*, 41(11):1187–1192, Regulation of Ethylene–Induced Transcription of Defense Genes.

Slusarenko, AJ, (1996), *Lipoxygenase and Lipoxygenase Pathway Enzymes (Piazza, G., Ed), AOCS Press*, pp. 176–197, "The Role of Lipoxygenase in Plant Resistance to Infection".

* cited by examiner

GAATTCGGATCGTTGGATAGGAGAGTA<u>TGAC</u>ACAAGGGAGTGCGTATCTATACAGAGGTACG
CGTATACAGCATAGCGTTAAGCC<u>GTCA</u>ATGAAAAACAAAATCTAGGGTTGGTTTGTTTTAGAT
TACAATATAACTAAAATATATAATCCAAGTTATTTTAAAATAACACTTAATTTAAAATAATTT
AGATTATATAATCTAAGTAGATTTATAATCCGAAACAAACCGCTACACAGTGAAACAGCTAGC
TAAGAGAT<u>GTTTGGT</u>TTTTATAGACTAAATTTTACTCTATCTATTTTATTTTATCTTAGTCTCTA
AATTGCTAAATATTTAGTTTCTATATTT<u>GTCA</u>ATTTAAAAACTAAAAAAGAACAAAGAGATTA
AAAATTAGTCTCTATAAACGTAACACGCCTAGTG<u>TGAC</u>CAGACCACCAATCTTCCATCTGGAA
AAACCGCTGTCGCCTTCTTGCATT<u>CCATCC</u>TGAGCTTGGTTTACAAGCAAAGCAAAGACGAAT
GATCTTTCTCGACCCGAGAGACTTGTCTGGGCCAAAAACAATCTGGAGGAGAAATTTATTGCT
CCTCTATTTTTCGAAGGCTCGCCTTCACCGTACCAAATGGCGTCCGGAATTGTTTAGTCCTGTA
GTATATATGTACGCGGAATCGGTCGCTCGTACGATCCGCCATCGGTTAGCACGAGAAGCTAGC
GCCTGGTGCAGATCTTCTCGGGGTAGTTTTTAGTGTT<u>GTCA</u>ACTATTATTATAAACAATTATTT
AGAAAGTGAGTCTAACTTCATTGGTTATGATATGAAGAAAGTTGAGCTACACAGCCATGTCCA
TCGGTGTCGGCGAAACGTGCAGCAACTGAAACCGAAACCGCGGCCTTTCTCTTCGTTCGAGTT
TTACACGGTGTCTATTCCGTGGCCCCGGCGGATGCCTTGCC<u>ATGAC</u>CGGGGCCGGGACCGGG
AGGATCAACACTACGCACCTCCTCAGCTACGTAATTTACTACTAACACAAGCCAGGCGCAATT
AAGACCGGCCG<u>GTCA</u>ATGTCCAGTCCCTGTTTCCCTGTTCTGCTTGCAGGGCGGACCACCGAG
AGGAAACAACGTTGAGGACGGCACGCGACCGTCACGACGCGCGGCCCTCACGGCCACTGTAC
ATGATCGTCGTCGACGGCAGCAGCTCCGTAGGACGACTCAGCGCTGGAGCCTAGTGAAGGGT
CTGCAGTGCACTCGCGACGACGTGTCTCGTGTGTGTCGTCGCCCTCGGAGTCGATGTGGGATG
CGCATGGCACCGCAGCCCGTTTCCGCCGCGGTTTCGGTCTCGGCGCTATGGACACAGTCAGCT
CGGCCTCTGGCCTCTGGGCTCGTCCGTGCTCGCTTGCAGGTTGCAATTACACACCTGCCGGTT
GCTGGCTCCGCCGGCGTGGACCAGCTGGAGCCGGAGAAACCGCGCATGTGCCCGGGGC<u>AGCC</u>
<u>GCC</u>AGCCGGCTCCCAGCCTGATGGCTTTCTGATCTCGTTTTTCGTTTGTGTCGGATTGGTGGGT
CGGAACGATTCTTAGCCGGATTGCTTCTCTAATT<u>TATATAA</u>ACTTTAATCAACTGGAACGATT
CCGGGTGCAATCCGACGTAAACGAACAAGGCCTTACCGGGATCACCATTACCATAAGCCGCA
CGGTCCCCAAACCCGTGACGCCGACGTATACCATACCATACCATACTATGTAATACGTACTAT
CCAATCTTAATCCCCGCATTTTTTAAACTAGTTTCTCATCATCATCGTCCTCGTCGTCATCTTCT
TCTTCACCCTTTCCTTATCGTGTAGTAGTACATGTCGTTGTCGCCTACATCACTGGCTGGCAGA
GCAGTAAGCAGTAAAGAGTAGGCGCAGCATAAAGCCGAGGCGAGCAGCCGTCGCCGCCTATA
TATCGCGGCGCAGGGCAGCAGGAGTTCCACACTTCCATACACGCCTGCCTTGTGCCTTCCCTT
CCCTTGCCTTGCTTCGCTTATTGCCGGCACATCACATCGGCAGGCGGCGAGGGACGGAGCGAGCAG
GGAAGCCCATCCACCAGCCAGCCACCGCGTTCCTGAGAAGCGAGGAGCGAGAAAAGCGAAG
AGCGGCCATGTTCTGGCACGGGGTCGCGGACCGGCTGACGGGAAAGAACAAGGAGGCGTGG
AGCGAGGGCAAGATCCGCGGCACGGTGAGGCTGGTCAAGAAGGAGGTGCTGGACGTCGGCG
ACTTCAACGCCTCGCTCCTCGACGGCGTCCACAGGATCCTCGGCTGGGACGACGGCGTCGCCT
TCCAGCTCGTCAGCGCCACCGCGGGCCGACCCCAgtaagcgagccctgccccacgccacctatctgaacacgcccgctcc
cggtggccacggggccgtgacgtgacgccgggccgcgctcgctcgccggctcgccgcccgtggccggaccggaacgcacgggcatgcggccaccg
cgcgtttcgccgtccatttcggtttctacgtttcgtctcttcctgcctgtactggactggtcacccgtccggcatggcaagcacacagtcagacggacaggagc
gacaccgcgcgacccgtgagagttggtcgctggtccatggtccgttgcacccgcggtggctgggtccgtgtctctgcgacgaactcatgattgcggttaag
aaacttgcttgcctgctctgcttccatggacacggacagacagtgagacagggatgtattttttttggaattttctccgggctggaacagttgttgtgtgtggggt
ggtgtggcattctgaatctcgaacgcgactgcggtttcatgttcgctatcgcttccacggcaacgctccagctagcgtcatctgattgcatgcaggcgtttagg
acccggccggccgtactgtaatctccgctgaaatgtcgtatagtaaaccttgtttattagtactattttttgtgtgtgtgtgtggagctaataatgtgcttaaacga
aacctcgccgtcatgctgtcatgggttggtggatcccagGCAACGGGGGCCGTGGCAAGGTGGGGAAGGCGGCGCAC
CTGGAGGAGGCGGTGGTGTCGCTCAAGTCCACGGCGGACGGGGAGACCGTGTACCGGGTGAG
CTTCGAGTGGGACGAGTCGCAGGGCATCCCGGGCGCCGTCCTGGTCAGGAACCTGCAGCACG
CCGAGTTCTTCCTCAAGACGCTCACCCTCGAGGGCGTCCCAGGCAAGGGCACCGTCGTCTTCG
TCGCCAACTCGTGGGTCTACCCGCACAAGCTCTACTCCCAGGAACGCATCTTCTTCGCCAACG
ACgtgagtattaatctttctgatgcatgtcacgattttttttttgaaaagcgaccagcaggaggagatctaccgggcatatattaacagagaaggagtttaaa
aaactaattacaaaaattgaggttacttttttttttgctgctagaagcaaaaatatggacaagacaaggacaatcattgctatatgtatctgtatactcctacacaac
acgtactacccaaacaaccgcatccacacactcatcacttcgtattattgttaggggctctctactgcatttacgtagcatatgactaaattaacgcaaagtagtgc
tgcttaattaggttgtggaaaggatccatcagggcatattcattatgctcgtttgttgacccagaaggccagaactggttgatccatcacggcatattcatccta
cgttttacttctgccagcactatattactccgtggctatatatagaaaaaaacaggccagtctcactctaatcctgtgttgcttgcagACCTATCTGCC
GAGCAAAATGCCGGCGGCGTTGGTGCCTTATCGGCAAGATGAGCTCAAGATTCTCCGTGGCG
ACGATAATCCTGGACCATACCAGGAGCATGATCGCGTCTACCGTTACGACTACTACAATGACC

FIGURE 1A

TTGGTGATCCCGACAAGGGCGAAGAGCACGCTCGGCCGATCCTCGGTGGCAGCCAAGAACAC
CCGTATCCCCGTCGCTGCAGAACTGGCCGGCACCCAACAAAGAAAGgtactagctcaagtcagctagtgctag
tccataccatacaggatgccagaaatttggctgaaatccttgctgagttaaccttttttacgcagACCCAAATTCGGAGAGCAGGCTTTT
CCTGCTGAACCTGAACATCTACGTCCCGCGTGACGAACGCTTTGGGCATCTCAAGATGTCGGA
CTTCCTTGGGTACTCGCTGAAGACGATCATCGAGGCTGTTCTTCCAACACTGGGGACTTTCGTC
GATGACACGCCCAAGGAGTTCGATTCGTTTGAGGATATCCTCGGGCTCTACGAGCTGGGCCCA
GAGGCACCCAACAACCCACTGATAGCAGAGATCAGGAAGAAGATCCCCAGCGAGTTCCTTCG
AAGCATTCTGCCGAACGGTAGCCATGACCACCCGCTAAAGATGCCCCTTCCAAATGTCATCAA
ATCAGgtaaacccaaatttcttttttttttggaatcttctatgttaaacggccggtgcctgaactagaaaaaaatttaccatggctaaggctgaatcttggttg
gtataaaaccagATGTGTTGAAAAAGGCTCCGGAGTTTAAGTTTGGCTGGAGGACTGACGAAGAGTT
CGCGAGAGAGACACTTGCAGGCGTGAACCCAGTAATCATCAAACGTCTGACGgttagcgttcttgcatca
tttggatcggcaaaaatacaccttgccccatatattaactgagtacagagccttaaaggccttttttttatatatatattcgtatctcagGAGTTCCCCGC
TAAAAGCACCCTGGACCCAAGGCAGTACGGAGACCACACCAGCAAGATCACTGAAGCTCACA
TCCGGCATAACATGGGAGGCCTGTCGGTGCAGAACgtatgctggactgcatgaacgcacgcacgtacaaccgaaagcc
gcttaaaaccatcgactgatctgatttccgcgtaacgaaccctgtgcagGCACTGAGGAACAAGAGGCTCTTCATCCTAGAC
CACCATGACCATTTCATGCCGTACCTCGACGAGATCAACGAGCTGGAGGGGAACTTCATCTAC
GCCAGCAGGACCCTACTGTTCCTGAAGGACGATGGCACGCTGAAGCCCCTGGCCATCGAGCT
GAGCCTGCCCCACCCTGACGGCCAGCAGCGCGGCGCGGTCAGCAAGGTGTACACCCCGGCTC
ACACCGGCGTCGAGGGCCACGTCTGGCAGCTCGCCAAGGCTTATGCCTGCGTAAACGACTCTG
CCTGGCATCAGCTGATCAGCCACTGgtataagaaatgtttctggtgccttttctcttttttttccttttaattaattaatgtacatagataact
gaagcactaatcttaattgtgtggcttgcattgcattcagGCTGAACACGCACGCGGTGATCGAGCCGTTCGTAATCGC
GACAAACCGGCAGCTCAGCGTGGTGCATCCCGTGCACAAGCTGCTGAGCCCGCACTACCGTG
ACACGCTGAACATCAACGCCCTGGCACGCCAGACACTCATCAACGCCGGCGGCGTCTTCGAG
CGCACCGTGTTCCCTGCAAAGTACGCGCTGGGGATGTCGGCAGACGTGTACAAGAGCTGGAA
TTTCAACGAGCAGGCTCTCCCAGCAGATCTCGTCAAGAGgtacgtagacaatacactgaggtgagcagcactaaacg
cctatagaaaactgttcggttcttgacgtggttgtggttgcgtgcgttcagAGGTGTGGCTGTGCCGGACCAGTCAAGCCCAT
ATGGTGTCCGACTGCTGATCAAGGACTACCCCTATGCCGTTGACGGGCTCGTCATCTGGTGGG
CGATCGAGCGGTGGGTCAAGGAGTACCTGGACATCTACTACCCTAACGACGGCGAGCTCCAG
CGTGACGTGGAGCTGCAGGCGTGGTGGAAGGAGGTGCGTGAGGAGGCGCACGGCGACCTCAA
GGACCGAGACTGGTGGCCCAGGATGGACACCGTCCAGCAGCTGGCTAGGGCGTGCACGACCA
TCATCTGGGTGGCATCCGCGCTGCACGCGGCTGTCAACTTTGGGCAGTACCCATACGCCGGGT
ACCTCCCGAACCGGCCGACGGCCAGCCGGCGCCCGATGCCGGAGCCAGGCAGCCACGACTAC
AAGAAGCTGGGAGCGGGGCAGAAGGAGGCGGACATGGTGTTCATCCGCACCATCACCAGCCA
GTTCCAGACCATCCTGGGCATCTCGCTCATCGAGATCCTCTCCAAGCACTCCTCCGACGAGGT
GTACCTCGGCCAGCGTGACGAGCCTGATCGCTGGACGTCAGACGCCAAGGCGCTGGATGCGT
TCAAAAGATTCGGGAGCCGGCTGGTGCAGATTGAGAATCGGATCAAGACGATGAACGACAGT
CCGGACTTGAAGAACCGGAAGGGGCCTGTGGAAATGCCGTACATGCTGCTGTACCCCAACAC
GTCGGACGTTACCGGCGAGAAGGCCGAGGGGCTTACTGCCATGGGCATTCCCAACAGCATCT
CCATATGAGCCTGGGCAGATTGTGTCTCGTAGTAAATTGTTGTGCTGCGCCGTGCGATGTGTT
TCTTCATTGGTTTTGTCAGTCTCAGGGTAGGGGATGGAGATCATACCATGATCTTTGTAGGGTT
GAGAGAGGAGTCCACGCTTGAATATTGTTGTCATGTATGTAATTCTTGGTTAATAATAAAGTT
CGTCAGTTCATTTCTTAGCCTATCAGTCTCCAGCCAAAACTTATACTTCAAAAAAAAGTAATA
GGCATTTGATTCCAATATGATAATAAAATAGGACTACTTTTTCCGTCCGTTCACGCATGTGAGT
GTTGCCGGTTCCGAAGACGATGACACGGGTATTCGTTTTGTCCCGGGCTTATTCCTTTATGCT
GGATTGGTGGGTCGAAACGATTTCTAACCGGATTGCTTATCTAATTTGTATAAATTTTTATTAG
CTCAAACGATTCCGGACGCAATCCAATACAAACGAACAAGCCGTCAGGTGTCATGGAGTACT
GTACTCATGTGTACTGTATTCCTGATGCCGCCGCCCGCCGACTTTGGCGGTTTGCCGGCCCTGC
GAATGCCACCGCTCTTCCTAGCTGGGGTCGTACACTCTCCACGCCTCCCACGTCTTACTGCTCA
CCGCCACCACCCGCCGCCTCTATCTCGGTCTGCGACGCGTTGGCCCATCCCTGCTCCCCGCCA
TGGTCTCTCGCCCACCGAGGTATGTTCGAGGAGCAAATAAGATGAGGAGCCAGTTTTCTTCTT
CCGTTCTTCTCTCGCATTAGCCAAGGAAGGCACCGTAGAAAGATCCCCAAAGCTTTCCAGAAA
TCCGCTTTTCACGATCAGTAGGGCTCGCAGTTTTTTTTTCTTTCCTACAGCGCATTTCTCGGTCTT
CACCTCGCTCCTGTTGTAGAGTTCTCGTGGCAGGGGAATTC

FIGURE 1B

SEQUENCE LISTING

<160> NUMBER OF SEQ ID NOS: 56

<210> SEQ ID NO 1
<211> LENGTH: 2912
<212> TYPE: DNA
<213> ORGANISM: Zea mays
<220> FEATURE:
<221> NAME/KEY: CDS
<222> LOCATION: (81)...(2702)
<223> OTHER INFORMATION: LOX1

<400> SEQUENCE: 1

```
cactcagtct gcaaataccc cacaaggcca ctccaaagag ctagtagttg cagttagctc      60
tgccggtagt ggaaccgaag atg ttc ggg aac atc gga aag atc ccc atc atc    113
                     Met Phe Gly Asn Ile Gly Lys Ile Pro Ile Ile
                      1               5                  10 ggc gac ctg acg ggc agc aac aag aat gcg cac ctc aag ggc aac gtg     161
Gly Asp Leu Thr Gly Ser Asn Lys Asn Ala His Leu Lys Gly Asn Val
             15                  20                  25 gtg ctc gtg cgc aag acc gtg ctc ggc ttg gac gtc acc agc atc gcc     209
Val Leu Val Arg Lys Thr Val Leu Gly Leu Asp Val Thr Ser Ile Ala
         30                  35                  40 ggc tcc ctc ctc gac ggc atc ggc gag ttc ctc ggc cgc ggc gtc acc     257
Gly Ser Leu Leu Asp Gly Ile Gly Glu Phe Leu Gly Arg Gly Val Thr
     45                  50                  55 tgc cag ctt atc agc tcc acc gtc gtc gac cct aac aac ggc aac cgc     305
Cys Gln Leu Ile Ser Ser Thr Val Val Asp Pro Asn Asn Gly Asn Arg
 60                  65                  70                  75 ggg aag ttg ggc gcg gag gcg agc ctg gag cag tgg ctg ctg aac ccg     353
Gly Lys Leu Gly Ala Glu Ala Ser Leu Glu Gln Trp Leu Leu Asn Pro
                 80                  85                  90 ccg ccg ctt ctg tcc agc gag aac cag ttc cgc gtc acc ttc gac tgg     401
Pro Pro Leu Leu Ser Ser Glu Asn Gln Phe Arg Val Thr Phe Asp Trp
             95                 100                 105 gag gtg gag aag cag ggc atc ccg ggc gcc atc atc gtc aag aac aac     449
Glu Val Glu Lys Gln Gly Ile Pro Gly Ala Ile Ile Val Lys Asn Asn
        110                 115                 120
```

```
cac gcc tcc gag ttc ttc ctc aag acc atc acc ctc aac gac gtc ccc    497
His Ala Ser Glu Phe Phe Leu Lys Thr Ile Thr Leu Asn Asp Val Pro
    125                 130                 135 ggc cac ggc acc atc gtc ttc gtc gcc aac tca tgg atc tac ccg cag    545
Gly His Gly Thr Ile Val Phe Val Ala Asn Ser Trp Ile Tyr Pro Gln
140                 145                 150                 155 tcc aag tac cgc tac aac cgc gtc ttc ttc tcc aac gac acg tac ctc    593
Ser Lys Tyr Arg Tyr Asn Arg Val Phe Phe Ser Asn Asp Thr Tyr Leu
                160                 165                 170 ccc agc cag atg ccg gcg gcg ctg aag ccc tac cgc gac gac gag ctc    641
Pro Ser Gln Met Pro Ala Ala Leu Lys Pro Tyr Arg Asp Asp Glu Leu
    175                 180                 185 cgg aac ctg agg ggc gac gac cag cag ggc ccg tac cag gag cac gac    689
Arg Asn Leu Arg Gly Asp Asp Gln Gln Gly Pro Tyr Gln Glu His Asp
            190                 195                 200 cgc gtc tac cgc tac gac gtc tac aac gac ctg ggc ctg cct gac agc    737
Arg Val Tyr Arg Tyr Asp Val Tyr Asn Asp Leu Gly Leu Pro Asp Ser
205                 210                 215 ggg aac ccg cgc ccc gtc ctc ggc ggc acc aag gag ctc ccc tac ccg    785
Gly Asn Pro Arg Pro Val Leu Gly Gly Thr Lys Glu Leu Pro Tyr Pro
220                 225                 230                 235 cgc cgc tgc cgc acc ggg cgg aag ccc acc aag agc gac ccc aac agc    833
Arg Arg Cys Arg Thr Gly Arg Lys Pro Thr Lys Ser Asp Pro Asn Ser
                240                 245                 250 gag agc agg ctc acg ctg gtc gac ggc gac gtc tac gtg ccg cgc gac    881
Glu Ser Arg Leu Thr Leu Val Asp Gly Asp Val Tyr Val Pro Arg Asp
            255                 260                 265 gag cgc ttc ggc cac atc aag aag tcg gac ttc tac ggc tac gcc atc    929
Glu Arg Phe Gly His Ile Lys Lys Ser Asp Phe Tyr Gly Tyr Ala Ile
        270                 275                 280 aag gcg ctg gtg aac gcc gtc atc ccg gca atc cgc acc tac gtc gac    977
Lys Ala Leu Val Asn Ala Val Ile Pro Ala Ile Arg Thr Tyr Val Asp
285                 290                 295 ctg tcg ccc ggc gag ttc gac tcc ttc aag gac atc atg aag ctg tac   1025
Leu Ser Pro Gly Glu Phe Asp Ser Phe Lys Asp Ile Met Lys Leu Tyr
300                 305                 310                 315 gag ggc ggg atc cag ctg ccc aaa ata cca gcc ctc gag gac ctg cgg   1073
Glu Gly Gly Ile Gln Leu Pro Lys Ile Pro Ala Leu Glu Asp Leu Arg
                320                 325                 330 aag cag ttc cca ctc gag ctc gtc aag gat gtc ctc ccg gtc ggc ggc   1121
Lys Gln Phe Pro Leu Glu Leu Val Lys Asp Val Leu Pro Val Gly Gly
            335                 340                 345 gac tac ctc ctc aag ctc ccc atg ccg cag atc atc aaa gag gac aag   1169
Asp Tyr Leu Leu Lys Leu Pro Met Pro Gln Ile Ile Lys Glu Asp Lys
        350                 355                 360 aca ggt tgg atg aca gat gag gag ttt gga cgg gag att ctc gcc ggc   1217
Thr Gly Trp Met Thr Asp Glu Glu Phe Gly Arg Glu Ile Leu Ala Gly
365                 370                 375 gtg aac ccc atg ctc gtc aag cgt ctc acg gag ttc cct ccg agg agc   1265
Val Asn Pro Met Leu Val Lys Arg Leu Thr Glu Phe Pro Pro Arg Ser
380                 385                 390                 395 agt ctt gac ccg agc aag tac ggc gac cac acc agc acc atc agg gag   1313
Ser Leu Asp Pro Ser Lys Tyr Gly Asp His Thr Ser Thr Ile Arg Glu
                400                 405                 410 gcg gac ctc gag aac aag ctc gag ggc ctg acg gtg cag cag gcg ctg   1361
Ala Asp Leu Glu Asn Lys Leu Glu Gly Leu Thr Val Gln Gln Ala Leu
            415                 420                 425 cac ggc aac cgg ctc tac atc ctg gac cac cac gac aac ttc atg ccg   1409
His Gly Asn Arg Leu Tyr Ile Leu Asp His His Asp Asn Phe Met Pro
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 430 |     |     |     |     | 435 |     |     |     |     | 440 |     |     |      |
| ttc | ctg | gtc | agg | gtg | aac | agc | ctg | gag | ggc | aac | ttc | atc | tac | gcc | acc | 1457 |
| Phe | Leu | Val | Arg | Val | Asn | Ser | Leu | Glu | Gly | Asn | Phe | Ile | Tyr | Ala | Thr |      |
|     |     | 445 |     |     |     |     | 450 |     |     |     |     | 455 |     |     |     |      |
| agg | acc | gtg | ctg | ttc | ctg | cgc | ggc | gac | ggc | acg | ctg | gtg | ccg | gtg | gcc | 1505 |
| Arg | Thr | Val | Leu | Phe | Leu | Arg | Gly | Asp | Gly | Thr | Leu | Val | Pro | Val | Ala |      |
| 460 |     |     |     |     | 465 |     |     |     |     | 470 |     |     |     |     | 475 |      |
| atc | gag | ctg | agc | ctg | ccc | gag | ctc | cgg | gac | ggc | ctg | acc | acc | gcc | aag | 1553 |
| Ile | Glu | Leu | Ser | Leu | Pro | Glu | Leu | Arg | Asp | Gly | Leu | Thr | Thr | Ala | Lys |      |
|     |     |     |     | 480 |     |     |     |     | 485 |     |     |     |     | 490 |     |      |
| agc | acc | gtg | tac | acg | ccc | aag | tcg | acc | acc | ggc | gcg | gag | gcg | tgg | gtg | 1601 |
| Ser | Thr | Val | Tyr | Thr | Pro | Lys | Ser | Thr | Thr | Gly | Ala | Glu | Ala | Trp | Val |      |
|     |     |     | 495 |     |     |     |     | 500 |     |     |     |     | 505 |     |     |      |
| tgg | cac | ctg | gcc | aag | gcc | tac | gcc | aac | gtg | aac | gac | tac | tgc | tgg | cac | 1649 |
| Trp | His | Leu | Ala | Lys | Ala | Tyr | Ala | Asn | Val | Asn | Asp | Tyr | Cys | Trp | His |      |
| 510 |     |     |     |     | 515 |     |     |     |     | 520 |     |     |     |     |     |      |
| cag | ctc | atc | agc | cac | tgg | ctc | aac | acc | cac | gcc | gtg | atg | gag | ccg | ttc | 1697 |
| Gln | Leu | Ile | Ser | His | Trp | Leu | Asn | Thr | His | Ala | Val | Met | Glu | Pro | Phe |      |
| 525 |     |     |     |     | 530 |     |     |     |     | 535 |     |     |     |     |     |      |
| gtg | atc | gcc | acc | aac | cgg | cag | ctc | agc | gtg | acg | cac | ccc | gtg | cac | aag | 1745 |
| Val | Ile | Ala | Thr | Asn | Arg | Gln | Leu | Ser | Val | Thr | His | Pro | Val | His | Lys |      |
| 540 |     |     |     |     | 545 |     |     |     |     | 550 |     |     |     |     | 555 |      |
| ctc | ctc | ctg | ccg | cac | tac | cgt | gac | acc | atg | aac | atc | aac | tcc | aac | gcg | 1793 |
| Leu | Leu | Leu | Pro | His | Tyr | Arg | Asp | Thr | Met | Asn | Ile | Asn | Ser | Asn | Ala |      |
|     |     |     |     | 560 |     |     |     |     | 565 |     |     |     |     | 570 |     |      |
| cgc | cag | atg | ctc | gtc | aac | gcc | ggc | ggc | atc | ttc | gag | acc | acc | gtc | ttc | 1841 |
| Arg | Gln | Met | Leu | Val | Asn | Ala | Gly | Gly | Ile | Phe | Glu | Thr | Thr | Val | Phe |      |
|     |     |     | 575 |     |     |     |     | 580 |     |     |     |     | 585 |     |     |      |
| ccg | cgc | cag | tac | gcg | ttc | gag | atg | tcc | tcc | gtc | atc | tac | aag | gac | tgg | 1889 |
| Pro | Arg | Gln | Tyr | Ala | Phe | Glu | Met | Ser | Ser | Val | Ile | Tyr | Lys | Asp | Trp |      |
|     |     | 590 |     |     |     |     | 595 |     |     |     |     | 600 |     |     |     |      |
| aac | ttc | aca | gag | cag | gct | ctc | cct | gac | gac | cta | atc | aag | aga | ggc | atg | 1937 |
| Asn | Phe | Thr | Glu | Gln | Ala | Leu | Pro | Asp | Asp | Leu | Ile | Lys | Arg | Gly | Met |      |
|     | 605 |     |     |     |     | 610 |     |     |     |     | 615 |     |     |     |     |      |
| gcg | gtc | gca | gac | ccg | tcg | agc | ccg | tac | aag | gta | cgg | ctg | ctg | gtg | gag | 1985 |
| Ala | Val | Ala | Asp | Pro | Ser | Ser | Pro | Tyr | Lys | Val | Arg | Leu | Leu | Val | Glu |      |
| 620 |     |     |     |     | 625 |     |     |     |     | 630 |     |     |     |     | 635 |      |
| gac | tac | ccg | tac | gcg | tcg | gac | ggg | ctg | gcc | atc | tgg | cac | gcc | atc | gag | 2033 |
| Asp | Tyr | Pro | Tyr | Ala | Ser | Asp | Gly | Leu | Ala | Ile | Trp | His | Ala | Ile | Glu |      |
|     |     |     |     | 640 |     |     |     |     | 645 |     |     |     |     | 650 |     |      |
| cag | tgg | gtg | acg | gag | tac | ctc | gcc | gtc | tac | tac | ccc | aac | gac | ggc | gtg | 2081 |
| Gln | Trp | Val | Thr | Glu | Tyr | Leu | Ala | Val | Tyr | Tyr | Pro | Asn | Asp | Gly | Val |      |
|     |     |     | 655 |     |     |     |     | 660 |     |     |     |     | 665 |     |     |      |
| ctg | cgg | gcg | gac | gtg | gag | ctg | cag | gcg | tgg | tgg | aag | gag | gcg | cgc | gag | 2129 |
| Leu | Arg | Ala | Asp | Val | Glu | Leu | Gln | Ala | Trp | Trp | Lys | Glu | Ala | Arg | Glu |      |
|     |     | 670 |     |     |     |     | 675 |     |     |     |     | 680 |     |     |     |      |
| gtc | ggg | cac | gcc | gac | ctc | aag | gac | gcg | ccc | tgg | tgg | ccc | aag | atg | cag | 2177 |
| Val | Gly | His | Ala | Asp | Leu | Lys | Asp | Ala | Pro | Trp | Trp | Pro | Lys | Met | Gln |      |
|     | 685 |     |     |     |     | 690 |     |     |     |     | 695 |     |     |     |     |      |
| acg | gtg | gcc | gag | ctg | gtc | aag | gcc | tgc | acc | acc | atc | atc | tgg | atc | gcg | 2225 |
| Thr | Val | Ala | Glu | Leu | Val | Lys | Ala | Cys | Thr | Thr | Ile | Ile | Trp | Ile | Ala |      |
| 700 |     |     |     |     | 705 |     |     |     |     | 710 |     |     |     |     | 715 |      |
| tcg | gcg | ctc | cac | gcg | gcc | gtc | aac | ttc | ggg | cag | tac | ccg | tac | gcc | ggg | 2273 |
| Ser | Ala | Leu | His | Ala | Ala | Val | Asn | Phe | Gly | Gln | Tyr | Pro | Tyr | Ala | Gly |      |
|     |     |     |     | 720 |     |     |     |     | 725 |     |     |     |     | 730 |     |      |
| tac | ctc | ccg | aac | cgc | ccg | tcc | gtc | agc | cgg | aag | ccg | atg | ccg | gcg | ccg | 2321 |
| Tyr | Leu | Pro | Asn | Arg | Pro | Ser | Val | Ser | Arg | Lys | Pro | Met | Pro | Ala | Pro |      |
|     |     |     | 735 |     |     |     |     | 740 |     |     |     |     | 745 |     |     |      |
| ggc | agc | gac | gag | tac | gcg | gag | ctg | gag | cgc | aag | ccg | gag | aag | gtg | ttc | 2369 |

-continued

```
Gly Ser Asp Glu Tyr Ala Glu Leu Glu Arg Lys Pro Glu Lys Val Phe
            750                 755                 760 gtg cgc acc atc acc agc cag ttc cag gcc ctc gtc ggc atc tcg ctg      2417
Val Arg Thr Ile Thr Ser Gln Phe Gln Ala Leu Val Gly Ile Ser Leu
765                 770                 775 ctg gag atc ctg tcc agc cac tcc tcc gac gag gtg tac ctc ggc cag      2465
Leu Glu Ile Leu Ser Ser His Ser Ser Asp Glu Val Tyr Leu Gly Gln
780                 785                 790                 795 cgc gac acc aag gag tgg acg tcg gac gcc aag gcg cag gag gcg ttc      2513
Arg Asp Thr Lys Glu Trp Thr Ser Asp Ala Lys Ala Gln Glu Ala Phe
                800                 805                 810 aag cgg ttc ggc gcg cgg ctg acc gag atc gag aaa cgc gtc gtc acc      2561
Lys Arg Phe Gly Ala Arg Leu Thr Glu Ile Glu Lys Arg Val Val Thr
            815                 820                 825 atg aac gcg gac cct cgc ctc aag aac cgc aac ggc ccg gcc gag ttc      2609
Met Asn Ala Asp Pro Arg Leu Lys Asn Arg Asn Gly Pro Ala Glu Phe
        830                 835                 840 ccc tac acg ctg ctc tac ccc aac acc tcc gac acg aag ggc gac gcc      2657
Pro Tyr Thr Leu Leu Tyr Pro Asn Thr Ser Asp Thr Lys Gly Asp Ala
    845                 850                 855 gcc ggc atc acc gcc aag ggc att cca aac agc atc tcc att tga          2702
Ala Gly Ile Thr Ala Lys Gly Ile Pro Asn Ser Ile Ser Ile *
860                 865                 870 gttctgtctg tctgagctga ggacgtacgg tcgtcgcact agttgtttgc gtttccccgt    2762
tccgttccgt gaagtgtggt tctcacttgc gcggtattgt gcaaatagcc aagtactcct    2822
tacagaagtc gctacgtgag gactgttgta ataaggctct attcagttcc tcaataatga    2882
agttactttg tgttcaaaaa aaaaaaaaaa                                     2912
```

<210> SEQ ID NO 2
<211> LENGTH: 873
<212> TYPE: PRT
<213> ORGANISM: Zea mays

<400> SEQUENCE: 2

```
Met Phe Gly Asn Ile Gly Lys Ile Pro Ile Ile Gly Asp Leu Thr Gly
 1               5                   10                  15

Ser Asn Lys Asn Ala His Leu Lys Gly Asn Val Val Leu Val Arg Lys
            20                  25                  30

Thr Val Leu Gly Leu Asp Val Thr Ser Ile Ala Gly Ser Leu Leu Asp
        35                  40                  45

Gly Ile Gly Glu Phe Leu Gly Arg Gly Val Thr Cys Gln Leu Ile Ser
    50                  55                  60

Ser Thr Val Val Asp Pro Asn Asn Gly Asn Arg Gly Lys Leu Gly Ala
65                  70                  75                  80

Glu Ala Ser Leu Glu Gln Trp Leu Leu Asn Pro Pro Leu Ser
                85                  90                  95

Ser Glu Asn Gln Phe Arg Val Thr Phe Asp Trp Glu Val Glu Lys Gln
            100                 105                 110

Gly Ile Pro Gly Ala Ile Ile Val Lys Asn Asn His Ala Ser Glu Phe
        115                 120                 125

Phe Leu Lys Thr Ile Thr Leu Asn Asp Val Pro Gly His Gly Thr Ile
    130                 135                 140

Val Phe Val Ala Asn Ser Trp Ile Tyr Pro Gln Ser Lys Tyr Arg Tyr
145                 150                 155                 160

Asn Arg Val Phe Phe Ser Asn Asp Thr Tyr Leu Pro Ser Gln Met Pro
                165                 170                 175
```

```
Ala Ala Leu Lys Pro Tyr Arg Asp Asp Glu Leu Arg Asn Leu Arg Gly
            180                 185                 190

Asp Asp Gln Gln Gly Pro Tyr Gln Glu His Asp Arg Val Tyr Arg Tyr
        195                 200                 205

Asp Val Tyr Asn Asp Leu Gly Leu Pro Asp Ser Gly Asn Pro Arg Pro
    210                 215                 220

Val Leu Gly Gly Thr Lys Glu Leu Pro Tyr Pro Arg Arg Cys Arg Thr
225                 230                 235                 240

Gly Arg Lys Pro Thr Lys Ser Asp Pro Asn Ser Glu Ser Arg Leu Thr
                245                 250                 255

Leu Val Asp Gly Asp Val Tyr Val Pro Arg Asp Glu Arg Phe Gly His
            260                 265                 270

Ile Lys Lys Ser Asp Phe Tyr Gly Tyr Ala Ile Lys Ala Leu Val Asn
        275                 280                 285

Ala Val Ile Pro Ala Ile Arg Thr Tyr Val Asp Leu Ser Pro Gly Glu
    290                 295                 300

Phe Asp Ser Phe Lys Asp Ile Met Lys Leu Tyr Glu Gly Gly Ile Gln
305                 310                 315                 320

Leu Pro Lys Ile Pro Ala Leu Glu Asp Leu Arg Lys Gln Phe Pro Leu
                325                 330                 335

Glu Leu Val Lys Asp Val Leu Pro Val Gly Gly Asp Tyr Leu Leu Lys
            340                 345                 350

Leu Pro Met Pro Gln Ile Ile Lys Glu Asp Lys Thr Gly Trp Met Thr
        355                 360                 365

Asp Glu Glu Phe Gly Arg Glu Ile Leu Ala Gly Val Asn Pro Met Leu
    370                 375                 380

Val Lys Arg Leu Thr Glu Phe Pro Pro Arg Ser Ser Leu Asp Pro Ser
385                 390                 395                 400

Lys Tyr Gly Asp His Thr Ser Thr Ile Arg Glu Ala Asp Leu Glu Asn
                405                 410                 415

Lys Leu Glu Gly Leu Thr Val Gln Gln Ala Leu His Gly Asn Arg Leu
            420                 425                 430

Tyr Ile Leu Asp His His Asp Asn Phe Met Pro Phe Leu Val Arg Val
        435                 440                 445

Asn Ser Leu Glu Gly Asn Phe Ile Tyr Ala Thr Arg Thr Val Leu Phe
    450                 455                 460

Leu Arg Gly Asp Gly Thr Leu Val Pro Val Ala Ile Glu Leu Ser Leu
465                 470                 475                 480

Pro Glu Leu Arg Asp Gly Leu Thr Thr Ala Lys Ser Thr Val Tyr Thr
                485                 490                 495

Pro Lys Ser Thr Thr Gly Ala Glu Ala Trp Val Trp His Leu Ala Lys
            500                 505                 510

Ala Tyr Ala Asn Val Asn Asp Tyr Cys Trp His Gln Leu Ile Ser His
        515                 520                 525

Trp Leu Asn Thr His Ala Val Met Glu Pro Phe Val Ile Ala Thr Asn
    530                 535                 540

Arg Gln Leu Ser Val Thr His Pro Val His Lys Leu Leu Leu Pro His
545                 550                 555                 560

Tyr Arg Asp Thr Met Asn Ile Asn Ser Asn Ala Arg Gln Met Leu Val
                565                 570                 575

Asn Ala Gly Gly Ile Phe Glu Thr Thr Val Phe Pro Arg Gln Tyr Ala
            580                 585                 590
```

-continued

```
Phe Glu Met Ser Ser Val Ile Tyr Lys Asp Trp Asn Phe Thr Glu Gln
            595                 600                 605

Ala Leu Pro Asp Asp Leu Ile Lys Arg Gly Met Ala Val Ala Asp Pro
        610                 615                 620

Ser Ser Pro Tyr Lys Val Arg Leu Leu Val Glu Asp Tyr Pro Tyr Ala
625                 630                 635                 640

Ser Asp Gly Leu Ala Ile Trp His Ala Ile Glu Gln Trp Val Thr Glu
                645                 650                 655

Tyr Leu Ala Val Tyr Tyr Pro Asn Asp Gly Val Leu Arg Ala Asp Val
            660                 665                 670

Glu Leu Gln Ala Trp Trp Lys Glu Ala Arg Glu Val Gly His Ala Asp
        675                 680                 685

Leu Lys Asp Ala Pro Trp Trp Pro Lys Met Gln Thr Val Ala Glu Leu
690                 695                 700

Val Lys Ala Cys Thr Thr Ile Ile Trp Ile Ala Ser Ala Leu His Ala
705                 710                 715                 720

Ala Val Asn Phe Gly Gln Tyr Pro Tyr Ala Gly Tyr Leu Pro Asn Arg
                725                 730                 735

Pro Ser Val Ser Arg Lys Pro Met Pro Ala Pro Gly Ser Asp Glu Tyr
            740                 745                 750

Ala Glu Leu Glu Arg Lys Pro Glu Lys Val Phe Val Arg Thr Ile Thr
        755                 760                 765

Ser Gln Phe Gln Ala Leu Val Gly Ile Ser Leu Leu Glu Ile Leu Ser
770                 775                 780

Ser His Ser Ser Asp Glu Val Tyr Leu Gly Gln Arg Asp Thr Lys Glu
785                 790                 795                 800

Trp Thr Ser Asp Ala Lys Ala Gln Glu Ala Phe Lys Arg Phe Gly Ala
                805                 810                 815

Arg Leu Thr Glu Ile Glu Lys Arg Val Val Thr Met Asn Ala Asp Pro
            820                 825                 830

Arg Leu Lys Asn Arg Asn Gly Pro Ala Glu Phe Pro Tyr Thr Leu Leu
        835                 840                 845

Tyr Pro Asn Thr Ser Asp Thr Lys Gly Asp Ala Ala Gly Ile Thr Ala
    850                 855                 860

Lys Gly Ile Pro Asn Ser Ile Ser Ile
865                 870
```

<210> SEQ ID NO 3
<211> LENGTH: 2622
<212> TYPE: DNA
<213> ORGANISM: Zea mays
<220> FEATURE:
<221> NAME/KEY: CDS
<222> LOCATION: (1)...(2622)

<400> SEQUENCE: 3

```
atg ttc ggg aac atc gga aag atc ccc atc atc ggc gac ctg acg ggc      48
Met Phe Gly Asn Ile Gly Lys Ile Pro Ile Ile Gly Asp Leu Thr Gly
 1               5                  10                  15 agc aac aag aat gcg cac ctc aag ggc aac gtg gtg ctc gtg cgc aag      96
Ser Asn Lys Asn Ala His Leu Lys Gly Asn Val Val Leu Val Arg Lys
            20                  25                  30 acc gtg ctc ggc ttg gac gtc acc agc atc gcc ggc tcc ctc ctc gac     144
Thr Val Leu Gly Leu Asp Val Thr Ser Ile Ala Gly Ser Leu Leu Asp
        35                  40                  45 ggc atc ggc gag ttc ctc ggc cgc ggc gtc acc tgc cag ctt atc agc     192
Gly Ile Gly Glu Phe Leu Gly Arg Gly Val Thr Cys Gln Leu Ile Ser
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 50  |     |     |     |     | 55  |     |     |     |     | 60  |     |     |      |
| tcc | acc | gtc | gtc | gac | cct | aac | aac | ggc | aac | cgc | ggg | aag | ttg | ggc | gcg | 240  |
| Ser | Thr | Val | Val | Asp | Pro | Asn | Asn | Gly | Asn | Arg | Gly | Lys | Leu | Gly | Ala |      |
| 65  |     |     |     |     | 70  |     |     |     |     | 75  |     |     |     |     | 80  |      |
| gag | gcg | agc | ctg | gag | cag | tgg | ctg | ctg | aac | ccg | ccg | ccg | ctt | ctg | tcc | 288  |
| Glu | Ala | Ser | Leu | Glu | Gln | Trp | Leu | Leu | Asn | Pro | Pro | Pro | Leu | Leu | Ser |      |
|     |     |     |     | 85  |     |     |     |     | 90  |     |     |     |     | 95  |     |      |
| agc | gag | aac | cag | ttc | cgc | gtc | acc | ttc | gac | tgg | gag | gtg | gag | aag | cag | 336  |
| Ser | Glu | Asn | Gln | Phe | Arg | Val | Thr | Phe | Asp | Trp | Glu | Val | Glu | Lys | Gln |      |
|     |     |     | 100 |     |     |     |     | 105 |     |     |     |     | 110 |     |     |      |
| ggc | atc | ccg | ggc | gcc | atc | atc | gtc | aag | aac | aac | cac | gcc | tcc | gag | ttc | 384  |
| Gly | Ile | Pro | Gly | Ala | Ile | Ile | Val | Lys | Asn | Asn | His | Ala | Ser | Glu | Phe |      |
|     |     | 115 |     |     |     |     | 120 |     |     |     |     | 125 |     |     |     |      |
| ttc | ctc | aag | acc | atc | acc | ctc | aac | gac | gtc | ccc | ggc | cac | ggc | acc | atc | 432  |
| Phe | Leu | Lys | Thr | Ile | Thr | Leu | Asn | Asp | Val | Pro | Gly | His | Gly | Thr | Ile |      |
|     | 130 |     |     |     |     | 135 |     |     |     |     | 140 |     |     |     |     |      |
| gtc | ttc | gtc | gcc | aac | tca | tgg | atc | tac | ccg | cag | tcc | aag | tac | cgc | tac | 480  |
| Val | Phe | Val | Ala | Asn | Ser | Trp | Ile | Tyr | Pro | Gln | Ser | Lys | Tyr | Arg | Tyr |      |
| 145 |     |     |     |     | 150 |     |     |     |     | 155 |     |     |     |     | 160 |      |
| aac | cgc | gtc | ttc | ttc | tcc | aac | gac | acg | tac | ctc | ccc | agc | cag | atg | ccg | 528  |
| Asn | Arg | Val | Phe | Phe | Ser | Asn | Asp | Thr | Tyr | Leu | Pro | Ser | Gln | Met | Pro |      |
|     |     |     |     | 165 |     |     |     |     | 170 |     |     |     |     | 175 |     |      |
| gcg | gcg | ctg | aag | ccc | tac | cgc | gac | gac | gag | ctc | cgg | aac | ctg | agg | ggc | 576  |
| Ala | Ala | Leu | Lys | Pro | Tyr | Arg | Asp | Asp | Glu | Leu | Arg | Asn | Leu | Arg | Gly |      |
|     |     |     | 180 |     |     |     |     | 185 |     |     |     |     | 190 |     |     |      |
| gac | gac | cag | cag | ggc | ccg | tac | cag | gag | cac | gac | cgc | gtc | tac | cgc | tac | 624  |
| Asp | Asp | Gln | Gln | Gly | Pro | Tyr | Gln | Glu | His | Asp | Arg | Val | Tyr | Arg | Tyr |      |
|     |     | 195 |     |     |     |     | 200 |     |     |     |     | 205 |     |     |     |      |
| gac | gtc | tac | aac | gac | ctg | ggc | ctg | cct | gac | agc | ggg | aac | ccg | cgc | ccc | 672  |
| Asp | Val | Tyr | Asn | Asp | Leu | Gly | Leu | Pro | Asp | Ser | Gly | Asn | Pro | Arg | Pro |      |
|     | 210 |     |     |     |     | 215 |     |     |     |     | 220 |     |     |     |     |      |
| gtc | ctc | ggc | ggc | acc | aag | gag | ctc | ccc | tac | ccg | cgc | cgc | tgc | cgc | acc | 720  |
| Val | Leu | Gly | Gly | Thr | Lys | Glu | Leu | Pro | Tyr | Pro | Arg | Arg | Cys | Arg | Thr |      |
| 225 |     |     |     |     | 230 |     |     |     |     | 235 |     |     |     |     | 240 |      |
| ggg | cgg | aag | ccc | acc | aag | agc | gac | ccc | aac | agc | gag | agc | agg | ctc | acg | 768  |
| Gly | Arg | Lys | Pro | Thr | Lys | Ser | Asp | Pro | Asn | Ser | Glu | Ser | Arg | Leu | Thr |      |
|     |     |     |     | 245 |     |     |     |     | 250 |     |     |     |     | 255 |     |      |
| ctg | gtc | gac | ggc | gac | gtc | tac | gtg | ccg | cgc | gac | gag | cgc | ttc | ggc | cac | 816  |
| Leu | Val | Asp | Gly | Asp | Val | Tyr | Val | Pro | Arg | Asp | Glu | Arg | Phe | Gly | His |      |
|     |     |     | 260 |     |     |     |     | 265 |     |     |     |     | 270 |     |     |      |
| atc | aag | aag | tcg | gac | ttc | tac | ggc | tac | gcc | atc | aag | gcg | ctg | gtg | aac | 864  |
| Ile | Lys | Lys | Ser | Asp | Phe | Tyr | Gly | Tyr | Ala | Ile | Lys | Ala | Leu | Val | Asn |      |
|     |     | 275 |     |     |     |     | 280 |     |     |     |     | 285 |     |     |     |      |
| gcc | gtc | atc | ccg | gca | atc | cgc | acc | tac | gtc | gac | ctg | tcg | ccc | ggc | gag | 912  |
| Ala | Val | Ile | Pro | Ala | Ile | Arg | Thr | Tyr | Val | Asp | Leu | Ser | Pro | Gly | Glu |      |
|     | 290 |     |     |     |     | 295 |     |     |     |     | 300 |     |     |     |     |      |
| ttc | gac | tcc | ttc | aag | gac | atc | atg | aag | ctg | tac | gag | ggc | ggg | atc | cag | 960  |
| Phe | Asp | Ser | Phe | Lys | Asp | Ile | Met | Lys | Leu | Tyr | Glu | Gly | Gly | Ile | Gln |      |
| 305 |     |     |     |     | 310 |     |     |     |     | 315 |     |     |     |     | 320 |      |
| ctg | ccc | aaa | ata | cca | gcc | ctc | gag | gac | ctg | cgg | aag | cag | ttc | cca | ctc | 1008 |
| Leu | Pro | Lys | Ile | Pro | Ala | Leu | Glu | Asp | Leu | Arg | Lys | Gln | Phe | Pro | Leu |      |
|     |     |     |     | 325 |     |     |     |     | 330 |     |     |     |     | 335 |     |      |
| gag | ctc | gtc | aag | gat | gtc | ctc | ccg | gtc | ggc | ggc | gac | tac | ctc | ctc | aag | 1056 |
| Glu | Leu | Val | Lys | Asp | Val | Leu | Pro | Val | Gly | Gly | Asp | Tyr | Leu | Leu | Lys |      |
|     |     |     | 340 |     |     |     |     | 345 |     |     |     |     | 350 |     |     |      |
| ctc | ccc | atg | ccg | cag | atc | atc | aaa | gag | gac | aag | aca | ggt | tgg | atg | aca | 1104 |
| Leu | Pro | Met | Pro | Gln | Ile | Ile | Lys | Glu | Asp | Lys | Thr | Gly | Trp | Met | Thr |      |
|     |     | 355 |     |     |     |     | 360 |     |     |     |     | 365 |     |     |     |      |
| gat | gag | gag | ttt | gga | cgg | gag | att | ctc | gcc | ggc | gtg | aac | ccc | atg | ctc | 1152 |

-continued

```
                    Asp Glu Glu Phe Gly Arg Glu Ile Leu Ala Gly Val Asn Pro Met Leu
                        370             375                 380 gtc aag cgt ctc acg gag ttc cct ccg agg agc agt ctt gac ccg agc              1200
Val Lys Arg Leu Thr Glu Phe Pro Pro Arg Ser Ser Leu Asp Pro Ser
385                 390                 395                 400 aag tac ggc gac cac acc agc acc atc agg gag gcg gac ctc gag aac              1248
Lys Tyr Gly Asp His Thr Ser Thr Ile Arg Glu Ala Asp Leu Glu Asn
                    405                 410                 415 aag ctc gag ggc ctg acg gtg cag cag gcg ctg cac ggc aac cgg ctc              1296
Lys Leu Glu Gly Leu Thr Val Gln Gln Ala Leu His Gly Asn Arg Leu
                420                 425                 430 tac atc ctg gac cac cac gac aac ttc atg ccg ttc ctg gtc agg gtg              1344
Tyr Ile Leu Asp His His Asp Asn Phe Met Pro Phe Leu Val Arg Val
            435                 440                 445 aac agc ctg gag ggc aac ttc atc tac gcc acc agg acc gtg ctg ttc              1392
Asn Ser Leu Glu Gly Asn Phe Ile Tyr Ala Thr Arg Thr Val Leu Phe
        450                 455                 460 ctg cgc ggc gac ggc acg ctg gtg ccg gtg gcc atc gag ctg agc ctg              1440
Leu Arg Gly Asp Gly Thr Leu Val Pro Val Ala Ile Glu Leu Ser Leu
465                 470                 475                 480 ccc gag ctc cgg gac ggc ctg acc acc gcc aag agc acc gtg tac acg              1488
Pro Glu Leu Arg Asp Gly Leu Thr Thr Ala Lys Ser Thr Val Tyr Thr
                485                 490                 495 ccc aag tcg acc acc ggc gcg gag gcg tgg gtg tgg cac ctg gcc aag              1536
Pro Lys Ser Thr Thr Gly Ala Glu Ala Trp Val Trp His Leu Ala Lys
                500                 505                 510 gcc tac gcc aac gtg aac gac tac tgc tgg cac cag ctc atc agc cac              1584
Ala Tyr Ala Asn Val Asn Asp Tyr Cys Trp His Gln Leu Ile Ser His
                    515                 520                 525 tgg ctc aac acc cac gcc gtg atg gag ccg ttc gtg atc gcc acc aac              1632
Trp Leu Asn Thr His Ala Val Met Glu Pro Phe Val Ile Ala Thr Asn
                530                 535                 540 cgg cag ctc agc gtg acg cac ccc gtg cac aag ctc ctc ctg ccg cac              1680
Arg Gln Leu Ser Val Thr His Pro Val His Lys Leu Leu Leu Pro His
545                 550                 555                 560 tac cgt gac acc atg aac atc aac tcc aac gcg cgc cag atg ctc gtc              1728
Tyr Arg Asp Thr Met Asn Ile Asn Ser Asn Ala Arg Gln Met Leu Val
                565                 570                 575 aac gcc ggc ggc atc ttc gag acc acc gtc ttc ccg cgc cag tac gcg              1776
Asn Ala Gly Gly Ile Phe Glu Thr Thr Val Phe Pro Arg Gln Tyr Ala
                580                 585                 590 ttc gag atg tcc tcc gtc atc tac aag gac tgg aac ttc aca gag cag              1824
Phe Glu Met Ser Ser Val Ile Tyr Lys Asp Trp Asn Phe Thr Glu Gln
                595                 600                 605 gct ctc cct gac gac cta atc aag aga ggc atg gcg gtc gca gac ccg              1872
Ala Leu Pro Asp Asp Leu Ile Lys Arg Gly Met Ala Val Ala Asp Pro
                    610                 615                 620 tcg agc ccg tac aag gta cgg ctg ctg gtg gag gac tac ccg tac gcg              1920
Ser Ser Pro Tyr Lys Val Arg Leu Leu Val Glu Asp Tyr Pro Tyr Ala
625                 630                 635                 640 tcg gac ggg ctg gcc atc tgg cac gcc atc gag cag tgg gtg acg gag              1968
Ser Asp Gly Leu Ala Ile Trp His Ala Ile Glu Gln Trp Val Thr Glu
                    645                 650                 655 tac ctc gcc gtc tac tac ccc aac gac ggc gtg ctg cgg gcg gac gtg              2016
Tyr Leu Ala Val Tyr Tyr Pro Asn Asp Gly Val Leu Arg Ala Asp Val
                    660                 665                 670 gag ctg cag gcg tgg tgg aag gag gcg cgc gag gtc ggg cac gcc gac              2064
Glu Leu Gln Ala Trp Trp Lys Glu Ala Arg Glu Val Gly His Ala Asp
                    675                 680                 685
```

```
ctc aag gac gcg ccc tgg tgg ccc aag atg cag acg gtg gcc gag ctg       2112
Leu Lys Asp Ala Pro Trp Trp Pro Lys Met Gln Thr Val Ala Glu Leu
690             695                 700 gtc aag gcc tgc acc acc atc atc tgg atc gcg tcg gcg ctc cac gcg       2160
Val Lys Ala Cys Thr Thr Ile Ile Trp Ile Ala Ser Ala Leu His Ala
705                 710                 715                 720 gcc gtc aac ttc ggg cag tac ccg tac gcc ggg tac ctc ccg aac cgc       2208
Ala Val Asn Phe Gly Gln Tyr Pro Tyr Ala Gly Tyr Leu Pro Asn Arg
                725                 730                 735 ccg tcc gtc agc cgg aag ccg atg ccg gcg ccg ggc agc gac gag tac       2256
Pro Ser Val Ser Arg Lys Pro Met Pro Ala Pro Gly Ser Asp Glu Tyr
            740                 745                 750 gcg gag ctg gag cgc aag ccg gag aag gtg ttc gtg cgc acc atc acc       2304
Ala Glu Leu Glu Arg Lys Pro Glu Lys Val Phe Val Arg Thr Ile Thr
        755                 760                 765 agc cag ttc cag gcc ctc gtc ggc atc tcg ctg ctg gag atc ctg tcc       2352
Ser Gln Phe Gln Ala Leu Val Gly Ile Ser Leu Leu Glu Ile Leu Ser
770                 775                 780 agc cac tcc tcc gac gag gtg tac ctc ggc cag cgc gac acc aag gag       2400
Ser His Ser Ser Asp Glu Val Tyr Leu Gly Gln Arg Asp Thr Lys Glu
785                 790                 795                 800 tgg acg tcg gac gcc aag gcg cag gag gcg ttc aag cgg ttc ggc gcg       2448
Trp Thr Ser Asp Ala Lys Ala Gln Glu Ala Phe Lys Arg Phe Gly Ala
                805                 810                 815 cgg ctg acc gag atc gag aaa cgc gtc gtc acc atg aac gcg gac cct       2496
Arg Leu Thr Glu Ile Glu Lys Arg Val Val Thr Met Asn Ala Asp Pro
            820                 825                 830 cgc ctc aag aac cgc aac ggc ccg gcc gag ttc ccc tac acg ctg ctc       2544
Arg Leu Lys Asn Arg Asn Gly Pro Ala Glu Phe Pro Tyr Thr Leu Leu
        835                 840                 845 tac ccc aac acc tcc gac acg aag ggc gac gcc gcc ggc atc acc gcc       2592
Tyr Pro Asn Thr Ser Asp Thr Lys Gly Asp Ala Ala Gly Ile Thr Ala
850                 855                 860 aag ggc att cca aac agc atc tcc att tga                               2622
Lys Gly Ile Pro Asn Ser Ile Ser Ile *
865                 870

<210> SEQ ID NO 4
<211> LENGTH: 873
<212> TYPE: PRT
<213> ORGANISM: Zea mays

<400> SEQUENCE: 4

Met Phe Gly Asn Ile Gly Lys Ile Pro Ile Ile Gly Asp Leu Thr Gly
1               5                   10                  15

Ser Asn Lys Asn Ala His Leu Lys Gly Asn Val Val Leu Val Arg Lys
            20                  25                  30

Thr Val Leu Gly Leu Asp Val Thr Ser Ile Ala Gly Ser Leu Leu Asp
        35                  40                  45

Gly Ile Gly Glu Phe Leu Gly Arg Gly Val Thr Cys Gln Leu Ile Ser
    50                  55                  60

Ser Thr Val Val Asp Pro Asn Asn Gly Asn Arg Gly Lys Leu Gly Ala
65                  70                  75                  80

Glu Ala Ser Leu Glu Gln Trp Leu Leu Asn Pro Pro Leu Leu Ser
                85                  90                  95

Ser Glu Asn Gln Phe Arg Val Thr Phe Asp Trp Glu Val Glu Lys Gln
            100                 105                 110

Gly Ile Pro Gly Ala Ile Ile Val Lys Asn Asn His Ala Ser Glu Phe
        115                 120                 125
```

-continued

```
Phe Leu Lys Thr Ile Thr Leu Asn Asp Val Pro Gly His Gly Thr Ile
    130                 135                 140
Val Phe Val Ala Asn Ser Trp Ile Tyr Pro Gln Ser Lys Tyr Arg Tyr
145                 150                 155                 160
Asn Arg Val Phe Phe Ser Asn Asp Thr Tyr Leu Pro Ser Gln Met Pro
                165                 170                 175
Ala Ala Leu Lys Pro Tyr Arg Asp Asp Glu Leu Arg Asn Leu Arg Gly
            180                 185                 190
Asp Asp Gln Gln Gly Pro Tyr Gln Glu His Asp Arg Val Tyr Arg Tyr
        195                 200                 205
Asp Val Tyr Asn Asp Leu Gly Leu Pro Asp Ser Gly Asn Pro Arg Pro
    210                 215                 220
Val Leu Gly Gly Thr Lys Glu Leu Pro Tyr Pro Arg Arg Cys Arg Thr
225                 230                 235                 240
Gly Arg Lys Pro Thr Lys Ser Asp Pro Asn Ser Glu Ser Arg Leu Thr
                245                 250                 255
Leu Val Asp Gly Asp Val Tyr Val Pro Arg Asp Glu Arg Phe Gly His
            260                 265                 270
Ile Lys Lys Ser Asp Phe Tyr Gly Tyr Ala Ile Lys Ala Leu Val Asn
        275                 280                 285
Ala Val Ile Pro Ala Ile Arg Thr Tyr Val Asp Leu Ser Pro Gly Glu
    290                 295                 300
Phe Asp Ser Phe Lys Asp Ile Met Lys Leu Tyr Glu Gly Gly Ile Gln
305                 310                 315                 320
Leu Pro Lys Ile Pro Ala Leu Glu Asp Leu Arg Lys Gln Phe Pro Leu
                325                 330                 335
Glu Leu Val Lys Asp Val Leu Pro Val Gly Gly Asp Tyr Leu Leu Lys
            340                 345                 350
Leu Pro Met Pro Gln Ile Ile Lys Glu Asp Lys Thr Gly Trp Met Thr
        355                 360                 365
Asp Glu Glu Phe Gly Arg Glu Ile Leu Ala Gly Val Asn Pro Met Leu
    370                 375                 380
Val Lys Arg Leu Thr Glu Phe Pro Pro Arg Ser Ser Leu Asp Pro Ser
385                 390                 395                 400
Lys Tyr Gly Asp His Thr Ser Thr Ile Arg Glu Ala Asp Leu Glu Asn
                405                 410                 415
Lys Leu Glu Gly Leu Thr Val Gln Gln Ala Leu His Gly Asn Arg Leu
            420                 425                 430
Tyr Ile Leu Asp His His Asp Asn Phe Met Pro Phe Leu Val Arg Val
        435                 440                 445
Asn Ser Leu Glu Gly Asn Phe Ile Tyr Ala Thr Arg Thr Val Leu Phe
    450                 455                 460
Leu Arg Gly Asp Gly Thr Leu Val Pro Val Ala Ile Glu Leu Ser Leu
465                 470                 475                 480
Pro Glu Leu Arg Asp Gly Leu Thr Thr Ala Lys Ser Thr Val Tyr Thr
                485                 490                 495
Pro Lys Ser Thr Thr Gly Ala Glu Ala Trp Val Trp His Leu Ala Lys
            500                 505                 510
Ala Tyr Ala Asn Val Asn Asp Tyr Cys Trp His Gln Leu Ile Ser His
        515                 520                 525
Trp Leu Asn Thr His Ala Val Met Glu Pro Phe Val Ile Ala Thr Asn
    530                 535                 540
```

```
Arg Gln Leu Ser Val Thr His Pro Val His Lys Leu Leu Pro His
545                 550                 555                 560

Tyr Arg Asp Thr Met Asn Ile Asn Ser Asn Ala Arg Gln Met Leu Val
                565                 570                 575

Asn Ala Gly Gly Ile Phe Glu Thr Thr Val Phe Pro Arg Gln Tyr Ala
            580                 585                 590

Phe Glu Met Ser Ser Val Ile Tyr Lys Asp Trp Asn Phe Thr Glu Gln
        595                 600                 605

Ala Leu Pro Asp Asp Leu Ile Lys Arg Gly Met Ala Val Ala Asp Pro
    610                 615                 620

Ser Ser Pro Tyr Lys Val Arg Leu Leu Val Glu Asp Tyr Pro Tyr Ala
625                 630                 635                 640

Ser Asp Gly Leu Ala Ile Trp His Ala Ile Glu Gln Trp Val Thr Glu
                645                 650                 655

Tyr Leu Ala Val Tyr Tyr Pro Asn Asp Gly Val Leu Arg Ala Asp Val
            660                 665                 670

Glu Leu Gln Ala Trp Trp Lys Glu Ala Arg Glu Val Gly His Ala Asp
        675                 680                 685

Leu Lys Asp Ala Pro Trp Trp Pro Lys Met Gln Thr Val Ala Glu Leu
    690                 695                 700

Val Lys Ala Cys Thr Thr Ile Ile Trp Ile Ala Ser Ala Leu His Ala
705                 710                 715                 720

Ala Val Asn Phe Gly Gln Tyr Pro Tyr Ala Gly Tyr Leu Pro Asn Arg
                725                 730                 735

Pro Ser Val Ser Arg Lys Pro Met Pro Ala Pro Gly Ser Asp Glu Tyr
            740                 745                 750

Ala Glu Leu Glu Arg Lys Pro Glu Lys Val Phe Val Arg Thr Ile Thr
        755                 760                 765

Ser Gln Phe Gln Ala Leu Val Gly Ile Ser Leu Leu Glu Ile Leu Ser
    770                 775                 780

Ser His Ser Ser Asp Glu Val Tyr Leu Gly Gln Arg Asp Thr Lys Glu
785                 790                 795                 800

Trp Thr Ser Asp Ala Lys Ala Gln Glu Ala Phe Lys Arg Phe Gly Ala
                805                 810                 815

Arg Leu Thr Glu Ile Glu Lys Arg Val Val Thr Met Asn Ala Asp Pro
            820                 825                 830

Arg Leu Lys Asn Arg Asn Gly Pro Ala Glu Phe Pro Tyr Thr Leu Leu
        835                 840                 845

Tyr Pro Asn Thr Ser Asp Thr Lys Gly Asp Ala Ala Gly Ile Thr Ala
    850                 855                 860

Lys Gly Ile Pro Asn Ser Ile Ser Ile
865                 870

<210> SEQ ID NO 5
<211> LENGTH: 911
<212> TYPE: DNA
<213> ORGANISM: Zea mays
<220> FEATURE:
<221> NAME/KEY: CDS
<222> LOCATION: (1)...(702)
<223> OTHER INFORMATION: LOX1b

<400> SEQUENCE: 5 cgg ggt cga ccc acg cgt ccg cca cca acc ggc agc tca gcg tga cgc      48
Arg Gly Arg Pro Thr Arg Pro Pro Thr Gly Ser Ser Ala  *  Arg
 1               5                  10                  15
```

```
acc ccg tgc aca agc tcc tcc tgc cgc act acc gtg atc gcc gtc tac      96
Thr Pro Cys Thr Ser Ser Ser Cys Arg Thr Thr Val Ile Ala Val Tyr
             20                  25                  30 tac ccc aac gac ggc gtg ctg cgg gcg cgc gag gtc ggg cac gcc gac     144
Tyr Pro Asn Asp Gly Val Leu Arg Ala Arg Glu Val Gly His Ala Asp
         35                  40                  45 ctc aag gac gcg ccc tgg tgg ccc aag atg cag acg gtg gcc gag ctg     192
Leu Lys Asp Ala Pro Trp Trp Pro Lys Met Gln Thr Val Ala Glu Leu
     50                  55                  60 gtc aag gcc tgc acc acc atc atc tgg atc gcg tcg gcg ctc cac gcg     240
Val Lys Ala Cys Thr Thr Ile Ile Trp Ile Ala Ser Ala Leu His Ala
 65                  70                  75 gcc gtc aac ttc ggg cag tac cca tac gcc ggg tac ctc ccg aac cgc     288
Ala Val Asn Phe Gly Gln Tyr Pro Tyr Ala Gly Tyr Leu Pro Asn Arg
 80                  85                  90                  95 ccg tcc gtc agc cgg aag ccg atg ccg gcg ccg ggc agc gac gag tac     336
Pro Ser Val Ser Arg Lys Pro Met Pro Ala Pro Gly Ser Asp Glu Tyr
                 100                 105                 110 gcg gag ctg gag cgc aag ccg gag aag gtg ttc gtg cgc acc atc acc     384
Ala Glu Leu Glu Arg Lys Pro Glu Lys Val Phe Val Arg Thr Ile Thr
             115                 120                 125 agc cag ttt cag gcc ctc gtc ggc atc tcg ctg ctg gag atc ctg tcc     432
Ser Gln Phe Gln Ala Leu Val Gly Ile Ser Leu Leu Glu Ile Leu Ser
         130                 135                 140 agc cac tcc tcc gac gag gtg tac ctc ggc cag cgc gac acc aag gag     480
Ser His Ser Ser Asp Glu Val Tyr Leu Gly Gln Arg Asp Thr Lys Glu
    145                 150                 155 tgg acg tcg gac gcc aag gcg cag gag gcg ttc aag cgg ttc ggc gcg     528
Trp Thr Ser Asp Ala Lys Ala Gln Glu Ala Phe Lys Arg Phe Gly Ala
160                 165                 170                 175 cgg ctg acc gaa atc gag aaa cgc gtc gtc acc atg aac gcg gac cct     576
Arg Leu Thr Glu Ile Glu Lys Arg Val Val Thr Met Asn Ala Asp Pro
                180                 185                 190 cgc ctc aag aac cga aac ggc ccg gcc gag ttc cct tac acg ctg ctt     624
Arg Leu Lys Asn Arg Asn Gly Pro Ala Glu Phe Pro Tyr Thr Leu Leu
            195                 200                 205 tac ccc aac acc tcc gac acg aag ggc gac gcc gct ggc atc acc gcc     672
Tyr Pro Asn Thr Ser Asp Thr Lys Gly Asp Ala Ala Gly Ile Thr Ala
        210                 215                 220 aag ggc att cca aac agc atc tcc att tga gttctgtctg agatgaggac       722
Lys Gly Ile Pro Asn Ser Ile Ser Ile *
225                 230 gtacggtcgt cgcactagtt gtttgcgttt ccccgttccg ttccgtgaag tgtggttctc   782
acttgcgcgg tattgtgcaa atagccaagt actccttacg gaagtcgcta cgtgaggact   842
gttgtaataa ggctctattc agttcctcaa taatgaagtt actttgtgtt tcaaaaaaaa   902
aaaaaaaaa                                                           911

<210> SEQ ID NO 6
<211> LENGTH: 232
<212> TYPE: PRT
<213> ORGANISM: Zea mays

<400> SEQUENCE: 6

Arg Gly Arg Pro Thr Arg Pro Pro Thr Gly Ser Ser Ala Arg Thr
 1               5                  10                  15

Pro Cys Thr Ser Ser Ser Cys Arg Thr Thr Val Ile Ala Val Tyr Tyr
             20                  25                  30

Pro Asn Asp Gly Val Leu Arg Ala Arg Glu Val Gly His Ala Asp Leu
```

-continued

```
                 35                  40                  45
Lys Asp Ala Pro Trp Trp Pro Lys Met Gln Thr Val Ala Glu Leu Val
 50                  55                  60

Lys Ala Cys Thr Thr Ile Ile Trp Ile Ala Ser Ala Leu His Ala Ala
 65                  70                  75                  80

Val Asn Phe Gly Gln Tyr Pro Tyr Ala Gly Tyr Leu Pro Asn Arg Pro
                 85                  90                  95

Ser Val Ser Arg Lys Pro Met Pro Ala Pro Gly Ser Asp Glu Tyr Ala
                100                 105                 110

Glu Leu Glu Arg Lys Pro Glu Lys Val Phe Val Arg Thr Ile Thr Ser
                115                 120                 125

Gln Phe Gln Ala Leu Val Gly Ile Ser Leu Leu Glu Ile Leu Ser Ser
130                 135                 140

His Ser Ser Asp Glu Val Tyr Leu Gly Gln Arg Asp Thr Lys Glu Trp
145                 150                 155                 160

Thr Ser Asp Ala Lys Ala Gln Glu Ala Phe Lys Arg Phe Gly Ala Arg
                165                 170                 175

Leu Thr Glu Ile Glu Lys Arg Val Val Thr Met Asn Ala Asp Pro Arg
                180                 185                 190

Leu Lys Asn Arg Asn Gly Pro Ala Glu Phe Pro Tyr Thr Leu Leu Tyr
                195                 200                 205

Pro Asn Thr Ser Asp Thr Lys Gly Asp Ala Ala Gly Ile Thr Ala Lys
                210                 215                 220

Gly Ile Pro Asn Ser Ile Ser Ile
225                 230
```

<210> SEQ ID NO 7
<211> LENGTH: 702
<212> TYPE: DNA
<213> ORGANISM: Zea mays
<220> FEATURE:
<221> NAME/KEY: CDS
<222> LOCATION: (1)...(702)

<400> SEQUENCE: 7

```
cgg ggt cga ccc acg cgt ccg cca cca acc ggc agc tca gcg tga cgc     48
Arg Gly Arg Pro Thr Arg Pro Pro Thr Gly Ser Ser Ala  *  Arg
 1               5                  10                  15 acc ccg tgc aca agc tcc tcc tgc cgc act acc gtg atc gcc gtc tac     96
Thr Pro Cys Thr Ser Ser Ser Cys Arg Thr Thr Val Ile Ala Val Tyr
                 20                  25                  30 tac ccc aac gac ggc gtg ctg cgg gcg cgc gag gtc ggg cac gcc gac    144
Tyr Pro Asn Asp Gly Val Leu Arg Ala Arg Glu Val Gly His Ala Asp
                 35                  40                  45 ctc aag gac gcg ccc tgg tgg ccc aag atg cag acg gtg gcc gag ctg    192
Leu Lys Asp Ala Pro Trp Trp Pro Lys Met Gln Thr Val Ala Glu Leu
 50                  55                  60 gtc aag gcc tgc acc acc atc atc tgg atc gcg tcg gcg ctc cac gcg    240
Val Lys Ala Cys Thr Thr Ile Ile Trp Ile Ala Ser Ala Leu His Ala
 65                  70                  75 gcc gtc aac ttc ggg cag tac cca tac gcc ggg tac ctc ccg aac cgc    288
Ala Val Asn Phe Gly Gln Tyr Pro Tyr Ala Gly Tyr Leu Pro Asn Arg
 80                  85                  90                  95 ccg tcc gtc agc cgg aag ccg atg ccg gcg ccg ggc agc gac gag tac    336
Pro Ser Val Ser Arg Lys Pro Met Pro Ala Pro Gly Ser Asp Glu Tyr
                100                 105                 110 gcg gag ctg gag cgc aag ccg gag aag gtg ttc gtg cgc acc atc acc    384
Ala Glu Leu Glu Arg Lys Pro Glu Lys Val Phe Val Arg Thr Ile Thr
```

-continued

```
                115                 120                 125
agc cag ttt cag gcc ctc gtc ggc atc tcg ctg ctg gag atc ctg tcc    432
Ser Gln Phe Gln Ala Leu Val Gly Ile Ser Leu Leu Glu Ile Leu Ser
        130                 135                 140 agc cac tcc tcc gac gag gtg tac ctc ggc cag cgc gac acc aag gag    480
Ser His Ser Ser Asp Glu Val Tyr Leu Gly Gln Arg Asp Thr Lys Glu
    145                 150                 155 tgg acg tcg gac gcc aag gcg cag gag gcg ttc aag cgg ttc ggc gcg    528
Trp Thr Ser Asp Ala Lys Ala Gln Glu Ala Phe Lys Arg Phe Gly Ala
160                 165                 170                 175 cgg ctg acc gaa atc gag aaa cgc gtc gtc acc atg aac gcg gac cct    576
Arg Leu Thr Glu Ile Glu Lys Arg Val Val Thr Met Asn Ala Asp Pro
                180                 185                 190 cgc ctc aag aac cga aac ggc ccg gcc gag ttc cct tac acg ctg ctt    624
Arg Leu Lys Asn Arg Asn Gly Pro Ala Glu Phe Pro Tyr Thr Leu Leu
            195                 200                 205 tac ccc aac acc tcc gac acg aag ggc gac gcc gct ggc atc acc gcc    672
Tyr Pro Asn Thr Ser Asp Thr Lys Gly Asp Ala Ala Gly Ile Thr Ala
        210                 215                 220 aag ggc att cca aac agc atc tcc att tga                            702
Lys Gly Ile Pro Asn Ser Ile Ser Ile *
    225                 230

<210> SEQ ID NO 8
<211> LENGTH: 226
<212> TYPE: PRT
<213> ORGANISM: Zea mays

<400> SEQUENCE: 8

Ala Thr Asn Arg Gln Leu Ser Val Thr His Pro Val His Lys Leu Leu
  1               5                  10                  15

Leu Pro His Tyr Arg Asp Ala Val Tyr Tyr Pro Asn Asp Gly Val Leu
             20                  25                  30

Arg Ala Arg Glu Val Gly His Ala Asp Leu Lys Asp Ala Pro Trp Trp
         35                  40                  45

Pro Lys Met Gln Thr Val Ala Glu Leu Val Lys Ala Cys Thr Thr Ile
     50                  55                  60

Ile Trp Ile Ala Ser Ala Leu His Ala Ala Val Asn Phe Gly Gln Tyr
 65                  70                  75                  80

Pro Tyr Ala Gly Tyr Leu Pro Asn Arg Pro Ser Val Ser Arg Lys Pro
                 85                  90                  95

Met Pro Ala Pro Gly Ser Asp Glu Tyr Ala Glu Leu Glu Arg Lys Pro
            100                 105                 110

Glu Lys Val Phe Val Arg Thr Ile Thr Ser Gln Phe Gln Ala Leu Val
        115                 120                 125

Gly Ile Ser Leu Leu Glu Ile Leu Ser Ser His Ser Ser Asp Glu Val
    130                 135                 140

Tyr Leu Gly Gln Arg Asp Thr Lys Glu Trp Thr Ser Asp Ala Lys Ala
145                 150                 155                 160

Gln Glu Ala Phe Lys Arg Phe Gly Ala Arg Leu Thr Glu Ile Glu Lys
                165                 170                 175

Arg Val Val Thr Met Asn Ala Asp Pro Arg Leu Lys Asn Arg Asn Gly
            180                 185                 190

Pro Ala Glu Phe Pro Tyr Thr Leu Leu Tyr Pro Asn Thr Ser Asp Thr
        195                 200                 205

Lys Gly Asp Ala Ala Gly Ile Thr Ala Lys Gly Ile Pro Asn Ser Ile
    210                 215                 220
```

Ser Ile
225

<210> SEQ ID NO 9
<211> LENGTH: 3007
<212> TYPE: DNA
<213> ORGANISM: Zea mays
<220> FEATURE:
<221> NAME/KEY: CDS
<222> LOCATION: (65)...(2659)
<223> OTHER INFORMATION: LOX2b

<400> SEQUENCE: 9

```
ccacgcgtcc gcacagacac caacgccact gcactgcaaa agcaagagca gctagctagt      60 aaag atg ctg agc ggg atc atc gac ggg ctg acg ggg gcg aac aag cat     109
     Met Leu Ser Gly Ile Ile Asp Gly Leu Thr Gly Ala Asn Lys His
       1               5                  10                  15 gcg cgg ctc aag ggc acg gtg gtg ctc atg cgc aag aac gtg ctg gac     157
Ala Arg Leu Lys Gly Thr Val Val Leu Met Arg Lys Asn Val Leu Asp
             20                  25                  30 ctc aac gac ttc ggc gcc acc gtc gtt gac agc atc agc gag ttc ctc     205
Leu Asn Asp Phe Gly Ala Thr Val Val Asp Ser Ile Ser Glu Phe Leu
         35                  40                  45 ggc aag ggg gtc acc tgc cag ctc atc agc tcc acc ctc gtc gac gcc     253
Gly Lys Gly Val Thr Cys Gln Leu Ile Ser Ser Thr Leu Val Asp Ala
     50                  55                  60 aac aac ggc aac cgc ggg cgg gtc ggg gcg gag gcg aac ctg gag cag     301
Asn Asn Gly Asn Arg Gly Arg Val Gly Ala Glu Ala Asn Leu Glu Gln
 65                  70                  75 tgg ctg acg agc ctg ccg tcg ctg acg acc ggc gag tcc aag ttc ggc     349
Trp Leu Thr Ser Leu Pro Ser Leu Thr Thr Gly Glu Ser Lys Phe Gly
 80                  85                  90                  95 gtc acg ttc gac tgg gag gtg gag aag ctg gga gtg ccg ggg gcc gtc     397
Val Thr Phe Asp Trp Glu Val Glu Lys Leu Gly Val Pro Gly Ala Val
                100                 105                 110 gtc gtc aag aac aac cac gcc gcc gag ttc ttc ctc aag aca atc acc     445
Val Val Lys Asn Asn His Ala Ala Glu Phe Phe Leu Lys Thr Ile Thr
            115                 120                 125 ctc gac gac gtg ccc ggc cgc ggc gcc gtc acc ttc gtc gcc aac tcc     493
Leu Asp Asp Val Pro Gly Arg Gly Ala Val Thr Phe Val Ala Asn Ser
        130                 135                 140 tgg gtc tac ccc gcg ggc aag tac cgc tac aac cgc gtc ttc ttc tcc     541
Trp Val Tyr Pro Ala Gly Lys Tyr Arg Tyr Asn Arg Val Phe Phe Ser
    145                 150                 155 aac gat acg tac ctg cca agc cag atg ccg gcg gcg ctg aag ccg tac     589
Asn Asp Thr Tyr Leu Pro Ser Gln Met Pro Ala Ala Leu Lys Pro Tyr
160                 165                 170                 175 cgc gac gac gag ctc cgc aac ctc cgc ggc gac gac cag cag ggc ccc     637
Arg Asp Asp Glu Leu Arg Asn Leu Arg Gly Asp Asp Gln Gln Gly Pro
                180                 185                 190 tac cag gag cac gac cgc gtg tac cgc tac gac gtc tac aac gac ctc     685
Tyr Gln Glu His Asp Arg Val Tyr Arg Tyr Asp Val Tyr Asn Asp Leu
            195                 200                 205 ggc gag ccc gac ggc ggc aac ccg cgc ccc atc ctc ggc ggc tcc gcc     733
Gly Glu Pro Asp Gly Gly Asn Pro Arg Pro Ile Leu Gly Gly Ser Ala
        210                 215                 220 gac cac ccg tac ccg cgc cgc tgc cgc acg ggc cgc aag ccc acc aaa     781
Asp His Pro Tyr Pro Arg Arg Cys Arg Thr Gly Arg Lys Pro Thr Lys
    225                 230                 235 acc gac ccc aac tcg gat agc cga ctg tcg ctg gtg gag cag atc tac     829
```

-continued

| | | |
|---|---|---|
| Thr Asp Pro Asn Ser Asp Ser Arg Leu Ser Leu Val Glu Gln Ile Tyr<br>240 245 250 255 | | |
| gtg ccg cgg gac gag cgc ttc ggc cac ctc aag atg tcc gac ttc ctg<br>Val Pro Arg Asp Glu Arg Phe Gly His Leu Lys Met Ser Asp Phe Leu<br>260 265 270 | | 877 |
| ggc tac tcc atc aag gcc atc acg cag ggc atc atc ccg gcg gtg cgc<br>Gly Tyr Ser Ile Lys Ala Ile Thr Gln Gly Ile Ile Pro Ala Val Arg<br>275 280 285 | | 925 |
| acg tac gtg gac acc acc ccg ggc gag ttc gac tcc ttc cag gac atc<br>Thr Tyr Val Asp Thr Thr Pro Gly Glu Phe Asp Ser Phe Gln Asp Ile<br>290 295 300 | | 973 |
| atc aac ctg tac gag ggc ggg atc aag ctg ccc aag atc cag gcg ctc<br>Ile Asn Leu Tyr Glu Gly Gly Ile Lys Leu Pro Lys Ile Gln Ala Leu<br>305 310 315 | | 1021 |
| gag gac atg cgc aag ctc ttc ccg ctc cag ctc gtc aag gac ctc ctc<br>Glu Asp Met Arg Lys Leu Phe Pro Leu Gln Leu Val Lys Asp Leu Leu<br>320 325 330 335 | | 1069 |
| ccc gcc ggc ggg gac tac ctg ctc aag ctc ccc atc cca cag atc atc<br>Pro Ala Gly Gly Asp Tyr Leu Leu Lys Leu Pro Ile Pro Gln Ile Ile<br>340 345 350 | | 1117 |
| caa gag gac aag aac gcg tgg agg acc gac gag gag ttc gcg cgg gag<br>Gln Glu Asp Lys Asn Ala Trp Arg Thr Asp Glu Glu Phe Ala Arg Glu<br>355 360 365 | | 1165 |
| gtg ctc gcc ggc gtc aac ccg atg gtg atc acg cgc ctc acg gag ttc<br>Val Leu Ala Gly Val Asn Pro Met Val Ile Thr Arg Leu Thr Glu Phe<br>370 375 380 | | 1213 |
| ccg ccc aag agc acg ctg gac ccc agc aag tac ggc gac cac acc agc<br>Pro Pro Lys Ser Thr Leu Asp Pro Ser Lys Tyr Gly Asp His Thr Ser<br>385 390 395 | | 1261 |
| acg atc acg gcg gag cac atc gag aag aac ctc gag ggc ctc acg gtg<br>Thr Ile Thr Ala Glu His Ile Glu Lys Asn Leu Glu Gly Leu Thr Val<br>400 405 410 415 | | 1309 |
| cag cag gcg ctg gac ggc aac agg ctc tac atc ctg gac cac cac gac<br>Gln Gln Ala Leu Asp Gly Asn Arg Leu Tyr Ile Leu Asp His His Asp<br>420 425 430 | | 1357 |
| cgc ttc atg ccg ttc ctc atc gac gtg aac aac ctg gag ggt aac ttc<br>Arg Phe Met Pro Phe Leu Ile Asp Val Asn Asn Leu Glu Gly Asn Phe<br>435 440 445 | | 1405 |
| atc tac gcc acc agg acc ctc ttc ttc ctg cgc ggc gac ggc agg ctc<br>Ile Tyr Ala Thr Arg Thr Leu Phe Phe Leu Arg Gly Asp Gly Arg Leu<br>450 455 460 | | 1453 |
| gcg ccc ctc gct atc gag ctc agc gag ccg tac atc gac ggg gac ctt<br>Ala Pro Leu Ala Ile Glu Leu Ser Glu Pro Tyr Ile Asp Gly Asp Leu<br>465 470 475 | | 1501 |
| acc gtg gcc aag agc aag gtc tac acg ccg gcg tcc agc ggc gtc gag<br>Thr Val Ala Lys Ser Lys Val Tyr Thr Pro Ala Ser Ser Gly Val Glu<br>480 485 490 495 | | 1549 |
| gcc tgg gtg tgg cag ctc gcc aag gcc tat gtc gcc gtc aac gac tct<br>Ala Trp Val Trp Gln Leu Ala Lys Ala Tyr Val Ala Val Asn Asp Ser<br>500 505 510 | | 1597 |
| ggc tgg cac caa ctc gtc agc cac tgg ctg aac acg cac gcg gtg atg<br>Gly Trp His Gln Leu Val Ser His Trp Leu Asn Thr His Ala Val Met<br>515 520 525 | | 1645 |
| gag ccg ttc gtg atc gcg acg aac cgg cag ctg agc gtg acg cac ccg<br>Glu Pro Phe Val Ile Ala Thr Asn Arg Gln Leu Ser Val Thr His Pro<br>530 535 540 | | 1693 |
| gtg cac aag ctc ctg agc tcg cac ttc cgc gac acc atg acc atc aac<br>Val His Lys Leu Leu Ser Ser His Phe Arg Asp Thr Met Thr Ile Asn<br>545 550 555 | | 1741 |

| | |
|---|---|
| gcg ctg gcg cgg cag acg ctc atc aac ggc ggc ggc atc ttc gag atg<br>Ala Leu Ala Arg Gln Thr Leu Ile Asn Gly Gly Gly Ile Phe Glu Met<br>560               565               570               575 | 1789 |
| acc gtc ttc ccg ggc aag tac gcg ctg ggc atg tcc tcc gtg gtg tac<br>Thr Val Phe Pro Gly Lys Tyr Ala Leu Gly Met Ser Ser Val Val Tyr<br>               580               585               590 | 1837 |
| aag agc tgg aac ttc acc gag cag ggc ctc ccc gcc gac ctc gtc aag<br>Lys Ser Trp Asn Phe Thr Glu Gln Gly Leu Pro Ala Asp Leu Val Lys<br>595               600               605 | 1885 |
| agg ggc gtg gcg gtg gcg gac ccg tcc agc ctg tac aag gtg cgg ctg<br>Arg Gly Val Ala Val Ala Asp Pro Ser Ser Leu Tyr Lys Val Arg Leu<br>               610               615               620 | 1933 |
| ctg atc gag gac tac ccg tac gcg agc gac ggg ctg gcc atc tgg cac<br>Leu Ile Glu Asp Tyr Pro Tyr Ala Ser Asp Gly Leu Ala Ile Trp His<br>625               630               635 | 1981 |
| gcc atc gag cag tgg gtg ggc gag tac ctg gcc atc tac tac ccc gac<br>Ala Ile Glu Gln Trp Val Gly Glu Tyr Leu Ala Ile Tyr Tyr Pro Asp<br>640               645               650               655 | 2029 |
| gac ggc gcg ctg cgg ggc gac gag gag ctg cag gcg tgg tgg aag gag<br>Asp Gly Ala Leu Arg Gly Asp Glu Glu Leu Gln Ala Trp Trp Lys Glu<br>               660               665               670 | 2077 |
| gtg cgc gag gtc ggg cac ggc gac cac aag gac gcg ccc tgg tgg ccc<br>Val Arg Glu Val Gly His Gly Asp His Lys Asp Ala Pro Trp Trp Pro<br>675               680               685 | 2125 |
| aag atg cag gcc gtg tcg gag ctc gcc agc gcc tgc acc acc atc atc<br>Lys Met Gln Ala Val Ser Glu Leu Ala Ser Ala Cys Thr Thr Ile Ile<br>               690               695               700 | 2173 |
| tgg atc gcg tcg gcg ctc cac gcc gcc gtc aac ttc ggc cag tac ccg<br>Trp Ile Ala Ser Ala Leu His Ala Ala Val Asn Phe Gly Gln Tyr Pro<br>705               710               715 | 2221 |
| tac gcg ggg tac ctc ccg aac agg ccc acg gtg agc cgg cgc cgg atg<br>Tyr Ala Gly Tyr Leu Pro Asn Arg Pro Thr Val Ser Arg Arg Arg Met<br>720               725               730               735 | 2269 |
| ccg gag ccc ggc agc aag gag tac gag gag ctg gag cgc gac ccg gag<br>Pro Glu Pro Gly Ser Lys Glu Tyr Glu Glu Leu Glu Arg Asp Pro Glu<br>               740               745               750 | 2317 |
| cgc ggc ttc atc cac acc atc acg agc cag atc cag acc atc atc ggc<br>Arg Gly Phe Ile His Thr Ile Thr Ser Gln Ile Gln Thr Ile Ile Gly<br>755               760               765 | 2365 |
| atc tcg ctc atc gag atc ctc tcc aag cac tcc tcc gac gag gtg tac<br>Ile Ser Leu Ile Glu Ile Leu Ser Lys His Ser Ser Asp Glu Val Tyr<br>               770               775               780 | 2413 |
| ctc ggc cag cgc gac acc ccc gag tgg acc tcc gac gcc cgg gcg ctg<br>Leu Gly Gln Arg Asp Thr Pro Glu Trp Thr Ser Asp Ala Arg Ala Leu<br>785               790               795 | 2461 |
| gcg gcg ttc aag agg ttc agc gac gcg ctg gtc aag atc gag ggc aag<br>Ala Ala Phe Lys Arg Phe Ser Asp Ala Leu Val Lys Ile Glu Gly Lys<br>800               805               810               815 | 2509 |
| gtg gtg ggc gag aac cgc gac ccg cag ctg agg aac agg aac ggc ccc<br>Val Val Gly Glu Asn Arg Asp Pro Gln Leu Arg Asn Arg Asn Gly Pro<br>               820               825               830 | 2557 |
| gcc gag ttc ccc tac atg ctg ctc tac ccc aac acc tct gac cac agt<br>Ala Glu Phe Pro Tyr Met Leu Leu Tyr Pro Asn Thr Ser Asp His Ser<br>835               840               845 | 2605 |
| ggc gcc gcc gca ggg ctc act gcc aag ggc atc ccc aac agc atc tcc<br>Gly Ala Ala Ala Gly Leu Thr Ala Lys Gly Ile Pro Asn Ser Ile Ser<br>               850               855               860 | 2653 |
| atc tga gcgactggta ccactaccac cccaggagtg ctacgtacga gctggtacat<br>Ile  * | 2709 |

```
gaataagcta atataagcaa tcgtgtaaac gggaagagag cggccggcac gagacggacc    2769
atgtattttg cgtaaacgtg tgggctggtg aatcgaatta ctaccacgta ataagtgaag    2829
tgcttgttgc aatcattggc ctgccagctt caagattctt gcagttacta ttctagtcgt    2889
ttcgcagtgc tcctcgatca caacatttca cgaggtgttt tattacaata atttggagct    2949
attcaatttc aaaaaaaaaa aaaaaaaaaa aaaaaaaaaa aaaaaaaaaa aaaaaaa       3007
```

<210> SEQ ID NO 10
<211> LENGTH: 864
<212> TYPE: PRT
<213> ORGANISM: Zea mays

<400> SEQUENCE: 10

```
Met Leu Ser Gly Ile Ile Asp Gly Leu Thr Gly Ala Asn Lys His Ala
 1               5                  10                  15

Arg Leu Lys Gly Thr Val Val Leu Met Arg Lys Asn Val Leu Asp Leu
             20                  25                  30

Asn Asp Phe Gly Ala Thr Val Asp Ser Ile Ser Glu Phe Leu Gly
         35                  40                  45

Lys Gly Val Thr Cys Gln Leu Ile Ser Ser Thr Leu Val Asp Ala Asn
 50                  55                  60

Asn Gly Asn Arg Gly Arg Val Gly Ala Glu Ala Asn Leu Glu Gln Trp
 65                  70                  75                  80

Leu Thr Ser Leu Pro Ser Leu Thr Thr Gly Glu Ser Lys Phe Gly Val
                 85                  90                  95

Thr Phe Asp Trp Glu Val Glu Lys Leu Gly Val Pro Gly Ala Val Val
            100                 105                 110

Val Lys Asn Asn His Ala Ala Glu Phe Phe Leu Lys Thr Ile Thr Leu
        115                 120                 125

Asp Asp Val Pro Gly Arg Gly Ala Val Thr Phe Val Ala Asn Ser Trp
130                 135                 140

Val Tyr Pro Ala Gly Lys Tyr Arg Tyr Asn Arg Val Phe Phe Ser Asn
145                 150                 155                 160

Asp Thr Tyr Leu Pro Ser Gln Met Pro Ala Ala Leu Lys Pro Tyr Arg
                165                 170                 175

Asp Asp Glu Leu Arg Asn Leu Arg Gly Asp Asp Gln Gln Gly Pro Tyr
            180                 185                 190

Gln Glu His Asp Arg Val Tyr Arg Tyr Asp Val Tyr Asn Asp Leu Gly
        195                 200                 205

Glu Pro Asp Gly Gly Asn Pro Arg Pro Ile Leu Gly Gly Ser Ala Asp
    210                 215                 220

His Pro Tyr Pro Arg Arg Cys Arg Thr Gly Arg Lys Pro Thr Lys Thr
225                 230                 235                 240

Asp Pro Asn Ser Asp Ser Arg Leu Ser Leu Val Glu Gln Ile Tyr Val
                245                 250                 255

Pro Arg Asp Glu Arg Phe Gly His Leu Lys Met Ser Asp Phe Leu Gly
            260                 265                 270

Tyr Ser Ile Lys Ala Ile Thr Gln Gly Ile Ile Pro Ala Val Arg Thr
        275                 280                 285

Tyr Val Asp Thr Thr Pro Gly Glu Phe Asp Ser Phe Gln Asp Ile Ile
    290                 295                 300

Asn Leu Tyr Glu Gly Gly Ile Lys Leu Pro Lys Ile Gln Ala Leu Glu
305                 310                 315                 320

Asp Met Arg Lys Leu Phe Pro Leu Gln Leu Val Lys Asp Leu Leu Pro
```

-continued

```
                325                 330                 335
Ala Gly Gly Asp Tyr Leu Leu Lys Leu Pro Ile Pro Gln Ile Ile Gln
                340                 345                 350
Glu Asp Lys Asn Ala Trp Arg Thr Asp Glu Glu Phe Ala Arg Glu Val
                355                 360                 365
Leu Ala Gly Val Asn Pro Met Val Ile Thr Arg Leu Thr Glu Phe Pro
                370                 375                 380
Pro Lys Ser Thr Leu Asp Pro Ser Lys Tyr Gly Asp His Thr Ser Thr
385                 390                 395                 400
Ile Thr Ala Glu His Ile Glu Lys Asn Leu Glu Gly Leu Thr Val Gln
                405                 410                 415
Gln Ala Leu Asp Gly Asn Arg Leu Tyr Ile Leu Asp His His Asp Arg
                420                 425                 430
Phe Met Pro Phe Leu Ile Asp Val Asn Asn Leu Glu Gly Asn Phe Ile
                435                 440                 445
Tyr Ala Thr Arg Thr Leu Phe Phe Leu Arg Gly Asp Gly Arg Leu Ala
                450                 455                 460
Pro Leu Ala Ile Glu Leu Ser Glu Pro Tyr Ile Asp Gly Asp Leu Thr
465                 470                 475                 480
Val Ala Lys Ser Lys Val Tyr Thr Pro Ala Ser Ser Gly Val Glu Ala
                485                 490                 495
Trp Val Trp Gln Leu Ala Lys Ala Tyr Val Ala Val Asn Asp Ser Gly
                500                 505                 510
Trp His Gln Leu Val Ser His Trp Leu Asn Thr His Ala Val Met Glu
                515                 520                 525
Pro Phe Val Ile Ala Thr Asn Arg Gln Leu Ser Val Thr His Pro Val
                530                 535                 540
His Lys Leu Leu Ser Ser His Phe Arg Asp Thr Met Thr Ile Asn Ala
545                 550                 555                 560
Leu Ala Arg Gln Thr Leu Ile Asn Gly Gly Gly Ile Phe Glu Met Thr
                565                 570                 575
Val Phe Pro Gly Lys Tyr Ala Leu Gly Met Ser Ser Val Val Tyr Lys
                580                 585                 590
Ser Trp Asn Phe Thr Glu Gln Gly Leu Pro Ala Asp Leu Val Lys Arg
                595                 600                 605
Gly Val Ala Val Ala Asp Pro Ser Ser Leu Tyr Lys Val Arg Leu Leu
                610                 615                 620
Ile Glu Asp Tyr Pro Tyr Ala Ser Asp Gly Leu Ala Ile Trp His Ala
625                 630                 635                 640
Ile Glu Gln Trp Val Gly Glu Tyr Leu Ala Ile Tyr Tyr Pro Asp Asp
                645                 650                 655
Gly Ala Leu Arg Gly Asp Glu Leu Gln Ala Trp Trp Lys Glu Val
                660                 665                 670
Arg Glu Val Gly His Gly Asp His Lys Asp Ala Pro Trp Pro Lys
                675                 680                 685
Met Gln Ala Val Ser Glu Leu Ala Ser Ala Cys Thr Thr Ile Ile Trp
                690                 695                 700
Ile Ala Ser Ala Leu His Ala Ala Val Asn Phe Gly Gln Tyr Pro Tyr
705                 710                 715                 720
Ala Gly Tyr Leu Pro Asn Arg Pro Thr Val Ser Arg Arg Met Pro
                725                 730                 735
Glu Pro Gly Ser Lys Glu Tyr Glu Glu Leu Glu Arg Asp Pro Glu Arg
                740                 745                 750
```

```
Gly Phe Ile His Thr Ile Thr Ser Gln Ile Gln Thr Ile Ile Gly Ile
            755                 760                 765

Ser Leu Ile Glu Ile Leu Ser Lys His Ser Ser Asp Glu Val Tyr Leu
            770                 775                 780

Gly Gln Arg Asp Thr Pro Glu Trp Thr Ser Asp Ala Arg Ala Leu Ala
785                 790                 795                 800

Ala Phe Lys Arg Phe Ser Asp Ala Leu Val Lys Ile Glu Gly Lys Val
            805                 810                 815

Val Gly Glu Asn Arg Asp Pro Gln Leu Arg Asn Arg Asn Gly Pro Ala
            820                 825                 830

Glu Phe Pro Tyr Met Leu Leu Tyr Pro Asn Thr Ser Asp His Ser Gly
            835                 840                 845

Ala Ala Ala Gly Leu Thr Ala Lys Gly Ile Pro Asn Ser Ile Ser Ile
            850                 855                 860

<210> SEQ ID NO 11
<211> LENGTH: 2595
<212> TYPE: DNA
<213> ORGANISM: Zea mays
<220> FEATURE:
<221> NAME/KEY: CDS
<222> LOCATION: (1)...(2595)

<400> SEQUENCE: 11 atg ctg agc ggg atc atc gac ggg ctg acg ggg gcg aac aag cat gcg      48
Met Leu Ser Gly Ile Ile Asp Gly Leu Thr Gly Ala Asn Lys His Ala
1               5                   10                  15 cgg ctc aag ggc acg gtg gtg ctc atg cgc aag aac gtg ctg gac ctc      96
Arg Leu Lys Gly Thr Val Val Leu Met Arg Lys Asn Val Leu Asp Leu
                20                  25                  30 aac gac ttc ggc gcc acc gtc gtt gac agc atc agc gag ttc ctc ggc     144
Asn Asp Phe Gly Ala Thr Val Val Asp Ser Ile Ser Glu Phe Leu Gly
            35                  40                  45 aag ggg gtc acc tgc cag ctc atc agc tcc acc ctc gtc gac gcc aac     192
Lys Gly Val Thr Cys Gln Leu Ile Ser Ser Thr Leu Val Asp Ala Asn
        50                  55                  60 aac ggc aac cgc ggg cgg gtc ggg gcg gag gcg aac ctg gag cag tgg     240
Asn Gly Asn Arg Gly Arg Val Gly Ala Glu Ala Asn Leu Glu Gln Trp
65                  70                  75                  80 ctg acg agc ctg ccg tcg ctg acg acc ggc gag tcc aag ttc ggc gtc     288
Leu Thr Ser Leu Pro Ser Leu Thr Thr Gly Glu Ser Lys Phe Gly Val
                85                  90                  95 acg ttc gac tgg gag gtg gag aag ctg gga gtg ccg ggg gcc gtc gtc     336
Thr Phe Asp Trp Glu Val Glu Lys Leu Gly Val Pro Gly Ala Val Val
                100                 105                 110 gtc aag aac aac cac gcc gcc gag ttc ttc ctc aag aca atc acc ctc     384
Val Lys Asn Asn His Ala Ala Glu Phe Phe Leu Lys Thr Ile Thr Leu
            115                 120                 125 gac gac gtg ccc ggc cgc ggc gcc gtc acc ttc gtc gcc aac tcc tgg     432
Asp Asp Val Pro Gly Arg Gly Ala Val Thr Phe Val Ala Asn Ser Trp
        130                 135                 140 gtc tac ccc gcg ggc aag tac cgc tac aac cgc gtc ttc ttc tcc aac     480
Val Tyr Pro Ala Gly Lys Tyr Arg Tyr Asn Arg Val Phe Phe Ser Asn
145                 150                 155                 160 gat acg tac ctg cca agc cag atg ccg gcg gcg ctg aag ccg tac cgc     528
Asp Thr Tyr Leu Pro Ser Gln Met Pro Ala Ala Leu Lys Pro Tyr Arg
                165                 170                 175 gac gac gag ctc cgc aac ctc cgc ggc gac gac cag cag ggc ccc tac     576
Asp Asp Glu Leu Arg Asn Leu Arg Gly Asp Asp Gln Gln Gly Pro Tyr
```

-continued

```
                180                 185                 190
cag gag cac gac cgc gtg tac cgc tac gac gtc tac aac gac ctc ggc         624
Gln Glu His Asp Arg Val Tyr Arg Tyr Asp Val Tyr Asn Asp Leu Gly
        195                 200                 205 gag ccc gac ggc ggc aac ccg cgc ccc atc ctc ggc ggc tcc gcc gac         672
Glu Pro Asp Gly Gly Asn Pro Arg Pro Ile Leu Gly Gly Ser Ala Asp
210                 215                 220 cac ccg tac ccg cgc cgc tgc cgc acg ggc cgc aag ccc acc aaa acc         720
His Pro Tyr Pro Arg Arg Cys Arg Thr Gly Arg Lys Pro Thr Lys Thr
225                 230                 235                 240 gac ccc aac tcg gat agc cga ctg tcg ctg gtg gag cag atc tac gtg         768
Asp Pro Asn Ser Asp Ser Arg Leu Ser Leu Val Glu Gln Ile Tyr Val
                245                 250                 255 ccg cgg gac gag cgc ttc ggc cac ctc aag atg tcc gac ttc ctg ggc         816
Pro Arg Asp Glu Arg Phe Gly His Leu Lys Met Ser Asp Phe Leu Gly
            260                 265                 270 tac tcc atc aag gcc atc acg cag ggc atc atc ccg gcg gtg cgc acg         864
Tyr Ser Ile Lys Ala Ile Thr Gln Gly Ile Ile Pro Ala Val Arg Thr
        275                 280                 285 tac gtg gac acc acc ccg ggc gag ttc gac tcc ttc cag gac atc atc         912
Tyr Val Asp Thr Thr Pro Gly Glu Phe Asp Ser Phe Gln Asp Ile Ile
290                 295                 300 aac ctg tac gag ggc ggg atc aag ctg ccc aag atc cag gcg ctc gag         960
Asn Leu Tyr Glu Gly Gly Ile Lys Leu Pro Lys Ile Gln Ala Leu Glu
305                 310                 315                 320 gac atg cgc aag ctc ttc ccg ctc cag ctc gtc aag gac ctc ctc ccc        1008
Asp Met Arg Lys Leu Phe Pro Leu Gln Leu Val Lys Asp Leu Leu Pro
                325                 330                 335 gcc ggc ggg gac tac ctg ctc aag ctc ccc atc cca cag atc atc caa        1056
Ala Gly Gly Asp Tyr Leu Leu Lys Leu Pro Ile Pro Gln Ile Ile Gln
            340                 345                 350 gag gac aag aac gcg tgg agg acc gac gag gag ttc gcg cgg gag gtg        1104
Glu Asp Lys Asn Ala Trp Arg Thr Asp Glu Glu Phe Ala Arg Glu Val
        355                 360                 365 ctc gcc ggc gtc aac ccg atg gtg atc acg cgc ctc acg gag ttc ccg        1152
Leu Ala Gly Val Asn Pro Met Val Ile Thr Arg Leu Thr Glu Phe Pro
370                 375                 380 ccc aag agc acg ctg gac ccc agc aag tac ggc gac cac acc agc acg        1200
Pro Lys Ser Thr Leu Asp Pro Ser Lys Tyr Gly Asp His Thr Ser Thr
385                 390                 395                 400 atc acg gcg gag cac atc gag aag aac ctc gag ggc ctc acg gtg cag        1248
Ile Thr Ala Glu His Ile Glu Lys Asn Leu Glu Gly Leu Thr Val Gln
                405                 410                 415 cag gcg ctg gac ggc aac agg ctc tac atc ctg gac cac cac gac cgc        1296
Gln Ala Leu Asp Gly Asn Arg Leu Tyr Ile Leu Asp His His Asp Arg
            420                 425                 430 ttc atg ccg ttc ctc atc gac gtc aac aac ctg gag ggt aac ttc atc        1344
Phe Met Pro Phe Leu Ile Asp Val Asn Asn Leu Glu Gly Asn Phe Ile
        435                 440                 445 tac gcc acc agg acc ctc ttc ttc ctg cgc ggc gac ggc agg ctc gcg        1392
Tyr Ala Thr Arg Thr Leu Phe Phe Leu Arg Gly Asp Gly Arg Leu Ala
450                 455                 460 ccc ctc gct atc gag ctc agc gag ccg tac atc gac ggg gac ctt acc        1440
Pro Leu Ala Ile Glu Leu Ser Glu Pro Tyr Ile Asp Gly Asp Leu Thr
465                 470                 475                 480 gtg gcc aag agc aag gtc tac acg ccg gcg tcc agc ggc gtc gag gcc        1488
Val Ala Lys Ser Lys Val Tyr Thr Pro Ala Ser Ser Gly Val Glu Ala
                485                 490                 495 tgg gtg tgg cag ctc gcc aag gcc tat gtc gcc gtc aac gac tct ggc        1536
```

```
                                              -continued

Trp Val Trp Gln Leu Ala Lys Ala Tyr Val Ala Val Asn Asp Ser Gly
            500                 505                 510 tgg cac caa ctc gtc agc cac tgg ctg aac acg cac gcg gtg atg gag      1584
Trp His Gln Leu Val Ser His Trp Leu Asn Thr His Ala Val Met Glu
        515                 520                 525 ccg ttc gtg atc gcg acg aac cgg cag ctg agc gtg acg cac ccg gtg      1632
Pro Phe Val Ile Ala Thr Asn Arg Gln Leu Ser Val Thr His Pro Val
    530                 535                 540 cac aag ctc ctg agc tcg cac ttc cgc gac acc atg acc atc aac gcg      1680
His Lys Leu Leu Ser Ser His Phe Arg Asp Thr Met Thr Ile Asn Ala
545                 550                 555                 560 ctg gcg cgg cag acg ctc atc aac ggc ggc ggc atc ttc gag atg acc      1728
Leu Ala Arg Gln Thr Leu Ile Asn Gly Gly Gly Ile Phe Glu Met Thr
                565                 570                 575 gtc ttc ccg ggc aag tac gcg ctg ggc atg tcc tcc gtg gtg tac aag      1776
Val Phe Pro Gly Lys Tyr Ala Leu Gly Met Ser Ser Val Val Tyr Lys
            580                 585                 590 agc tgg aac ttc acc gag cag ggc ctc ccc gcc gac ctc gtc aag agg      1824
Ser Trp Asn Phe Thr Glu Gln Gly Leu Pro Ala Asp Leu Val Lys Arg
        595                 600                 605 ggc gtg gcg gtg gcg gac ccg tcc agc ctg tac aag gtg cgg ctg ctg      1872
Gly Val Ala Val Ala Asp Pro Ser Ser Leu Tyr Lys Val Arg Leu Leu
    610                 615                 620 atc gag gac tac ccg tac gcg agc gac ggg ctg gcc atc tgg cac gcc      1920
Ile Glu Asp Tyr Pro Tyr Ala Ser Asp Gly Leu Ala Ile Trp His Ala
625                 630                 635                 640 atc gag cag tgg gtg ggc gag tac ctg gcc atc tac tac ccc gac gac      1968
Ile Glu Gln Trp Val Gly Glu Tyr Leu Ala Ile Tyr Tyr Pro Asp Asp
                645                 650                 655 ggc gcg ctg cgg ggc gac gag gag ctg cag gcg tgg tgg aag gag gtg      2016
Gly Ala Leu Arg Gly Asp Glu Glu Leu Gln Ala Trp Trp Lys Glu Val
            660                 665                 670 cgc gag gtc ggg cac ggc gac cac aag gac gcg ccc tgg tgg ccc aag      2064
Arg Glu Val Gly His Gly Asp His Lys Asp Ala Pro Trp Trp Pro Lys
        675                 680                 685 atg cag gcc gtg tcg gag ctc gcc agc gcc tgc acc acc atc atc tgg      2112
Met Gln Ala Val Ser Glu Leu Ala Ser Ala Cys Thr Thr Ile Ile Trp
    690                 695                 700 atc gcg tcg gcg ctc cac gcc gcc gtc aac ttc ggc cag tac ccg tac      2160
Ile Ala Ser Ala Leu His Ala Ala Val Asn Phe Gly Gln Tyr Pro Tyr
705                 710                 715                 720 gcg ggg tac ctc ccg aac agg ccc acg gtg agc cgg cgc cgg atg ccg      2208
Ala Gly Tyr Leu Pro Asn Arg Pro Thr Val Ser Arg Arg Arg Met Pro
                725                 730                 735 gag ccc ggc agc aag gag tac gag gag ctg gag cgc gac ccg gag cgc      2256
Glu Pro Gly Ser Lys Glu Tyr Glu Glu Leu Glu Arg Asp Pro Glu Arg
            740                 745                 750 ggc ttc atc cac acc atc acg agc cag atc cag acc atc atc ggc atc      2304
Gly Phe Ile His Thr Ile Thr Ser Gln Ile Gln Thr Ile Ile Gly Ile
        755                 760                 765 tcg ctc atc gag atc ctc tcc aag cac tcc tcc gac gag gtg tac ctc      2352
Ser Leu Ile Glu Ile Leu Ser Lys His Ser Ser Asp Glu Val Tyr Leu
    770                 775                 780 ggc cag cgc gac acc ccc gag tgg acc tcc gac gcc cgg gcg ctg gcg      2400
Gly Gln Arg Asp Thr Pro Glu Trp Thr Ser Asp Ala Arg Ala Leu Ala
785                 790                 795                 800 gcg ttc aag agg ttc agc gac gcg ctg gtc aag atc gag ggc aag gtg      2448
Ala Phe Lys Arg Phe Ser Asp Ala Leu Val Lys Ile Glu Gly Lys Val
                805                 810                 815
```

```
gtg ggc gag aac cgc gac ccg cag ctg agg aac agg aac ggc ccc gcc   2496
Val Gly Glu Asn Arg Asp Pro Gln Leu Arg Asn Arg Asn Gly Pro Ala
            820                 825                 830 gag ttc ccc tac atg ctg ctc tac ccc aac acc tct gac cac agt ggc   2544
Glu Phe Pro Tyr Met Leu Leu Tyr Pro Asn Thr Ser Asp His Ser Gly
        835                 840                 845 gcc gcc gca ggg ctc act gcc aag ggc atc ccc aac agc atc tcc atc   2592
Ala Ala Ala Gly Leu Thr Ala Lys Gly Ile Pro Asn Ser Ile Ser Ile
    850                 855                 860 tga                                                                2595
 *

<210> SEQ ID NO 12
<211> LENGTH: 864
<212> TYPE: PRT
<213> ORGANISM: Zea mays

<400> SEQUENCE: 12

Met Leu Ser Gly Ile Ile Asp Gly Leu Thr Gly Ala Asn Lys His Ala
 1               5                  10                  15

Arg Leu Lys Gly Thr Val Val Leu Met Arg Lys Asn Val Leu Asp Leu
            20                  25                  30

Asn Asp Phe Gly Ala Thr Val Asp Ser Ile Ser Glu Phe Leu Gly
        35                  40                  45

Lys Gly Val Thr Cys Gln Leu Ile Ser Ser Thr Leu Val Asp Ala Asn
    50                  55                  60

Asn Gly Asn Arg Gly Arg Val Gly Ala Glu Ala Asn Leu Glu Gln Trp
65                  70                  75                  80

Leu Thr Ser Leu Pro Ser Leu Thr Thr Gly Glu Ser Lys Phe Gly Val
                85                  90                  95

Thr Phe Asp Trp Glu Val Glu Lys Leu Gly Val Pro Gly Ala Val Val
            100                 105                 110

Val Lys Asn Asn His Ala Ala Glu Phe Phe Leu Lys Thr Ile Thr Leu
        115                 120                 125

Asp Asp Val Pro Gly Arg Gly Ala Val Thr Phe Val Ala Asn Ser Trp
    130                 135                 140

Val Tyr Pro Ala Gly Lys Tyr Arg Tyr Asn Arg Val Phe Phe Ser Asn
145                 150                 155                 160

Asp Thr Tyr Leu Pro Ser Gln Met Pro Ala Ala Leu Lys Pro Tyr Arg
                165                 170                 175

Asp Asp Glu Leu Arg Asn Leu Arg Gly Asp Gln Gln Gly Pro Tyr
            180                 185                 190

Gln Glu His Asp Arg Val Tyr Arg Tyr Asp Val Tyr Asn Asp Leu Gly
        195                 200                 205

Glu Pro Asp Gly Gly Asn Pro Arg Pro Ile Leu Gly Gly Ser Ala Asp
    210                 215                 220

His Pro Tyr Pro Arg Arg Cys Arg Thr Gly Arg Lys Pro Thr Lys Thr
225                 230                 235                 240

Asp Pro Asn Ser Asp Ser Arg Leu Ser Leu Val Glu Gln Ile Tyr Val
                245                 250                 255

Pro Arg Asp Glu Arg Phe Gly His Leu Lys Met Ser Asp Phe Leu Gly
            260                 265                 270

Tyr Ser Ile Lys Ala Ile Thr Gln Gly Ile Ile Pro Ala Val Arg Thr
        275                 280                 285

Tyr Val Asp Thr Thr Pro Gly Glu Phe Asp Ser Phe Gln Asp Ile Ile
    290                 295                 300
```

-continued

```
Asn Leu Tyr Glu Gly Gly Ile Lys Leu Pro Lys Ile Gln Ala Leu Glu
305                 310                 315                 320

Asp Met Arg Lys Leu Phe Pro Leu Gln Leu Val Lys Asp Leu Leu Pro
            325                 330                 335

Ala Gly Gly Asp Tyr Leu Leu Lys Leu Pro Ile Pro Gln Ile Ile Gln
                340                 345                 350

Glu Asp Lys Asn Ala Trp Arg Thr Asp Glu Glu Phe Ala Arg Glu Val
            355                 360                 365

Leu Ala Gly Val Asn Pro Met Val Ile Thr Arg Leu Thr Glu Phe Pro
370                 375                 380

Pro Lys Ser Thr Leu Asp Pro Ser Lys Tyr Gly Asp His Thr Ser Thr
385                 390                 395                 400

Ile Thr Ala Glu His Ile Glu Lys Asn Leu Glu Gly Leu Thr Val Gln
                405                 410                 415

Gln Ala Leu Asp Gly Asn Arg Leu Tyr Ile Leu Asp His His Asp Arg
            420                 425                 430

Phe Met Pro Phe Leu Ile Asp Val Asn Asn Leu Glu Gly Asn Phe Ile
            435                 440                 445

Tyr Ala Thr Arg Thr Leu Phe Phe Leu Arg Gly Asp Gly Arg Leu Ala
450                 455                 460

Pro Leu Ala Ile Glu Leu Ser Glu Pro Tyr Ile Asp Gly Asp Leu Thr
465                 470                 475                 480

Val Ala Lys Ser Lys Val Tyr Thr Pro Ala Ser Ser Gly Val Glu Ala
            485                 490                 495

Trp Val Trp Gln Leu Ala Lys Ala Tyr Val Ala Val Asn Asp Ser Gly
            500                 505                 510

Trp His Gln Leu Val Ser His Trp Leu Asn Thr His Ala Val Met Glu
            515                 520                 525

Pro Phe Val Ile Ala Thr Asn Arg Gln Leu Ser Val Thr His Pro Val
530                 535                 540

His Lys Leu Leu Ser Ser His Phe Arg Asp Thr Met Thr Ile Asn Ala
545                 550                 555                 560

Leu Ala Arg Gln Thr Leu Ile Asn Gly Gly Gly Ile Phe Glu Met Thr
            565                 570                 575

Val Phe Pro Gly Lys Tyr Ala Leu Gly Met Ser Ser Val Val Tyr Lys
            580                 585                 590

Ser Trp Asn Phe Thr Glu Gln Gly Leu Pro Ala Asp Leu Val Lys Arg
            595                 600                 605

Gly Val Ala Val Ala Asp Pro Ser Ser Leu Tyr Lys Val Arg Leu Leu
610                 615                 620

Ile Glu Asp Tyr Pro Tyr Ala Ser Asp Gly Leu Ala Ile Trp His Ala
625                 630                 635                 640

Ile Glu Gln Trp Val Gly Glu Tyr Leu Ala Ile Tyr Tyr Pro Asp Asp
            645                 650                 655

Gly Ala Leu Arg Gly Asp Glu Glu Leu Gln Ala Trp Trp Lys Glu Val
            660                 665                 670

Arg Glu Val Gly His Gly Asp His Lys Asp Ala Pro Trp Trp Pro Lys
            675                 680                 685

Met Gln Ala Val Ser Glu Leu Ala Ser Ala Cys Thr Thr Ile Ile Trp
            690                 695                 700

Ile Ala Ser Ala Leu His Ala Ala Val Asn Phe Gly Gln Tyr Pro Tyr
705                 710                 715                 720
```

```
Ala Gly Tyr Leu Pro Asn Arg Pro Thr Val Ser Arg Arg Met Pro
            725                 730                 735
Glu Pro Gly Ser Lys Glu Tyr Glu Glu Leu Glu Arg Asp Pro Glu Arg
            740                 745                 750
Gly Phe Ile His Thr Ile Thr Ser Gln Ile Gln Thr Ile Ile Gly Ile
            755                 760                 765
Ser Leu Ile Glu Ile Leu Ser Lys His Ser Ser Asp Glu Val Tyr Leu
770                 775                 780
Gly Gln Arg Asp Thr Pro Glu Trp Thr Ser Asp Ala Arg Ala Leu Ala
785                 790                 795                 800
Ala Phe Lys Arg Phe Ser Asp Ala Leu Val Lys Ile Glu Gly Lys Val
                805                 810                 815
Val Gly Glu Asn Arg Asp Pro Gln Leu Arg Asn Arg Asn Gly Pro Ala
            820                 825                 830
Glu Phe Pro Tyr Met Leu Leu Tyr Pro Asn Thr Ser Asp His Ser Gly
            835                 840                 845
Ala Ala Ala Gly Leu Thr Ala Lys Gly Ile Pro Asn Ser Ile Ser Ile
850                 855                 860

<210> SEQ ID NO 13
<211> LENGTH: 2949
<212> TYPE: DNA
<213> ORGANISM: Zea mays
<220> FEATURE:
<221> NAME/KEY: CDS
<222> LOCATION: (47)...(2662)
<223> OTHER INFORMATION: LOX3

<400> SEQUENCE: 13
gttcactcac acagcaaata cccacagtcc acagcaagaa ccgaag atg ttc gga        55
                                                    Met Phe Gly
                                                     1 aac atc gga aag atc ccg atc atc ggc gac ctg acg ggc agc aac aag     103
Asn Ile Gly Lys Ile Pro Ile Ile Gly Asp Leu Thr Gly Ser Asn Lys
        5                   10                  15 aat gcg cac ctc aag ggc aac ctg gtg ctc atg cgc aag acc gtg ctc     151
Asn Ala His Leu Lys Gly Asn Leu Val Leu Met Arg Lys Thr Val Leu
 20                  25                  30                  35 ggc ttc gac gtc acc agc atc gcc ggc tcc ctc atg gac ggc ctc ggc     199
Gly Phe Asp Val Thr Ser Ile Ala Gly Ser Leu Met Asp Gly Leu Gly
                40                  45                  50 gag ttc ctc ggc cgc ggc gtc acc tgc caa ctc gtc agc tcc acc gtc     247
Glu Phe Leu Gly Arg Gly Val Thr Cys Gln Leu Val Ser Ser Thr Val
            55                  60                  65 gtc gac ccc aac aac ggg aac cgc ggg aag gtg ggt cag gag gcg agc     295
Val Asp Pro Asn Asn Gly Asn Arg Gly Lys Val Gly Gln Glu Ala Ser
        70                  75                  80 ctg gag cag tgg ctg ctg cac ccg ccg ccg ctt ctg gcc ggc gag gac     343
Leu Glu Gln Trp Leu Leu His Pro Pro Pro Leu Leu Ala Gly Glu Asp
    85                  90                  95 cag ttc cgc gtc acc ttc gac tgg gag gtg gag aag cac ggc gtc ccg     391
Gln Phe Arg Val Thr Phe Asp Trp Glu Val Glu Lys His Gly Val Pro
100                 105                 110                 115 ggc gcc atc atc gtg aag aac aac cac gcc tcc gag ttc ttc ctc aag     439
Gly Ala Ile Ile Val Lys Asn Asn His Ala Ser Glu Phe Phe Leu Lys
                120                 125                 130 acc atc acc atc gac gac gtc ccc ggc cac ggc ccc atc gtc ttc gtc     487
Thr Ile Thr Ile Asp Asp Val Pro Gly His Gly Pro Ile Val Phe Val
            135                 140                 145
```

```
gcc aac tca tgg gtg tac ccg cag tac aag tac cgc tac aac cgc gtc        535
Ala Asn Ser Trp Val Tyr Pro Gln Tyr Lys Tyr Arg Tyr Asn Arg Val
            150                 155                 160 ttc ttc tcc aac gac acg tac ctc ccc agc cag atg ccg gcg gcg ctg        583
Phe Phe Ser Asn Asp Thr Tyr Leu Pro Ser Gln Met Pro Ala Ala Leu
165                 170                 175 aag cct tac cgc gac gac gag ctc cgc aac ctg agg ggc gac gac cag        631
Lys Pro Tyr Arg Asp Asp Glu Leu Arg Asn Leu Arg Gly Asp Asp Gln
180                 185                 190                 195 cag ggc ccg tac cag gag cac gac cgc gtc tac cgc tac gac gtc tac        679
Gln Gly Pro Tyr Gln Glu His Asp Arg Val Tyr Arg Tyr Asp Val Tyr
                200                 205                 210 aac gac ctc ggc aac ccc gac gcc aaa aac ccg cgc ccc gtc ctc ggc        727
Asn Asp Leu Gly Asn Pro Asp Ala Lys Asn Pro Arg Pro Val Leu Gly
            215                 220                 225 ggc tcc aag cac cac ccc tac ccg cgc cgg cgg ccc acg ggc cgg aag        775
Gly Ser Lys His His Pro Tyr Pro Arg Arg Arg Pro Thr Gly Arg Lys
        230                 235                 240 ccg acg cag aca gac ccc aac agc gag agc agg ctg acg ctg acc gac        823
Pro Thr Gln Thr Asp Pro Asn Ser Glu Ser Arg Leu Thr Leu Thr Asp
245                 250                 255 ggc gac gtc tac gtg ccg cgc gac gag cgc ttc ggc cac atc aag aac        871
Gly Asp Val Tyr Val Pro Arg Asp Glu Arg Phe Gly His Ile Lys Asn
260                 265                 270                 275 tcc gac ttc tac ggc tac acc atc aag gcg ttc gtc gac ggc ctg gtg        919
Ser Asp Phe Tyr Gly Tyr Thr Ile Lys Ala Phe Val Asp Gly Leu Val
                280                 285                 290 ccc atc ctg gaa ggc tac ctc ctc ggc atc gag ttc aac tcc ttc aag        967
Pro Ile Leu Glu Gly Tyr Leu Leu Gly Ile Glu Phe Asn Ser Phe Lys
            295                 300                 305 gac atc ctg cag ctg tac gag ggc ggt atc aag ctg ccc gac atc ccc       1015
Asp Ile Leu Gln Leu Tyr Glu Gly Gly Ile Lys Leu Pro Asp Ile Pro
        310                 315                 320 gcc ctc gag gag ttc cgc aag cag ttc ccg cta cag atg gtc aag gac       1063
Ala Leu Glu Glu Phe Arg Lys Gln Phe Pro Leu Gln Met Val Lys Asp
325                 330                 335 ctc atg ccc gcc ggc ggc gac tac gtc ctc aat ctc ccc atg ccc aaa       1111
Leu Met Pro Ala Gly Gly Asp Tyr Val Leu Asn Leu Pro Met Pro Lys
340                 345                 350                 355 atc atc aaa gag gac aag aaa gct tgg atg agt gac gag gag ttc gca       1159
Ile Ile Lys Glu Asp Lys Lys Ala Trp Met Ser Asp Glu Glu Phe Ala
                360                 365                 370 agg gag acc ctc gcc ggc gtg aac ccc ttg atc atc agg cgt ctc acg       1207
Arg Glu Thr Leu Ala Gly Val Asn Pro Leu Ile Ile Arg Arg Leu Thr
            375                 380                 385 gag ttc cct ccg aaa agc acc ctt gat ccg agc aag tac ggc gac cag       1255
Glu Phe Pro Pro Lys Ser Thr Leu Asp Pro Ser Lys Tyr Gly Asp Gln
        390                 395                 400 acg agc acc atc acg gag gcg cac atc gcg ggg agc ctg gag ggc ctc       1303
Thr Ser Thr Ile Thr Glu Ala His Ile Ala Gly Ser Leu Glu Gly Leu
405                 410                 415 acc gtg cag cag gcg ctg gac agc aac cgg ctc tac atc ctg gac cac       1351
Thr Val Gln Gln Ala Leu Asp Ser Asn Arg Leu Tyr Ile Leu Asp His
420                 425                 430                 435 cac gac cac tac atg ccg ttc ctg atc gag gtc aac agc ctg aac gac       1399
His Asp His Tyr Met Pro Phe Leu Ile Glu Val Asn Ser Leu Asn Asp
                440                 445                 450 aac ttc atc tac gcc acc agg acg ctc ctg ttc ctg cgc ggc gac ggc       1447
Asn Phe Ile Tyr Ala Thr Arg Thr Leu Leu Phe Leu Arg Gly Asp Gly
            455                 460                 465
```

```
acg ctc gcg ccg gtg gcc atc gag atg agc ctc ccc gag ctc cgg gac    1495
Thr Leu Ala Pro Val Ala Ile Glu Met Ser Leu Pro Glu Leu Arg Asp
        470                 475                 480 ggc atc acg gcc gcg aag agc acg gtg tac acg ccg gcg ccg ccg acg    1543
Gly Ile Thr Ala Ala Lys Ser Thr Val Tyr Thr Pro Ala Pro Pro Thr
    485                 490                 495 gcc ggc gcg gag gcg tgg gtg tgg cgc ctg gcc aag gcc tac gtg aac    1591
Ala Gly Ala Glu Ala Trp Val Trp Arg Leu Ala Lys Ala Tyr Val Asn
500                 505                 510                 515 gtg aac gac tac tgc tgg cac cag ggc atc agc cac tgg ctc aac acg    1639
Val Asn Asp Tyr Cys Trp His Gln Gly Ile Ser His Trp Leu Asn Thr
                520                 525                 530 cac gcg gtg atg gag ccg ttc gtg atc gcc acc aac cgg cag ctc agc    1687
His Ala Val Met Glu Pro Phe Val Ile Ala Thr Asn Arg Gln Leu Ser
            535                 540                 545 gtg acg cac ccc gtg cac agg ctg ctg ctg ccg cac tac cgc gac acc    1735
Val Thr His Pro Val His Arg Leu Leu Leu Pro His Tyr Arg Asp Thr
        550                 555                 560 atg aac atc aac gcc ctc gcg cgc cag aag ctc atc aac gcc ggc ggc    1783
Met Asn Ile Asn Ala Leu Ala Arg Gln Lys Leu Ile Asn Ala Gly Gly
    565                 570                 575 atc ttc gag att acc gtc ttc ccg cgc aag tac gcc atc gag atc tcc    1831
Ile Phe Glu Ile Thr Val Phe Pro Arg Lys Tyr Ala Ile Glu Ile Ser
580                 585                 590                 595 tcc aaa gtc tac ggc agc tgg aac ttc acc gag cag gcc ctc ccc gac    1879
Ser Lys Val Tyr Gly Ser Trp Asn Phe Thr Glu Gln Ala Leu Pro Asp
                600                 605                 610 gac ctc atc aag cga ggc atg gcc gtt cca gat ccg tcg agc ccc tac    1927
Asp Leu Ile Lys Arg Gly Met Ala Val Pro Asp Pro Ser Ser Pro Tyr
            615                 620                 625 aag gtg cgg ctg ctg atc gag gac tac ccg tac gcc tcg gac ggg ctg    1975
Lys Val Arg Leu Leu Ile Glu Asp Tyr Pro Tyr Ala Ser Asp Gly Leu
        630                 635                 640 gcc gtg tgg cac gcc atc gag cag tgg gtg acg gag tac ctg gcc atc    2023
Ala Val Trp His Ala Ile Glu Gln Trp Val Thr Glu Tyr Leu Ala Ile
    645                 650                 655 tac tac ccc aac gac ggc gtg ctg cag gcc gac gtg gag ctg cag gcg    2071
Tyr Tyr Pro Asn Asp Gly Val Leu Gln Ala Asp Val Glu Leu Gln Ala
660                 665                 670                 675 tgg tgg aag gag gcg cgc gag gtc ggg cac gcc gac ctc aag gac gag    2119
Trp Trp Lys Glu Ala Arg Glu Val Gly His Ala Asp Leu Lys Asp Glu
                680                 685                 690 cac tgg tgg ccc aag atg cag acg gtg ccg gag ctc gtg aag gcc tgc    2167
His Trp Trp Pro Lys Met Gln Thr Val Pro Glu Leu Val Lys Ala Cys
            695                 700                 705 acc acc atc atc tgg atc gcg tcg gcg cta cac gct gcc gtc aac ttc    2215
Thr Thr Ile Ile Trp Ile Ala Ser Ala Leu His Ala Ala Val Asn Phe
        710                 715                 720 ggg cag tac ccg tac tgc ggg tac cac ccg aac cgg ccg tcc gtg agc    2263
Gly Gln Tyr Pro Tyr Cys Gly Tyr His Pro Asn Arg Pro Ser Val Ser
    725                 730                 735 cgg cgg ccc atg ccg gtg ccg ggc tcc gac gcg tac aag gag ctg gag    2311
Arg Arg Pro Met Pro Val Pro Gly Ser Asp Ala Tyr Lys Glu Leu Glu
740                 745                 750                 755 aag aac ccg gag aag ttc ttc gtg cgc tcc atc acc gcc caa ttc cag    2359
Lys Asn Pro Glu Lys Phe Phe Val Arg Ser Ile Thr Ala Gln Phe Gln
                760                 765                 770 gcc gtc gtc ggc atc tcg ctg ctg gag atc ctg tcc agc cac tcc tcc    2407
Ala Val Val Gly Ile Ser Leu Leu Glu Ile Leu Ser Ser His Ser Ser
```

```
                775                 780                 785
gac gag gtg tac ctc ggc cag cgc gac acc aag gag tgg acg tcg gac    2455
Asp Glu Val Tyr Leu Gly Gln Arg Asp Thr Lys Glu Trp Thr Ser Asp
        790                 795                 800 gcc aag gcg cag gag gcg ttc aag cgg ttc ggc gcg cgg ctg acc gag    2503
Ala Lys Ala Gln Glu Ala Phe Lys Arg Phe Gly Ala Arg Leu Thr Glu
805                 810                 815 atc gag aaa cgc gtg gag gcc atg aac aag gac ccg cgc ttc aag aac    2551
Ile Glu Lys Arg Val Glu Ala Met Asn Lys Asp Pro Arg Phe Lys Asn
820                 825                 830                 835 cgc tac agc gcg gcc cag ttc ccc tac acc ctg ctc ttc ccc aac acc    2599
Arg Tyr Ser Ala Ala Gln Phe Pro Tyr Thr Leu Leu Phe Pro Asn Thr
                840                 845                 850 tcc gac aag ggc gat aac acc ggc gtc acc gcc aag ggc atc ccc aac    2647
Ser Asp Lys Gly Asp Asn Thr Gly Val Thr Ala Lys Gly Ile Pro Asn
            855                 860                 865 agc att tcc atc tga ttcgatcgag tcctggccag cgtttcaccc aaaaaagcag    2702
Ser Ile Ser Ile *
        870 agctagcggt gattcccgta tgtcatccgt ttcattttt acatgaatga gaagcgtggt    2762 aataaaaagg tttgtagttg cgtgcgcgcc gtgtattcct tggtgtactg gtgctggcgg    2822 taaccactta ttaccaggga tccttgtaat ttttcctgtt ggtttcccaa taataatgtg    2882 aatatattgg tcaaaaaaaa aaaaaaaaaa aaaaaaaaaa aaaaaaaaaa aaaaaaaaaa    2942 aaaaaaa                                                             2949

<210> SEQ ID NO 14
<211> LENGTH: 871
<212> TYPE: PRT
<213> ORGANISM: Zea mays

<400> SEQUENCE: 14

Met Phe Gly Asn Ile Gly Lys Ile Pro Ile Ile Gly Asp Leu Thr Gly
 1               5                  10                  15

Ser Asn Lys Asn Ala His Leu Lys Gly Asn Leu Val Leu Met Arg Lys
            20                  25                  30

Thr Val Leu Gly Phe Asp Val Thr Ser Ile Ala Gly Ser Leu Met Asp
        35                  40                  45

Gly Leu Gly Glu Phe Leu Gly Arg Gly Val Thr Cys Gln Leu Val Ser
    50                  55                  60

Ser Thr Val Val Asp Pro Asn Gly Asn Arg Gly Lys Val Gly Gln
65                  70                  75                  80

Glu Ala Ser Leu Glu Gln Trp Leu Leu His Pro Pro Leu Leu Ala
                85                  90                  95

Gly Glu Asp Gln Phe Arg Val Thr Phe Asp Trp Glu Val Glu Lys His
            100                 105                 110

Gly Val Pro Gly Ala Ile Ile Val Lys Asn Asn His Ala Ser Glu Phe
        115                 120                 125

Phe Leu Lys Thr Ile Thr Ile Asp Asp Val Pro Gly His Gly Pro Ile
    130                 135                 140

Val Phe Val Ala Asn Ser Trp Val Tyr Pro Gln Tyr Lys Tyr Arg Tyr
145                 150                 155                 160

Asn Arg Val Phe Phe Ser Asn Asp Thr Tyr Leu Pro Ser Gln Met Pro
                165                 170                 175

Ala Ala Leu Lys Pro Tyr Arg Asp Asp Glu Leu Arg Asn Leu Arg Gly
            180                 185                 190
```

-continued

```
Asp Asp Gln Gln Gly Pro Tyr Gln Glu His Asp Arg Val Tyr Arg Tyr
        195                 200                 205

Asp Val Tyr Asn Asp Leu Gly Asn Pro Asp Ala Lys Asn Pro Arg Pro
        210                 215                 220

Val Leu Gly Gly Ser Lys His His Pro Tyr Pro Arg Arg Arg Pro Thr
225                 230                 235                 240

Gly Arg Lys Pro Thr Gln Thr Asp Pro Asn Ser Glu Ser Arg Leu Thr
                245                 250                 255

Leu Thr Asp Gly Asp Val Tyr Val Pro Arg Asp Glu Arg Phe Gly His
                260                 265                 270

Ile Lys Asn Ser Asp Phe Tyr Gly Tyr Thr Ile Lys Ala Phe Val Asp
        275                 280                 285

Gly Leu Val Pro Ile Leu Glu Gly Tyr Leu Leu Gly Ile Glu Phe Asn
        290                 295                 300

Ser Phe Lys Asp Ile Leu Gln Leu Tyr Glu Gly Gly Ile Lys Leu Pro
305                 310                 315                 320

Asp Ile Pro Ala Leu Glu Glu Phe Arg Lys Gln Phe Pro Leu Gln Met
                325                 330                 335

Val Lys Asp Leu Met Pro Ala Gly Gly Asp Tyr Val Leu Asn Leu Pro
                340                 345                 350

Met Pro Lys Ile Ile Lys Glu Asp Lys Lys Ala Trp Met Ser Asp Glu
        355                 360                 365

Glu Phe Ala Arg Glu Thr Leu Ala Gly Val Asn Pro Leu Ile Ile Arg
        370                 375                 380

Arg Leu Thr Glu Phe Pro Pro Lys Ser Thr Leu Asp Pro Ser Lys Tyr
385                 390                 395                 400

Gly Asp Gln Thr Ser Thr Ile Thr Glu Ala His Ile Ala Gly Ser Leu
                405                 410                 415

Glu Gly Leu Thr Val Gln Gln Ala Leu Asp Ser Asn Arg Leu Tyr Ile
                420                 425                 430

Leu Asp His His Asp His Tyr Met Pro Phe Leu Ile Glu Val Asn Ser
        435                 440                 445

Leu Asn Asp Asn Phe Ile Tyr Ala Thr Arg Thr Leu Leu Phe Leu Arg
450                 455                 460

Gly Asp Gly Thr Leu Ala Pro Val Ala Ile Glu Met Ser Leu Pro Glu
465                 470                 475                 480

Leu Arg Asp Gly Ile Thr Ala Ala Lys Ser Thr Val Tyr Thr Pro Ala
                485                 490                 495

Pro Pro Thr Ala Gly Ala Glu Ala Trp Val Trp Arg Leu Ala Lys Ala
                500                 505                 510

Tyr Val Asn Val Asn Asp Tyr Cys Trp His Gln Gly Ile Ser His Trp
        515                 520                 525

Leu Asn Thr His Ala Val Met Glu Pro Phe Val Ile Ala Thr Asn Arg
        530                 535                 540

Gln Leu Ser Val Thr His Pro Val His Arg Leu Leu Leu Pro His Tyr
545                 550                 555                 560

Arg Asp Thr Met Asn Ile Asn Ala Leu Ala Arg Gln Lys Leu Ile Asn
                565                 570                 575

Ala Gly Gly Ile Phe Glu Ile Thr Val Phe Pro Arg Lys Tyr Ala Ile
                580                 585                 590

Glu Ile Ser Ser Lys Val Tyr Gly Ser Trp Asn Phe Thr Glu Gln Ala
        595                 600                 605
```

```
Leu Pro Asp Asp Leu Ile Lys Arg Gly Met Ala Val Pro Asp Pro Ser
    610                 615                 620

Ser Pro Tyr Lys Val Arg Leu Leu Ile Glu Asp Tyr Pro Tyr Ala Ser
625                 630                 635                 640

Asp Gly Leu Ala Val Trp His Ala Ile Glu Gln Trp Val Thr Glu Tyr
                645                 650                 655

Leu Ala Ile Tyr Tyr Pro Asn Asp Gly Val Leu Gln Ala Asp Val Glu
            660                 665                 670

Leu Gln Ala Trp Trp Lys Glu Ala Arg Glu Val Gly His Ala Asp Leu
        675                 680                 685

Lys Asp Glu His Trp Trp Pro Lys Met Gln Thr Val Pro Glu Leu Val
    690                 695                 700

Lys Ala Cys Thr Thr Ile Ile Trp Ile Ala Ser Ala Leu His Ala Ala
705                 710                 715                 720

Val Asn Phe Gly Gln Tyr Pro Tyr Cys Gly Tyr His Pro Asn Arg Pro
                725                 730                 735

Ser Val Ser Arg Arg Pro Met Pro Val Pro Gly Ser Asp Ala Tyr Lys
            740                 745                 750

Glu Leu Glu Lys Asn Pro Glu Lys Phe Phe Val Arg Ser Ile Thr Ala
        755                 760                 765

Gln Phe Gln Ala Val Val Gly Ile Ser Leu Leu Glu Ile Leu Ser Ser
    770                 775                 780

His Ser Ser Asp Glu Val Tyr Leu Gly Gln Arg Asp Thr Lys Glu Trp
785                 790                 795                 800

Thr Ser Asp Ala Lys Ala Gln Glu Ala Phe Lys Arg Phe Gly Ala Arg
                805                 810                 815

Leu Thr Glu Ile Glu Lys Arg Val Glu Ala Met Asn Lys Asp Pro Arg
            820                 825                 830

Phe Lys Asn Arg Tyr Ser Ala Ala Gln Phe Pro Tyr Thr Leu Leu Phe
        835                 840                 845

Pro Asn Thr Ser Asp Lys Gly Asp Asn Thr Gly Val Thr Ala Lys Gly
    850                 855                 860

Ile Pro Asn Ser Ile Ser Ile
865                 870

<210> SEQ ID NO 15
<211> LENGTH: 2616
<212> TYPE: DNA
<213> ORGANISM: Zea mays
<220> FEATURE:
<221> NAME/KEY: CDS
<222> LOCATION: (1)...(2616)

<400> SEQUENCE: 15 atg ttc gga aac atc gga aag atc ccg atc atc ggc gac ctg acg ggc    48
Met Phe Gly Asn Ile Gly Lys Ile Pro Ile Ile Gly Asp Leu Thr Gly
 1               5                  10                  15 agc aac aag aat gcg cac ctc aag ggc aac ctg gtg ctc atg cgc aag    96
Ser Asn Lys Asn Ala His Leu Lys Gly Asn Leu Val Leu Met Arg Lys
                20                  25                  30 acc gtg ctc ggc ttc gac gtc acc agc atc gcc ggc tcc ctc atg gac   144
Thr Val Leu Gly Phe Asp Val Thr Ser Ile Ala Gly Ser Leu Met Asp
            35                  40                  45 ggc ctc ggc gag ttc ctc ggc cgc ggc gtc acc tgc caa ctc gtc agc   192
Gly Leu Gly Glu Phe Leu Gly Arg Gly Val Thr Cys Gln Leu Val Ser
        50                  55                  60 tcc acc gtc gtc gac ccc aac aac ggg aac cgc ggg aag gtg ggt cag   240
```

```
Ser Thr Val Val Asp Pro Asn Asn Gly Asn Arg Gly Lys Val Gly Gln
 65                  70                  75                  80 gag gcg agc ctg gag cag tgg ctg ctg cac ccg ccg ccg ctt ctg gcc        288
Glu Ala Ser Leu Glu Gln Trp Leu Leu His Pro Pro Pro Leu Leu Ala
                 85                  90                  95 ggc gag gac cag ttc cgc gtc acc ttc gac tgg gag gtg gag aag cac        336
Gly Glu Asp Gln Phe Arg Val Thr Phe Asp Trp Glu Val Glu Lys His
            100                 105                 110 ggc gtc ccg ggc gcc atc atc gtg aag aac aac cac gcc tcc gag ttc        384
Gly Val Pro Gly Ala Ile Ile Val Lys Asn Asn His Ala Ser Glu Phe
        115                 120                 125 ttc ctc aag acc atc acc atc gac gac gtc ccc ggc cac ggc ccc atc        432
Phe Leu Lys Thr Ile Thr Ile Asp Asp Val Pro Gly His Gly Pro Ile
    130                 135                 140 gtc ttc gtc gcc aac tca tgg gtg tac ccg cag tac aag tac cgc tac        480
Val Phe Val Ala Asn Ser Trp Val Tyr Pro Gln Tyr Lys Tyr Arg Tyr
145                 150                 155                 160 aac cgc gtc ttc ttc tcc aac gac acg tac ctc ccc agc cag atg ccg        528
Asn Arg Val Phe Phe Ser Asn Asp Thr Tyr Leu Pro Ser Gln Met Pro
                165                 170                 175 gcg gcg ctg aag cct tac cgc gac gac gag ctc cgc aac ctg agg ggc        576
Ala Ala Leu Lys Pro Tyr Arg Asp Asp Glu Leu Arg Asn Leu Arg Gly
            180                 185                 190 gac gac cag cag ggc ccg tac cag gag cac gac cgc gtc tac cgc tac        624
Asp Asp Gln Gln Gly Pro Tyr Gln Glu His Asp Arg Val Tyr Arg Tyr
        195                 200                 205 gac gtc tac aac gac ctc ggc aac ccc gac gcc aaa aac ccg cgc ccc        672
Asp Val Tyr Asn Asp Leu Gly Asn Pro Asp Ala Lys Asn Pro Arg Pro
    210                 215                 220 gtc ctc ggc ggc tcc aag cac cac ccc tac ccg cgc cgg cgg ccc acg        720
Val Leu Gly Gly Ser Lys His His Pro Tyr Pro Arg Arg Arg Pro Thr
225                 230                 235                 240 ggc cgg aag ccg acg cag aca gac ccc aac agc gag agc agg ctg acg        768
Gly Arg Lys Pro Thr Gln Thr Asp Pro Asn Ser Glu Ser Arg Leu Thr
                245                 250                 255 ctg acc gac ggc gac gtc tac gtg ccg cgc gac gag cgc ttc ggc cac        816
Leu Thr Asp Gly Asp Val Tyr Val Pro Arg Asp Glu Arg Phe Gly His
            260                 265                 270 atc aag aac tcc gac ttc tac ggc tac acc atc aag gcg ttc gtc gac        864
Ile Lys Asn Ser Asp Phe Tyr Gly Tyr Thr Ile Lys Ala Phe Val Asp
        275                 280                 285 ggc ctg gtg ccc atc ctg gaa ggc tac ctc ctc ggc atc gag ttc aac        912
Gly Leu Val Pro Ile Leu Glu Gly Tyr Leu Leu Gly Ile Glu Phe Asn
    290                 295                 300 tcc ttc aag gac atc ctg cag ctg tac gag ggc ggt atc aag ctg ccc        960
Ser Phe Lys Asp Ile Leu Gln Leu Tyr Glu Gly Gly Ile Lys Leu Pro
305                 310                 315                 320 gac atc ccc gcc ctc gag gag ttc cgc aag cag ttc ccg cta cag atg       1008
Asp Ile Pro Ala Leu Glu Glu Phe Arg Lys Gln Phe Pro Leu Gln Met
                325                 330                 335 gtc aag gac ctc atg ccc gcc ggc ggc gac tac gtc ctc aat ctc ccc       1056
Val Lys Asp Leu Met Pro Ala Gly Gly Asp Tyr Val Leu Asn Leu Pro
            340                 345                 350 atg ccc aaa atc atc aaa gag gac aag aaa gct tgg atg agt gac gag       1104
Met Pro Lys Ile Ile Lys Glu Asp Lys Lys Ala Trp Met Ser Asp Glu
        355                 360                 365 gag ttc gca agg gag acc ctc gcc ggc gtg aac ccc ttg atc atc agg       1152
Glu Phe Ala Arg Glu Thr Leu Ala Gly Val Asn Pro Leu Ile Ile Arg
    370                 375                 380
```

-continued

```
cgt ctc acg gag ttc cct ccg aaa agc acc ctt gat ccg agc aag tac       1200
Arg Leu Thr Glu Phe Pro Pro Lys Ser Thr Leu Asp Pro Ser Lys Tyr
385                 390                 395                 400 ggc gac cag acg agc acc atc acg gag gcg cac atc gcg ggg agc ctg       1248
Gly Asp Gln Thr Ser Thr Ile Thr Glu Ala His Ile Ala Gly Ser Leu
                405                 410                 415 gag ggc ctc acc gtg cag cag gcg ctg gac agc aac cgg ctc tac atc       1296
Glu Gly Leu Thr Val Gln Gln Ala Leu Asp Ser Asn Arg Leu Tyr Ile
            420                 425                 430 ctg gac cac cac gac cac tac atg ccg ttc ctg atc gag gtc aac agc       1344
Leu Asp His His Asp His Tyr Met Pro Phe Leu Ile Glu Val Asn Ser
        435                 440                 445 ctg aac gac aac ttc atc tac gcc acc agg acg ctc ctg ttc ctg cgc       1392
Leu Asn Asp Asn Phe Ile Tyr Ala Thr Arg Thr Leu Leu Phe Leu Arg
450                 455                 460 ggc gac ggc acg ctc gcg ccg gtg gcc atc gag atg agc ctc ccc gag       1440
Gly Asp Gly Thr Leu Ala Pro Val Ala Ile Glu Met Ser Leu Pro Glu
465                 470                 475                 480 ctc cgg gac ggc atc acg gcc gcg aag agc acg gtg tac acg ccg gcg       1488
Leu Arg Asp Gly Ile Thr Ala Ala Lys Ser Thr Val Tyr Thr Pro Ala
                485                 490                 495 ccg ccg acg gcc ggc gcg gag gcg tgg gtg tgg cgc ctg gcc aag gcc       1536
Pro Pro Thr Ala Gly Ala Glu Ala Trp Val Trp Arg Leu Ala Lys Ala
            500                 505                 510 tac gtg aac gtg aac gac tac tgc tgg cac cag ggc atc agc cac tgg       1584
Tyr Val Asn Val Asn Asp Tyr Cys Trp His Gln Gly Ile Ser His Trp
        515                 520                 525 ctc aac acg cac gcg gtg atg gag ccg ttc gtg atc gcc acc aac cgg       1632
Leu Asn Thr His Ala Val Met Glu Pro Phe Val Ile Ala Thr Asn Arg
530                 535                 540 cag ctc agc gtg acg cac ccc gtg cac agg ctg ctg ctg ccg cac tac       1680
Gln Leu Ser Val Thr His Pro Val His Arg Leu Leu Leu Pro His Tyr
545                 550                 555                 560 cgc gac acc atg aac atc aac gcc ctc gcg cgc cag aag ctc atc aac       1728
Arg Asp Thr Met Asn Ile Asn Ala Leu Ala Arg Gln Lys Leu Ile Asn
                565                 570                 575 gcc ggc ggc atc ttc gag att acc gtc ttc ccg cgc aag tac gcc atc       1776
Ala Gly Gly Ile Phe Glu Ile Thr Val Phe Pro Arg Lys Tyr Ala Ile
            580                 585                 590 gag atc tcc tcc aaa gtc tac ggc agc tgg aac ttc acc gag cag gcc       1824
Glu Ile Ser Ser Lys Val Tyr Gly Ser Trp Asn Phe Thr Glu Gln Ala
        595                 600                 605 ctc ccc gac gac ctc atc aag cga ggc atg gcc gtt cca gat ccg tcg       1872
Leu Pro Asp Asp Leu Ile Lys Arg Gly Met Ala Val Pro Asp Pro Ser
610                 615                 620 agc ccc tac aag gtg cgg ctg ctg atc gag gac tac ccg tac gcc tcg       1920
Ser Pro Tyr Lys Val Arg Leu Leu Ile Glu Asp Tyr Pro Tyr Ala Ser
625                 630                 635                 640 gac ggg ctg gcc gtg tgg cac gcc atc gag cag tgg gtg acg gag tac       1968
Asp Gly Leu Ala Val Trp His Ala Ile Glu Gln Trp Val Thr Glu Tyr
                645                 650                 655 ctg gcc atc tac tac ccc aac gac ggc gtg ctg cag gcc gac gtg gag       2016
Leu Ala Ile Tyr Tyr Pro Asn Asp Gly Val Leu Gln Ala Asp Val Glu
            660                 665                 670 ctg cag gcg tgg tgg aag gag gcg cgc gag gtc ggg cac gcc gac ctc       2064
Leu Gln Ala Trp Trp Lys Glu Ala Arg Glu Val Gly His Ala Asp Leu
        675                 680                 685 aag gac gag cac tgg tgg ccc aag atg cag acg gtg ccg gag ctc gtg       2112
Lys Asp Glu His Trp Trp Pro Lys Met Gln Thr Val Pro Glu Leu Val
690                 695                 700
```

```
aag gcc tgc acc acc atc atc tgg atc gcg tcg gcg cta cac gct gcc    2160
Lys Ala Cys Thr Thr Ile Ile Trp Ile Ala Ser Ala Leu His Ala Ala
705                 710                 715                 720 gtc aac ttc ggg cag tac ccg tac tgc ggg tac cac ccg aac cgg ccg    2208
Val Asn Phe Gly Gln Tyr Pro Tyr Cys Gly Tyr His Pro Asn Arg Pro
                725                 730                 735 tcc gtg agc cgg cgg ccc atg ccg gtg ccg ggc tcc gac gcg tac aag    2256
Ser Val Ser Arg Arg Pro Met Pro Val Pro Gly Ser Asp Ala Tyr Lys
            740                 745                 750 gag ctg gag aag aac ccg gag aag ttc ttc gtg cgc tcc atc acc gcc    2304
Glu Leu Glu Lys Asn Pro Glu Lys Phe Phe Val Arg Ser Ile Thr Ala
        755                 760                 765 caa ttc cag gcc gtc gtc ggc atc tcg ctg ctg gag atc ctg tcc agc    2352
Gln Phe Gln Ala Val Val Gly Ile Ser Leu Leu Glu Ile Leu Ser Ser
    770                 775                 780 cac tcc tcc gac gag gtg tac ctc ggc cag cgc gac acc aag gag tgg    2400
His Ser Ser Asp Glu Val Tyr Leu Gly Gln Arg Asp Thr Lys Glu Trp
785                 790                 795                 800 acg tcg gac gcc aag gcg cag gag gcg ttc aag cgg ttc ggc gcg cgg    2448
Thr Ser Asp Ala Lys Ala Gln Glu Ala Phe Lys Arg Phe Gly Ala Arg
                805                 810                 815 ctg acc gag atc gag aaa cgc gtg gag gcc atg aac aag gac ccg cgc    2496
Leu Thr Glu Ile Glu Lys Arg Val Glu Ala Met Asn Lys Asp Pro Arg
            820                 825                 830 ttc aag aac cgc tac agc gcg gcc cag ttc ccc tac acc ctg ctc ttc    2544
Phe Lys Asn Arg Tyr Ser Ala Ala Gln Phe Pro Tyr Thr Leu Leu Phe
        835                 840                 845 ccc aac acc tcc gac aag ggc gat aac acc ggc gtc acc gcc aag ggc    2592
Pro Asn Thr Ser Asp Lys Gly Asp Asn Thr Gly Val Thr Ala Lys Gly
    850                 855                 860 atc ccc aac agc att tcc atc tga                                    2616
Ile Pro Asn Ser Ile Ser Ile *
865                 870

<210> SEQ ID NO 16
<211> LENGTH: 871
<212> TYPE: PRT
<213> ORGANISM: Zea mays

<400> SEQUENCE: 16

Met Phe Gly Asn Ile Gly Lys Ile Pro Ile Ile Gly Asp Leu Thr Gly
1               5                   10                  15

Ser Asn Lys Asn Ala His Leu Lys Gly Asn Leu Val Leu Met Arg Lys
            20                  25                  30

Thr Val Leu Gly Phe Asp Val Thr Ser Ile Ala Gly Ser Leu Met Asp
        35                  40                  45

Gly Leu Gly Glu Phe Leu Gly Arg Gly Val Thr Cys Gln Leu Val Ser
    50                  55                  60

Ser Thr Val Val Asp Pro Asn Asn Gly Asn Arg Gly Lys Val Gly Gln
65                  70                  75                  80

Glu Ala Ser Leu Glu Gln Trp Leu Leu His Pro Pro Leu Leu Ala
                85                  90                  95

Gly Glu Asp Gln Phe Arg Val Thr Phe Asp Trp Glu Val Lys His
            100                 105                 110

Gly Val Pro Gly Ala Ile Ile Val Lys Asn Asn His Ala Ser Glu Phe
        115                 120                 125

Phe Leu Lys Thr Ile Thr Ile Asp Asp Val Pro Gly His Gly Pro Ile
    130                 135                 140
```

```
Val Phe Val Ala Asn Ser Trp Val Tyr Pro Gln Tyr Lys Tyr Arg Tyr
145                 150                 155                 160

Asn Arg Val Phe Phe Ser Asn Asp Thr Tyr Leu Pro Ser Gln Met Pro
                165                 170                 175

Ala Ala Leu Lys Pro Tyr Arg Asp Asp Glu Leu Arg Asn Leu Arg Gly
            180                 185                 190

Asp Asp Gln Gln Gly Pro Tyr Gln Glu His Asp Arg Val Tyr Arg Tyr
        195                 200                 205

Asp Val Tyr Asn Asp Leu Gly Asn Pro Asp Ala Lys Asn Pro Arg Pro
210                 215                 220

Val Leu Gly Gly Ser Lys His His Pro Tyr Pro Arg Arg Pro Thr
225                 230                 235                 240

Gly Arg Lys Pro Thr Gln Thr Asp Pro Asn Ser Glu Ser Arg Leu Thr
                245                 250                 255

Leu Thr Asp Gly Asp Val Tyr Val Pro Arg Asp Glu Arg Phe Gly His
            260                 265                 270

Ile Lys Asn Ser Asp Phe Tyr Gly Tyr Thr Ile Lys Ala Phe Val Asp
        275                 280                 285

Gly Leu Val Pro Ile Leu Glu Gly Tyr Leu Leu Gly Ile Glu Phe Asn
290                 295                 300

Ser Phe Lys Asp Ile Leu Gln Leu Tyr Glu Gly Gly Ile Lys Leu Pro
305                 310                 315                 320

Asp Ile Pro Ala Leu Glu Glu Phe Arg Lys Gln Phe Pro Leu Gln Met
                325                 330                 335

Val Lys Asp Leu Met Pro Ala Gly Gly Asp Tyr Val Leu Asn Leu Pro
            340                 345                 350

Met Pro Lys Ile Ile Lys Glu Asp Lys Lys Ala Trp Met Ser Asp Glu
        355                 360                 365

Glu Phe Ala Arg Glu Thr Leu Ala Gly Val Asn Pro Leu Ile Ile Arg
    370                 375                 380

Arg Leu Thr Glu Phe Pro Pro Lys Ser Thr Leu Asp Pro Ser Lys Tyr
385                 390                 395                 400

Gly Asp Gln Thr Ser Thr Ile Thr Glu Ala His Ile Ala Gly Ser Leu
                405                 410                 415

Glu Gly Leu Thr Val Gln Gln Ala Leu Asp Ser Asn Arg Leu Tyr Ile
            420                 425                 430

Leu Asp His His Asp His Tyr Met Pro Phe Leu Ile Glu Val Asn Ser
        435                 440                 445

Leu Asn Asp Asn Phe Ile Tyr Ala Thr Arg Thr Leu Leu Phe Leu Arg
450                 455                 460

Gly Asp Gly Thr Leu Ala Pro Val Ala Ile Glu Met Ser Leu Pro Glu
465                 470                 475                 480

Leu Arg Asp Gly Ile Thr Ala Ala Lys Ser Thr Val Tyr Thr Pro Ala
                485                 490                 495

Pro Pro Thr Ala Gly Ala Glu Ala Trp Val Trp Arg Leu Ala Lys Ala
            500                 505                 510

Tyr Val Asn Val Asn Asp Tyr Cys Trp His Gln Gly Ile Ser His Trp
        515                 520                 525

Leu Asn Thr His Ala Val Met Glu Pro Phe Val Ile Ala Thr Asn Arg
530                 535                 540

Gln Leu Ser Val Thr His Pro Val His Arg Leu Leu Leu Pro His Tyr
545                 550                 555                 560
```

-continued

```
Arg Asp Thr Met Asn Ile Asn Ala Leu Ala Arg Gln Lys Leu Ile Asn
            565                 570                 575

Ala Gly Gly Ile Phe Glu Ile Thr Val Phe Pro Arg Lys Tyr Ala Ile
        580                 585                 590

Glu Ile Ser Ser Lys Val Tyr Gly Ser Trp Asn Phe Thr Glu Gln Ala
    595                 600                 605

Leu Pro Asp Asp Leu Ile Lys Arg Gly Met Ala Val Pro Asp Pro Ser
610                 615                 620

Ser Pro Tyr Lys Val Arg Leu Leu Ile Glu Asp Tyr Pro Tyr Ala Ser
625                 630                 635                 640

Asp Gly Leu Ala Val Trp His Ala Ile Glu Gln Trp Val Thr Glu Tyr
                645                 650                 655

Leu Ala Ile Tyr Tyr Pro Asn Asp Gly Val Leu Gln Ala Asp Val Glu
            660                 665                 670

Leu Gln Ala Trp Trp Lys Glu Ala Arg Glu Val Gly His Ala Asp Leu
        675                 680                 685

Lys Asp Glu His Trp Trp Pro Lys Met Gln Thr Val Pro Glu Leu Val
    690                 695                 700

Lys Ala Cys Thr Thr Ile Ile Trp Ile Ala Ser Ala Leu His Ala Ala
705                 710                 715                 720

Val Asn Phe Gly Gln Tyr Pro Tyr Cys Gly Tyr His Pro Asn Arg Pro
                725                 730                 735

Ser Val Ser Arg Arg Pro Met Pro Val Pro Gly Ser Asp Ala Tyr Lys
            740                 745                 750

Glu Leu Glu Lys Asn Pro Glu Lys Phe Phe Val Arg Ser Ile Thr Ala
        755                 760                 765

Gln Phe Gln Ala Val Val Gly Ile Ser Leu Leu Glu Ile Leu Ser Ser
    770                 775                 780

His Ser Ser Asp Glu Val Tyr Leu Gly Gln Arg Asp Thr Lys Glu Trp
785                 790                 795                 800

Thr Ser Asp Ala Lys Ala Gln Glu Ala Phe Lys Arg Phe Gly Ala Arg
                805                 810                 815

Leu Thr Glu Ile Glu Lys Arg Val Glu Ala Met Asn Lys Asp Pro Arg
            820                 825                 830

Phe Lys Asn Arg Tyr Ser Ala Ala Gln Phe Pro Tyr Thr Leu Leu Phe
        835                 840                 845

Pro Asn Thr Ser Asp Lys Gly Asp Asn Thr Gly Val Thr Ala Lys Gly
    850                 855                 860

Ile Pro Asn Ser Ile Ser Ile
865                 870
```

<210> SEQ ID NO 17
<211> LENGTH: 3080
<212> TYPE: DNA
<213> ORGANISM: Zea mays
<220> FEATURE:
<221> NAME/KEY: CDS
<222> LOCATION: (152)...(2815)
<223> OTHER INFORMATION: LOX4

<400> SEQUENCE: 17

```
caaccgtgcg tgaaggaagg cctttgctcg ccgccacatc acattggcag gcgaggcgag      60
ggagcgagca gcagggcaag gcatccacac ccacacccac cggacactcc ctgagaagcg     120
agaagcgaga agcgaagagc ggccggccac c atg ttc tgg cac ggg gtc gcg        172
                                   Met Phe Trp His Gly Val Ala
                                    1               5
```

| | | |
|---|---|---|
| gac cgg ctg acg ggg aag aac aag gag gcg tgg aac gag gga aag atc<br>Asp Arg Leu Thr Gly Lys Asn Lys Glu Ala Trp Asn Glu Gly Lys Ile<br>        10                     15                    20 | 220 |
| cgc ggc acg gtg agg ctg gtc aag aag gag gtg ctg gac gtc ggc gac<br>Arg Gly Thr Val Arg Leu Val Lys Lys Glu Val Leu Asp Val Gly Asp<br>    25                     30                     35 | 268 |
| ttc aac gcc tcg ctc ctc gac ggc gta cac agg atc ctc ggc tgg gac<br>Phe Asn Ala Ser Leu Leu Asp Gly Val His Arg Ile Leu Gly Trp Asp<br>40                     45                     50                     55 | 316 |
| gac ggc gtc gcc ttc cag ctc gtc agc gcc acc gcg gcc gac ccc agc<br>Asp Gly Val Ala Phe Gln Leu Val Ser Ala Thr Ala Ala Asp Pro Ser<br>                60                     65                     70 | 364 |
| aac ggg agc cgc ggc aag gtc ggg aag gcg gcg cac ctg gag gag gcg<br>Asn Gly Ser Arg Gly Lys Val Gly Lys Ala Ala His Leu Glu Glu Ala<br>         75                     80                     85 | 412 |
| gtg gtg tcg ctc aag tcg acg acg gac ggg gag acc gtg tac cgg gtg<br>Val Val Ser Leu Lys Ser Thr Thr Asp Gly Glu Thr Val Tyr Arg Val<br>               90                     95                    100 | 460 |
| agc ttc gag tgg gac ggg tcg cag ggc gtc cct ggc gcc gtc ctg gtc<br>Ser Phe Glu Trp Asp Gly Ser Gln Gly Val Pro Gly Ala Val Leu Val<br>105                    110                   115 | 508 |
| agg aac ctg cag cac gcc gag ttc ttc ctc aag tcg ctc acc ctc gag<br>Arg Asn Leu Gln His Ala Glu Phe Phe Leu Lys Ser Leu Thr Leu Glu<br>120                  125                   130                  135 | 556 |
| ggc gtc ccc ggc agg ggc acc gtc gtc ttc gtc gcc aac tcg tgg atc<br>Gly Val Pro Gly Arg Gly Thr Val Val Phe Val Ala Asn Ser Trp Ile<br>              140                   145                   150 | 604 |
| tac ccg cac aat ctc tac tcc cag gaa cgc gtc ttc ttc gcc aac gac<br>Tyr Pro His Asn Leu Tyr Ser Gln Glu Arg Val Phe Phe Ala Asn Asp<br>        155                    160                   165 | 652 |
| act tat ctg cca agc aaa atg cct gcg gca ttg gtg cct tac cgg cag<br>Thr Tyr Leu Pro Ser Lys Met Pro Ala Ala Leu Val Pro Tyr Arg Gln<br>          170                    175                   180 | 700 |
| gac gag ctc aag att ctc cgc ggc gac gat aat cct gga cca tac aag<br>Asp Glu Leu Lys Ile Leu Arg Gly Asp Asp Asn Pro Gly Pro Tyr Lys<br>185                    190                   195 | 748 |
| gag cac gac cgc gtc tac cgt tac gac tac tac aac gac ctc ggt gag<br>Glu His Asp Arg Val Tyr Arg Tyr Asp Tyr Tyr Asn Asp Leu Gly Glu<br>200                    205                   210                  215 | 796 |
| cca gac aag ggt gaa gac cat gcc cgg cct gtc ctc ggg ggc agc caa<br>Pro Asp Lys Gly Glu Asp His Ala Arg Pro Val Leu Gly Gly Ser Gln<br>              220                   225                   230 | 844 |
| gaa cac ccg tat ccc cgt cgc tgc agg acc ggc cgg cgt cca aca gag<br>Glu His Pro Tyr Pro Arg Arg Cys Arg Thr Gly Arg Arg Pro Thr Glu<br>          235                    240                   245 | 892 |
| aca gac ccc aac tcg gag agc agg ctg ttt ctg ctg aac ctg aac atc<br>Thr Asp Pro Asn Ser Glu Ser Arg Leu Phe Leu Leu Asn Leu Asn Ile<br>              250                   255                   260 | 940 |
| tac gtc ccg cgc gac gag cgg ttt ggg cat ctc aag atg tcg gac ttc<br>Tyr Val Pro Arg Asp Glu Arg Phe Gly His Leu Lys Met Ser Asp Phe<br>265                    270                   275 | 988 |
| ctc ggg tac tca ctg aag gcg atc atc gag gct gtc ctt ccg acg ctg<br>Leu Gly Tyr Ser Leu Lys Ala Ile Ile Glu Ala Val Leu Pro Thr Leu<br>280                    285                   290                  295 | 1036 |
| gga cgt ttc gtc gac gat acg ccc aag gag ttc gat tcg ttc gaa gac<br>Gly Arg Phe Val Asp Asp Thr Pro Lys Glu Phe Asp Ser Phe Glu Asp<br>              300                   305                   310 | 1084 |
| atc ctt ggg ctc tac gag ccg ggt cca gag gcg ccc aac aac cca ctg<br>Ile Leu Gly Leu Tyr Glu Pro Gly Pro Glu Ala Pro Asn Asn Pro Leu | 1132 |

-continued

```
                  315                 320                 325
gta gca gag gtc agg aag aga atc ccc agc gag ttc ctc aga agc att      1180
Val Ala Glu Val Arg Lys Arg Ile Pro Ser Glu Phe Leu Arg Ser Ile
            330                 335                 340 ctg ccc gat ggt agc cat gac cac ccc ctg aag atg ccc ctt cca aat      1228
Leu Pro Asp Gly Ser His Asp His Pro Leu Lys Met Pro Leu Pro Asn
345                 350                 355 atc atc aga tca gat gtg ttg aaa aag gct cca gag ttt aag ttt ggc      1276
Ile Ile Arg Ser Asp Val Leu Lys Lys Ala Pro Glu Phe Lys Phe Gly
360                 365                 370                 375 tgg agg acc gac gaa gag ttt gcg agg gag acg ctt gca ggc gtg aac      1324
Trp Arg Thr Asp Glu Glu Phe Ala Arg Glu Thr Leu Ala Gly Val Asn
            380                 385                 390 cca gtg ctc atc aaa cgt ctg acg gag ttc cca gct aaa agt acc ctg      1372
Pro Val Leu Ile Lys Arg Leu Thr Glu Phe Pro Ala Lys Ser Thr Leu
                395                 400                 405 gac cca agt caa tac gga gac cat acg agc aag atc acc gaa gct cac      1420
Asp Pro Ser Gln Tyr Gly Asp His Thr Ser Lys Ile Thr Glu Ala His
            410                 415                 420 atc cag cat aac atg gaa ggc ctg tcg gtg cag aat gca ctg aag aag      1468
Ile Gln His Asn Met Glu Gly Leu Ser Val Gln Asn Ala Leu Lys Lys
425                 430                 435 aac agg ctc ttc atc cta gac cat cat gac cat ttc atg ccg tac ctc      1516
Asn Arg Leu Phe Ile Leu Asp His His Asp His Phe Met Pro Tyr Leu
440                 445                 450                 455 aac aag atc aac gag ttg gag ggg aac ttc atc tac gcc agc agg acc      1564
Asn Lys Ile Asn Glu Leu Glu Gly Asn Phe Ile Tyr Ala Ser Arg Thr
            460                 465                 470 cta ctg ttc ctg aag gac gat ggc acc ctg aag ccc ctg gcc gtc gag      1612
Leu Leu Phe Leu Lys Asp Asp Gly Thr Leu Lys Pro Leu Ala Val Glu
                475                 480                 485 ctg agc ctg ccc cac ccc gat ggc cag cag cac ggc gcg gtc agc aag      1660
Leu Ser Leu Pro His Pro Asp Gly Gln Gln His Gly Ala Val Ser Lys
            490                 495                 500 gtg tac acc cca gct cac tcc ggc gct gag ggc cac gtc tgg caa ctt      1708
Val Tyr Thr Pro Ala His Ser Gly Ala Glu Gly His Val Trp Gln Leu
505                 510                 515 gcc aag gct tat gcc tgc gtg aac gac tct gcc tgg cat cag ctg atc      1756
Ala Lys Ala Tyr Ala Cys Val Asn Asp Ser Ala Trp His Gln Leu Ile
520                 525                 530                 535 agc cac tgg ctg aac acg cac gcg gtg atc gag ccg ttc gtc atc gca      1804
Ser His Trp Leu Asn Thr His Ala Val Ile Glu Pro Phe Val Ile Ala
            540                 545                 550 acg aac cgg cag ctg agc gtg gtg cat ccc gtg cac aag ctg ctg agc      1852
Thr Asn Arg Gln Leu Ser Val Val His Pro Val His Lys Leu Leu Ser
            555                 560                 565 cca cac tac cgt gac acg ctg aac atc aac gcc ctg gca cgc cag acg      1900
Pro His Tyr Arg Asp Thr Leu Asn Ile Asn Ala Leu Ala Arg Gln Thr
            570                 575                 580 ctc atc aac gcc gac ggc atc ttc gag cgc acc gtg ttc cct gca aag      1948
Leu Ile Asn Ala Asp Gly Ile Phe Glu Arg Thr Val Phe Pro Ala Lys
585                 590                 595 tac gcg ctg ggg atg tcc tcc gac gtg tac aag agc tgg aat ttc aac      1996
Tyr Ala Leu Gly Met Ser Ser Asp Val Tyr Lys Ser Trp Asn Phe Asn
600                 605                 610                 615 gag cag gct ctc cca gca gac ctc gtc aag aga ggt gtg gct gtg ccg      2044
Glu Gln Ala Leu Pro Ala Asp Leu Val Lys Arg Gly Val Ala Val Pro
            620                 625                 630 gac cag tca agc ccc tac ggt gtc cgg ctg ctg atc aag gac tac cct      2092
```

```
Asp Gln Ser Ser Pro Tyr Gly Val Arg Leu Leu Ile Lys Asp Tyr Pro
            635                 640                 645 tac gcc gtg gac ggg ctg gtc atc tgg tgg gcg atc gag cgg tgg gtc    2140
Tyr Ala Val Asp Gly Leu Val Ile Trp Trp Ala Ile Glu Arg Trp Val
        650                 655                 660 aag gag tac ctg gac gtc tac tac ccc aac gac ggc gag ctc cag cgc    2188
Lys Glu Tyr Leu Asp Val Tyr Tyr Pro Asn Asp Gly Glu Leu Gln Arg
    665                 670                 675 gac gtg gag ctg cag gcg tgg tgg aag gag gtg cgc gag gag gcg cac    2236
Asp Val Glu Leu Gln Ala Trp Trp Lys Glu Val Arg Glu Glu Ala His
680                 685                 690                 695 ggc gac ctc aag gac cga gac tgg tgg ccc agg atg gac gcc gtc cag    2284
Gly Asp Leu Lys Asp Arg Asp Trp Trp Pro Arg Met Asp Ala Val Gln
                700                 705                 710 cgg ctg gcc agg gcg tgc acg acc gtc atc tgg gta gcg tcc gcg ctg    2332
Arg Leu Ala Arg Ala Cys Thr Thr Val Ile Trp Val Ala Ser Ala Leu
            715                 720                 725 cac gcg gcc gtc aac ttc ggg cag tac ccg tac gcc ggg tac ctg ccg    2380
His Ala Ala Val Asn Phe Gly Gln Tyr Pro Tyr Ala Gly Tyr Leu Pro
        730                 735                 740 aac cgg ccg acc gtg agc cgg cgg ccg atg ccg gag ccg ggc agc gac    2428
Asn Arg Pro Thr Val Ser Arg Arg Pro Met Pro Glu Pro Gly Ser Asp
    745                 750                 755 gac tac aag aag ctg gag gcg ggg cag aag gag gcg gac gcg gtg ttc    2476
Asp Tyr Lys Lys Leu Glu Ala Gly Gln Lys Glu Ala Asp Ala Val Phe
760                 765                 770                 775 atc cgc acc atc acc agc cag ttc cag acc atc ctg ggc atc tcg ctc    2524
Ile Arg Thr Ile Thr Ser Gln Phe Gln Thr Ile Leu Gly Ile Ser Leu
                780                 785                 790 atc gag atc ctc tcc aag cac tcc tcc gac gag gtg tac ctc ggc cag    2572
Ile Glu Ile Leu Ser Lys His Ser Ser Asp Glu Val Tyr Leu Gly Gln
            795                 800                 805 cgc gac gag cct gag cgc tgg acg tcg gac gcc agg gcg ctg gac gcg    2620
Arg Asp Glu Pro Glu Arg Trp Thr Ser Asp Ala Arg Ala Leu Asp Ala
        810                 815                 820 ttc aga agg ttc gga agc cgg ctg gtg gag atc gag aag cgg atc agg    2668
Phe Arg Arg Phe Gly Ser Arg Leu Val Glu Ile Glu Lys Arg Ile Arg
    825                 830                 835 acg atg aac gac agc ccg acg ttg aag aac cgg aag ggg ccg gtg gag    2716
Thr Met Asn Asp Ser Pro Thr Leu Lys Asn Arg Lys Gly Pro Val Glu
840                 845                 850                 855 atg ccg tac atg ctg ctg tac ccc aac acg tcg gat gtc acc ggc gag    2764
Met Pro Tyr Met Leu Leu Tyr Pro Asn Thr Ser Asp Val Thr Gly Glu
                860                 865                 870 aag ggc gag ggg ctc act gcc atg ggc att ccc aac agc atc tcc ata    2812
Lys Gly Glu Gly Leu Thr Ala Met Gly Ile Pro Asn Ser Ile Ser Ile
            875                 880                 885 tga gcctcctcac tgcctgagcg gatggtttgt agatgctctg ttacgctgtg         2865
 * tgtaatgtgt cgtttattcg ttggttttgt cagtctggta gggaatggag atgttgattg  2925
gatccatgat ctgtagggtt gagagaggag ccacgtctgg ataatgttgt catgtgtgtt  2985
tctttcttgg ttaagaataa aaattcgtct gctcaaaaaa aaaaaaaaaa aaaaaaaaaa  3045
aaaaaaaaaa aaaaaaaaaa aaaaaaaaaa aaaa                              3080

<210> SEQ ID NO 18
<211> LENGTH: 887
<212> TYPE: PRT
<213> ORGANISM: Zea mays
```

<400> SEQUENCE: 18

```
Met Phe Trp His Gly Val Ala Asp Arg Leu Thr Gly Lys Asn Lys Glu
 1               5                  10                  15
Ala Trp Asn Glu Gly Lys Ile Arg Gly Thr Val Arg Leu Val Lys Lys
            20                  25                  30
Glu Val Leu Asp Val Gly Asp Phe Asn Ala Ser Leu Leu Asp Gly Val
        35                  40                  45
His Arg Ile Leu Gly Trp Asp Asp Gly Val Ala Phe Gln Leu Val Ser
    50                  55                  60
Ala Thr Ala Ala Asp Pro Ser Asn Gly Ser Arg Gly Lys Val Gly Lys
65                  70                  75                  80
Ala Ala His Leu Glu Glu Ala Val Val Ser Leu Lys Ser Thr Thr Asp
                85                  90                  95
Gly Glu Thr Val Tyr Arg Val Ser Phe Glu Trp Asp Gly Ser Gln Gly
            100                 105                 110
Val Pro Gly Ala Val Leu Val Arg Asn Leu Gln His Ala Glu Phe Phe
        115                 120                 125
Leu Lys Ser Leu Thr Leu Glu Gly Val Pro Gly Arg Gly Thr Val Val
    130                 135                 140
Phe Val Ala Asn Ser Trp Ile Tyr Pro His Asn Leu Tyr Ser Gln Glu
145                 150                 155                 160
Arg Val Phe Phe Ala Asn Asp Thr Tyr Leu Pro Ser Lys Met Pro Ala
                165                 170                 175
Ala Leu Val Pro Tyr Arg Gln Asp Glu Leu Lys Ile Leu Arg Gly Asp
            180                 185                 190
Asp Asn Pro Gly Pro Tyr Lys Glu His Asp Arg Val Tyr Arg Tyr Asp
        195                 200                 205
Tyr Tyr Asn Asp Leu Gly Glu Pro Asp Lys Gly Glu Asp His Ala Arg
    210                 215                 220
Pro Val Leu Gly Gly Ser Gln Glu His Pro Tyr Pro Arg Arg Cys Arg
225                 230                 235                 240
Thr Gly Arg Arg Pro Thr Glu Thr Asp Pro Asn Ser Glu Ser Arg Leu
                245                 250                 255
Phe Leu Leu Asn Leu Asn Ile Tyr Val Pro Arg Asp Glu Arg Phe Gly
            260                 265                 270
His Leu Lys Met Ser Asp Phe Leu Gly Tyr Ser Leu Lys Ala Ile Ile
        275                 280                 285
Glu Ala Val Leu Pro Thr Leu Gly Arg Phe Val Asp Asp Thr Pro Lys
    290                 295                 300
Glu Phe Asp Ser Phe Glu Asp Ile Leu Gly Leu Tyr Glu Pro Gly Pro
305                 310                 315                 320
Glu Ala Pro Asn Asn Pro Leu Val Ala Glu Val Arg Lys Arg Ile Pro
                325                 330                 335
Ser Glu Phe Leu Arg Ser Ile Leu Pro Asp Gly Ser His Asp His Pro
            340                 345                 350
Leu Lys Met Pro Leu Pro Asn Ile Ile Arg Ser Asp Val Leu Lys Lys
        355                 360                 365
Ala Pro Glu Phe Lys Phe Gly Trp Arg Thr Asp Glu Glu Phe Ala Arg
    370                 375                 380
Glu Thr Leu Ala Gly Val Asn Pro Val Leu Ile Lys Arg Leu Thr Glu
385                 390                 395                 400
Phe Pro Ala Lys Ser Thr Leu Asp Pro Ser Gln Tyr Gly Asp His Thr
```

-continued

```
                405                 410                 415
Ser Lys Ile Thr Glu Ala His Ile Gln His Asn Met Glu Gly Leu Ser
            420                 425                 430

Val Gln Asn Ala Leu Lys Lys Asn Arg Leu Phe Ile Leu Asp His His
            435                 440                 445

Asp His Phe Met Pro Tyr Leu Asn Lys Ile Asn Glu Leu Glu Gly Asn
450                 455                 460

Phe Ile Tyr Ala Ser Arg Thr Leu Leu Phe Leu Lys Asp Asp Gly Thr
465                 470                 475                 480

Leu Lys Pro Leu Ala Val Glu Leu Ser Leu Pro His Pro Asp Gly Gln
                485                 490                 495

Gln His Gly Ala Val Ser Lys Val Tyr Thr Pro Ala His Ser Gly Ala
            500                 505                 510

Glu Gly His Val Trp Gln Leu Ala Lys Ala Tyr Ala Cys Val Asn Asp
            515                 520                 525

Ser Ala Trp His Gln Leu Ile Ser His Trp Leu Asn Thr His Ala Val
            530                 535                 540

Ile Glu Pro Phe Val Ile Ala Thr Asn Arg Gln Leu Ser Val Val His
545                 550                 555                 560

Pro Val His Lys Leu Leu Ser Pro His Tyr Arg Asp Thr Leu Asn Ile
                565                 570                 575

Asn Ala Leu Ala Arg Gln Thr Leu Ile Asn Ala Asp Gly Ile Phe Glu
            580                 585                 590

Arg Thr Val Phe Pro Ala Lys Tyr Ala Leu Gly Met Ser Ser Asp Val
            595                 600                 605

Tyr Lys Ser Trp Asn Phe Asn Glu Gln Ala Leu Pro Ala Asp Leu Val
            610                 615                 620

Lys Arg Gly Val Ala Val Pro Asp Gln Ser Ser Pro Tyr Gly Val Arg
625                 630                 635                 640

Leu Leu Ile Lys Asp Tyr Pro Tyr Ala Val Asp Gly Leu Val Ile Trp
                645                 650                 655

Trp Ala Ile Glu Arg Trp Val Lys Glu Tyr Leu Asp Val Tyr Tyr Pro
            660                 665                 670

Asn Asp Gly Glu Leu Gln Arg Asp Val Glu Leu Gln Ala Trp Trp Lys
            675                 680                 685

Glu Val Arg Glu Glu Ala His Gly Asp Leu Lys Asp Arg Asp Trp Trp
            690                 695                 700

Pro Arg Met Asp Ala Val Gln Arg Leu Ala Arg Ala Cys Thr Thr Val
705                 710                 715                 720

Ile Trp Val Ala Ser Ala Leu His Ala Ala Val Asn Phe Gly Gln Tyr
                725                 730                 735

Pro Tyr Ala Gly Tyr Leu Pro Asn Arg Pro Thr Val Ser Arg Arg Pro
            740                 745                 750

Met Pro Glu Pro Gly Ser Asp Tyr Lys Lys Leu Glu Ala Gly Gln
            755                 760                 765

Lys Glu Ala Asp Ala Val Phe Ile Arg Thr Ile Thr Ser Gln Phe Gln
            770                 775                 780

Thr Ile Leu Gly Ile Ser Leu Ile Glu Ile Leu Ser Lys His Ser Ser
785                 790                 795                 800

Asp Glu Val Tyr Leu Gly Gln Arg Asp Glu Pro Glu Arg Trp Thr Ser
                805                 810                 815

Asp Ala Arg Ala Leu Asp Ala Phe Arg Arg Phe Gly Ser Arg Leu Val
            820                 825                 830
```

```
Glu Ile Glu Lys Arg Ile Arg Thr Met Asn Asp Ser Pro Thr Leu Lys
            835                 840                 845

Asn Arg Lys Gly Pro Val Glu Met Pro Tyr Met Leu Leu Tyr Pro Asn
850                 855                 860

Thr Ser Asp Val Thr Gly Glu Lys Gly Glu Gly Leu Thr Ala Met Gly
865                 870                 875                 880

Ile Pro Asn Ser Ile Ser Ile
                885

<210> SEQ ID NO 19
<211> LENGTH: 2664
<212> TYPE: DNA
<213> ORGANISM: Zea mays
<220> FEATURE:
<221> NAME/KEY: CDS
<222> LOCATION: (1)...(2664)

<400> SEQUENCE: 19 atg ttc tgg cac ggg gtc gcg gac cgg ctg acg ggg aag aac aag gag      48
Met Phe Trp His Gly Val Ala Asp Arg Leu Thr Gly Lys Asn Lys Glu
1               5                  10                  15 gcg tgg aac gag gga aag atc cgc ggc acg gtg agg ctg gtc aag aag      96
Ala Trp Asn Glu Gly Lys Ile Arg Gly Thr Val Arg Leu Val Lys Lys
            20                  25                  30 gag gtg ctg gac gtc ggc gac ttc aac gcc tcg ctc ctc gac ggc gta     144
Glu Val Leu Asp Val Gly Asp Phe Asn Ala Ser Leu Leu Asp Gly Val
        35                  40                  45 cac agg atc ctc ggc tgg gac gac ggc gtc gcc ttc cag ctc gtc agc     192
His Arg Ile Leu Gly Trp Asp Asp Gly Val Ala Phe Gln Leu Val Ser
    50                  55                  60 gcc acc gcg gcc gac ccc agc aac ggg agc cgc ggc aag gtc ggg aag     240
Ala Thr Ala Ala Asp Pro Ser Asn Gly Ser Arg Gly Lys Val Gly Lys
65                  70                  75                  80 gcg gcg cac ctg gag gag gcg gtg gtg tcg ctc aag tcg acg acg gac     288
Ala Ala His Leu Glu Glu Ala Val Val Ser Leu Lys Ser Thr Thr Asp
                85                  90                  95 ggg gag acc gtg tac cgg gtg agc ttc gag tgg gac ggg tcg cag ggc     336
Gly Glu Thr Val Tyr Arg Val Ser Phe Glu Trp Asp Gly Ser Gln Gly
            100                 105                 110 gtc cct ggc gcc gtc ctg gtc agg aac ctg cag cac gcc gag ttc ttc     384
Val Pro Gly Ala Val Leu Val Arg Asn Leu Gln His Ala Glu Phe Phe
        115                 120                 125 ctc aag tcg ctc acc ctc gag ggc gtc ccc ggc agg ggc acc gtc gtc     432
Leu Lys Ser Leu Thr Leu Glu Gly Val Pro Gly Arg Gly Thr Val Val
    130                 135                 140 ttc gtc gcc aac tcg tgg atc tac ccg cac aat ctc tac tcc cag gaa     480
Phe Val Ala Asn Ser Trp Ile Tyr Pro His Asn Leu Tyr Ser Gln Glu
145                 150                 155                 160 cgc gtc ttc ttc gcc aac gac act tat ctg cca agc aaa atg cct gcg     528
Arg Val Phe Phe Ala Asn Asp Thr Tyr Leu Pro Ser Lys Met Pro Ala
                165                 170                 175 gca ttg gtg cct tac cgg cag gac gag ctc aag att ctc cgc ggc gac     576
Ala Leu Val Pro Tyr Arg Gln Asp Glu Leu Lys Ile Leu Arg Gly Asp
            180                 185                 190 gat aat cct gga cca tac aag gag cac gac cgc gtc tac cgt tac gac     624
Asp Asn Pro Gly Pro Tyr Lys Glu His Asp Arg Val Tyr Arg Tyr Asp
        195                 200                 205 tac tac aac gac ctc ggt gag cca gac aag ggt gaa gac cat gcc cgg     672
Tyr Tyr Asn Asp Leu Gly Glu Pro Asp Lys Gly Glu Asp His Ala Arg
    210                 215                 220
```

```
                                                            -continued cct gtc ctc ggg ggc agc caa gaa cac ccg tat ccc cgt cgc tgc agg      720
Pro Val Leu Gly Gly Ser Gln Glu His Pro Tyr Pro Arg Arg Cys Arg
225                 230                 235                 240 acc ggc cgg cgt cca aca gag aca gac ccc aac tcg gag agc agg ctg      768
Thr Gly Arg Arg Pro Thr Glu Thr Asp Pro Asn Ser Glu Ser Arg Leu
                245                 250                 255 ttt ctg ctg aac ctg aac atc tac gtc ccg cgc gac gag cgg ttt ggg      816
Phe Leu Leu Asn Leu Asn Ile Tyr Val Pro Arg Asp Glu Arg Phe Gly
                260                 265                 270 cat ctc aag atg tcg gac ttc ctc ggg tac tca ctg aag gcg atc atc      864
His Leu Lys Met Ser Asp Phe Leu Gly Tyr Ser Leu Lys Ala Ile Ile
            275                 280                 285 gag gct gtc ctt ccg acg ctg gga cgt ttc gtc gac gat acg ccc aag      912
Glu Ala Val Leu Pro Thr Leu Gly Arg Phe Val Asp Asp Thr Pro Lys
        290                 295                 300 gag ttc gat tcg ttc gaa gac atc ctt ggg ctc tac gag ccg ggt cca      960
Glu Phe Asp Ser Phe Glu Asp Ile Leu Gly Leu Tyr Glu Pro Gly Pro
305                 310                 315                 320 gag gcg ccc aac aac cca ctg gta gca gag gtc agg aag aga atc ccc     1008
Glu Ala Pro Asn Asn Pro Leu Val Ala Glu Val Arg Lys Arg Ile Pro
                325                 330                 335 agc gag ttc ctc aga agc att ctg ccc gat ggt agc cat gac cac ccc     1056
Ser Glu Phe Leu Arg Ser Ile Leu Pro Asp Gly Ser His Asp His Pro
                340                 345                 350 ctg aag atg ccc ctt cca aat atc atc aga tca gat gtg ttg aaa aag     1104
Leu Lys Met Pro Leu Pro Asn Ile Ile Arg Ser Asp Val Leu Lys Lys
            355                 360                 365 gct cca gag ttt aag ttt ggc tgg agg acc gac gaa gag ttt gcg agg     1152
Ala Pro Glu Phe Lys Phe Gly Trp Arg Thr Asp Glu Glu Phe Ala Arg
        370                 375                 380 gag acg ctt gca ggc gtg aac cca gtg ctc atc aaa cgt ctg acg gag     1200
Glu Thr Leu Ala Gly Val Asn Pro Val Leu Ile Lys Arg Leu Thr Glu
385                 390                 395                 400 ttc cca gct aaa agt acc ctg gac cca agt caa tac gga gac cat acg     1248
Phe Pro Ala Lys Ser Thr Leu Asp Pro Ser Gln Tyr Gly Asp His Thr
                405                 410                 415 agc aag atc acc gaa gct cac atc cag cat aac atg gaa ggc ctg tcg     1296
Ser Lys Ile Thr Glu Ala His Ile Gln His Asn Met Glu Gly Leu Ser
                420                 425                 430 gtg cag aat gca ctg aag aag aac agg ctc ttc atc cta gac cat cat     1344
Val Gln Asn Ala Leu Lys Lys Asn Arg Leu Phe Ile Leu Asp His His
            435                 440                 445 gac cat ttc atg ccg tac ctc aac aag atc aac gag ttg gag ggg aac     1392
Asp His Phe Met Pro Tyr Leu Asn Lys Ile Asn Glu Leu Glu Gly Asn
        450                 455                 460 ttc atc tac gcc agc agg acc cta ctg ttc ctg aag gac gat ggc acc     1440
Phe Ile Tyr Ala Ser Arg Thr Leu Leu Phe Leu Lys Asp Asp Gly Thr
465                 470                 475                 480 ctg aag ccc ctg gcc gtc gag ctg agc ctg ccc cac ccc gat ggc cag     1488
Leu Lys Pro Leu Ala Val Glu Leu Ser Leu Pro His Pro Asp Gly Gln
                485                 490                 495 cag cac ggc gcg gtc agc aag gtg tac acc cca gct cac tcc ggc gct     1536
Gln His Gly Ala Val Ser Lys Val Tyr Thr Pro Ala His Ser Gly Ala
                500                 505                 510 gag ggc cac gtc tgg caa ctt gcc aag gct tat gcc tgc gtg aac gac     1584
Glu Gly His Val Trp Gln Leu Ala Lys Ala Tyr Ala Cys Val Asn Asp
            515                 520                 525 tct gcc tgg cat cag ctg atc agc cac tgg ctg aac acg cac gcg gtg     1632
Ser Ala Trp His Gln Leu Ile Ser His Trp Leu Asn Thr His Ala Val
```

-continued

```
        530                 535                 540
atc gag ccg ttc gtc atc gca acg aac cgg cag ctg agc gtg gtg cat      1680
Ile Glu Pro Phe Val Ile Ala Thr Asn Arg Gln Leu Ser Val Val His
545                 550                 555                 560 ccc gtg cac aag ctg ctg agc cca cac tac cgt gac acg ctg aac atc      1728
Pro Val His Lys Leu Leu Ser Pro His Tyr Arg Asp Thr Leu Asn Ile
                565                 570                 575 aac gcc ctg gca cgc cag acg ctc atc aac gcc gac ggc atc ttc gag      1776
Asn Ala Leu Ala Arg Gln Thr Leu Ile Asn Ala Asp Gly Ile Phe Glu
            580                 585                 590 cgc acc gtg ttc cct gca aag tac gcg ctg ggg atg tcc tcc gac gtg      1824
Arg Thr Val Phe Pro Ala Lys Tyr Ala Leu Gly Met Ser Ser Asp Val
        595                 600                 605 tac aag agc tgg aat ttc aac gag cag gct ctc cca gca gac ctc gtc      1872
Tyr Lys Ser Trp Asn Phe Asn Glu Gln Ala Leu Pro Ala Asp Leu Val
610                 615                 620 aag aga ggt gtg gct gtg ccg gac cag tca agc ccc tac ggt gtc cgg      1920
Lys Arg Gly Val Ala Val Pro Asp Gln Ser Ser Pro Tyr Gly Val Arg
625                 630                 635                 640 ctg ctg atc aag gac tac cct tac gcc gtg gac ggg ctg gtc atc tgg      1968
Leu Leu Ile Lys Asp Tyr Pro Tyr Ala Val Asp Gly Leu Val Ile Trp
                645                 650                 655 tgg gcg atc gag cgg tgg gtc aag gag tac ctg gac gtc tac tac ccc      2016
Trp Ala Ile Glu Arg Trp Val Lys Glu Tyr Leu Asp Val Tyr Tyr Pro
            660                 665                 670 aac gac ggc gag ctc cag cgc gac gtg gag ctg cag gcg tgg tgg aag      2064
Asn Asp Gly Glu Leu Gln Arg Asp Val Glu Leu Gln Ala Trp Trp Lys
        675                 680                 685 gag gtg cgc gag gag gcg cac ggc gac ctc aag gac cga gac tgg tgg      2112
Glu Val Arg Glu Glu Ala His Gly Asp Leu Lys Asp Arg Asp Trp Trp
    690                 695                 700 ccc agg atg gac gcc gtc cag cgg ctg gcc agg gcg tgc acg acc gtc      2160
Pro Arg Met Asp Ala Val Gln Arg Leu Ala Arg Ala Cys Thr Thr Val
705                 710                 715                 720 atc tgg gta gcg tcc gcg ctg cac gcg gcc gtc aac ttc ggg cag tac      2208
Ile Trp Val Ala Ser Ala Leu His Ala Ala Val Asn Phe Gly Gln Tyr
                725                 730                 735 ccg tac gcc ggg tac ctg ccg aac cgg ccg acc gtg agc cgg cgg ccg      2256
Pro Tyr Ala Gly Tyr Leu Pro Asn Arg Pro Thr Val Ser Arg Arg Pro
            740                 745                 750 atg ccg gag ccg ggc agc gac gac tac aag aag ctg gag gcg ggg cag      2304
Met Pro Glu Pro Gly Ser Asp Asp Tyr Lys Lys Leu Glu Ala Gly Gln
        755                 760                 765 aag gag gcg gac gcg gtg ttc atc cgc acc atc acc agc cag ttc cag      2352
Lys Glu Ala Asp Ala Val Phe Ile Arg Thr Ile Thr Ser Gln Phe Gln
770                 775                 780 acc atc ctg ggc atc tcg ctc atc gag atc ctc tcc aag cac tcc tcc      2400
Thr Ile Leu Gly Ile Ser Leu Ile Glu Ile Leu Ser Lys His Ser Ser
785                 790                 795                 800 gac gag gtg tac ctc ggc cag cgc gac gag cct gag cgc tgg acg tcg      2448
Asp Glu Val Tyr Leu Gly Gln Arg Asp Glu Pro Glu Arg Trp Thr Ser
                805                 810                 815 gac gcc agg gcg ctg gac gcg ttc aga agg ttc gga agc cgg ctg gtg      2496
Asp Ala Arg Ala Leu Asp Ala Phe Arg Arg Phe Gly Ser Arg Leu Val
            820                 825                 830 gag atc gag aag cgg atc agg acg atg aac gac agc ccg acg ttg aag      2544
Glu Ile Glu Lys Arg Ile Arg Thr Met Asn Asp Ser Pro Thr Leu Lys
        835                 840                 845 aac cgg aag ggg ccg gtg gag atg ccg tac atg ctg ctg tac ccc aac      2592
```

```
Asn Arg Lys Gly Pro Val Glu Met Pro Tyr Met Leu Leu Tyr Pro Asn
        850                 855                 860 acg tcg gat gtc acc ggc gag aag ggc gag ggg ctc act gcc atg ggc      2640
Thr Ser Asp Val Thr Gly Glu Lys Gly Glu Gly Leu Thr Ala Met Gly
865                 870                 875                 880 att ccc aac agc atc tcc ata tga                                      2664
Ile Pro Asn Ser Ile Ser Ile  *
                885
```

<210> SEQ ID NO 20
<211> LENGTH: 887
<212> TYPE: PRT
<213> ORGANISM: Zea mays

<400> SEQUENCE: 20

```
Met Phe Trp His Gly Val Ala Asp Arg Leu Thr Gly Lys Asn Lys Glu
 1               5                  10                  15

Ala Trp Asn Glu Gly Lys Ile Arg Gly Thr Val Arg Leu Val Lys Lys
            20                  25                  30

Glu Val Leu Asp Val Gly Asp Phe Asn Ala Ser Leu Leu Asp Gly Val
        35                  40                  45

His Arg Ile Leu Gly Trp Asp Asp Gly Val Ala Phe Gln Leu Val Ser
    50                  55                  60

Ala Thr Ala Ala Asp Pro Ser Asn Gly Ser Arg Gly Lys Val Gly Lys
65                  70                  75                  80

Ala Ala His Leu Glu Glu Ala Val Val Ser Leu Lys Ser Thr Thr Asp
                85                  90                  95

Gly Glu Thr Val Tyr Arg Val Ser Phe Glu Trp Asp Gly Ser Gln Gly
            100                 105                 110

Val Pro Gly Ala Val Leu Val Arg Asn Leu Gln His Ala Glu Phe Phe
        115                 120                 125

Leu Lys Ser Leu Thr Leu Glu Gly Val Pro Gly Arg Gly Thr Val Val
    130                 135                 140

Phe Val Ala Asn Ser Trp Ile Tyr Pro His Asn Leu Tyr Ser Gln Glu
145                 150                 155                 160

Arg Val Phe Phe Ala Asn Asp Thr Tyr Leu Pro Ser Lys Met Pro Ala
                165                 170                 175

Ala Leu Val Pro Tyr Arg Gln Asp Glu Leu Lys Ile Leu Arg Gly Asp
            180                 185                 190

Asp Asn Pro Gly Pro Tyr Lys Glu His Asp Arg Val Tyr Arg Tyr Asp
        195                 200                 205

Tyr Tyr Asn Asp Leu Gly Glu Pro Asp Lys Gly Glu Asp His Ala Arg
    210                 215                 220

Pro Val Leu Gly Gly Ser Gln Glu His Pro Tyr Pro Arg Arg Cys Arg
225                 230                 235                 240

Thr Gly Arg Arg Pro Thr Glu Thr Asp Pro Asn Ser Glu Ser Arg Leu
                245                 250                 255

Phe Leu Leu Asn Leu Asn Ile Tyr Val Pro Arg Asp Glu Arg Phe Gly
            260                 265                 270

His Leu Lys Met Ser Asp Phe Leu Gly Tyr Ser Leu Lys Ala Ile Ile
        275                 280                 285

Glu Ala Val Leu Pro Thr Leu Gly Arg Phe Val Asp Asp Thr Pro Lys
    290                 295                 300

Glu Phe Asp Ser Phe Glu Asp Ile Leu Gly Leu Tyr Glu Pro Gly Pro
305                 310                 315                 320
```

```
Glu Ala Pro Asn Asn Pro Leu Val Ala Glu Val Arg Lys Arg Ile Pro
                325                 330                 335

Ser Glu Phe Leu Arg Ser Ile Leu Pro Asp Gly Ser His Asp His Pro
            340                 345                 350

Leu Lys Met Pro Leu Pro Asn Ile Ile Arg Ser Asp Val Leu Lys Lys
        355                 360                 365

Ala Pro Glu Phe Lys Phe Gly Trp Arg Thr Asp Glu Glu Phe Ala Arg
370                 375                 380

Glu Thr Leu Ala Gly Val Asn Pro Val Leu Ile Lys Arg Leu Thr Glu
385                 390                 395                 400

Phe Pro Ala Lys Ser Thr Leu Asp Pro Ser Gln Tyr Gly Asp His Thr
                405                 410                 415

Ser Lys Ile Thr Glu Ala His Ile Gln His Asn Met Glu Gly Leu Ser
            420                 425                 430

Val Gln Asn Ala Leu Lys Lys Asn Arg Leu Phe Ile Leu Asp His His
        435                 440                 445

Asp His Phe Met Pro Tyr Leu Asn Lys Ile Asn Glu Leu Glu Gly Asn
    450                 455                 460

Phe Ile Tyr Ala Ser Arg Thr Leu Leu Phe Leu Lys Asp Asp Gly Thr
465                 470                 475                 480

Leu Lys Pro Leu Ala Val Glu Leu Ser Leu Pro His Pro Asp Gly Gln
                485                 490                 495

Gln His Gly Ala Val Ser Lys Val Tyr Thr Pro Ala His Ser Gly Ala
            500                 505                 510

Glu Gly His Val Trp Gln Leu Ala Lys Ala Tyr Ala Cys Val Asn Asp
        515                 520                 525

Ser Ala Trp His Gln Leu Ile Ser His Trp Leu Asn Thr His Ala Val
    530                 535                 540

Ile Glu Pro Phe Val Ile Ala Thr Asn Arg Gln Leu Ser Val Val His
545                 550                 555                 560

Pro Val His Lys Leu Leu Ser Pro His Tyr Arg Asp Thr Leu Asn Ile
                565                 570                 575

Asn Ala Leu Ala Arg Gln Thr Leu Ile Asn Ala Asp Gly Ile Phe Glu
            580                 585                 590

Arg Thr Val Phe Pro Ala Lys Tyr Ala Leu Gly Met Ser Ser Asp Val
        595                 600                 605

Tyr Lys Ser Trp Asn Phe Asn Glu Gln Ala Leu Pro Ala Asp Leu Val
    610                 615                 620

Lys Arg Gly Val Ala Val Pro Asp Gln Ser Ser Pro Tyr Gly Val Arg
625                 630                 635                 640

Leu Leu Ile Lys Asp Tyr Pro Tyr Ala Val Asp Gly Leu Val Ile Trp
                645                 650                 655

Trp Ala Ile Glu Arg Trp Val Lys Glu Tyr Leu Asp Val Tyr Tyr Pro
            660                 665                 670

Asn Asp Gly Glu Leu Gln Arg Asp Val Glu Leu Gln Ala Trp Trp Lys
        675                 680                 685

Glu Val Arg Glu Glu Ala His Gly Asp Leu Lys Asp Arg Asp Trp Trp
    690                 695                 700

Pro Arg Met Asp Ala Val Gln Arg Leu Ala Arg Ala Cys Thr Thr Val
705                 710                 715                 720

Ile Trp Val Ala Ser Ala Leu His Ala Ala Val Asn Phe Gly Gln Tyr
                725                 730                 735

Pro Tyr Ala Gly Tyr Leu Pro Asn Arg Pro Thr Val Ser Arg Arg Pro
```

-continued

```
                        740                 745                 750
        Met Pro Glu Pro Gly Ser Asp Asp Tyr Lys Lys Leu Glu Ala Gly Gln
                755                 760                 765
        Lys Glu Ala Asp Ala Val Phe Ile Arg Thr Ile Thr Ser Gln Phe Gln
            770                 775                 780
        Thr Ile Leu Gly Ile Ser Leu Ile Glu Ile Leu Ser Lys His Ser Ser
        785                 790                 795                 800
        Asp Glu Val Tyr Leu Gly Gln Arg Asp Glu Pro Glu Arg Trp Thr Ser
                        805                 810                 815
        Asp Ala Arg Ala Leu Asp Ala Phe Arg Arg Phe Gly Ser Arg Leu Val
                    820                 825                 830
        Glu Ile Glu Lys Arg Ile Arg Thr Met Asn Asp Ser Pro Thr Leu Lys
                835                 840                 845
        Asn Arg Lys Gly Pro Val Glu Met Pro Tyr Met Leu Leu Tyr Pro Asn
            850                 855                 860
        Thr Ser Asp Val Thr Gly Glu Lys Gly Glu Gly Leu Thr Ala Met Gly
        865                 870                 875                 880
        Ile Pro Asn Ser Ile Ser Ile
                        885
```

<210> SEQ ID NO 21
<211> LENGTH: 3122
<212> TYPE: DNA
<213> ORGANISM: Zea mays
<220> FEATURE:
<221> NAME/KEY: CDS
<222> LOCATION: (224)...(2887)
<223> OTHER INFORMATION: LOX5

<400> SEQUENCE: 21

```
gccgaggcga gcagccgtcg ccgcctatat atcgcggcgc agggcagcag gagttccaca       60
cttccataca cgcctgcctt gtgccttccc ttcccttgcc ttgcttcgct tattgccggc      120
acatcacatc ggcaggcgag ggacggagcg agcagggaag cccatccacc agccagccac      180
cgcgttcctg agaagcgagg agcgagaaaa gcgaagagcg gcc atg ttc tgg cac        235
                                            Met Phe Trp His
                                              1 ggg gtc gcg gac cgg ctg acg gga aag aac aag gag gcg tgg agc gag        283
Gly Val Ala Asp Arg Leu Thr Gly Lys Asn Lys Glu Ala Trp Ser Glu
  5              10                  15                  20 ggc aag atc cgc ggc acg gtg agg ctg gtc aag aag gag gtg ctg gac        331
Gly Lys Ile Arg Gly Thr Val Arg Leu Val Lys Lys Glu Val Leu Asp
             25                  30                  35 gtc ggc gac ttc aac gcc tcg ctc ctc gac ggc gtc cac agg atc ctc        379
Val Gly Asp Phe Asn Ala Ser Leu Leu Asp Gly Val His Arg Ile Leu
         40                  45                  50 ggc tgg gac gac ggc gtc gcc ttc cag ctc gtc agc gcc acc gcg gcc        427
Gly Trp Asp Asp Gly Val Ala Phe Gln Leu Val Ser Ala Thr Ala Ala
     55                  60                  65 gac ccc agc aac ggg ggc cgt ggc aag gtg ggg aag gcg gcg cac ctg        475
Asp Pro Ser Asn Gly Gly Arg Gly Lys Val Gly Lys Ala Ala His Leu
 70                  75                  80 gag gag gcg gtg gtg tcg ctc aag tcc acg gcg gac ggg gag acc gtg        523
Glu Glu Ala Val Val Ser Leu Lys Ser Thr Ala Asp Gly Glu Thr Val
 85                  90                  95                 100 tac cgg gtg agc ttc gag tgg gac gag tcg cag ggc atc ccg ggc gcc        571
Tyr Arg Val Ser Phe Glu Trp Asp Glu Ser Gln Gly Ile Pro Gly Ala
                105                 110                 115
```

```
gtc ctg gtc agg aac ctg cag cac gcc gag ttc ttc ctc aag acg ctc      619
Val Leu Val Arg Asn Leu Gln His Ala Glu Phe Phe Leu Lys Thr Leu
        120                 125                 130 acc ctc gag ggc gtc cca ggc aag ggc acc gtc gtc ttc gtc gcc aac      667
Thr Leu Glu Gly Val Pro Gly Lys Gly Thr Val Val Phe Val Ala Asn
            135                 140                 145 tcg tgg gtc tac ccg cac aag ctc tac tcc cag gaa cgc atc ttc ttc      715
Ser Trp Val Tyr Pro His Lys Leu Tyr Ser Gln Glu Arg Ile Phe Phe
    150                 155                 160 gcc aac gac acc tat ctg ccg agc aaa atg ccg gcg gcg ttg gtg cct      763
Ala Asn Asp Thr Tyr Leu Pro Ser Lys Met Pro Ala Ala Leu Val Pro
165                 170                 175                 180 tat cgg caa gat gag ctc aag att ctc cgt ggc gac gat aat cct gga      811
Tyr Arg Gln Asp Glu Leu Lys Ile Leu Arg Gly Asp Asp Asn Pro Gly
                185                 190                 195 cca tac cag gag cat gat cgc gtc tac cgt tac gac tac tac aat gac      859
Pro Tyr Gln Glu His Asp Arg Val Tyr Arg Tyr Asp Tyr Tyr Asn Asp
            200                 205                 210 ctt ggt gat ccc gac aag ggc gaa gag cac gct cgg ccg atc ctc ggt      907
Leu Gly Asp Pro Asp Lys Gly Glu Glu His Ala Arg Pro Ile Leu Gly
    215                 220                 225 ggc agc caa gaa cac ccg tat ccc cgt cgc tgc aga act ggc cgg cac      955
Gly Ser Gln Glu His Pro Tyr Pro Arg Arg Cys Arg Thr Gly Arg His
230                 235                 240 cca aca aag aaa gac cca aat tcg gag agc agg ctt ttc ctg ctg aac     1003
Pro Thr Lys Lys Asp Pro Asn Ser Glu Ser Arg Leu Phe Leu Leu Asn
245                 250                 255                 260 ctg aac atc tac gtc ccg cgt gac gaa cgc ttt ggg cat ctc aag atg     1051
Leu Asn Ile Tyr Val Pro Arg Asp Glu Arg Phe Gly His Leu Lys Met
                265                 270                 275 tcg gac ttc ctt ggg tac tcg ctg aag acg atc atc gag gct gtt ctt     1099
Ser Asp Phe Leu Gly Tyr Ser Leu Lys Thr Ile Ile Glu Ala Val Leu
            280                 285                 290 cca aca ctg ggg act ttc gtc gat gac acg ccc aag gag ttc gat tcg     1147
Pro Thr Leu Gly Thr Phe Val Asp Asp Thr Pro Lys Glu Phe Asp Ser
    295                 300                 305 ttt gag gat atc ctc ggg ctc tac gag ctg ggc cca gag gca ccc aac     1195
Phe Glu Asp Ile Leu Gly Leu Tyr Glu Leu Gly Pro Glu Ala Pro Asn
310                 315                 320 aac cca ctg ata gca gag atc agg aag aag atc ccc agc gag ttc ctt     1243
Asn Pro Leu Ile Ala Glu Ile Arg Lys Lys Ile Pro Ser Glu Phe Leu
325                 330                 335                 340 cga agc att ctg ccg aac ggt agc cat gac cac ccg cta aag atg ccc     1291
Arg Ser Ile Leu Pro Asn Gly Ser His Asp His Pro Leu Lys Met Pro
                345                 350                 355 ctt cca aat gtc atc aaa tca gat gtg ttg aaa aag gct ccg gag ttt     1339
Leu Pro Asn Val Ile Lys Ser Asp Val Leu Lys Lys Ala Pro Glu Phe
            360                 365                 370 aag ttt ggc tgg agg act gac gaa gag ttc gcg aga gag aca ctt gca     1387
Lys Phe Gly Trp Arg Thr Asp Glu Glu Phe Ala Arg Glu Thr Leu Ala
    375                 380                 385 ggc gtg aac cca gta atc atc aaa cgt ctg acg gag ttc ccc gct aaa     1435
Gly Val Asn Pro Val Ile Ile Lys Arg Leu Thr Glu Phe Pro Ala Lys
390                 395                 400 agc acc ctg gac cca agg cag tac gga gac cac acc agc aag atc act     1483
Ser Thr Leu Asp Pro Arg Gln Tyr Gly Asp His Thr Ser Lys Ile Thr
405                 410                 415                 420 gaa gct cac atc cgg cat aac atg gga ggc ctg tcg gtg cag aac gca     1531
Glu Ala His Ile Arg His Asn Met Gly Gly Leu Ser Val Gln Asn Ala
                425                 430                 435
```

```
                                    -continued ctg agg aac aag agg ctc ttc atc cta gac cac cat gac cat ttc atg    1579
Leu Arg Asn Lys Arg Leu Phe Ile Leu Asp His His Asp His Phe Met
        440                 445                 450 ccg tac ctc gac gag atc aac gag ctg gag ggg aac ttc atc tac gcc    1627
Pro Tyr Leu Asp Glu Ile Asn Glu Leu Glu Gly Asn Phe Ile Tyr Ala
            455                 460                 465 agc agg acc cta ctg ttc ctg aag gac gat ggc acg ctg aag ccc ctg    1675
Ser Arg Thr Leu Leu Phe Leu Lys Asp Asp Gly Thr Leu Lys Pro Leu
470                 475                 480 gcc atc gag ctg agc ctg ccc cac cct gac ggc cag cag cgc ggc gcg    1723
Ala Ile Glu Leu Ser Leu Pro His Pro Asp Gly Gln Gln Arg Gly Ala
485                 490                 495                 500 gtc agc aag gtg tac acc ccg gct cac acc ggc gtc gag ggc cac gtc    1771
Val Ser Lys Val Tyr Thr Pro Ala His Thr Gly Val Glu Gly His Val
                505                 510                 515 tgg cag ctc gcc aag gct tat gcc tgc gta aac gac tct gcc tgg cat    1819
Trp Gln Leu Ala Lys Ala Tyr Ala Cys Val Asn Asp Ser Ala Trp His
            520                 525                 530 cag ctg atc agc cac tgg ctg aac acg cac gcg gtg atc gag ccg ttc    1867
Gln Leu Ile Ser His Trp Leu Asn Thr His Ala Val Ile Glu Pro Phe
        535                 540                 545 gta atc gcg aca aac cgg cag ctc agc gtg gtg cat ccc gtg cac aag    1915
Val Ile Ala Thr Asn Arg Gln Leu Ser Val Val His Pro Val His Lys
550                 555                 560 ctg ctg agc ccg cac tac cgt gac acg ctg aac atc aac gcc ctg gca    1963
Leu Leu Ser Pro His Tyr Arg Asp Thr Leu Asn Ile Asn Ala Leu Ala
565                 570                 575                 580 cgc cag aca ctc atc aac gcc ggc ggc gtc ttc gag cgc acc gtg ttc    2011
Arg Gln Thr Leu Ile Asn Ala Gly Gly Val Phe Glu Arg Thr Val Phe
                585                 590                 595 cct gca aag tac gcg ctg ggg atg tcg gca gac gtg tac aag agc tgg    2059
Pro Ala Lys Tyr Ala Leu Gly Met Ser Ala Asp Val Tyr Lys Ser Trp
            600                 605                 610 aat ttc aac gag cag gct ctc cca gca gat ctc gtc aag aga ggt gtg    2107
Asn Phe Asn Glu Gln Ala Leu Pro Ala Asp Leu Val Lys Arg Gly Val
        615                 620                 625 gct gtg ccg gac cag tca agc cca tat ggt gtc cga ctg ctg atc aag    2155
Ala Val Pro Asp Gln Ser Ser Pro Tyr Gly Val Arg Leu Leu Ile Lys
630                 635                 640 gac tac ccc tat gcc gtt gac ggg ctc gtc atc tgg tgg gcg atc gag    2203
Asp Tyr Pro Tyr Ala Val Asp Gly Leu Val Ile Trp Trp Ala Ile Glu
645                 650                 655                 660 cgg tgg gtc aag gag tac ctg gac atc tac tac cct aac gac ggc gag    2251
Arg Trp Val Lys Glu Tyr Leu Asp Ile Tyr Tyr Pro Asn Asp Gly Glu
                665                 670                 675 ctc cag cgt gac gtg gag ctg cag gcg tgg tgg aag gag gtg cgt gag    2299
Leu Gln Arg Asp Val Glu Leu Gln Ala Trp Trp Lys Glu Val Arg Glu
            680                 685                 690 gag gcg cac ggc gac ctc aag gac cga gac tgg tgg ccc agg atg gac    2347
Glu Ala His Gly Asp Leu Lys Asp Arg Asp Trp Trp Pro Arg Met Asp
        695                 700                 705 acc gtc cag cag ctg gct agg gcg tgc acg acc atc atc tgg gtg gca    2395
Thr Val Gln Gln Leu Ala Arg Ala Cys Thr Thr Ile Ile Trp Val Ala
710                 715                 720 tcc gcg ctg cac gcg gct gtc aac ttt ggg cag tac cca tac gcc ggg    2443
Ser Ala Leu His Ala Ala Val Asn Phe Gly Gln Tyr Pro Tyr Ala Gly
725                 730                 735                 740 tac ctc ccg aac cgg ccg acg gcc agc cgg cgc ccg atg ccg gag cca    2491
Tyr Leu Pro Asn Arg Pro Thr Ala Ser Arg Arg Pro Met Pro Glu Pro
```

```
                745                 750                 755
ggc agc cac gac tac aag aag ctg gga gcg ggg cag aag gag gcg gac      2539
Gly Ser His Asp Tyr Lys Lys Leu Gly Ala Gly Gln Lys Glu Ala Asp
            760                 765                 770 atg gtg ttc atc cgc acc atc acc agc cag ttc cag acc atc ctg ggc      2587
Met Val Phe Ile Arg Thr Ile Thr Ser Gln Phe Gln Thr Ile Leu Gly
        775                 780                 785 atc tcg ctc atc gag atc ctc tcc aag cac tcc tcc gac gag gtg tac      2635
Ile Ser Leu Ile Glu Ile Leu Ser Lys His Ser Ser Asp Glu Val Tyr
    790                 795                 800 ctc ggc cag cgt gac gag cct gat cgc tgg acg tca gac gcc aag gcg      2683
Leu Gly Gln Arg Asp Glu Pro Asp Arg Trp Thr Ser Asp Ala Lys Ala
805                 810                 815                 820 ctg gat gcg ttc aaa aga ttc ggg agc cgg ctg gtg cag att gag aat      2731
Leu Asp Ala Phe Lys Arg Phe Gly Ser Arg Leu Val Gln Ile Glu Asn
                825                 830                 835 cgg atc aag acg atg aac gac agt ccg gac ttg aag aac cgg aag ggg      2779
Arg Ile Lys Thr Met Asn Asp Ser Pro Asp Leu Lys Asn Arg Lys Gly
            840                 845                 850 cct gtg gaa atg ccg tac atg ctg ctg tac ccc aac acg tcg gac gtt      2827
Pro Val Glu Met Pro Tyr Met Leu Leu Tyr Pro Asn Thr Ser Asp Val
        855                 860                 865 acc ggc gag aag gcc gag ggg ctt act gcc atg ggc att ccc aac agc      2875
Thr Gly Glu Lys Ala Glu Gly Leu Thr Ala Met Gly Ile Pro Asn Ser
    870                 875                 880 atc tcc ata tga gcctgggcag attgtgtctc gtagtaaatt gttgtgctgc          2927
Ile Ser Ile  *
885 gccgtgcgat gtgtttcttc attggttttg tcagtctcag ggtagggat ggagatcata     2987 ccatgatctt tgtagggttg agagaggagt ccacgcttga atattgttgt catgtatgta    3047 attcttggtt aataataaag ttcgtcagtt catttcttaa aaaaaaaaaa aaaaaaaaaa    3107 aaaaaaaaaa aaaaa                                                     3122

<210> SEQ ID NO 22
<211> LENGTH: 887
<212> TYPE: PRT
<213> ORGANISM: Zea mays

<400> SEQUENCE: 22

Met Phe Trp His Gly Val Ala Asp Arg Leu Thr Gly Lys Asn Lys Glu
 1               5                  10                  15

Ala Trp Ser Glu Gly Lys Ile Arg Gly Thr Val Arg Leu Val Lys Lys
            20                  25                  30

Glu Val Leu Asp Val Gly Asp Phe Asn Ala Ser Leu Leu Asp Gly Val
        35                  40                  45

His Arg Ile Leu Gly Trp Asp Asp Gly Val Ala Phe Gln Leu Val Ser
    50                  55                  60

Ala Thr Ala Ala Asp Pro Ser Asn Gly Arg Gly Lys Val Gly Lys
65                  70                  75                  80

Ala Ala His Leu Glu Glu Ala Val Val Ser Leu Lys Ser Thr Ala Asp
                85                  90                  95

Gly Glu Thr Val Tyr Arg Val Ser Phe Glu Trp Asp Glu Ser Gln Gly
            100                 105                 110

Ile Pro Gly Ala Val Leu Val Arg Asn Leu Gln His Ala Glu Phe Phe
        115                 120                 125

Leu Lys Thr Leu Thr Leu Glu Gly Val Pro Gly Lys Gly Thr Val Val
```

```
            130                 135                 140
Phe Val Ala Asn Ser Trp Val Tyr Pro His Lys Leu Tyr Ser Gln Glu
145                 150                 155                 160

Arg Ile Phe Phe Ala Asn Asp Thr Tyr Leu Pro Ser Lys Met Pro Ala
                165                 170                 175

Ala Leu Val Pro Tyr Arg Gln Asp Glu Leu Lys Ile Leu Arg Gly Asp
                180                 185                 190

Asp Asn Pro Gly Pro Tyr Gln Glu His Asp Arg Val Tyr Arg Tyr Asp
            195                 200                 205

Tyr Tyr Asn Asp Leu Gly Asp Pro Asp Lys Gly Glu Glu His Ala Arg
210                 215                 220

Pro Ile Leu Gly Gly Ser Gln Glu His Pro Tyr Pro Arg Arg Cys Arg
225                 230                 235                 240

Thr Gly Arg His Pro Thr Lys Lys Asp Pro Asn Ser Glu Ser Arg Leu
                245                 250                 255

Phe Leu Leu Asn Leu Asn Ile Tyr Val Pro Arg Asp Glu Arg Phe Gly
                260                 265                 270

His Leu Lys Met Ser Asp Phe Leu Gly Tyr Ser Leu Lys Thr Ile Ile
                275                 280                 285

Glu Ala Val Leu Pro Thr Leu Gly Thr Phe Val Asp Asp Thr Pro Lys
290                 295                 300

Glu Phe Asp Ser Phe Glu Asp Ile Leu Gly Leu Tyr Glu Leu Gly Pro
305                 310                 315                 320

Glu Ala Pro Asn Asn Pro Leu Ile Ala Glu Ile Arg Lys Lys Ile Pro
                325                 330                 335

Ser Glu Phe Leu Arg Ser Ile Leu Pro Asn Gly Ser His Asp His Pro
                340                 345                 350

Leu Lys Met Pro Leu Pro Asn Val Ile Lys Ser Asp Val Leu Lys Lys
                355                 360                 365

Ala Pro Glu Phe Lys Phe Gly Trp Arg Thr Asp Glu Glu Phe Ala Arg
                370                 375                 380

Glu Thr Leu Ala Gly Val Asn Pro Val Ile Ile Lys Arg Leu Thr Glu
385                 390                 395                 400

Phe Pro Ala Lys Ser Thr Leu Asp Pro Arg Gln Tyr Gly Asp His Thr
                405                 410                 415

Ser Lys Ile Thr Glu Ala His Ile Arg His Asn Met Gly Gly Leu Ser
                420                 425                 430

Val Gln Asn Ala Leu Arg Asn Lys Arg Leu Phe Ile Leu Asp His His
                435                 440                 445

Asp His Phe Met Pro Tyr Leu Asp Glu Ile Asn Glu Leu Glu Gly Asn
            450                 455                 460

Phe Ile Tyr Ala Ser Arg Thr Leu Leu Phe Leu Lys Asp Asp Gly Thr
465                 470                 475                 480

Leu Lys Pro Leu Ala Ile Glu Leu Ser Leu Pro His Pro Asp Gly Gln
                485                 490                 495

Gln Arg Gly Ala Val Ser Lys Val Tyr Thr Pro Ala His Thr Gly Val
            500                 505                 510

Glu Gly His Val Trp Gln Leu Ala Lys Ala Tyr Ala Cys Val Asn Asp
            515                 520                 525

Ser Ala Trp His Gln Leu Ile Ser His Trp Leu Asn Thr His Ala Val
            530                 535                 540

Ile Glu Pro Phe Val Ile Ala Thr Asn Arg Gln Leu Ser Val Val His
545                 550                 555                 560
```

-continued

```
Pro Val His Lys Leu Leu Ser Pro His Tyr Arg Asp Thr Leu Asn Ile
            565                 570                 575
Asn Ala Leu Ala Arg Gln Thr Leu Ile Asn Ala Gly Gly Val Phe Glu
            580                 585                 590
Arg Thr Val Phe Pro Ala Lys Tyr Ala Leu Gly Met Ser Ala Asp Val
            595                 600                 605
Tyr Lys Ser Trp Asn Phe Asn Glu Gln Ala Leu Pro Ala Asp Leu Val
            610                 615                 620
Lys Arg Gly Val Ala Val Pro Asp Gln Ser Ser Pro Tyr Gly Val Arg
625                 630                 635                 640
Leu Leu Ile Lys Asp Tyr Pro Tyr Ala Val Asp Gly Leu Val Ile Trp
            645                 650                 655
Trp Ala Ile Glu Arg Trp Val Lys Glu Tyr Leu Asp Ile Tyr Tyr Pro
            660                 665                 670
Asn Asp Gly Glu Leu Gln Arg Asp Val Glu Leu Gln Ala Trp Trp Lys
            675                 680                 685
Glu Val Arg Glu Glu Ala His Gly Asp Leu Lys Asp Arg Asp Trp Trp
            690                 695                 700
Pro Arg Met Asp Thr Val Gln Gln Leu Ala Arg Ala Cys Thr Thr Ile
705                 710                 715                 720
Ile Trp Val Ala Ser Ala Leu His Ala Ala Val Asn Phe Gly Gln Tyr
            725                 730                 735
Pro Tyr Ala Gly Tyr Leu Pro Asn Arg Pro Thr Ala Ser Arg Arg Pro
            740                 745                 750
Met Pro Glu Pro Gly Ser His Asp Tyr Lys Lys Leu Gly Ala Gly Gln
            755                 760                 765
Lys Glu Ala Asp Met Val Phe Ile Arg Thr Ile Thr Ser Gln Phe Gln
            770                 775                 780
Thr Ile Leu Gly Ile Ser Leu Ile Glu Ile Leu Ser Lys His Ser Ser
785                 790                 795                 800
Asp Glu Val Tyr Leu Gly Gln Arg Asp Glu Pro Asp Arg Trp Thr Ser
            805                 810                 815
Asp Ala Lys Ala Leu Asp Ala Phe Lys Arg Phe Gly Ser Arg Leu Val
            820                 825                 830
Gln Ile Glu Asn Arg Ile Lys Thr Met Asn Asp Ser Pro Asp Leu Lys
            835                 840                 845
Asn Arg Lys Gly Pro Val Glu Met Pro Tyr Met Leu Leu Tyr Pro Asn
            850                 855                 860
Thr Ser Asp Val Thr Gly Glu Lys Ala Glu Gly Leu Thr Ala Met Gly
865                 870                 875                 880
Ile Pro Asn Ser Ile Ser Ile
            885
```

<210> SEQ ID NO 23
<211> LENGTH: 2664
<212> TYPE: DNA
<213> ORGANISM: Zea mays
<220> FEATURE:
<221> NAME/KEY: CDS
<222> LOCATION: (1)...(2664)

<400> SEQUENCE: 23

```
atg ttc tgg cac ggg gtc gcg gac cgg ctg acg gga aag aac aag gag      48
Met Phe Trp His Gly Val Ala Asp Arg Leu Thr Gly Lys Asn Lys Glu
 1               5                  10                  15
```

```
gcg tgg agc gag ggc aag atc cgc ggc acg gtg agg ctg gtc aag aag      96
Ala Trp Ser Glu Gly Lys Ile Arg Gly Thr Val Arg Leu Val Lys Lys
         20                  25                  30 gag gtg ctg gac gtc ggc gac ttc aac gcc tcg ctc ctc gac ggc gtc     144
Glu Val Leu Asp Val Gly Asp Phe Asn Ala Ser Leu Leu Asp Gly Val
     35                  40                  45 cac agg atc ctc ggc tgg gac gac ggc gtc gcc ttc cag ctc gtc agc     192
His Arg Ile Leu Gly Trp Asp Asp Gly Val Ala Phe Gln Leu Val Ser
 50                  55                  60 gcc acc gcg gcc gac ccc agc aac ggg ggc cgt ggc aag gtg ggg aag     240
Ala Thr Ala Ala Asp Pro Ser Asn Gly Gly Arg Gly Lys Val Gly Lys
 65                  70                  75                  80 gcg gcg cac ctg gag gag gcg gtg gtg tcg ctc aag tcc acg gcg gac     288
Ala Ala His Leu Glu Glu Ala Val Val Ser Leu Lys Ser Thr Ala Asp
             85                  90                  95 ggg gag acc gtg tac cgg gtg agc ttc gag tgg gac gag tcg cag ggc     336
Gly Glu Thr Val Tyr Arg Val Ser Phe Glu Trp Asp Glu Ser Gln Gly
            100                 105                 110 atc ccg ggc gcc gtc ctg gtc agg aac ctg cag cac gcc gag ttc ttc     384
Ile Pro Gly Ala Val Leu Val Arg Asn Leu Gln His Ala Glu Phe Phe
        115                 120                 125 ctc aag acg ctc acc ctc gag ggc gtc cca ggc aag ggc acc gtc gtc     432
Leu Lys Thr Leu Thr Leu Glu Gly Val Pro Gly Lys Gly Thr Val Val
130                 135                 140 ttc gtc gcc aac tcg tgg gtc tac ccg cac aag ctc tac tcc cag gaa     480
Phe Val Ala Asn Ser Trp Val Tyr Pro His Lys Leu Tyr Ser Gln Glu
145                 150                 155                 160 cgc atc ttc ttc gcc aac gac acc tat ctg ccg agc aaa atg ccg gcg     528
Arg Ile Phe Phe Ala Asn Asp Thr Tyr Leu Pro Ser Lys Met Pro Ala
                165                 170                 175 gcg ttg gtg cct tat cgg caa gat gag ctc aag att ctc cgt ggc gac     576
Ala Leu Val Pro Tyr Arg Gln Asp Glu Leu Lys Ile Leu Arg Gly Asp
            180                 185                 190 gat aat cct gga cca tac cag gag cat gat cgc gtc tac cgt tac gac     624
Asp Asn Pro Gly Pro Tyr Gln Glu His Asp Arg Val Tyr Arg Tyr Asp
        195                 200                 205 tac tac aat gac ctt ggt gat ccc gac aag ggc gaa gag cac gct cgg     672
Tyr Tyr Asn Asp Leu Gly Asp Pro Asp Lys Gly Glu Glu His Ala Arg
    210                 215                 220 ccg atc ctc ggt ggc agc caa gaa cac ccg tat ccc cgt cgc tgc aga     720
Pro Ile Leu Gly Gly Ser Gln Glu His Pro Tyr Pro Arg Arg Cys Arg
225                 230                 235                 240 act ggc cgg cac cca aca aag aaa gac cca aat tcg gag agc agg ctt     768
Thr Gly Arg His Pro Thr Lys Lys Asp Pro Asn Ser Glu Ser Arg Leu
                245                 250                 255 ttc ctg ctg aac ctg aac atc tac gtc ccg cgt gac gaa cgc ttt ggg     816
Phe Leu Leu Asn Leu Asn Ile Tyr Val Pro Arg Asp Glu Arg Phe Gly
            260                 265                 270 cat ctc aag atg tcg gac ttc ctt ggg tac tcg ctg aag acg atc atc     864
His Leu Lys Met Ser Asp Phe Leu Gly Tyr Ser Leu Lys Thr Ile Ile
        275                 280                 285 gag gct gtt ctt cca aca ctg ggg act ttc gtc gat gac acg ccc aag     912
Glu Ala Val Leu Pro Thr Leu Gly Thr Phe Val Asp Asp Thr Pro Lys
    290                 295                 300 gag ttc gat tcg ttt gag gat atc ctc ggg ctc tac gag ctg ggc cca     960
Glu Phe Asp Ser Phe Glu Asp Ile Leu Gly Leu Tyr Glu Leu Gly Pro
305                 310                 315                 320 gag gca ccc aac aac cca ctg ata gca gag atc agg aag aag atc ccc    1008
Glu Ala Pro Asn Asn Pro Leu Ile Ala Glu Ile Arg Lys Lys Ile Pro
                325                 330                 335
```

```
agc gag ttc ctt cga agc att ctg ccg aac ggt agc cat gac cac ccg      1056
Ser Glu Phe Leu Arg Ser Ile Leu Pro Asn Gly Ser His Asp His Pro
            340                 345                 350 cta aag atg ccc ctt cca aat gtc atc aaa tca gat gtg ttg aaa aag      1104
Leu Lys Met Pro Leu Pro Asn Val Ile Lys Ser Asp Val Leu Lys Lys
            355                 360                 365 gct ccg gag ttt aag ttt ggc tgg agg act gac gaa gag ttc gcg aga      1152
Ala Pro Glu Phe Lys Phe Gly Trp Arg Thr Asp Glu Glu Phe Ala Arg
            370                 375                 380 gag aca ctt gca ggc gtg aac cca gta atc atc aaa cgt ctg acg gag      1200
Glu Thr Leu Ala Gly Val Asn Pro Val Ile Ile Lys Arg Leu Thr Glu
385                 390                 395                 400 ttc ccc gct aaa agc acc ctg gac cca agg cag tac gga gac cac acc      1248
Phe Pro Ala Lys Ser Thr Leu Asp Pro Arg Gln Tyr Gly Asp His Thr
            405                 410                 415 agc aag atc act gaa gct cac atc cgg cat aac atg gga ggc ctg tcg      1296
Ser Lys Ile Thr Glu Ala His Ile Arg His Asn Met Gly Gly Leu Ser
            420                 425                 430 gtg cag aac gca ctg agg aac aag agg ctc ttc atc cta gac cac cat      1344
Val Gln Asn Ala Leu Arg Asn Lys Arg Leu Phe Ile Leu Asp His His
            435                 440                 445 gac cat ttc atg ccg tac ctc gac gag atc aac gag ctg gag ggg aac      1392
Asp His Phe Met Pro Tyr Leu Asp Glu Ile Asn Glu Leu Glu Gly Asn
450                 455                 460 ttc atc tac gcc agc agg acc cta ctg ttc ctg aag gac gat ggc acg      1440
Phe Ile Tyr Ala Ser Arg Thr Leu Leu Phe Leu Lys Asp Asp Gly Thr
465                 470                 475                 480 ctg aag ccc ctg gcc atc gag ctg agc ctg ccc cac cct gac ggc cag      1488
Leu Lys Pro Leu Ala Ile Glu Leu Ser Leu Pro His Pro Asp Gly Gln
            485                 490                 495 cag cgc ggc gcg gtc agc aag gtg tac acc ccg gct cac acc ggc gtc      1536
Gln Arg Gly Ala Val Ser Lys Val Tyr Thr Pro Ala His Thr Gly Val
            500                 505                 510 gag ggc cac gtc tgg cag ctc gcc aag gct tat gcc tgc gta aac gac      1584
Glu Gly His Val Trp Gln Leu Ala Lys Ala Tyr Ala Cys Val Asn Asp
            515                 520                 525 tct gcc tgg cat cag ctg atc agc cac tgg ctg aac acg cac gcg gtg      1632
Ser Ala Trp His Gln Leu Ile Ser His Trp Leu Asn Thr His Ala Val
530                 535                 540 atc gag ccg ttc gta atc gcg aca aac cgg cag ctc agc gtg gtg cat      1680
Ile Glu Pro Phe Val Ile Ala Thr Asn Arg Gln Leu Ser Val Val His
545                 550                 555                 560 ccc gtg cac aag ctg ctg agc ccg cac tac cgt gac acg ctg aac atc      1728
Pro Val His Lys Leu Leu Ser Pro His Tyr Arg Asp Thr Leu Asn Ile
            565                 570                 575 aac gcc ctg gca cgc cag aca ctc atc aac gcc ggc ggc gtc ttc gag      1776
Asn Ala Leu Ala Arg Gln Thr Leu Ile Asn Ala Gly Gly Val Phe Glu
            580                 585                 590 cgc acc gtg ttc cct gca aag tac gcg ctg ggg atg tcg gca gac gtg      1824
Arg Thr Val Phe Pro Ala Lys Tyr Ala Leu Gly Met Ser Ala Asp Val
            595                 600                 605 tac aag agc tgg aat ttc aac gag cag gct ctc cca gca gat ctc gtc      1872
Tyr Lys Ser Trp Asn Phe Asn Glu Gln Ala Leu Pro Ala Asp Leu Val
            610                 615                 620 aag aga ggt gtg gct gtg ccg gac cag tca agc cca tat ggt gtc cga      1920
Lys Arg Gly Val Ala Val Pro Asp Gln Ser Ser Pro Tyr Gly Val Arg
625                 630                 635                 640 ctg ctg atc aag gac tac ccc tat gcc gtt gac ggg ctc gtc atc tgg      1968
Leu Leu Ile Lys Asp Tyr Pro Tyr Ala Val Asp Gly Leu Val Ile Trp
```

```
                        645                 650                 655
tgg gcg atc gag cgg tgg gtc aag gag tac ctg gac atc tac tac cct      2016
Trp Ala Ile Glu Arg Trp Val Lys Glu Tyr Leu Asp Ile Tyr Tyr Pro
            660                 665                 670 aac gac ggc gag ctc cag cgt gac gtg gag ctg cag gcg tgg tgg aag      2064
Asn Asp Gly Glu Leu Gln Arg Asp Val Glu Leu Gln Ala Trp Trp Lys
        675                 680                 685 gag gtg cgt gag gag gcg cac ggc gac ctc aag gac cga gac tgg tgg      2112
Glu Val Arg Glu Glu Ala His Gly Asp Leu Lys Asp Arg Asp Trp Trp
    690                 695                 700 ccc agg atg gac acc gtc cag cag ctg gct agg gcg tgc acg acc atc      2160
Pro Arg Met Asp Thr Val Gln Gln Leu Ala Arg Ala Cys Thr Thr Ile
705                 710                 715                 720 atc tgg gtg gca tcc gcg ctg cac gcg gct gtc aac ttt ggg cag tac      2208
Ile Trp Val Ala Ser Ala Leu His Ala Ala Val Asn Phe Gly Gln Tyr
                725                 730                 735 cca tac gcc ggg tac ctc ccg aac cgg ccg acg gcc agc cgg cgc ccg      2256
Pro Tyr Ala Gly Tyr Leu Pro Asn Arg Pro Thr Ala Ser Arg Arg Pro
            740                 745                 750 atg ccg gag cca ggc agc cac gac tac aag aag ctg gga gcg ggg cag      2304
Met Pro Glu Pro Gly Ser His Asp Tyr Lys Lys Leu Gly Ala Gly Gln
        755                 760                 765 aag gag gcg gac atg gtg ttc atc cgc acc atc acc agc cag ttc cag      2352
Lys Glu Ala Asp Met Val Phe Ile Arg Thr Ile Thr Ser Gln Phe Gln
    770                 775                 780 acc atc ctg ggc atc tcg ctc atc gag atc ctc tcc aag cac tcc tcc      2400
Thr Ile Leu Gly Ile Ser Leu Ile Glu Ile Leu Ser Lys His Ser Ser
785                 790                 795                 800 gac gag gtg tac ctc ggc cag cgt gac gag cct gat cgc tgg acg tca      2448
Asp Glu Val Tyr Leu Gly Gln Arg Asp Glu Pro Asp Arg Trp Thr Ser
                805                 810                 815 gac gcc aag gcg ctg gat gcg ttc aaa aga ttc ggg agc cgg ctg gtg      2496
Asp Ala Lys Ala Leu Asp Ala Phe Lys Arg Phe Gly Ser Arg Leu Val
            820                 825                 830 cag att gag aat cgg atc aag acg atg aac gac agt ccg gac ttg aag      2544
Gln Ile Glu Asn Arg Ile Lys Thr Met Asn Asp Ser Pro Asp Leu Lys
        835                 840                 845 aac cgg aag ggg cct gtg gaa atg ccg tac atg ctg ctg tac ccc aac      2592
Asn Arg Lys Gly Pro Val Glu Met Pro Tyr Met Leu Leu Tyr Pro Asn
    850                 855                 860 acg tcg gac gtt acc ggc gag aag gcc gag ggg ctt act gcc atg ggc      2640
Thr Ser Asp Val Thr Gly Glu Lys Ala Glu Gly Leu Thr Ala Met Gly
865                 870                 875                 880 att ccc aac agc atc tcc ata tga                                      2664
Ile Pro Asn Ser Ile Ser Ile *
                885

<210> SEQ ID NO 24
<211> LENGTH: 887
<212> TYPE: PRT
<213> ORGANISM: Zea mays

<400> SEQUENCE: 24

Met Phe Trp His Gly Val Ala Asp Arg Leu Thr Gly Lys Asn Lys Glu
1               5                   10                  15

Ala Trp Ser Glu Gly Lys Ile Arg Gly Thr Val Arg Leu Val Lys Lys
            20                  25                  30

Glu Val Leu Asp Val Gly Asp Phe Asn Ala Ser Leu Leu Asp Gly Val
        35                  40                  45
```

```
His Arg Ile Leu Gly Trp Asp Asp Gly Val Ala Phe Gln Leu Val Ser
 50                  55                  60

Ala Thr Ala Ala Asp Pro Ser Asn Gly Gly Arg Gly Lys Val Gly Lys
 65                  70                  75                  80

Ala Ala His Leu Glu Glu Ala Val Val Ser Leu Lys Ser Thr Ala Asp
                 85                  90                  95

Gly Glu Thr Val Tyr Arg Val Ser Phe Glu Trp Asp Glu Ser Gln Gly
                100                 105                 110

Ile Pro Gly Ala Val Leu Val Arg Asn Leu Gln His Ala Glu Phe Phe
                115                 120                 125

Leu Lys Thr Leu Thr Leu Glu Gly Val Pro Gly Lys Gly Thr Val Val
    130                 135                 140

Phe Val Ala Asn Ser Trp Val Tyr Pro His Lys Leu Tyr Ser Gln Glu
145                 150                 155                 160

Arg Ile Phe Phe Ala Asn Asp Thr Tyr Leu Pro Ser Lys Met Pro Ala
                165                 170                 175

Ala Leu Val Pro Tyr Arg Gln Asp Glu Leu Lys Ile Leu Arg Gly Asp
                180                 185                 190

Asp Asn Pro Gly Pro Tyr Gln Glu His Asp Arg Val Tyr Arg Tyr Asp
                195                 200                 205

Tyr Tyr Asn Asp Leu Gly Asp Pro Asp Lys Gly Glu Glu His Ala Arg
    210                 215                 220

Pro Ile Leu Gly Gly Ser Gln Glu His Pro Tyr Pro Arg Arg Cys Arg
225                 230                 235                 240

Thr Gly Arg His Pro Thr Lys Lys Asp Pro Asn Ser Glu Ser Arg Leu
                245                 250                 255

Phe Leu Leu Asn Leu Asn Ile Tyr Val Pro Arg Asp Glu Arg Phe Gly
                260                 265                 270

His Leu Lys Met Ser Asp Phe Leu Gly Tyr Ser Leu Lys Thr Ile Ile
                275                 280                 285

Glu Ala Val Leu Pro Thr Leu Gly Thr Phe Val Asp Asp Thr Pro Lys
    290                 295                 300

Glu Phe Asp Ser Phe Glu Asp Ile Leu Gly Leu Tyr Glu Leu Gly Pro
305                 310                 315                 320

Glu Ala Pro Asn Asn Pro Leu Ile Ala Glu Ile Arg Lys Lys Ile Pro
                325                 330                 335

Ser Glu Phe Leu Arg Ser Ile Leu Pro Asn Gly Ser His Asp His Pro
                340                 345                 350

Leu Lys Met Pro Leu Pro Asn Val Ile Lys Ser Asp Val Leu Lys Lys
    355                 360                 365

Ala Pro Glu Phe Lys Phe Gly Trp Arg Thr Asp Glu Glu Phe Ala Arg
    370                 375                 380

Glu Thr Leu Ala Gly Val Asn Pro Val Ile Ile Lys Arg Leu Thr Glu
385                 390                 395                 400

Phe Pro Ala Lys Ser Thr Leu Asp Pro Arg Gln Tyr Gly Asp His Thr
                405                 410                 415

Ser Lys Ile Thr Glu Ala His Ile Arg His Asn Met Gly Gly Leu Ser
                420                 425                 430

Val Gln Asn Ala Leu Arg Asn Lys Arg Leu Phe Ile Leu Asp His His
    435                 440                 445

Asp His Phe Met Pro Tyr Leu Asp Glu Ile Asn Glu Leu Glu Gly Asn
    450                 455                 460

Phe Ile Tyr Ala Ser Arg Thr Leu Leu Phe Leu Lys Asp Asp Gly Thr
```

-continued

```
             465                 470                 475                 480
Leu Lys Pro Leu Ala Ile Glu Leu Ser Leu Pro His Pro Asp Gly Gln
                    485                 490                 495
Gln Arg Gly Ala Val Ser Lys Val Tyr Thr Pro Ala His Thr Gly Val
                500                 505                 510
Glu Gly His Val Trp Gln Leu Ala Lys Ala Tyr Ala Cys Val Asn Asp
            515                 520                 525
Ser Ala Trp His Gln Leu Ile Ser His Trp Leu Asn Thr His Ala Val
        530                 535                 540
Ile Glu Pro Phe Val Ile Ala Thr Asn Arg Gln Leu Ser Val Val His
545                 550                 555                 560
Pro Val His Lys Leu Leu Ser Pro His Tyr Arg Asp Thr Leu Asn Ile
                565                 570                 575
Asn Ala Leu Ala Arg Gln Thr Leu Ile Asn Ala Gly Val Phe Glu
            580                 585                 590
Arg Thr Val Phe Pro Ala Lys Tyr Ala Leu Gly Met Ser Ala Asp Val
                595                 600                 605
Tyr Lys Ser Trp Asn Phe Asn Glu Gln Ala Leu Pro Ala Asp Leu Val
            610                 615                 620
Lys Arg Gly Val Ala Val Pro Asp Gln Ser Ser Pro Tyr Gly Val Arg
625                 630                 635                 640
Leu Leu Ile Lys Asp Tyr Pro Tyr Ala Val Asp Gly Leu Val Ile Trp
                645                 650                 655
Trp Ala Ile Glu Arg Trp Val Lys Glu Tyr Leu Asp Ile Tyr Tyr Pro
            660                 665                 670
Asn Asp Gly Glu Leu Gln Arg Asp Val Glu Leu Gln Ala Trp Trp Lys
            675                 680                 685
Glu Val Arg Glu Glu Ala His Gly Asp Leu Lys Asp Arg Asp Trp Trp
        690                 695                 700
Pro Arg Met Asp Thr Val Gln Gln Leu Ala Arg Ala Cys Thr Thr Ile
705                 710                 715                 720
Ile Trp Val Ala Ser Ala Leu His Ala Ala Val Asn Phe Gly Gln Tyr
                725                 730                 735
Pro Tyr Ala Gly Tyr Leu Pro Asn Arg Pro Thr Ala Ser Arg Arg Pro
            740                 745                 750
Met Pro Glu Pro Gly Ser His Asp Tyr Lys Lys Leu Gly Ala Gly Gln
            755                 760                 765
Lys Glu Ala Asp Met Val Phe Ile Arg Thr Ile Thr Ser Gln Phe Gln
        770                 775                 780
Thr Ile Leu Gly Ile Ser Leu Ile Glu Ile Leu Ser Lys His Ser Ser
785                 790                 795                 800
Asp Glu Val Tyr Leu Gly Gln Arg Asp Glu Pro Asp Arg Trp Thr Ser
                805                 810                 815
Asp Ala Lys Ala Leu Asp Ala Phe Lys Arg Phe Gly Ser Arg Leu Val
            820                 825                 830
Gln Ile Glu Asn Arg Ile Lys Thr Met Asn Asp Ser Pro Asp Leu Lys
            835                 840                 845
Asn Arg Lys Gly Pro Val Glu Met Pro Tyr Met Leu Leu Tyr Pro Asn
        850                 855                 860
Thr Ser Asp Val Thr Gly Glu Lys Ala Glu Gly Leu Thr Ala Met Gly
865                 870                 875                 880
Ile Pro Asn Ser Ile Ser Ile
                885
```

<210> SEQ ID NO 25
<211> LENGTH: 2909
<212> TYPE: DNA
<213> ORGANISM: Zea mays
<220> FEATURE:
<221> NAME/KEY: CDS
<222> LOCATION: (62)...(2740)
<223> OTHER INFORMATION: LOX6

<400> SEQUENCE: 25

| | | |
|---|---|---|
| aacccacgga agcaagacaa aagctcgtgc tggacgacat ctccccctgtc gatccacgac | | 60 |
| c atg atg cag cag ctc cgt cac agc cag ccg agc ccg tgc ctc tgc ggc<br>  Met Met Gln Gln Leu Arg His Ser Gln Pro Ser Pro Cys Leu Cys Gly<br>   1             5                10              15 | | 109 |
| ctg cgg gcg gca cgg cct atg ctc gcc ctc ggc gca gca gca tcc cgt<br>Leu Arg Ala Ala Arg Pro Met Leu Ala Leu Gly Ala Ala Ala Ser Arg<br>              20                25               30 | | 157 |
| tcg cgg ccc gcc gga aaa ctg caa ccg agc gtc tgc ctc ggc ctc ggc<br>Ser Arg Pro Ala Gly Lys Leu Gln Pro Ser Val Cys Leu Gly Leu Gly<br>        35                40               45 | | 205 |
| cat gta gcc cca gcc gcg gcg aga gga cag ccc cgt ccc cgt gcc gtt<br>His Val Ala Pro Ala Ala Ala Arg Gly Gln Pro Arg Pro Arg Ala Val<br>    50                    55                 60 | | 253 |
| gcc gac tcg gcg ctg gga gca tcg cct acg agc gtg cat gtc gga ggc<br>Ala Asp Ser Ala Leu Gly Ala Ser Pro Thr Ser Val His Val Gly Gly<br> 65                  70               75               80 | | 301 |
| aag ctg ctg ctg cag aac ttc gcc gcc gac agc cag cag cgg ctc aag<br>Lys Leu Leu Leu Gln Asn Phe Ala Ala Asp Ser Gln Gln Arg Leu Lys<br>              85                90               95 | | 349 |
| ctc tcc atc cag ctt gtc agc gcc acc gtg gcc gat ccc gac ggg cgc<br>Leu Ser Ile Gln Leu Val Ser Ala Thr Val Ala Asp Pro Asp Gly Arg<br>              100               105             110 | | 397 |
| ggg gtg aag gcg gag gcg tcg gtg ctg gac gcc gtc gtg ggc agc ggg<br>Gly Val Lys Ala Glu Ala Ser Val Leu Asp Ala Val Val Gly Ser Gly<br>             115               120             125 | | 445 |
| gac agc gag ctc gac gtg gac ctg atc tgg gac gag gcg ctg ggc gcg<br>Asp Ser Glu Leu Asp Val Asp Leu Ile Trp Asp Glu Ala Leu Gly Ala<br>130                 135               140 | | 493 |
| ccc ggc gcg gtg gtg gtg aag aac cac tcc gac ttc ccc gtg tac ctg<br>Pro Gly Ala Val Val Val Lys Asn His Ser Asp Phe Pro Val Tyr Leu<br>145                 150               155               160 | | 541 |
| agg ctg ctg agc gtg ccg gcc ggc gtc ggc ggc gcc gac gac gag gcc<br>Arg Leu Leu Ser Val Pro Ala Gly Val Gly Gly Ala Asp Asp Glu Ala<br>             165               170             175 | | 589 |
| gcc gcc gtc cac ttc gcc tgc aac gga tgg gtg tac ccc gtc gac aag<br>Ala Ala Val His Phe Ala Cys Asn Gly Trp Val Tyr Pro Val Asp Lys<br>               180               185             190 | | 637 |
| cac ccg tac cgc ctc ttc ttc acc aac gac gcg tgt gtc aag gaa gaa<br>His Pro Tyr Arg Leu Phe Phe Thr Asn Asp Ala Cys Val Lys Glu Glu<br>             195               200             205 | | 685 |
| acg ccg agc gcc ctg ctc aag tac cgg gag gac gag ctc ggc gcg ctc<br>Thr Pro Ser Ala Leu Leu Lys Tyr Arg Glu Asp Glu Leu Gly Ala Leu<br>210                 215               220 | | 733 |
| cgg gga gac ggc gag acg acg gag cga ccg ttc cag ccg tgg gac cgc<br>Arg Gly Asp Gly Glu Thr Thr Glu Arg Pro Phe Gln Pro Trp Asp Arg<br>225                 230               235               240 | | 781 |
| gtg tac gac tac gcg ctg tac aac gac ctg ggg aac cca gac ctg cgc<br>Val Tyr Asp Tyr Ala Leu Tyr Asn Asp Leu Gly Asn Pro Asp Leu Arg<br>               245               250             255 | | 829 |

```
cag gac ctg gcg cgc ccc gtg ctg gga gga tcc cag gag tac ccg tac      877
Gln Asp Leu Ala Arg Pro Val Leu Gly Gly Ser Gln Glu Tyr Pro Tyr
        260                 265                 270 cct cgg cgt acc aag acc ggc cga cca gcc gcc aaa aca gat cct cgg      925
Pro Arg Arg Thr Lys Thr Gly Arg Pro Ala Ala Lys Thr Asp Pro Arg
275                 280                 285 tcg gag agc aga gcg ccg ctg gac gaa gag atc tac gtc ccc tgc gac      973
Ser Glu Ser Arg Ala Pro Leu Asp Glu Glu Ile Tyr Val Pro Cys Asp
        290                 295                 300 gag cgc gtc ggc ttc gcc agc atc ccc gcg ccg acg ctt ccg ccg ctg     1021
Glu Arg Val Gly Phe Ala Ser Ile Pro Ala Pro Thr Leu Pro Pro Leu
305                 310                 315                 320 ggc ggg cac ttc agg tcc ctc gcc gat gtc tac cgc ctc ttc ggc ctc     1069
Gly Gly His Phe Arg Ser Leu Ala Asp Val Tyr Arg Leu Phe Gly Leu
                325                 330                 335 gac gac ctc ggc cgg ctc ccg gag gcc aag gcg gtc atc aac agc ggc     1117
Asp Asp Leu Gly Arg Leu Pro Glu Ala Lys Ala Val Ile Asn Ser Gly
                340                 345                 350 gcg ccg ttc ccc gtc gtg cct cag gtc att tca gtg aac ccg aca cat     1165
Ala Pro Phe Pro Val Val Pro Gln Val Ile Ser Val Asn Pro Thr His
        355                 360                 365 tgg cgg aag gac gaa gag ttc gcg cgg cag atg atc gcc ggg gcg aac     1213
Trp Arg Lys Asp Glu Glu Phe Ala Arg Gln Met Ile Ala Gly Ala Asn
370                 375                 380 ccg gtg tgc atc aag cgc gtc acc aag ttc ccg ctg gcg agc gag ctt     1261
Pro Val Cys Ile Lys Arg Val Thr Lys Phe Pro Leu Ala Ser Glu Leu
385                 390                 395                 400 gac cgc ggg gtg ttc ggc gac cag gac agc aag ata acc aag gac cat     1309
Asp Arg Gly Val Phe Gly Asp Gln Asp Ser Lys Ile Thr Lys Asp His
                405                 410                 415 gtc gag aag aac atg ggc ggc atg acg gtg cag cag gcc gta gag gag     1357
Val Glu Lys Asn Met Gly Gly Met Thr Val Gln Gln Ala Val Glu Glu
                420                 425                 430 ggg agg ctg tac gtc gtg gac cac cac gac tgg gtg atg cca tac ctg     1405
Gly Arg Leu Tyr Val Val Asp His His Asp Trp Val Met Pro Tyr Leu
        435                 440                 445 aag cgc atc aac gag ctc cct gcg agc gag gag aag gcg gag gtg tcg     1453
Lys Arg Ile Asn Glu Leu Pro Ala Ser Glu Glu Lys Ala Glu Val Ser
450                 455                 460 cag agg aag gtg tac gcc gcc aga acg ctc ctg ttc ctg gac ggc gag     1501
Gln Arg Lys Val Tyr Ala Ala Arg Thr Leu Leu Phe Leu Asp Gly Glu
465                 470                 475                 480 gac tcg tcg atg ctc aga ccg ctg gcg atc gag ctc agc tcg ccg cac     1549
Asp Ser Ser Met Leu Arg Pro Leu Ala Ile Glu Leu Ser Ser Pro His
                485                 490                 495 ccg gag aag gag cag ctc ggc gcg gtc agc acg gtg tac act cca ccg     1597
Pro Glu Lys Glu Gln Leu Gly Ala Val Ser Thr Val Tyr Thr Pro Pro
                500                 505                 510 gac agc ggg gac gac ggc atc acg gcc ggg agg ttc tca acc tgg gaa     1645
Asp Ser Gly Asp Asp Gly Ile Thr Ala Gly Arg Phe Ser Thr Trp Glu
        515                 520                 525 ctg gca aag gtt tac gcc tct gcc aac gac gca gcc gag aac aac ttc     1693
Leu Ala Lys Val Tyr Ala Ser Ala Asn Asp Ala Ala Glu Asn Asn Phe
530                 535                 540 gtc act cac tgg ctc aac acg cac gca tcc atg gag ccg atc gtg atc     1741
Val Thr His Trp Leu Asn Thr His Ala Ser Met Glu Pro Ile Val Ile
545                 550                 555                 560 gcg gcg aac cgg cag ctg agc gtg ctg cac cca atc cac agg ctc ctc     1789
Ala Ala Asn Arg Gln Leu Ser Val Leu His Pro Ile His Arg Leu Leu
                565                 570                 575
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aag | ccg | cac | ttc | cgg | aag | acg | ctc | cac | atc | aac | gcc | gtc | gca | cgc | cag | 1837 |
| Lys | Pro | His | Phe | Arg | Lys | Thr | Leu | His | Ile | Asn | Ala | Val | Ala | Arg | Gln |      |
|     |     |     |     | 580 |     |     |     |     | 585 |     |     |     |     | 590 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| atc | atc | gtc | ggc | tcg | ggt | gac | cag | agg | aag | gac | ggc | agc | gtc | ttc | cgt | 1885 |
| Ile | Ile | Val | Gly | Ser | Gly | Asp | Gln | Arg | Lys | Asp | Gly | Ser | Val | Phe | Arg |      |
|     | 595 |     |     |     |     | 600 |     |     |     |     | 605 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ggc | ata | gac | gag | gtc | acg | tac | ttc | ccc | agc | aag | tac | aac | atg | gag | atg | 1933 |
| Gly | Ile | Asp | Glu | Val | Thr | Tyr | Phe | Pro | Ser | Lys | Tyr | Asn | Met | Glu | Met |      |
| 610 |     |     |     |     | 615 |     |     |     |     | 620 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tcc | tcc | aag | gcg | tac | aaa | gcc | tgg | aac | ttc | acg | gac | ctt | gct | ctt | ccc | 1981 |
| Ser | Ser | Lys | Ala | Tyr | Lys | Ala | Trp | Asn | Phe | Thr | Asp | Leu | Ala | Leu | Pro |      |
| 625 |     |     |     |     | 630 |     |     |     |     | 635 |     |     |     |     | 640 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aac | gat | ctc | atc | aag | aga | ggt | ctg | gca | aaa | gga | gat | cca | aag | aag | cca | 2029 |
| Asn | Asp | Leu | Ile | Lys | Arg | Gly | Leu | Ala | Lys | Gly | Asp | Pro | Lys | Lys | Pro |      |
|     |     |     |     | 645 |     |     |     |     | 650 |     |     |     |     | 655 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gag | acg | gtg | gag | ctg | gcg | ata | aag | gac | tac | ccg | tac | gcg | gtg | gac | ggg | 2077 |
| Glu | Thr | Val | Glu | Leu | Ala | Ile | Lys | Asp | Tyr | Pro | Tyr | Ala | Val | Asp | Gly |      |
|     |     |     | 660 |     |     |     |     | 665 |     |     |     |     | 670 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctc | gac | atg | tgg | gcg | gcg | atc | aag | aag | tgg | gtg | gct | gac | tac | tgc | gcc | 2125 |
| Leu | Asp | Met | Trp | Ala | Ala | Ile | Lys | Lys | Trp | Val | Ala | Asp | Tyr | Cys | Ala |      |
|     |     |     | 675 |     |     |     |     | 680 |     |     |     |     | 685 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| atc | tac | tac | gcc | gac | gac | ggc | gcg | gtg | gcg | agg | gac | agc | gag | ctg | cag | 2173 |
| Ile | Tyr | Tyr | Ala | Asp | Asp | Gly | Ala | Val | Ala | Arg | Asp | Ser | Glu | Leu | Gln |      |
|     | 690 |     |     |     |     | 695 |     |     |     |     | 700 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ggg | tgg | tgg | agc | gag | gtc | agg | aac | gtg | ggg | cac | ggc | gac | ctg | gcg | gac | 2221 |
| Gly | Trp | Trp | Ser | Glu | Val | Arg | Asn | Val | Gly | His | Gly | Asp | Leu | Ala | Asp |      |
| 705 |     |     |     |     | 710 |     |     |     |     | 715 |     |     |     |     | 720 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gcg | ccg | tgg | tgg | ccg | gcg | atg | gac | tgc | gtc | gcc | gac | ctc | gtg | gag | acc | 2269 |
| Ala | Pro | Trp | Trp | Pro | Ala | Met | Asp | Cys | Val | Ala | Asp | Leu | Val | Glu | Thr |      |
|     |     |     |     | 725 |     |     |     |     | 730 |     |     |     |     | 735 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tgc | gcc | acc | gtc | gtc | tgg | ctg | agc | tcg | gcg | tac | cac | gcg | tcc | atc | agc | 2317 |
| Cys | Ala | Thr | Val | Val | Trp | Leu | Ser | Ser | Ala | Tyr | His | Ala | Ser | Ile | Ser |      |
|     |     |     | 740 |     |     |     |     | 745 |     |     |     |     | 750 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttc | ggg | cag | tac | gac | tac | ctg | ggc | ttc | gtc | ccg | aac | ggg | ccc | tcc | atc | 2365 |
| Phe | Gly | Gln | Tyr | Asp | Tyr | Leu | Gly | Phe | Val | Pro | Asn | Gly | Pro | Ser | Ile |      |
|     |     | 755 |     |     |     |     | 760 |     |     |     |     | 765 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| acc | acg | cgg | ccg | gtg | ccg | ggc | ccg | gac | gcc | ggg | gcg | gag | gtc | acg | gag | 2413 |
| Thr | Thr | Arg | Pro | Val | Pro | Gly | Pro | Asp | Ala | Gly | Ala | Glu | Val | Thr | Glu |      |
| 770 |     |     |     |     | 775 |     |     |     |     | 780 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tcg | gac | ttc | ctg | gcg | agc | gtc | acg | ccg | gtc | acc | gag | gcg | ctc | ggc | ttc | 2461 |
| Ser | Asp | Phe | Leu | Ala | Ser | Val | Thr | Pro | Val | Thr | Glu | Ala | Leu | Gly | Phe |      |
| 785 |     |     |     | 790 |     |     |     |     | 795 |     |     |     |     | 800 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| atg | tcc | atc | gcc | tcg | ggg | ccg | atg | ggg | ctc | aag | ggc | acg | gag | gtg | tac | 2509 |
| Met | Ser | Ile | Ala | Ser | Gly | Pro | Met | Gly | Leu | Lys | Gly | Thr | Glu | Val | Tyr |      |
|     |     |     |     | 805 |     |     |     |     | 810 |     |     |     |     | 815 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctg | ggg | cag | cgc | ccg | gac | acg | gag | cag | tgg | acg | cgc | gag | cgg | agg | gcg | 2557 |
| Leu | Gly | Gln | Arg | Pro | Asp | Thr | Glu | Gln | Trp | Thr | Arg | Glu | Arg | Arg | Ala |      |
|     |     |     |     | 820 |     |     |     |     | 825 |     |     |     |     | 830 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gcc | gag | gcg | ctg | gcg | gag | ttc | cgg | gcg | agg | ttg | gag | gag | gtc | gcg | ggc | 2605 |
| Ala | Glu | Ala | Leu | Ala | Glu | Phe | Arg | Ala | Arg | Leu | Glu | Glu | Val | Ala | Gly |      |
|     |     | 835 |     |     |     |     | 840 |     |     |     |     | 845 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aac | atc | gac | agg | cgg | aac | gcg | gac | cct | gcg | ctg | aag | aac | cgg | acg | ggg | 2653 |
| Asn | Ile | Asp | Arg | Arg | Asn | Ala | Asp | Pro | Ala | Leu | Lys | Asn | Arg | Thr | Gly |      |
| 850 |     |     |     |     | 855 |     |     |     |     | 860 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cag | gtg | gag | gtg | ccc | tat | acg | ctg | ctc | aag | ccg | acg | gca | cag | ccc | gga | 2701 |
| Gln | Val | Glu | Val | Pro | Tyr | Thr | Leu | Leu | Lys | Pro | Thr | Ala | Gln | Pro | Gly |      |
| 865 |     |     |     |     | 870 |     |     |     |     | 875 |     |     |     |     | 880 |      |

|     |     |     |     |     |     |     |     |     |     |     |      |
| --- | --- | --- | --- | --- | --- | --- | --- | --- | --- | --- | ---- |
| ctg | gtg | ctc | cgt | ggc | ata | ccc | aac | agc | atc | acc | gtt tga gcagcagagc | 2750 |
| Leu | Val | Leu | Arg | Gly | Ile | Pro | Asn | Ser | Ile | Thr | Val * |      |

```
                        885                 890
gccgtcggca gctgtcagct gtgtacagta cagaataata aggtggtcgt gtttggcgct     2810
atctccacca cataaacgtg aaaatgtttt tttttgaaaa aaaaaaaaaa aaaaaaaaa      2870 aaaaaaaaaa aaaaaaaaaa aaaaaaaaaa aaaaaaaa                             2909

<210> SEQ ID NO 26
<211> LENGTH: 892
<212> TYPE: PRT
<213> ORGANISM: Zea mays

<400> SEQUENCE: 26

Met Met Gln Gln Leu Arg His Ser Gln Pro Ser Pro Cys Leu Cys Gly
 1               5                  10                  15

Leu Arg Ala Ala Arg Pro Met Leu Ala Leu Gly Ala Ala Ala Ser Arg
                20                  25                  30

Ser Arg Pro Ala Gly Lys Leu Gln Pro Ser Val Cys Leu Gly Leu Gly
            35                  40                  45

His Val Ala Pro Ala Ala Ala Arg Gly Gln Pro Arg Pro Arg Ala Val
        50                  55                  60

Ala Asp Ser Ala Leu Gly Ala Ser Pro Thr Ser Val His Val Gly Gly
65                  70                  75                  80

Lys Leu Leu Leu Gln Asn Phe Ala Ala Asp Ser Gln Gln Arg Leu Lys
                85                  90                  95

Leu Ser Ile Gln Leu Val Ser Ala Thr Val Ala Asp Pro Asp Gly Arg
            100                 105                 110

Gly Val Lys Ala Glu Ala Ser Val Leu Asp Ala Val Gly Ser Gly
        115                 120                 125

Asp Ser Glu Leu Asp Val Asp Leu Ile Trp Asp Glu Ala Leu Gly Ala
130                 135                 140

Pro Gly Ala Val Val Lys Asn His Ser Asp Phe Pro Val Tyr Leu
145                 150                 155                 160

Arg Leu Leu Ser Val Pro Ala Gly Val Gly Gly Ala Asp Asp Glu Ala
                165                 170                 175

Ala Ala Val His Phe Ala Cys Asn Gly Trp Val Tyr Pro Val Asp Lys
            180                 185                 190

His Pro Tyr Arg Leu Phe Phe Thr Asn Asp Ala Cys Val Lys Glu Glu
        195                 200                 205

Thr Pro Ser Ala Leu Leu Lys Tyr Arg Glu Asp Glu Leu Gly Ala Leu
    210                 215                 220

Arg Gly Asp Gly Glu Thr Thr Glu Arg Pro Phe Gln Pro Trp Asp Arg
225                 230                 235                 240

Val Tyr Asp Tyr Ala Leu Tyr Asn Asp Leu Gly Asn Pro Asp Leu Arg
                245                 250                 255

Gln Asp Leu Ala Arg Pro Val Leu Gly Gly Ser Gln Glu Tyr Pro Tyr
            260                 265                 270

Pro Arg Arg Thr Lys Thr Gly Arg Pro Ala Ala Lys Thr Asp Pro Arg
        275                 280                 285

Ser Glu Ser Arg Ala Pro Leu Asp Glu Glu Ile Tyr Val Pro Cys Asp
    290                 295                 300

Glu Arg Val Gly Phe Ala Ser Ile Pro Ala Pro Thr Leu Pro Pro Leu
305                 310                 315                 320

Gly Gly His Phe Arg Ser Leu Ala Asp Val Tyr Arg Leu Phe Gly Leu
                325                 330                 335
```

-continued

```
Asp Asp Leu Gly Arg Leu Pro Glu Ala Lys Ala Val Ile Asn Ser Gly
            340                 345                 350

Ala Pro Phe Pro Val Pro Gln Val Ile Ser Val Asn Pro Thr His
        355                 360                 365

Trp Arg Lys Asp Glu Phe Ala Arg Gln Met Ile Ala Gly Ala Asn
    370                 375                 380

Pro Val Cys Ile Lys Arg Val Thr Lys Phe Pro Leu Ala Ser Glu Leu
385                 390                 395                 400

Asp Arg Gly Val Phe Gly Asp Gln Asp Ser Lys Ile Thr Lys Asp His
                405                 410                 415

Val Glu Lys Asn Met Gly Met Thr Val Gln Gln Ala Val Glu Glu
                420                 425                 430

Gly Arg Leu Tyr Val Val Asp His His Asp Trp Val Met Pro Tyr Leu
            435                 440                 445

Lys Arg Ile Asn Glu Leu Pro Ala Ser Glu Glu Lys Ala Glu Val Ser
450                 455                 460

Gln Arg Lys Val Tyr Ala Ala Arg Thr Leu Leu Phe Leu Asp Gly Glu
465                 470                 475                 480

Asp Ser Ser Met Leu Arg Pro Leu Ala Ile Glu Leu Ser Ser Pro His
                485                 490                 495

Pro Glu Lys Glu Gln Leu Gly Ala Val Ser Thr Val Tyr Thr Pro Pro
                500                 505                 510

Asp Ser Gly Asp Asp Gly Ile Thr Ala Gly Arg Phe Ser Thr Trp Glu
                515                 520                 525

Leu Ala Lys Val Tyr Ala Ser Ala Asn Asp Ala Ala Glu Asn Asn Phe
    530                 535                 540

Val Thr His Trp Leu Asn Thr His Ala Ser Met Glu Pro Ile Val Ile
545                 550                 555                 560

Ala Ala Asn Arg Gln Leu Ser Val Leu His Pro Ile His Arg Leu Leu
                565                 570                 575

Lys Pro His Phe Arg Lys Thr Leu His Ile Asn Ala Val Ala Arg Gln
            580                 585                 590

Ile Ile Val Gly Ser Gly Asp Gln Arg Lys Asp Gly Ser Val Phe Arg
            595                 600                 605

Gly Ile Asp Glu Val Thr Tyr Phe Pro Ser Lys Tyr Asn Met Glu Met
    610                 615                 620

Ser Ser Lys Ala Tyr Lys Ala Trp Asn Phe Thr Asp Leu Ala Leu Pro
625                 630                 635                 640

Asn Asp Leu Ile Lys Arg Gly Leu Ala Lys Gly Asp Pro Lys Lys Pro
                645                 650                 655

Glu Thr Val Glu Leu Ala Ile Lys Asp Tyr Pro Tyr Ala Val Asp Gly
                660                 665                 670

Leu Asp Met Trp Ala Ala Ile Lys Lys Trp Val Ala Asp Tyr Cys Ala
    675                 680                 685

Ile Tyr Tyr Ala Asp Asp Gly Ala Val Ala Arg Asp Ser Glu Leu Gln
    690                 695                 700

Gly Trp Trp Ser Glu Val Arg Asn Val Gly His Gly Asp Leu Ala Asp
705                 710                 715                 720

Ala Pro Trp Trp Pro Ala Met Asp Cys Val Ala Asp Leu Val Glu Thr
                725                 730                 735

Cys Ala Thr Val Val Trp Leu Ser Ser Ala Tyr His Ala Ser Ile Ser
            740                 745                 750

Phe Gly Gln Tyr Asp Tyr Leu Gly Phe Val Pro Asn Gly Pro Ser Ile
```

-continued

```
                755                 760                 765
Thr Thr Arg Pro Val Pro Gly Pro Asp Ala Gly Ala Glu Val Thr Glu
    770                 775                 780

Ser Asp Phe Leu Ala Ser Val Thr Pro Val Thr Glu Ala Leu Gly Phe
785                 790                 795                 800

Met Ser Ile Ala Ser Gly Pro Met Gly Leu Lys Gly Thr Glu Val Tyr
                805                 810                 815

Leu Gly Gln Arg Pro Asp Thr Glu Gln Trp Thr Arg Glu Arg Arg Ala
            820                 825                 830

Ala Glu Ala Leu Ala Glu Phe Arg Ala Arg Leu Glu Glu Val Ala Gly
            835                 840                 845

Asn Ile Asp Arg Arg Asn Ala Asp Pro Ala Leu Lys Asn Arg Thr Gly
        850                 855                 860

Gln Val Glu Val Pro Tyr Thr Leu Leu Lys Pro Thr Ala Gln Pro Gly
865                 870                 875                 880

Leu Val Leu Arg Gly Ile Pro Asn Ser Ile Thr Val
                885                 890

<210> SEQ ID NO 27
<211> LENGTH: 2664
<212> TYPE: DNA
<213> ORGANISM: Zea mays
<220> FEATURE:
<221> NAME/KEY: CDS
<222> LOCATION: (1)...(2664)

<400> SEQUENCE: 27 atg ttc tgg cac ggg gtc gcg gac cgg ctg acg gga aag aac aag gag      48
Met Phe Trp His Gly Val Ala Asp Arg Leu Thr Gly Lys Asn Lys Glu
1               5                   10                  15 gcg tgg agc gag ggc aag atc cgc ggc acg gtg agg ctg gtc aag aag      96
Ala Trp Ser Glu Gly Lys Ile Arg Gly Thr Val Arg Leu Val Lys Lys
                20                  25                  30 gag gtg ctg gac gtc ggc gac ttc aac gcc tcg ctc ctc gac ggc gtc     144
Glu Val Leu Asp Val Gly Asp Phe Asn Ala Ser Leu Leu Asp Gly Val
            35                  40                  45 cac agg atc ctc ggc tgg gac gac ggc gtc gcc ttc cag ctc gtc agc     192
His Arg Ile Leu Gly Trp Asp Asp Gly Val Ala Phe Gln Leu Val Ser
        50                  55                  60 gcc acc gcg gcc gac ccc agc aac ggg ggc cgt ggc aag gtg ggg aag     240
Ala Thr Ala Ala Asp Pro Ser Asn Gly Gly Arg Gly Lys Val Gly Lys
65                  70                  75                  80 gcg gcg cac ctg gag gag gcg gtg gtg tcg ctc aag tcc acg gcg gac     288
Ala Ala His Leu Glu Glu Ala Val Val Ser Leu Lys Ser Thr Ala Asp
                85                  90                  95 ggg gag acc gtg tac cgg gtg agc ttc gag tgg gac gag tcg cag ggc     336
Gly Glu Thr Val Tyr Arg Val Ser Phe Glu Trp Asp Glu Ser Gln Gly
            100                 105                 110 atc ccg ggc gcc gtc ctg gtc agg aac ctg cag cac gcc gag ttc ttc     384
Ile Pro Gly Ala Val Leu Val Arg Asn Leu Gln His Ala Glu Phe Phe
        115                 120                 125 ctc aag acg ctc acc ctc gag ggc gtc cca ggc aag ggc acc gtc gtc     432
Leu Lys Thr Leu Thr Leu Glu Gly Val Pro Gly Lys Gly Thr Val Val
    130                 135                 140 ttc gtc gcc aac tcg tgg gtc tac ccg cac aag ctc tac tcc cag gaa     480
Phe Val Ala Asn Ser Trp Val Tyr Pro His Lys Leu Tyr Ser Gln Glu
145                 150                 155                 160 cgc atc ttc ttc gcc aac gac acc tat ctg ccg agc aaa atg ccg gcg     528
Arg Ile Phe Phe Ala Asn Asp Thr Tyr Leu Pro Ser Lys Met Pro Ala
```

-continued

```
              165                 170                 175
gcg ttg gtg cct tat cgg caa gat gag ctc aag att ctc cgt ggc gac      576
Ala Leu Val Pro Tyr Arg Gln Asp Glu Leu Lys Ile Leu Arg Gly Asp
                180                 185                 190 gat aat cct gga cca tac cag gag cat gat cgc gtc tac cgt tac gac      624
Asp Asn Pro Gly Pro Tyr Gln Glu His Asp Arg Val Tyr Arg Tyr Asp
            195                 200                 205 tac tac aat gac ctt ggt gat ccc gac aag ggc gaa gag cac gct cgg      672
Tyr Tyr Asn Asp Leu Gly Asp Pro Asp Lys Gly Glu Glu His Ala Arg
        210                 215                 220 ccg atc ctc ggt ggc agc caa gaa cac ccg tat ccc cgt cgc tgc aga      720
Pro Ile Leu Gly Gly Ser Gln Glu His Pro Tyr Pro Arg Arg Cys Arg
225                 230                 235                 240 act ggc cgg cac cca aca aag aaa gac cca aat tcg gag agc agg ctt      768
Thr Gly Arg His Pro Thr Lys Lys Asp Pro Asn Ser Glu Ser Arg Leu
                245                 250                 255 ttc ctg ctg aac ctg aac atc tac gtc ccg cgt gac gaa cgc ttt ggg      816
Phe Leu Leu Asn Leu Asn Ile Tyr Val Pro Arg Asp Glu Arg Phe Gly
            260                 265                 270 cat ctc aag atg tcg gac ttc ctt ggg tac tcg ctg aag acg atc atc      864
His Leu Lys Met Ser Asp Phe Leu Gly Tyr Ser Leu Lys Thr Ile Ile
        275                 280                 285 gag gct gtt ctt cca aca ctg ggg act ttc gtc gat gac acg ccc aag      912
Glu Ala Val Leu Pro Thr Leu Gly Thr Phe Val Asp Asp Thr Pro Lys
    290                 295                 300 gag ttc gat tcg ttt gag gat atc ctc ggg ctc tac gag ctg ggc cca      960
Glu Phe Asp Ser Phe Glu Asp Ile Leu Gly Leu Tyr Glu Leu Gly Pro
305                 310                 315                 320 gag gca ccc aac aac cca ctg ata gca gag atc agg aag aag atc ccc     1008
Glu Ala Pro Asn Asn Pro Leu Ile Ala Glu Ile Arg Lys Lys Ile Pro
                325                 330                 335 agc gag ttc ctt cga agc att ctg ccg aac ggt agc cat gac cac ccg     1056
Ser Glu Phe Leu Arg Ser Ile Leu Pro Asn Gly Ser His Asp His Pro
            340                 345                 350 cta aag atg ccc ctt cca aat gtc atc aaa tca gat gtg ttg aaa aag     1104
Leu Lys Met Pro Leu Pro Asn Val Ile Lys Ser Asp Val Leu Lys Lys
        355                 360                 365 gct ccg gag ttt aag ttt ggc tgg agg act gac gaa gag ttc gcg aga     1152
Ala Pro Glu Phe Lys Phe Gly Trp Arg Thr Asp Glu Glu Phe Ala Arg
370                 375                 380 gag aca ctt gca ggc gtg aac cca gta atc atc aaa cgt ctg acg gag     1200
Glu Thr Leu Ala Gly Val Asn Pro Val Ile Ile Lys Arg Leu Thr Glu
385                 390                 395                 400 ttc ccc gct aaa agc acc ctg gac cca agg cag tac gga gac cac acc     1248
Phe Pro Ala Lys Ser Thr Leu Asp Pro Arg Gln Tyr Gly Asp His Thr
                405                 410                 415 agc aag atc act gaa gct cac atc cgg cat aac atg gga ggc ctg tcg     1296
Ser Lys Ile Thr Glu Ala His Ile Arg His Asn Met Gly Gly Leu Ser
            420                 425                 430 gtg cag aac gca ctg agg aac aag agg ctc ttc atc cta gac cac cat     1344
Val Gln Asn Ala Leu Arg Asn Lys Arg Leu Phe Ile Leu Asp His His
        435                 440                 445 gac cat ttc atg ccg tac ctc gac gag atc aac gag ctg gag ggg aac     1392
Asp His Phe Met Pro Tyr Leu Asp Glu Ile Asn Glu Leu Glu Gly Asn
    450                 455                 460 ttc atc tac gcc agc agg acc cta ctg ttc ctg aag gac gat ggc acg     1440
Phe Ile Tyr Ala Ser Arg Thr Leu Leu Phe Leu Lys Asp Asp Gly Thr
465                 470                 475                 480 ctg aag ccc ctg gcc atc gag ctg agc ctg ccc cac cct gac ggc cag     1488
```

```
                                                              -continued

Leu Lys Pro Leu Ala Ile Glu Leu Ser Leu Pro His Pro Asp Gly Gln
            485                 490                 495 cag cgc ggc gcg gtc agc aag gtg tac acc ccg gct cac acc ggc gtc      1536
Gln Arg Gly Ala Val Ser Lys Val Tyr Thr Pro Ala His Thr Gly Val
            500                 505                 510 gag ggc cac gtc tgg cag ctc gcc aag gct tat gcc tgc gta aac gac      1584
Glu Gly His Val Trp Gln Leu Ala Lys Ala Tyr Ala Cys Val Asn Asp
            515                 520                 525 tct gcc tgg cat cag ctg atc agc cac tgg ctg aac acg cac gcg gtg      1632
Ser Ala Trp His Gln Leu Ile Ser His Trp Leu Asn Thr His Ala Val
            530                 535                 540 atc gag ccg ttc gta atc gcg aca aac cgg cag ctc agc gtg gtg cat      1680
Ile Glu Pro Phe Val Ile Ala Thr Asn Arg Gln Leu Ser Val Val His
545                 550                 555                 560 ccc gtg cac aag ctg ctg agc ccg cac tac cgt gac acg ctg aac atc      1728
Pro Val His Lys Leu Leu Ser Pro His Tyr Arg Asp Thr Leu Asn Ile
            565                 570                 575 aac gcc ctg gca cgc cag aca ctc atc aac gcc ggc ggc gtc ttc gag      1776
Asn Ala Leu Ala Arg Gln Thr Leu Ile Asn Ala Gly Gly Val Phe Glu
            580                 585                 590 cgc acc gtg ttc cct gca aag tac gcg ctg ggg atg tcg gca gac gtg      1824
Arg Thr Val Phe Pro Ala Lys Tyr Ala Leu Gly Met Ser Ala Asp Val
            595                 600                 605 tac aag agc tgg aat ttc aac gag cag gct ctc cca gca gat ctc gtc      1872
Tyr Lys Ser Trp Asn Phe Asn Glu Gln Ala Leu Pro Ala Asp Leu Val
            610                 615                 620 aag aga ggt gtg gct gtg ccg gac cag tca agc cca tat ggt gtc cga      1920
Lys Arg Gly Val Ala Val Pro Asp Gln Ser Ser Pro Tyr Gly Val Arg
625                 630                 635                 640 ctg ctg atc aag gac tac ccc tat gcc gtt gac ggg ctc gtc atc tgg      1968
Leu Leu Ile Lys Asp Tyr Pro Tyr Ala Val Asp Gly Leu Val Ile Trp
            645                 650                 655 tgg gcg atc gag cgg tgg gtc aag gag tac ctg gac atc tac tac cct      2016
Trp Ala Ile Glu Arg Trp Val Lys Glu Tyr Leu Asp Ile Tyr Tyr Pro
            660                 665                 670 aac gac ggc gag ctc cag cgt gac gtg gag ctg cag gcg tgg tgg aag      2064
Asn Asp Gly Glu Leu Gln Arg Asp Val Glu Leu Gln Ala Trp Trp Lys
            675                 680                 685 gag gtg cgt gag gag gcg cac ggc gac ctc aag gac cga gac tgg tgg      2112
Glu Val Arg Glu Glu Ala His Gly Asp Leu Lys Asp Arg Asp Trp Trp
            690                 695                 700 ccc agg atg gac acc gtc cag cag ctg gct agg gcg tgc acg acc atc      2160
Pro Arg Met Asp Thr Val Gln Gln Leu Ala Arg Ala Cys Thr Thr Ile
705                 710                 715                 720 atc tgg gtg gca tcc gcg ctg cac gcg gct gtc aac ttt ggg cag tac      2208
Ile Trp Val Ala Ser Ala Leu His Ala Ala Val Asn Phe Gly Gln Tyr
            725                 730                 735 cca tac gcc ggg tac ctc ccg aac cgg ccg acg gcc agc cgg cgc ccg      2256
Pro Tyr Ala Gly Tyr Leu Pro Asn Arg Pro Thr Ala Ser Arg Arg Pro
            740                 745                 750 atg ccg gag cca ggc agc cac gac tac aag aag ctg gga gcg ggg cag      2304
Met Pro Glu Pro Gly Ser His Asp Tyr Lys Lys Leu Gly Ala Gly Gln
            755                 760                 765 aag gag gcg gac atg gtg ttc atc cgc acc atc acc agc cag ttc cag      2352
Lys Glu Ala Asp Met Val Phe Ile Arg Thr Ile Thr Ser Gln Phe Gln
            770                 775                 780 acc atc ctg ggc atc tcg ctc atc gag atc ctc tcc aag cac tcc tcc      2400
Thr Ile Leu Gly Ile Ser Leu Ile Glu Ile Leu Ser Lys His Ser Ser
785                 790                 795                 800
```

-continued

```
gac gag gtg tac ctc ggc cag cgt gac gag cct gat cgc tgg acg tca    2448
Asp Glu Val Tyr Leu Gly Gln Arg Asp Glu Pro Asp Arg Trp Thr Ser
            805                 810                 815 gac gcc aag gcg ctg gat gcg ttc aaa aga ttc ggg agc cgg ctg gtg    2496
Asp Ala Lys Ala Leu Asp Ala Phe Lys Arg Phe Gly Ser Arg Leu Val
820                 825                 830 cag att gag aat cgg atc aag acg atg aac gac agt ccg gac ttg aag    2544
Gln Ile Glu Asn Arg Ile Lys Thr Met Asn Asp Ser Pro Asp Leu Lys
        835                 840                 845 aac cgg aag ggg cct gtg gaa atg ccg tac atg ctg ctg tac ccc aac    2592
Asn Arg Lys Gly Pro Val Glu Met Pro Tyr Met Leu Leu Tyr Pro Asn
    850                 855                 860 acg tcg gac gtt acc ggc gag aag gcc gag ggg ctt act gcc atg ggc    2640
Thr Ser Asp Val Thr Gly Glu Lys Ala Glu Gly Leu Thr Ala Met Gly
865                 870                 875                 880 att ccc aac agc atc tcc ata tga                                    2664
Ile Pro Asn Ser Ile Ser Ile *
                885

<210> SEQ ID NO 28
<211> LENGTH: 892
<212> TYPE: PRT
<213> ORGANISM: Zea mays

<400> SEQUENCE: 28

Met Met Gln Gln Leu Arg His Ser Gln Pro Ser Pro Cys Leu Cys Gly
1               5                   10                  15

Leu Arg Ala Ala Arg Pro Met Leu Ala Leu Gly Ala Ala Ala Ser Arg
            20                  25                  30

Ser Arg Pro Ala Gly Lys Leu Gln Pro Ser Val Cys Leu Gly Leu Gly
        35                  40                  45

His Val Ala Pro Ala Ala Ala Arg Gly Gln Pro Arg Pro Arg Ala Val
    50                  55                  60

Ala Asp Ser Ala Leu Gly Ala Ser Pro Thr Ser Val His Val Gly Gly
65                  70                  75                  80

Lys Leu Leu Leu Gln Asn Phe Ala Ala Asp Ser Gln Gln Arg Leu Lys
                85                  90                  95

Leu Ser Ile Gln Leu Val Ser Ala Thr Val Ala Asp Pro Asp Gly Arg
            100                 105                 110

Gly Val Lys Ala Glu Ala Ser Val Leu Asp Ala Val Gly Ser Gly
        115                 120                 125

Asp Ser Glu Leu Asp Val Asp Leu Ile Trp Asp Glu Ala Leu Gly Ala
    130                 135                 140

Pro Gly Ala Val Val Lys Asn His Ser Asp Phe Pro Val Tyr Leu
145                 150                 155                 160

Arg Leu Leu Ser Val Pro Ala Gly Val Gly Gly Ala Asp Asp Glu Ala
                165                 170                 175

Ala Ala Val His Phe Ala Cys Asn Gly Trp Val Tyr Pro Val Asp Lys
            180                 185                 190

His Pro Tyr Arg Leu Phe Phe Thr Asn Asp Ala Cys Val Lys Glu Glu
        195                 200                 205

Thr Pro Ser Ala Leu Leu Lys Tyr Arg Glu Asp Glu Leu Gly Ala Leu
    210                 215                 220

Arg Gly Asp Gly Glu Thr Thr Glu Arg Pro Phe Gln Pro Trp Asp Arg
225                 230                 235                 240

Val Tyr Asp Tyr Ala Leu Tyr Asn Asp Leu Gly Asn Pro Asp Leu Arg
                245                 250                 255
```

-continued

Gln Asp Leu Ala Arg Pro Val Leu Gly Gly Ser Gln Glu Tyr Pro Tyr
                260                 265                 270

Pro Arg Arg Thr Lys Thr Gly Arg Pro Ala Ala Lys Thr Asp Pro Arg
                275                 280                 285

Ser Glu Ser Arg Ala Pro Leu Asp Glu Glu Ile Tyr Val Pro Cys Asp
                290                 295                 300

Glu Arg Val Gly Phe Ala Ser Ile Pro Ala Pro Thr Leu Pro Pro Leu
305                 310                 315                 320

Gly Gly His Phe Arg Ser Leu Ala Asp Val Tyr Arg Leu Phe Gly Leu
                325                 330                 335

Asp Asp Leu Gly Arg Leu Pro Glu Ala Lys Ala Val Ile Asn Ser Gly
                340                 345                 350

Ala Pro Phe Pro Val Val Pro Gln Val Ile Ser Val Asn Pro Thr His
                355                 360                 365

Trp Arg Lys Asp Glu Glu Phe Ala Arg Gln Met Ile Ala Gly Ala Asn
                370                 375                 380

Pro Val Cys Ile Lys Arg Val Thr Lys Phe Pro Leu Ala Ser Glu Leu
385                 390                 395                 400

Asp Arg Gly Val Phe Gly Asp Gln Asp Ser Lys Ile Thr Lys Asp His
                405                 410                 415

Val Glu Lys Asn Met Gly Met Thr Val Gln Gln Ala Val Glu Glu
                420                 425                 430

Gly Arg Leu Tyr Val Val Asp His His Asp Trp Val Met Pro Tyr Leu
                435                 440                 445

Lys Arg Ile Asn Glu Leu Pro Ala Ser Glu Glu Lys Ala Glu Val Ser
                450                 455                 460

Gln Arg Lys Val Tyr Ala Ala Arg Thr Leu Leu Phe Leu Asp Gly Glu
465                 470                 475                 480

Asp Ser Ser Met Leu Arg Pro Leu Ala Ile Glu Leu Ser Ser Pro His
                485                 490                 495

Pro Glu Lys Glu Gln Leu Gly Ala Val Ser Thr Val Tyr Thr Pro Pro
                500                 505                 510

Asp Ser Gly Asp Asp Gly Ile Thr Ala Gly Arg Phe Ser Thr Trp Glu
                515                 520                 525

Leu Ala Lys Val Tyr Ala Ser Ala Asn Asp Ala Ala Glu Asn Asn Phe
                530                 535                 540

Val Thr His Trp Leu Asn Thr His Ala Ser Met Glu Pro Ile Val Ile
545                 550                 555                 560

Ala Ala Asn Arg Gln Leu Ser Val Leu His Pro Ile His Arg Leu Leu
                565                 570                 575

Lys Pro His Phe Arg Lys Thr Leu His Ile Asn Ala Val Ala Arg Gln
                580                 585                 590

Ile Ile Val Gly Ser Gly Asp Gln Arg Lys Asp Gly Ser Val Phe Arg
                595                 600                 605

Gly Ile Asp Glu Val Thr Tyr Phe Pro Ser Lys Tyr Asn Met Glu Met
                610                 615                 620

Ser Ser Lys Ala Tyr Lys Ala Trp Asn Phe Thr Asp Leu Ala Leu Pro
625                 630                 635                 640

Asn Asp Leu Ile Lys Arg Gly Leu Ala Lys Gly Asp Pro Lys Lys Pro
                645                 650                 655

Glu Thr Val Glu Leu Ala Ile Lys Asp Tyr Pro Tyr Ala Val Asp Gly
                660                 665                 670

```
Leu Asp Met Trp Ala Ala Ile Lys Lys Trp Val Ala Asp Tyr Cys Ala
            675                 680                 685

Ile Tyr Tyr Ala Asp Asp Gly Ala Val Ala Arg Asp Ser Glu Leu Gln
        690                 695                 700

Gly Trp Trp Ser Glu Val Arg Asn Val Gly His Gly Asp Leu Ala Asp
705                 710                 715                 720

Ala Pro Trp Trp Pro Ala Met Asp Cys Val Ala Asp Leu Val Glu Thr
                725                 730                 735

Cys Ala Thr Val Val Trp Leu Ser Ser Ala Tyr His Ala Ser Ile Ser
            740                 745                 750

Phe Gly Gln Tyr Asp Tyr Leu Gly Phe Val Pro Asn Gly Pro Ser Ile
        755                 760                 765

Thr Thr Arg Pro Val Pro Gly Pro Asp Ala Gly Ala Glu Val Thr Glu
770                 775                 780

Ser Asp Phe Leu Ala Ser Val Thr Pro Val Thr Glu Ala Leu Gly Phe
785                 790                 795                 800

Met Ser Ile Ala Ser Gly Pro Met Gly Leu Lys Gly Thr Glu Val Tyr
            805                 810                 815

Leu Gly Gln Arg Pro Asp Thr Glu Gln Trp Thr Arg Glu Arg Arg Ala
        820                 825                 830

Ala Glu Ala Leu Ala Glu Phe Arg Ala Arg Leu Glu Glu Val Ala Gly
    835                 840                 845

Asn Ile Asp Arg Arg Asn Ala Asp Pro Ala Leu Lys Asn Arg Thr Gly
850                 855                 860

Gln Val Glu Val Pro Tyr Thr Leu Leu Lys Pro Thr Ala Gln Pro Gly
865                 870                 875                 880

Leu Val Leu Arg Gly Ile Pro Asn Ser Ile Thr Val
            885                 890

<210> SEQ ID NO 29
<211> LENGTH: 670
<212> TYPE: DNA
<213> ORGANISM: Zea mays
<220> FEATURE:
<221> NAME/KEY: CDS
<222> LOCATION: (1)...(670)
<223> OTHER INFORMATION: LOX7

<400> SEQUENCE: 29 gtg agc tcg ttc gcg tac cgg gag ctc tgg cgg ctc gac cag gag ggc      48
Val Ser Ser Phe Ala Tyr Arg Glu Leu Trp Arg Leu Asp Gln Glu Gly
  1               5                  10                  15 ctc ccc gcc gat ctc atc aga aga gga atg gcc gtg gag gac ccg acg      96
Leu Pro Ala Asp Leu Ile Arg Arg Gly Met Ala Val Glu Asp Pro Thr
             20                  25                  30 aag ccg cac ggt ctg cgg ctg ctc atc gag gac tac ccg tac gcc acc     144
Lys Pro His Gly Leu Arg Leu Leu Ile Glu Asp Tyr Pro Tyr Ala Thr
         35                  40                  45 gac ggg ctg ctc ctc tgg tcg gcc atc acg cgg tgg tgc ggc gcc tac     192
Asp Gly Leu Leu Leu Trp Ser Ala Ile Thr Arg Trp Cys Gly Ala Tyr
     50                  55                  60 gtg gcc acg tac tac ccg tcg gac gag tcg gtg cag gcc gac acc gag     240
Val Ala Thr Tyr Tyr Pro Ser Asp Glu Ser Val Gln Ala Asp Thr Glu
 65                  70                  75                  80 ctg cag tcg tgg tac acg gag gcg gtg cag acg ggg cac gcg gac aag     288
Leu Gln Ser Trp Tyr Thr Glu Ala Val Gln Thr Gly His Ala Asp Lys
                 85                  90                  95 cgc ggc gca ccg tgg tgg ccg cgc ctg acg acg ccc ggg gac ctg gcg     336
```

```
Arg Gly Ala Pro Trp Trp Pro Arg Leu Thr Thr Pro Gly Asp Leu Ala
            100                 105                 110 tcg ctg ctc acg acg ctg ctg tgg ctg acc tcg gcg cag cac gcg gcg      384
Ser Leu Leu Thr Thr Leu Leu Trp Leu Thr Ser Ala Gln His Ala Ala
            115                 120                 125 ctc aac ttc ggg cag tac ccg cta ggc ggc tac atc ccg aac cgg ccg      432
Leu Asn Phe Gly Gln Tyr Pro Leu Gly Gly Tyr Ile Pro Asn Arg Pro
    130                 135                 140 ccg ctg atg cgg cgg ctg gtg ccc gcc gag ggg gac ccg gag cac gcg      480
Pro Leu Met Arg Arg Leu Val Pro Ala Glu Gly Asp Pro Glu His Ala
145                 150                 155                 160 cac ctg gtg gcc gac ccg cac cgc tta ttc ctg tcg gcg ctg ccc ggc      528
His Leu Val Ala Asp Pro His Arg Leu Phe Leu Ser Ala Leu Pro Gly
                165                 170                 175 ctg acg cag gcc acc acg ttc atg acc gtc atc gac acg ctg tcc acg      576
Leu Thr Gln Ala Thr Thr Phe Met Thr Val Ile Asp Thr Leu Ser Thr
            180                 185                 190 cac tcc gcc gac gag cag tac ctc ggg gag cgc ccc gac gag gcg tgg      624
His Ser Ala Asp Glu Gln Tyr Leu Gly Glu Arg Pro Asp Glu Ala Trp
        195                 200                 205 acg gcc gac ccg gcc gcg ctg gcg gcc gct cta gag gat cca agc t        670
Thr Ala Asp Pro Ala Ala Leu Ala Ala Ala Leu Glu Asp Pro Ser
    210                 215                 220

<210> SEQ ID NO 30
<211> LENGTH: 223
<212> TYPE: PRT
<213> ORGANISM: Zea mays

<400> SEQUENCE: 30

Val Ser Ser Phe Ala Tyr Arg Glu Leu Trp Arg Leu Asp Gln Glu Gly
 1               5                  10                  15

Leu Pro Ala Asp Leu Ile Arg Arg Gly Met Ala Val Glu Asp Pro Thr
            20                  25                  30

Lys Pro His Gly Leu Arg Leu Leu Ile Glu Asp Tyr Pro Tyr Ala Thr
        35                  40                  45

Asp Gly Leu Leu Leu Trp Ser Ala Ile Thr Arg Trp Cys Gly Ala Tyr
    50                  55                  60

Val Ala Thr Tyr Tyr Pro Ser Asp Glu Ser Val Gln Ala Asp Thr Glu
65                  70                  75                  80

Leu Gln Ser Trp Tyr Thr Glu Ala Val Gln Thr Gly His Ala Asp Lys
                85                  90                  95

Arg Gly Ala Pro Trp Trp Pro Arg Leu Thr Thr Pro Gly Asp Leu Ala
            100                 105                 110

Ser Leu Leu Thr Thr Leu Leu Trp Leu Thr Ser Ala Gln His Ala Ala
        115                 120                 125

Leu Asn Phe Gly Gln Tyr Pro Leu Gly Gly Tyr Ile Pro Asn Arg Pro
    130                 135                 140

Pro Leu Met Arg Arg Leu Val Pro Ala Glu Gly Asp Pro Glu His Ala
145                 150                 155                 160

His Leu Val Ala Asp Pro His Arg Leu Phe Leu Ser Ala Leu Pro Gly
                165                 170                 175

Leu Thr Gln Ala Thr Thr Phe Met Thr Val Ile Asp Thr Leu Ser Thr
            180                 185                 190

His Ser Ala Asp Glu Gln Tyr Leu Gly Glu Arg Pro Asp Glu Ala Trp
        195                 200                 205

Thr Ala Asp Pro Ala Ala Leu Ala Ala Ala Leu Glu Asp Pro Ser
```

-continued

<210> SEQ ID NO 31
<211> LENGTH: 670
<212> TYPE: DNA
<213> ORGANISM: Zea mays
<220> FEATURE:
<221> NAME/KEY: CDS
<222> LOCATION: (1)...(670)

<400> SEQUENCE: 31

| | | | | | | | | | | | | | | | | |
|---|---|---|---|---|---|---|---|---|---|---|---|---|---|---|---|---|
| gtg | agc | tcg | ttc | gcg | tac | cgg | gag | ctc | tgg | cgg | ctc | gac | cag | gag | ggc | 48 |
| Val | Ser | Ser | Phe | Ala | Tyr | Arg | Glu | Leu | Trp | Arg | Leu | Asp | Gln | Glu | Gly | |
| 1 | | | | 5 | | | | | 10 | | | | | 15 | | |
| ctc | ccc | gcc | gat | ctc | atc | aga | aga | gga | atg | gcc | gtg | gag | gac | ccg | acg | 96 |
| Leu | Pro | Ala | Asp | Leu | Ile | Arg | Arg | Gly | Met | Ala | Val | Glu | Asp | Pro | Thr | |
| | | | 20 | | | | | 25 | | | | | 30 | | | |
| aag | ccg | cac | ggt | ctg | cgg | ctg | ctc | atc | gag | gac | tac | ccg | tac | gcc | acc | 144 |
| Lys | Pro | His | Gly | Leu | Arg | Leu | Leu | Ile | Glu | Asp | Tyr | Pro | Tyr | Ala | Thr | |
| | | 35 | | | | | 40 | | | | | 45 | | | | |
| gac | ggg | ctg | ctc | ctc | tgg | tcg | gcc | atc | acg | cgg | tgg | tgc | ggc | gcc | tac | 192 |
| Asp | Gly | Leu | Leu | Leu | Trp | Ser | Ala | Ile | Thr | Arg | Trp | Cys | Gly | Ala | Tyr | |
| | 50 | | | | | 55 | | | | | 60 | | | | | |
| gtg | gcc | acg | tac | tac | ccg | tcg | gac | gag | tcg | gtg | cag | gcc | gac | acc | gag | 240 |
| Val | Ala | Thr | Tyr | Tyr | Pro | Ser | Asp | Glu | Ser | Val | Gln | Ala | Asp | Thr | Glu | |
| 65 | | | | | 70 | | | | | 75 | | | | | 80 | |
| ctg | cag | tcg | tgg | tac | acg | gag | gcg | gtg | cag | acg | ggg | cac | gcg | gac | aag | 288 |
| Leu | Gln | Ser | Trp | Tyr | Thr | Glu | Ala | Val | Gln | Thr | Gly | His | Ala | Asp | Lys | |
| | | | | 85 | | | | | 90 | | | | | 95 | | |
| cgc | ggc | gca | ccg | tgg | tgg | ccg | cgc | ctg | acg | acg | ccc | ggg | gac | ctg | gcg | 336 |
| Arg | Gly | Ala | Pro | Trp | Trp | Pro | Arg | Leu | Thr | Thr | Pro | Gly | Asp | Leu | Ala | |
| | | | 100 | | | | | 105 | | | | | 110 | | | |
| tcg | ctg | ctc | acg | acg | ctg | ctg | tgg | ctg | acc | tcg | gcg | cag | cac | gcg | gcg | 384 |
| Ser | Leu | Leu | Thr | Thr | Leu | Leu | Trp | Leu | Thr | Ser | Ala | Gln | His | Ala | Ala | |
| | | 115 | | | | | 120 | | | | | 125 | | | | |
| ctc | aac | ttc | ggg | cag | tac | ccg | cta | ggc | ggc | tac | atc | ccg | aac | cgg | ccg | 432 |
| Leu | Asn | Phe | Gly | Gln | Tyr | Pro | Leu | Gly | Gly | Tyr | Ile | Pro | Asn | Arg | Pro | |
| | 130 | | | | | 135 | | | | | 140 | | | | | |
| ccg | ctg | atg | cgg | cgg | ctg | gtg | ccc | gcc | gag | ggg | gac | ccg | gag | cac | gcg | 480 |
| Pro | Leu | Met | Arg | Arg | Leu | Val | Pro | Ala | Glu | Gly | Asp | Pro | Glu | His | Ala | |
| 145 | | | | | 150 | | | | | 155 | | | | | 160 | |
| cac | ctg | gtg | gcc | gac | ccg | cac | cgc | tta | ttc | ctg | tcg | gcg | ctg | ccc | ggc | 528 |
| His | Leu | Val | Ala | Asp | Pro | His | Arg | Leu | Phe | Leu | Ser | Ala | Leu | Pro | Gly | |
| | | | | 165 | | | | | 170 | | | | | 175 | | |
| ctg | acg | cag | gcc | acc | acg | ttc | atg | acc | gtc | atc | gac | acg | ctg | tcc | acg | 576 |
| Leu | Thr | Gln | Ala | Thr | Thr | Phe | Met | Thr | Val | Ile | Asp | Thr | Leu | Ser | Thr | |
| | | | 180 | | | | | 185 | | | | | 190 | | | |
| cac | tcc | gcc | gac | gag | cag | tac | ctc | ggg | gag | cgc | ccc | gac | gag | gcg | tgg | 624 |
| His | Ser | Ala | Asp | Glu | Gln | Tyr | Leu | Gly | Glu | Arg | Pro | Asp | Glu | Ala | Trp | |
| | | 195 | | | | | 200 | | | | | 205 | | | | |
| acg | gcc | gac | ccg | gcc | gcg | ctg | gcg | gcc | gct | cta | gag | gat | cca | agc | t | 670 |
| Thr | Ala | Asp | Pro | Ala | Ala | Leu | Ala | Ala | Ala | Leu | Glu | Asp | Pro | Ser | | |
| | 210 | | | | | 215 | | | | | 220 | | | | | |

<210> SEQ ID NO 32
<211> LENGTH: 223
<212> TYPE: PRT
<213> ORGANISM: Zea mays

<400> SEQUENCE: 32

| | | | | | | | | | | | | | | | |
|---|---|---|---|---|---|---|---|---|---|---|---|---|---|---|---|
| Val | Ser | Ser | Phe | Ala | Tyr | Arg | Glu | Leu | Trp | Arg | Leu | Asp | Gln | Glu | Gly |
| 1 | | | | 5 | | | | | 10 | | | | | 15 | |

```
Leu Pro Ala Asp Leu Ile Arg Arg Gly Met Ala Val Glu Asp Pro Thr
             20                  25                  30

Lys Pro His Gly Leu Arg Leu Leu Ile Glu Asp Tyr Pro Tyr Ala Thr
         35                  40                  45

Asp Gly Leu Leu Leu Trp Ser Ala Ile Thr Arg Trp Cys Gly Ala Tyr
     50                  55                  60

Val Ala Thr Tyr Tyr Pro Ser Asp Glu Ser Val Gln Ala Asp Thr Glu
 65                  70                  75                  80

Leu Gln Ser Trp Tyr Thr Glu Ala Val Gln Thr Gly His Ala Asp Lys
                 85                  90                  95

Arg Gly Ala Pro Trp Trp Pro Arg Leu Thr Thr Pro Gly Asp Leu Ala
            100                 105                 110

Ser Leu Leu Thr Thr Leu Leu Trp Leu Thr Ser Ala Gln His Ala Ala
            115                 120                 125

Leu Asn Phe Gly Gln Tyr Pro Leu Gly Gly Tyr Ile Pro Asn Arg Pro
        130                 135                 140

Pro Leu Met Arg Arg Leu Val Pro Ala Glu Gly Asp Pro Glu His Ala
145                 150                 155                 160

His Leu Val Ala Asp Pro His Arg Leu Phe Leu Ser Ala Leu Pro Gly
                165                 170                 175

Leu Thr Gln Ala Thr Thr Phe Met Thr Val Ile Asp Thr Leu Ser Thr
            180                 185                 190

His Ser Ala Asp Glu Gln Tyr Leu Gly Glu Arg Pro Asp Glu Ala Trp
        195                 200                 205

Thr Ala Asp Pro Ala Ala Leu Ala Ala Leu Glu Asp Pro Ser
    210                 215                 220

<210> SEQ ID NO 33
<211> LENGTH: 140
<212> TYPE: DNA
<213> ORGANISM: Zea mays
<220> FEATURE:
<221> NAME/KEY: CDS
<222> LOCATION: (1)...(140)
<223> OTHER INFORMATION: LOX8

<400> SEQUENCE: 33 tat gta cct cag gat gag gcg ttt gag gag ctg aag caa ggc gcc ttc      48
Tyr Val Pro Gln Asp Glu Ala Phe Glu Glu Leu Lys Gln Gly Ala Phe
 1               5                  10                  15 tca tca cgg agg ctg cga gca gta ctt cac acg ctt atc cca tcg atg      96
Ser Ser Arg Arg Leu Arg Ala Val Leu His Thr Leu Ile Pro Ser Met
             20                  25                  30 att gca acc atg tca gct gag acc cat ggc ttc caa ggc ttc ca          140
Ile Ala Thr Met Ser Ala Glu Thr His Gly Phe Gln Gly Phe
         35                  40                  45

<210> SEQ ID NO 34
<211> LENGTH: 46
<212> TYPE: PRT
<213> ORGANISM: Zea mays

<400> SEQUENCE: 34

Tyr Val Pro Gln Asp Glu Ala Phe Glu Glu Leu Lys Gln Gly Ala Phe
 1               5                  10                  15

Ser Ser Arg Arg Leu Arg Ala Val Leu His Thr Leu Ile Pro Ser Met
             20                  25                  30

Ile Ala Thr Met Ser Ala Glu Thr His Gly Phe Gln Gly Phe
```

```
<210> SEQ ID NO 35
<211> LENGTH: 140
<212> TYPE: DNA
<213> ORGANISM: Zea mays
<220> FEATURE:
<221> NAME/KEY: CDS
<222> LOCATION: (1)...(140)

<400> SEQUENCE: 35 tat gta cct cag gat gag gcg ttt gag gag ctg aag caa ggc gcc ttc      48
Tyr Val Pro Gln Asp Glu Ala Phe Glu Glu Leu Lys Gln Gly Ala Phe
 1               5                  10                  15 tca tca cgg agg ctg cga gca gta ctt cac acg ctt atc cca tcg atg      96
Ser Ser Arg Arg Leu Arg Ala Val Leu His Thr Leu Ile Pro Ser Met
            20                  25                  30 att gca acc atg tca gct gag acc cat ggc ttc caa ggc ttc ca          140
Ile Ala Thr Met Ser Ala Glu Thr His Gly Phe Gln Gly Phe
        35                  40                  45

<210> SEQ ID NO 36
<211> LENGTH: 46
<212> TYPE: PRT
<213> ORGANISM: Zea mays

<400> SEQUENCE: 36

Tyr Val Pro Gln Asp Glu Ala Phe Glu Glu Leu Lys Gln Gly Ala Phe
 1               5                  10                  15

Ser Ser Arg Arg Leu Arg Ala Val Leu His Thr Leu Ile Pro Ser Met
            20                  25                  30

Ile Ala Thr Met Ser Ala Glu Thr His Gly Phe Gln Gly Phe
        35                  40                  45

<210> SEQ ID NO 37
<211> LENGTH: 1803
<212> TYPE: DNA
<213> ORGANISM: Zea mays
<220> FEATURE:
<221> NAME/KEY: CDS
<222> LOCATION: (1)...(1632)
<223> OTHER INFORMATION: LOX9

<400> SEQUENCE: 37 cgc ctg aag cag gcc ctg cag gac cag ctg ttc cag aag atc ccc ttc      48
Arg Leu Lys Gln Ala Leu Gln Asp Gln Leu Phe Gln Lys Ile Pro Phe
 1               5                  10                  15 gtg cgc aag atc cag gag aac agc gag ggc ctc ctc cgc tac gac act      96
Val Arg Lys Ile Gln Glu Asn Ser Glu Gly Leu Leu Arg Tyr Asp Thr
            20                  25                  30 ccc gac atc atc aag aag gac aag ttt gct tgg ctg cgg gac gac gag     144
Pro Asp Ile Ile Lys Lys Asp Lys Phe Ala Trp Leu Arg Asp Asp Glu
        35                  40                  45 ttc gcg agg cag gcg ctg gct ggc atc aac ccc gtc aac atc gaa cgt     192
Phe Ala Arg Gln Ala Leu Ala Gly Ile Asn Pro Val Asn Ile Glu Arg
    50                  55                  60 ctt cag gcg ttc ccg ccg atg agc aag ctg gac ccg gcc gtg tac ggc     240
Leu Gln Ala Phe Pro Pro Met Ser Lys Leu Asp Pro Ala Val Tyr Gly
65                  70                  75                  80 ccg ccg gag tcg gcc atc acg gag gag cac atc atc gga cag ctc gac     288
Pro Pro Glu Ser Ala Ile Thr Glu Glu His Ile Ile Gly Gln Leu Asp
                85                  90                  95 ggc atg tcg gtg cag cag gcg ctg cag gac gac agg ctg tac atg ctg     336
```

```
                                                                                                -continued Gly Met Ser Val Gln Gln Ala Leu Gln Asp Asp Arg Leu Tyr Met Leu
            100                 105                 110 gac tac cac gac atc ttc atg ccg ttc ctg gac cgg atc aac gcg ctg        384
Asp Tyr His Asp Ile Phe Met Pro Phe Leu Asp Arg Ile Asn Ala Leu
            115                 120                 125 gac ggg cgg aag gcc tac ggc acg cgc acg ctc ttc ttc ctg acg gcc        432
Asp Gly Arg Lys Ala Tyr Gly Thr Arg Thr Leu Phe Phe Leu Thr Ala
130             135                 140 gcg ggc acg ctg aag ccc atc gcg atc gag ctg tgc ctg ccg ccg atg        480
Ala Gly Thr Leu Lys Pro Ile Ala Ile Glu Leu Cys Leu Pro Pro Met
145             150                 155                 160 acc gac ggg tgc gcg cgc gcc aag cgg gtg ttc acg ccg ccc gcc gat        528
Thr Asp Gly Cys Ala Arg Ala Lys Arg Val Phe Thr Pro Pro Ala Asp
                165                 170                 175 gcc acc agc aac tgg ctg tgg cag ctc gcc aag gca cac gtc tgc tcc        576
Ala Thr Ser Asn Trp Leu Trp Gln Leu Ala Lys Ala His Val Cys Ser
                180                 185                 190 aat gac gcc ggc gtc cac cag ctc atc aac cac tgg ctg agg acg cac        624
Asn Asp Ala Gly Val His Gln Leu Ile Asn His Trp Leu Arg Thr His
                195                 200                 205 gcg gcc atg gag ccg ttc atc atc gcg gcg cac cgg cac ctg agc acg        672
Ala Ala Met Glu Pro Phe Ile Ile Ala Ala His Arg His Leu Ser Thr
210                 215                 220 atg cac ccc atc ttc aag ctg ctc aag cct cac atg cgg tac acg ctc        720
Met His Pro Ile Phe Lys Leu Leu Lys Pro His Met Arg Tyr Thr Leu
225             230                 235                 240 aag atc aac gcg ctg gcg cgg cag atc ctc atc aac ggc gac ggc gtc        768
Lys Ile Asn Ala Leu Ala Arg Gln Ile Leu Ile Asn Gly Asp Gly Val
                245                 250                 255 atc gag tcc ggg ttc acc cct ggc cgc tac tgc atg gag atg agc tcg        816
Ile Glu Ser Gly Phe Thr Pro Gly Arg Tyr Cys Met Glu Met Ser Ser
                260                 265                 270 ttc gcg tac cgg gag ctc tgg cgg cta gac cag gag ggc ctc cct gcc        864
Phe Ala Tyr Arg Glu Leu Trp Arg Leu Asp Gln Glu Gly Leu Pro Ala
                275                 280                 285 gat ctc atc aga aga gga atg gcc gtg gag gac ccg acg cag ccg cac        912
Asp Leu Ile Arg Arg Gly Met Ala Val Glu Asp Pro Thr Gln Pro His
290                 295                 300 ggt ctc cgg ctg ctc atc gag gac tac ccg tac gcc acc gac ggg ttg        960
Gly Leu Arg Leu Leu Ile Glu Asp Tyr Pro Tyr Ala Thr Asp Gly Leu
305             310                 315                 320 ctg ctc tgg tcg gcc atc agg cgg tgg tgc gac gcc tac gtg gcc atg       1008
Leu Leu Trp Ser Ala Ile Arg Arg Trp Cys Asp Ala Tyr Val Ala Met
                325                 330                 335 tac tac ccg tcc gac gag tcc gtg cag ggc gac acc gag ctg cag tcg       1056
Tyr Tyr Pro Ser Asp Glu Ser Val Gln Gly Asp Thr Glu Leu Gln Ser
                340                 345                 350 tgg tac agg gag gcc gtg cac acg ggg cac gcg gac aag cgc gac gcg       1104
Trp Tyr Arg Glu Ala Val His Thr Gly His Ala Asp Lys Arg Asp Ala
                355                 360                 365 ccg tgg tgg ccg cgc ctg tcg acg ccc gcg gac ctg gcg tcg ctg ctg       1152
Pro Trp Trp Pro Arg Leu Ser Thr Pro Ala Asp Leu Ala Ser Leu Leu
370                 375                 380 acg acg ctg ctg tgg ctc acc tcg gcg cag cac gcg gcg ctc aac ttc       1200
Thr Thr Leu Leu Trp Leu Thr Ser Ala Gln His Ala Ala Leu Asn Phe
385                 390                 395                 400 ggg cag tac ccg ctg ggc ggc tac atc ccg aac cgg ccg ccg ctg atg       1248
Gly Gln Tyr Pro Leu Gly Gly Tyr Ile Pro Asn Arg Pro Pro Leu Met
                405                 410                 415
```

-continued

```
cgg cgg ctg gtg ccc gcc gag ggc gac ccg gag tac gcg cac ctg gtg      1296
Arg Arg Leu Val Pro Ala Glu Gly Asp Pro Glu Tyr Ala His Leu Val
        420                 425                 430 gcc gac ccg cac cgc ttc ttc ctg tcg gcg ctg ccc agc ctg acg cag      1344
Ala Asp Pro His Arg Phe Phe Leu Ser Ala Leu Pro Ser Leu Thr Gln
435                 440                 445 acc acc acg ttc atg acc gtc atc gac acg ctg tcc acg cac tcc gcc      1392
Thr Thr Thr Phe Met Thr Val Ile Asp Thr Leu Ser Thr His Ser Ala
    450                 455                 460 gac gag cag tac ctc ggg gag cgg cct gat gag gcg tgg acg gcc gac      1440
Asp Glu Gln Tyr Leu Gly Glu Arg Pro Asp Glu Ala Trp Thr Ala Asp
465                 470                 475                 480 ccg gcg gcg ttg gcg gcc gcg cgc gag ttc gcg gac gag gtg cgc cgc      1488
Pro Ala Ala Leu Ala Ala Ala Arg Glu Phe Ala Asp Glu Val Arg Arg
                485                 490                 495 gcc gag gag gag atc gaa cgg cgc aac gct gac act ggc cgc cgc aac      1536
Ala Glu Glu Glu Ile Glu Arg Arg Asn Ala Asp Thr Gly Arg Arg Asn
            500                 505                 510 cgg tgc ggc gct ggc gtg ctg ccg tac gag ctc atg gcg ccc aca tcg      1584
Arg Cys Gly Ala Gly Val Leu Pro Tyr Glu Leu Met Ala Pro Thr Ser
        515                 520                 525 ggg ccg ggc atc acc tgc cgc ggc gtc ccc aac agc gtt acc att tag      1632
Gly Pro Gly Ile Thr Cys Arg Gly Val Pro Asn Ser Val Thr Ile *
530                 535                 540 cctctcagta ccgacagaca gccatgggcg catgacagag atgatctgaa aggagatttt   1692
ttttccactc attatagtcg ggtggggaga atctaagca gaagcaaatg aattctgcat    1752
tatttctccc cccatttcca aattgccatt gatttggtgg tccgaaacaa g            1803
```

<210> SEQ ID NO 38
<211> LENGTH: 543
<212> TYPE: PRT
<213> ORGANISM: Zea mays

<400> SEQUENCE: 38

```
Arg Leu Lys Gln Ala Leu Gln Asp Gln Leu Phe Gln Lys Ile Pro Phe
1               5                   10                  15

Val Arg Lys Ile Gln Glu Asn Ser Glu Gly Leu Leu Arg Tyr Asp Thr
            20                  25                  30

Pro Asp Ile Ile Lys Lys Asp Lys Phe Ala Trp Leu Arg Asp Asp Glu
        35                  40                  45

Phe Ala Arg Gln Ala Leu Ala Gly Ile Asn Pro Val Asn Ile Glu Arg
    50                  55                  60

Leu Gln Ala Phe Pro Pro Met Ser Lys Leu Asp Pro Ala Val Tyr Gly
65                  70                  75                  80

Pro Pro Glu Ser Ala Ile Thr Glu Glu His Ile Ile Gly Gln Leu Asp
                85                  90                  95

Gly Met Ser Val Gln Gln Ala Leu Gln Asp Asp Arg Leu Tyr Met Leu
            100                 105                 110

Asp Tyr His Asp Ile Phe Met Pro Phe Leu Asp Arg Ile Asn Ala Leu
        115                 120                 125

Asp Gly Arg Lys Ala Tyr Gly Thr Arg Thr Leu Phe Phe Leu Thr Ala
    130                 135                 140

Ala Gly Thr Leu Lys Pro Ile Ala Ile Glu Leu Cys Leu Pro Pro Met
145                 150                 155                 160

Thr Asp Gly Cys Ala Arg Ala Lys Arg Val Phe Thr Pro Pro Ala Asp
                165                 170                 175
```

```
Ala Thr Ser Asn Trp Leu Trp Gln Leu Ala Lys Ala His Val Cys Ser
            180                 185                 190

Asn Asp Ala Gly Val His Gln Leu Ile Asn His Trp Leu Arg Thr His
            195                 200                 205

Ala Ala Met Glu Pro Phe Ile Ile Ala Ala His Arg His Leu Ser Thr
            210                 215                 220

Met His Pro Ile Phe Lys Leu Leu Lys Pro His Met Arg Tyr Thr Leu
225                 230                 235                 240

Lys Ile Asn Ala Leu Ala Arg Gln Ile Leu Ile Asn Gly Asp Gly Val
                245                 250                 255

Ile Glu Ser Gly Phe Thr Pro Gly Arg Tyr Cys Met Glu Met Ser Ser
            260                 265                 270

Phe Ala Tyr Arg Glu Leu Trp Arg Leu Asp Gln Glu Gly Leu Pro Ala
            275                 280                 285

Asp Leu Ile Arg Arg Gly Met Ala Val Glu Asp Pro Thr Gln Pro His
            290                 295                 300

Gly Leu Arg Leu Leu Ile Glu Asp Tyr Pro Tyr Ala Thr Asp Gly Leu
305                 310                 315                 320

Leu Leu Trp Ser Ala Ile Arg Arg Trp Cys Asp Ala Tyr Val Ala Met
                325                 330                 335

Tyr Tyr Pro Ser Asp Glu Ser Val Gln Gly Asp Thr Glu Leu Gln Ser
            340                 345                 350

Trp Tyr Arg Glu Ala Val His Thr Gly His Ala Asp Lys Arg Asp Ala
            355                 360                 365

Pro Trp Trp Pro Arg Leu Ser Thr Pro Ala Asp Leu Ala Ser Leu Leu
            370                 375                 380

Thr Thr Leu Leu Trp Leu Thr Ser Ala Gln His Ala Ala Leu Asn Phe
385                 390                 395                 400

Gly Gln Tyr Pro Leu Gly Gly Tyr Ile Pro Asn Arg Pro Leu Met
                405                 410                 415

Arg Arg Leu Val Pro Ala Glu Gly Asp Pro Glu Tyr Ala His Leu Val
            420                 425                 430

Ala Asp Pro His Arg Phe Phe Leu Ser Ala Leu Pro Ser Leu Thr Gln
            435                 440                 445

Thr Thr Thr Phe Met Thr Val Ile Asp Thr Leu Ser Thr His Ser Ala
            450                 455                 460

Asp Glu Gln Tyr Leu Gly Glu Arg Pro Asp Glu Ala Trp Thr Ala Asp
465                 470                 475                 480

Pro Ala Ala Leu Ala Ala Arg Glu Phe Ala Asp Glu Val Arg Arg
                485                 490                 495

Ala Glu Glu Glu Ile Glu Arg Arg Asn Ala Asp Thr Gly Arg Arg Asn
            500                 505                 510

Arg Cys Gly Ala Gly Val Leu Pro Tyr Glu Leu Met Ala Pro Thr Ser
            515                 520                 525

Gly Pro Gly Ile Thr Cys Arg Gly Val Pro Asn Ser Val Thr Ile
            530                 535                 540

<210> SEQ ID NO 39
<211> LENGTH: 1632
<212> TYPE: DNA
<213> ORGANISM: Zea mays
<220> FEATURE:
<221> NAME/KEY: CDS
<222> LOCATION: (1)...(1632)

<400> SEQUENCE: 39
```

-continued

| | |
|---|---|
| cgc ctg aag cag gcc ctg cag gac cag ctg ttc cag aag atc ccc ttc<br>Arg Leu Lys Gln Ala Leu Gln Asp Gln Leu Phe Gln Lys Ile Pro Phe<br>1                  5                  10                15 | 48 |
| gtg cgc aag atc cag gag aac agc gag ggc ctc ctc cgc tac gac act<br>Val Arg Lys Ile Gln Glu Asn Ser Glu Gly Leu Leu Arg Tyr Asp Thr<br>            20                  25                  30 | 96 |
| ccc gac atc atc aag aag gac aag ttt gct tgg ctg cgg gac gac gag<br>Pro Asp Ile Ile Lys Lys Asp Lys Phe Ala Trp Leu Arg Asp Asp Glu<br>35                  40                  45 | 144 |
| ttc gcg agg cag gcg ctg gct ggc atc aac ccc gtc aac atc gaa cgt<br>Phe Ala Arg Gln Ala Leu Ala Gly Ile Asn Pro Val Asn Ile Glu Arg<br>50                  55                  60 | 192 |
| ctt cag gcg ttc ccg ccg atg agc aag ctg gac ccg gcc gtg tac ggc<br>Leu Gln Ala Phe Pro Pro Met Ser Lys Leu Asp Pro Ala Val Tyr Gly<br>65                  70                  75                80 | 240 |
| ccg ccg gag tcg gcc atc acg gag gag cac atc atc gga cag ctc gac<br>Pro Pro Glu Ser Ala Ile Thr Glu Glu His Ile Ile Gly Gln Leu Asp<br>            85                  90                  95 | 288 |
| ggc atg tcg gtg cag cag gcg ctg cag gac gac agg ctg tac atg ctg<br>Gly Met Ser Val Gln Gln Ala Leu Gln Asp Asp Arg Leu Tyr Met Leu<br>            100                105               110 | 336 |
| gac tac cac gac atc ttc atg ccg ttc ctg gac cgg atc aac gcg ctg<br>Asp Tyr His Asp Ile Phe Met Pro Phe Leu Asp Arg Ile Asn Ala Leu<br>            115                120               125 | 384 |
| gac ggg cgg aag gcc tac ggc acg cgc acg ctc ttc ttc ctg acg gcc<br>Asp Gly Arg Lys Ala Tyr Gly Thr Arg Thr Leu Phe Phe Leu Thr Ala<br>130                 135               140 | 432 |
| gcg ggc acg ctg aag ccc atc gcg atc gag ctg tgc ctg ccg ccg atg<br>Ala Gly Thr Leu Lys Pro Ile Ala Ile Glu Leu Cys Leu Pro Pro Met<br>145                 150               155               160 | 480 |
| acc gac ggg tgc gcg cgc gcc aag cgg gtg ttc acg ccg ccc gcc gat<br>Thr Asp Gly Cys Ala Arg Ala Lys Arg Val Phe Thr Pro Pro Ala Asp<br>                165               170               175 | 528 |
| gcc acc agc aac tgg ctg tgg cag ctc gcc aag gca cac gtc tgc tcc<br>Ala Thr Ser Asn Trp Leu Trp Gln Leu Ala Lys Ala His Val Cys Ser<br>            180                185               190 | 576 |
| aat gac gcc ggc gtc cac cag ctc atc aac cac tgg ctg agg acg cac<br>Asn Asp Ala Gly Val His Gln Leu Ile Asn His Trp Leu Arg Thr His<br>            195                200               205 | 624 |
| gcg gcc atg gag ccg ttc atc atc gcg gcg cac cgg cac ctg agc acg<br>Ala Ala Met Glu Pro Phe Ile Ile Ala Ala His Arg His Leu Ser Thr<br>210                 215               220 | 672 |
| atg cac ccc atc ttc aag ctg ctc aag cct cac atg cgg tac acg ctc<br>Met His Pro Ile Phe Lys Leu Leu Lys Pro His Met Arg Tyr Thr Leu<br>225                 230               235               240 | 720 |
| aag atc aac gcg ctg gcg cgg cag atc ctc atc aac ggc gac ggc gtc<br>Lys Ile Asn Ala Leu Ala Arg Gln Ile Leu Ile Asn Gly Asp Gly Val<br>            245                250               255 | 768 |
| atc gag tcc ggg ttc acc cct ggc cgc tac tgc atg gag atg agc tcg<br>Ile Glu Ser Gly Phe Thr Pro Gly Arg Tyr Cys Met Glu Met Ser Ser<br>            260                265               270 | 816 |
| ttc gcg tac cgg gag ctc tgg cgg cta gac cag gag ggc ctc cct gcc<br>Phe Ala Tyr Arg Glu Leu Trp Arg Leu Asp Gln Glu Gly Leu Pro Ala<br>275                 280               285 | 864 |
| gat ctc atc aga aga gga atg gcc gtg gag gac ccg acg cag ccg cac<br>Asp Leu Ile Arg Arg Gly Met Ala Val Glu Asp Pro Thr Gln Pro His<br>290                 295               300 | 912 |
| ggt ctc cgg ctg ctc atc gag gac tac ccg tac gcc acc gac ggg ttg<br>Gly Leu Arg Leu Leu Ile Glu Asp Tyr Pro Tyr Ala Thr Asp Gly Leu | 960 |

```
ctg ctc tgg tcg gcc atc agg cgg tgg tgc gac gcc tac gtg gcc atg    1008
Leu Leu Trp Ser Ala Ile Arg Arg Trp Cys Asp Ala Tyr Val Ala Met
            325                 330                 335 tac tac ccg tcc gac gag tcc gtg cag ggc gac acc gag ctg cag tcg    1056
Tyr Tyr Pro Ser Asp Glu Ser Val Gln Gly Asp Thr Glu Leu Gln Ser
        340                 345                 350 tgg tac agg gag gcc gtg cac acg ggc cac gcg gac aag cgc gac gcg    1104
Trp Tyr Arg Glu Ala Val His Thr Gly His Ala Asp Lys Arg Asp Ala
    355                 360                 365 ccg tgg tgg ccg cgc ctg tcg acg ccc gcg gac ctg gcg tcg ctg ctg    1152
Pro Trp Trp Pro Arg Leu Ser Thr Pro Ala Asp Leu Ala Ser Leu Leu
370                 375                 380 acg acg ctg ctg tgg ctc acc tcg gcg cag cac gcg gcg ctc aac ttc    1200
Thr Thr Leu Leu Trp Leu Thr Ser Ala Gln His Ala Ala Leu Asn Phe
385                 390                 395                 400 ggg cag tac ccg ctg ggc ggc tac atc ccg aac cgg ccg ccg ctg atg    1248
Gly Gln Tyr Pro Leu Gly Gly Tyr Ile Pro Asn Arg Pro Pro Leu Met
                405                 410                 415 cgg cgg ctg gtg ccc gcc gag ggc gac ccg gag tac gcg cac ctg gtg    1296
Arg Arg Leu Val Pro Ala Glu Gly Asp Pro Glu Tyr Ala His Leu Val
            420                 425                 430 gcc gac ccg cac cgc ttc ttc ctg tcg gcg ctg ccc agc ctg acg cag    1344
Ala Asp Pro His Arg Phe Phe Leu Ser Ala Leu Pro Ser Leu Thr Gln
        435                 440                 445 acc acc acg ttc atg acc gtc atc gac acg ctg tcc acg cac tcc gcc    1392
Thr Thr Thr Phe Met Thr Val Ile Asp Thr Leu Ser Thr His Ser Ala
    450                 455                 460 gac gag cag tac ctc ggg gag cgg cct gat gag gcg tgg acg gcc gac    1440
Asp Glu Gln Tyr Leu Gly Glu Arg Pro Asp Glu Ala Trp Thr Ala Asp
465                 470                 475                 480 ccg gcg gcg ttg gcg gcc gcg cgc gag ttc gcg gac gag gtg cgc cgc    1488
Pro Ala Ala Leu Ala Ala Ala Arg Glu Phe Ala Asp Glu Val Arg Arg
                485                 490                 495 gcc gag gag gag atc gaa cgg cgc aac gct gac act ggc cgc cgc aac    1536
Ala Glu Glu Glu Ile Glu Arg Arg Asn Ala Asp Thr Gly Arg Arg Asn
            500                 505                 510 cgg tgc ggc gct ggc gtg ctg ccg tac gag ctc atg gcg ccc aca tcg    1584
Arg Cys Gly Ala Gly Val Leu Pro Tyr Glu Leu Met Ala Pro Thr Ser
        515                 520                 525 ggg ccg ggc atc acc tgc cgc ggc gtc ccc aac agc gtt acc att tag    1632
Gly Pro Gly Ile Thr Cys Arg Gly Val Pro Asn Ser Val Thr Ile *
    530                 535                 540
```

<210> SEQ ID NO 40
<211> LENGTH: 543
<212> TYPE: PRT
<213> ORGANISM: Zea mays

<400> SEQUENCE: 40

```
Arg Leu Lys Gln Ala Leu Gln Asp Gln Leu Phe Gln Lys Ile Pro Phe
1               5                   10                  15

Val Arg Lys Ile Gln Glu Asn Ser Glu Gly Leu Leu Arg Tyr Asp Thr
            20                  25                  30

Pro Asp Ile Ile Lys Lys Asp Lys Phe Ala Trp Leu Arg Asp Asp Glu
        35                  40                  45

Phe Ala Arg Gln Ala Leu Ala Gly Ile Asn Pro Val Asn Ile Glu Arg
    50                  55                  60

Leu Gln Ala Phe Pro Pro Met Ser Lys Leu Asp Pro Ala Val Tyr Gly
```

```
            65                  70                  75                  80
Pro Pro Glu Ser Ala Ile Thr Glu Glu His Ile Ile Gly Gln Leu Asp
                    85                  90                  95
Gly Met Ser Val Gln Gln Ala Leu Gln Asp Asp Arg Leu Tyr Met Leu
                100                 105                 110
Asp Tyr His Asp Ile Phe Met Pro Phe Leu Asp Arg Ile Asn Ala Leu
            115                 120                 125
Asp Gly Arg Lys Ala Tyr Gly Thr Arg Thr Leu Phe Phe Leu Thr Ala
        130                 135                 140
Ala Gly Thr Leu Lys Pro Ile Ala Ile Glu Leu Cys Leu Pro Pro Met
145                 150                 155                 160
Thr Asp Gly Cys Ala Arg Ala Lys Arg Val Phe Thr Pro Pro Ala Asp
                165                 170                 175
Ala Thr Ser Asn Trp Leu Trp Gln Leu Ala Lys Ala His Val Cys Ser
                180                 185                 190
Asn Asp Ala Gly Val His Gln Leu Ile Asn His Trp Leu Arg Thr His
            195                 200                 205
Ala Ala Met Glu Pro Phe Ile Ile Ala Ala His Arg His Leu Ser Thr
        210                 215                 220
Met His Pro Ile Phe Lys Leu Leu Lys Pro His Met Arg Tyr Thr Leu
225                 230                 235                 240
Lys Ile Asn Ala Leu Ala Arg Gln Ile Leu Ile Asn Gly Asp Gly Val
                245                 250                 255
Ile Glu Ser Gly Phe Thr Pro Gly Arg Tyr Cys Met Glu Met Ser Ser
                260                 265                 270
Phe Ala Tyr Arg Glu Leu Trp Arg Leu Asp Gln Glu Gly Leu Pro Ala
            275                 280                 285
Asp Leu Ile Arg Arg Gly Met Ala Val Glu Asp Pro Thr Gln Pro His
        290                 295                 300
Gly Leu Arg Leu Leu Ile Glu Asp Tyr Pro Tyr Ala Thr Asp Gly Leu
305                 310                 315                 320
Leu Leu Trp Ser Ala Ile Arg Arg Trp Cys Asp Ala Tyr Val Ala Met
                325                 330                 335
Tyr Tyr Pro Ser Asp Glu Ser Val Gln Gly Asp Thr Glu Leu Gln Ser
                340                 345                 350
Trp Tyr Arg Glu Ala Val His Thr Gly His Ala Asp Lys Arg Asp Ala
            355                 360                 365
Pro Trp Trp Pro Arg Leu Ser Thr Pro Ala Asp Leu Ala Ser Leu Leu
        370                 375                 380
Thr Thr Leu Leu Trp Leu Thr Ser Ala Gln His Ala Ala Leu Asn Phe
385                 390                 395                 400
Gly Gln Tyr Pro Leu Gly Gly Tyr Ile Pro Asn Arg Pro Pro Leu Met
                405                 410                 415
Arg Arg Leu Val Pro Ala Glu Gly Asp Pro Glu Tyr Ala His Leu Val
                420                 425                 430
Ala Asp Pro His Arg Phe Phe Leu Ser Ala Leu Pro Ser Leu Thr Gln
            435                 440                 445
Thr Thr Thr Phe Met Thr Val Ile Asp Thr Leu Ser Thr His Ser Ala
        450                 455                 460
Asp Glu Gln Tyr Leu Gly Glu Arg Pro Asp Glu Ala Trp Thr Ala Asp
465                 470                 475                 480
Pro Ala Ala Leu Ala Ala Arg Glu Phe Ala Asp Glu Val Arg Arg
                485                 490                 495
```

-continued

```
Ala Glu Glu Glu Ile Glu Arg Arg Asn Ala Asp Thr Gly Arg Arg Asn
            500                 505                 510

Arg Cys Gly Ala Gly Val Leu Pro Tyr Glu Leu Met Ala Pro Thr Ser
        515                 520                 525

Gly Pro Gly Ile Thr Cys Arg Gly Val Pro Asn Ser Val Thr Ile
    530                 535                 540

<210> SEQ ID NO 41
<211> LENGTH: 2835
<212> TYPE: DNA
<213> ORGANISM: Zea mays
<220> FEATURE:
<221> NAME/KEY: CDS
<222> LOCATION: (223)...(2646)
<223> OTHER INFORMATION: LOX10

<400> SEQUENCE: 41
agggaaagct ggtacgcctg caggtaccgg tccggaattc ccgggtcgac ccacgcgtcc      60
ggcgaggacc tgccgaggct cgcggcgccc gggaccggga agggcgcgcc ggagggcagg     120
cggccggaga aggtgctggt gcgggccgcg ctcacggtgc ccgcaagca caaggaggac     180 ctcaaggagg cgctggccgg ccacctcgac gcgctatggg ac atg gtt ggc cgg      234
                                              Met Val Gly Arg
                                                1 agc gtc gcg ctc gag ctc att agc acc aag atc cac ccc agg acc aag     282
Ser Val Ala Leu Glu Leu Ile Ser Thr Lys Ile His Pro Arg Thr Lys
 5                  10                  15                  20 aag ccg ttg cac agc ggt cag gca tcg atc aaa gac tgg tgc cag aag     330
Lys Pro Leu His Ser Gly Gln Ala Ser Ile Lys Asp Trp Cys Gln Lys
                 25                  30                  35 agg ggc gtc aag gga gag cac gtc gtg tac acg gct gag ttc atg gtg     378
Arg Gly Val Lys Gly Glu His Val Val Tyr Thr Ala Glu Phe Met Val
             40                  45                  50 gat tca gac ttc ggc gag cct ggc gcc atc acc gtg gcc aac cgg cac     426
Asp Ser Asp Phe Gly Glu Pro Gly Ala Ile Thr Val Ala Asn Arg His
         55                  60                  65 cat cgg gag ttc ttt ctg gaa agc atc gtc gtc gag ggt ggg ctg ccg     474
His Arg Glu Phe Phe Leu Glu Ser Ile Val Val Glu Gly Gly Leu Pro
     70                  75                  80 tgt ggt ccg gtg cac ttc gcc tgc aac tcc tgg gtg cag tcc acc agg     522
Cys Gly Pro Val His Phe Ala Cys Asn Ser Trp Val Gln Ser Thr Arg
 85                  90                  95                 100 gaa ctg ccg gga aag agg gtg ttc ttc agt aac aag ccg tac tta cca     570
Glu Leu Pro Gly Lys Arg Val Phe Phe Ser Asn Lys Pro Tyr Leu Pro
                105                 110                 115 tct gaa aca cca ccc ggg ctt aga gaa cta cgg gat aag gaa ttg aag     618
Ser Glu Thr Pro Pro Gly Leu Arg Glu Leu Arg Asp Lys Glu Leu Lys
            120                 125                 130 gac ctt aga gga gat ggc aca gga gta cgg aag cta tct gac aga atc     666
Asp Leu Arg Gly Asp Gly Thr Gly Val Arg Lys Leu Ser Asp Arg Ile
        135                 140                 145 tat gat tat gca aca tac aat gat ttg ggg aat cca gat cgg ggg aaa     714
Tyr Asp Tyr Ala Thr Tyr Asn Asp Leu Gly Asn Pro Asp Arg Gly Lys
    150                 155                 160 gag ttc atc agg cca atc ctt gga ggt gac aac atc cct tat cca cgg     762
Glu Phe Ile Arg Pro Ile Leu Gly Gly Asp Asn Ile Pro Tyr Pro Arg
165                 170                 175                 180 cga tgc cga act ggt cgc cca cca act gat aca aac atg cta gct gag     810
Arg Cys Arg Thr Gly Arg Pro Pro Thr Asp Thr Asn Met Leu Ala Glu
                185                 190                 195
```

-continued

| | | |
|---|---|---|
| agc aga gta gag aaa cct cac agg ata tat gta cct cgg gat gag gcg<br>Ser Arg Val Glu Lys Pro His Arg Ile Tyr Val Pro Arg Asp Glu Ala<br>200                        205                  210 | 858 |
| ttt gag gag ctg aag caa ggt gcc ttc tca tca ggg agg ctg cgg gca<br>Phe Glu Glu Leu Lys Gln Gly Ala Phe Ser Ser Gly Arg Leu Arg Ala<br>215                      220                  225 | 906 |
| gta ctt cat acg ctt atc cca tcg atg att gca acc atc tca gct gag<br>Val Leu His Thr Leu Ile Pro Ser Met Ile Ala Thr Ile Ser Ala Glu<br>230                      235                  240 | 954 |
| acc cac agc ttc caa ggc ttt cac cac gtt gat aat cta tac aag gaa<br>Thr His Ser Phe Gln Gly Phe His His Val Asp Asn Leu Tyr Lys Glu<br>245                      250                  255                  260 | 1002 |
| ggc ctc agg ctg aag ttg ggt ctc cag gag cac ctg ttc cag aaa ata<br>Gly Leu Arg Leu Lys Leu Gly Leu Gln Glu His Leu Phe Gln Lys Ile<br>265                      270                  275 | 1050 |
| ccc ctt gtt cag aag att cag gaa tca agt gag ggg atg ctt cgc tat<br>Pro Leu Val Gln Lys Ile Gln Glu Ser Ser Glu Gly Met Leu Arg Tyr<br>280                      285                  290 | 1098 |
| gat aca cct aga att ctt tcc aag gac aag ttt gca tgg ctc cgt gac<br>Asp Thr Pro Arg Ile Leu Ser Lys Asp Lys Phe Ala Trp Leu Arg Asp<br>295                      300                  305 | 1146 |
| gat gag ttt gct cga cag act gtg gca gga ata aac cca gtt agc atc<br>Asp Glu Phe Ala Arg Gln Thr Val Ala Gly Ile Asn Pro Val Ser Ile<br>310                      315                  320 | 1194 |
| acc agg ctc acg gtt ttc cca cca gta agc aag atg gat cct gca atc<br>Thr Arg Leu Thr Val Phe Pro Pro Val Ser Lys Met Asp Pro Ala Ile<br>325                      330                  335                  340 | 1242 |
| tat ggc ccg cca gaa tca tcg atc aca gaa gcg cac atc act gga cag<br>Tyr Gly Pro Pro Glu Ser Ser Ile Thr Glu Ala His Ile Thr Gly Gln<br>345                      350                  355 | 1290 |
| ctc aat gga ctc acg gta caa cag gcg gtg gac gag gca aag ctg ttc<br>Leu Asn Gly Leu Thr Val Gln Gln Ala Val Asp Glu Ala Lys Leu Phe<br>360                      365                  370 | 1338 |
| ata ttg gac tac cat gat gta tat atg cca ttc ctg gac cgg atc aat<br>Ile Leu Asp Tyr His Asp Val Tyr Met Pro Phe Leu Asp Arg Ile Asn<br>375                      380                  385 | 1386 |
| gca ata gag ggg cgg aag gcg tat gca acc cgg aca atc ttg ttt ctt<br>Ala Ile Glu Gly Arg Lys Ala Tyr Ala Thr Arg Thr Ile Leu Phe Leu<br>390                      395                  400 | 1434 |
| acc aaa gct ggc aca ttg aaa ccg att gct att gaa ctt agc ctt cct<br>Thr Lys Ala Gly Thr Leu Lys Pro Ile Ala Ile Glu Leu Ser Leu Pro<br>405                      410                  415                  420 | 1482 |
| ccg agc aag gca ggc gag ccc cgg cca agc aag gtc ctt act cct ccc<br>Pro Ser Lys Ala Gly Glu Pro Arg Pro Ser Lys Val Leu Thr Pro Pro<br>425                      430                  435 | 1530 |
| gct gat gct acc tcc aat tgg cta tgg atg ctt gcc aaa gct cat gtc<br>Ala Asp Ala Thr Ser Asn Trp Leu Trp Met Leu Ala Lys Ala His Val<br>440                      445                  450 | 1578 |
| agc tcc aac gac gcc ggt gtt cac cag ctc gtt aat cac tgg ctg agg<br>Ser Ser Asn Asp Ala Gly Val His Gln Leu Val Asn His Trp Leu Arg<br>455                      460                  465 | 1626 |
| aca cat gct gta atg gag ccg ttc ata ttg gca gcg cat cgg cgt atg<br>Thr His Ala Val Met Glu Pro Phe Ile Leu Ala Ala His Arg Arg Met<br>470                      475                  480 | 1674 |
| agc gca atg cac cca gtc ttc aag ctc ctg cac ccc cac atg cgg tac<br>Ser Ala Met His Pro Val Phe Lys Leu Leu His Pro His Met Arg Tyr<br>485                      490                  495                  500 | 1722 |
| acg ctg gag atc aat gcg ctt gca cgg cag agc ctg atc agc gcg gac<br>Thr Leu Glu Ile Asn Ala Leu Ala Arg Gln Ser Leu Ile Ser Ala Asp | 1770 |

-continued

| | | | | | | | | | | | | | | | |
|---|---|---|---|---|---|---|---|---|---|---|---|---|---|---|---|
| | | | 505 | | | | | 510 | | | | | 515 | | |
| ggt | gtc | atc | gag | tcg | tgc | ttc | acc | cct | ggt | ccc | gtc | tcc | ttc | gag | atc |
| Gly | Val | Ile | Glu | Ser | Cys | Phe | Thr | Pro | Gly | Pro | Val | Ser | Phe | Glu | Ile |
| | | | 520 | | | | | 525 | | | | | 530 | | |

1818 agc gct gca tac tac cgc gac cac tgg cgg ttc gac cta gag ggc ctc   1866
Ser Ala Ala Tyr Tyr Arg Asp His Trp Arg Phe Asp Leu Glu Gly Leu
            535                 540                 545 cct tct gac ctc gtc cgc agg aga gtg gcc gtg gag gat gcg tcg cag   1914
Pro Ser Asp Leu Val Arg Arg Arg Val Ala Val Glu Asp Ala Ser Gln
550                 555                 560 cct cat ggc atc aga ctc ctc atc gag gac tac cct tac gca aac gac   1962
Pro His Gly Ile Arg Leu Leu Ile Glu Asp Tyr Pro Tyr Ala Asn Asp
565                 570                 575                 580 ggg ctc ctg ctg tgg tcg gcc att cgc agc tgg gtg gag tcg tat gtg   2010
Gly Leu Leu Leu Trp Ser Ala Ile Arg Ser Trp Val Glu Ser Tyr Val
            585                 590                 595 cag ctc tac tac ccg gac gcc ggc acc gtt cag tcc gac gac gag ctc   2058
Gln Leu Tyr Tyr Pro Asp Ala Gly Thr Val Gln Ser Asp Asp Glu Leu
            600                 605                 610 caa ggg tgg tac cac gaa acg gtc cac gtc ggg cac gcc gac atc cgg   2106
Gln Gly Trp Tyr His Glu Thr Val His Val Gly His Ala Asp Ile Arg
            615                 620                 625 cac gcg ccc tgg tgg ccc tcg ctc tcc acg ccg ggg gac ctc gcg tcc   2154
His Ala Pro Trp Trp Pro Ser Leu Ser Thr Pro Gly Asp Leu Ala Ser
            630                 635                 640 atc ctg acc acg ctc gtc tgg ctc gcg tcg gcg cag cac gcg gcg ctc   2202
Ile Leu Thr Thr Leu Val Trp Leu Ala Ser Ala Gln His Ala Ala Leu
645                 650                 655                 660 aac ttc ggg cag tac ccg ctg ggc ggg tac gtc ccg aac cgc ccg ccg   2250
Asn Phe Gly Gln Tyr Pro Leu Gly Gly Tyr Val Pro Asn Arg Pro Pro
            665                 670                 675 ctg atg cgc cgg ctg cta ccg gac ccg gag cgc gac gcc gcc gag tac   2298
Leu Met Arg Arg Leu Leu Pro Asp Pro Glu Arg Asp Ala Ala Glu Tyr
            680                 685                 690 gcg acg ttc atg gcg gac ccg cac cgg ttc ttc ctg aac gcg atg ccc   2346
Ala Thr Phe Met Ala Asp Pro His Arg Phe Phe Leu Asn Ala Met Pro
            695                 700                 705 ggg gtg ctg gag gcc acc aag ttc atg gct gtg gtg gac acg ctg tcg   2394
Gly Val Leu Glu Ala Thr Lys Phe Met Ala Val Val Asp Thr Leu Ser
            710                 715                 720 acg cac tcc ccc gac gag gag tac ctc ggc gag gag cgc gac gag ccg   2442
Thr His Ser Pro Asp Glu Glu Tyr Leu Gly Glu Glu Arg Asp Glu Pro
725                 730                 735                 740 tgg acg ggc gac gct gcc gcc gtg gcg gcg cac gac atg ttc acg gcc   2490
Trp Thr Gly Asp Ala Ala Ala Val Ala Ala His Asp Met Phe Thr Ala
            745                 750                 755 gac gtg cgc cgc gcc gag gaa gcc atc gat agt cga aac gcg gac cag   2538
Asp Val Arg Arg Ala Glu Glu Ala Ile Asp Ser Arg Asn Ala Asp Gln
            760                 765                 770 cgc agg aag aac cgg tgc ggc gcc ggg gtg ctg ccg tac gag ctg ctg   2586
Arg Arg Lys Asn Arg Cys Gly Ala Gly Val Leu Pro Tyr Glu Leu Leu
            775                 780                 785 gcg ccc agc tcg ccg ccg ggg gtc acg tgc cgc ggc gtg cct aac agc   2634
Ala Pro Ser Ser Pro Pro Gly Val Thr Cys Arg Gly Val Pro Asn Ser
            790                 795                 800 atc tcc ata tga atgagtgcat cgttcgttgt ttttccacat tttttttcta      2686
Ile Ser Ile  *
805 cgggtactat tatgtattgg ttttcaagca aattcgtgcc tacgccagca cttgtagaga  2746

-continued

```
atacactacg aacatatatc gaaaatacca aatctgccaa gaatgaggat tgaacaaaaa    2806
aaaaaaaaaa aaaaaaaaaa aaaaaaaaa                                      2835
```

<210> SEQ ID NO 42
<211> LENGTH: 807
<212> TYPE: PRT
<213> ORGANISM: Zea mays

<400> SEQUENCE: 42

```
Met Val Gly Arg Ser Val Ala Leu Glu Leu Ile Ser Thr Lys Ile His
 1               5                  10                  15

Pro Arg Thr Lys Lys Pro Leu His Ser Gly Gln Ala Ser Ile Lys Asp
            20                  25                  30

Trp Cys Gln Lys Arg Gly Val Lys Gly Glu His Val Val Tyr Thr Ala
        35                  40                  45

Glu Phe Met Val Asp Ser Asp Phe Gly Glu Pro Gly Ala Ile Thr Val
    50                  55                  60

Ala Asn Arg His His Arg Glu Phe Phe Leu Glu Ser Ile Val Val Glu
65                  70                  75                  80

Gly Gly Leu Pro Cys Gly Pro Val His Phe Ala Cys Asn Ser Trp Val
                85                  90                  95

Gln Ser Thr Arg Glu Leu Pro Gly Lys Arg Val Phe Ser Asn Lys
            100                 105                 110

Pro Tyr Leu Pro Ser Glu Thr Pro Pro Gly Leu Arg Glu Leu Arg Asp
        115                 120                 125

Lys Glu Leu Lys Asp Leu Arg Gly Asp Gly Thr Gly Val Arg Lys Leu
    130                 135                 140

Ser Asp Arg Ile Tyr Asp Tyr Ala Thr Tyr Asn Asp Leu Gly Asn Pro
145                 150                 155                 160

Asp Arg Gly Lys Glu Phe Ile Arg Pro Ile Leu Gly Gly Asp Asn Ile
                165                 170                 175

Pro Tyr Pro Arg Arg Cys Arg Thr Gly Arg Pro Pro Thr Asp Thr Asn
            180                 185                 190

Met Leu Ala Glu Ser Arg Val Glu Lys Pro His Arg Ile Tyr Val Pro
        195                 200                 205

Arg Asp Glu Ala Phe Glu Glu Leu Lys Gln Gly Ala Phe Ser Ser Gly
    210                 215                 220

Arg Leu Arg Ala Val Leu His Thr Leu Ile Pro Ser Met Ile Ala Thr
225                 230                 235                 240

Ile Ser Ala Glu Thr His Ser Phe Gln Gly Phe His His Val Asp Asn
                245                 250                 255

Leu Tyr Lys Glu Gly Leu Arg Leu Lys Leu Gly Leu Gln Glu His Leu
            260                 265                 270

Phe Gln Lys Ile Pro Leu Val Gln Lys Ile Gln Glu Ser Ser Glu Gly
        275                 280                 285

Met Leu Arg Tyr Asp Thr Pro Arg Ile Leu Ser Lys Asp Lys Phe Ala
    290                 295                 300

Trp Leu Arg Asp Asp Glu Phe Ala Arg Gln Thr Val Ala Gly Ile Asn
305                 310                 315                 320

Pro Val Ser Ile Thr Arg Leu Thr Val Phe Pro Pro Val Ser Lys Met
                325                 330                 335

Asp Pro Ala Ile Tyr Gly Pro Pro Glu Ser Ser Ile Thr Glu Ala His
            340                 345                 350
```

-continued

```
Ile Thr Gly Gln Leu Asn Gly Leu Thr Val Gln Gln Ala Val Asp Glu
        355                 360                 365

Ala Lys Leu Phe Ile Leu Asp Tyr His Asp Val Tyr Met Pro Phe Leu
        370                 375                 380

Asp Arg Ile Asn Ala Ile Glu Gly Arg Lys Ala Tyr Ala Thr Arg Thr
385                 390                 395                 400

Ile Leu Phe Leu Thr Lys Ala Gly Thr Leu Lys Pro Ile Ala Ile Glu
                405                 410                 415

Leu Ser Leu Pro Pro Ser Lys Ala Gly Glu Pro Arg Pro Ser Lys Val
                420                 425                 430

Leu Thr Pro Pro Ala Asp Ala Thr Ser Asn Trp Leu Trp Met Leu Ala
                435                 440                 445

Lys Ala His Val Ser Ser Asn Asp Ala Gly Val His Gln Leu Val Asn
        450                 455                 460

His Trp Leu Arg Thr His Ala Val Met Glu Pro Phe Ile Leu Ala Ala
465                 470                 475                 480

His Arg Arg Met Ser Ala Met His Pro Val Phe Lys Leu Leu His Pro
                485                 490                 495

His Met Arg Tyr Thr Leu Glu Ile Asn Ala Leu Ala Arg Gln Ser Leu
        500                 505                 510

Ile Ser Ala Asp Gly Val Ile Glu Ser Cys Phe Thr Pro Gly Pro Val
        515                 520                 525

Ser Phe Glu Ile Ser Ala Ala Tyr Tyr Arg Asp His Trp Arg Phe Asp
        530                 535                 540

Leu Glu Gly Leu Pro Ser Asp Leu Val Arg Arg Val Ala Val Glu
545                 550                 555                 560

Asp Ala Ser Gln Pro His Gly Ile Arg Leu Leu Ile Glu Asp Tyr Pro
                565                 570                 575

Tyr Ala Asn Asp Gly Leu Leu Leu Trp Ser Ala Ile Arg Ser Trp Val
                580                 585                 590

Glu Ser Tyr Val Gln Leu Tyr Tyr Pro Asp Ala Gly Thr Val Gln Ser
        595                 600                 605

Asp Asp Glu Leu Gln Gly Trp Tyr His Glu Thr Val His Val Gly His
        610                 615                 620

Ala Asp Ile Arg His Ala Pro Trp Trp Pro Ser Leu Ser Thr Pro Gly
625                 630                 635                 640

Asp Leu Ala Ser Ile Leu Thr Thr Leu Val Trp Leu Ala Ser Ala Gln
                645                 650                 655

His Ala Ala Leu Asn Phe Gly Gln Tyr Pro Leu Gly Gly Tyr Val Pro
                660                 665                 670

Asn Arg Pro Pro Leu Met Arg Arg Leu Leu Pro Asp Pro Glu Arg Asp
                675                 680                 685

Ala Ala Glu Tyr Ala Thr Phe Met Ala Asp Pro His Arg Phe Phe Leu
        690                 695                 700

Asn Ala Met Pro Gly Val Leu Glu Ala Thr Lys Phe Met Ala Val Val
705                 710                 715                 720

Asp Thr Leu Ser Thr His Ser Pro Asp Glu Glu Tyr Leu Gly Glu Glu
                725                 730                 735

Arg Asp Glu Pro Trp Thr Gly Asp Ala Ala Val Ala Ala His Asp
                740                 745                 750

Met Phe Thr Ala Asp Val Arg Arg Ala Glu Glu Ala Ile Asp Ser Arg
        755                 760                 765

Asn Ala Asp Gln Arg Arg Lys Asn Arg Cys Gly Ala Gly Val Leu Pro
```

```
                 770               775               780
Tyr Glu Leu Leu Ala Pro Ser Ser Pro Pro Gly Val Thr Cys Arg Gly
785               790               795               800

Val Pro Asn Ser Ile Ser Ile
            805

<210> SEQ ID NO 43
<211> LENGTH: 2424
<212> TYPE: DNA
<213> ORGANISM: Zea mays
<220> FEATURE:
<221> NAME/KEY: CDS
<222> LOCATION: (1)...(2424)

<400> SEQUENCE: 43 atg gtt ggc cgg agc gtc gcg ctc gag ctc att agc acc aag atc cac      48
Met Val Gly Arg Ser Val Ala Leu Glu Leu Ile Ser Thr Lys Ile His
  1               5                  10                  15 ccc agg acc aag aag ccg ttg cac agc ggt cag gca tcg atc aaa gac      96
Pro Arg Thr Lys Lys Pro Leu His Ser Gly Gln Ala Ser Ile Lys Asp
             20                  25                  30 tgg tgc cag aag agg ggc gtc aag gga gag cac gtc gtg tac acg gct     144
Trp Cys Gln Lys Arg Gly Val Lys Gly Glu His Val Val Tyr Thr Ala
         35                  40                  45 gag ttc atg gtg gat tca gac ttc ggc gag cct ggc gcc atc acc gtg     192
Glu Phe Met Val Asp Ser Asp Phe Gly Glu Pro Gly Ala Ile Thr Val
 50                  55                  60 gcc aac cgg cac cat cgg gag ttc ttt ctg gaa agc atc gtc gtc gag     240
Ala Asn Arg His His Arg Glu Phe Phe Leu Glu Ser Ile Val Val Glu
 65                  70                  75                  80 ggt ggg ctg ccg tgt ggt ccg gtg cac ttc gcc tgc aac tcc tgg gtg     288
Gly Gly Leu Pro Cys Gly Pro Val His Phe Ala Cys Asn Ser Trp Val
                 85                  90                  95 cag tcc acc agg gaa ctg ccg gga aag agg gtg ttc ttc agt aac aag     336
Gln Ser Thr Arg Glu Leu Pro Gly Lys Arg Val Phe Phe Ser Asn Lys
            100                 105                 110 ccg tac tta cca tct gaa aca cca ccc ggg ctt aga gaa cta cgg gat     384
Pro Tyr Leu Pro Ser Glu Thr Pro Pro Gly Leu Arg Glu Leu Arg Asp
        115                 120                 125 aag gaa ttg aag gac ctt aga gga gat ggc aca gga gta cgg aag cta     432
Lys Glu Leu Lys Asp Leu Arg Gly Asp Gly Thr Gly Val Arg Lys Leu
    130                 135                 140 tct gac aga atc tat gat tat gca aca tac aat gat ttg ggg aat cca     480
Ser Asp Arg Ile Tyr Asp Tyr Ala Thr Tyr Asn Asp Leu Gly Asn Pro
145                 150                 155                 160 gat cgg ggg aaa gag ttc atc agg cca atc ctt gga ggt gac aac atc     528
Asp Arg Gly Lys Glu Phe Ile Arg Pro Ile Leu Gly Gly Asp Asn Ile
                165                 170                 175 cct tat cca cgg cga tgc cga act ggt cgc cca cca act gat aca aac     576
Pro Tyr Pro Arg Arg Cys Arg Thr Gly Arg Pro Pro Thr Asp Thr Asn
            180                 185                 190 atg cta gct gag agc aga gta gag aaa cct cac agg ata tat gta cct     624
Met Leu Ala Glu Ser Arg Val Glu Lys Pro His Arg Ile Tyr Val Pro
        195                 200                 205 cgg gat gag gcg ttt gag gag ctg aag caa ggt gcc ttc tca tca ggg     672
Arg Asp Glu Ala Phe Glu Glu Leu Lys Gln Gly Ala Phe Ser Ser Gly
    210                 215                 220 agg ctg cgg gca gta ctt cat acg ctt atc cca tcg atg att gca acc     720
Arg Leu Arg Ala Val Leu His Thr Leu Ile Pro Ser Met Ile Ala Thr
225                 230                 235                 240
```

-continued

| | |
|---|---|
| atc tca gct gag acc cac agc ttc caa ggc ttt cac cac gtt gat aat<br>Ile Ser Ala Glu Thr His Ser Phe Gln Gly Phe His His Val Asp Asn<br>245 250 255 | 768 |
| cta tac aag gaa ggc ctc agg ctg aag ttg ggt ctc cag gag cac ctg<br>Leu Tyr Lys Glu Gly Leu Arg Leu Lys Leu Gly Leu Gln Glu His Leu<br>260 265 270 | 816 |
| ttc cag aaa ata ccc ctt gtt cag aag att cag gaa tca agt gag ggg<br>Phe Gln Lys Ile Pro Leu Val Gln Lys Ile Gln Glu Ser Ser Glu Gly<br>275 280 285 | 864 |
| atg ctt cgc tat gat aca cct aga att ctt tcc aag gac aag ttt gca<br>Met Leu Arg Tyr Asp Thr Pro Arg Ile Leu Ser Lys Asp Lys Phe Ala<br>290 295 300 | 912 |
| tgg ctc cgt gac gat gag ttt gct cga cag act gtg gca gga ata aac<br>Trp Leu Arg Asp Asp Glu Phe Ala Arg Gln Thr Val Ala Gly Ile Asn<br>305 310 315 320 | 960 |
| cca gtt agc atc acc agg ctc acg gtt ttc cca cca gta agc aag atg<br>Pro Val Ser Ile Thr Arg Leu Thr Val Phe Pro Pro Val Ser Lys Met<br>325 330 335 | 1008 |
| gat cct gca atc tat ggc ccg cca gaa tca tcg atc aca gaa gcg cac<br>Asp Pro Ala Ile Tyr Gly Pro Pro Glu Ser Ser Ile Thr Glu Ala His<br>340 345 350 | 1056 |
| atc act gga cag ctc aat gga ctc acg gta caa cag gcg gtg gac gag<br>Ile Thr Gly Gln Leu Asn Gly Leu Thr Val Gln Gln Ala Val Asp Glu<br>355 360 365 | 1104 |
| gca aag ctg ttc ata ttg gac tac cat gat gta tat atg cca ttc ctg<br>Ala Lys Leu Phe Ile Leu Asp Tyr His Asp Val Tyr Met Pro Phe Leu<br>370 375 380 | 1152 |
| gac cgg atc aat gca ata gag ggg cgg aag gcg tat gca acc cgg aca<br>Asp Arg Ile Asn Ala Ile Glu Gly Arg Lys Ala Tyr Ala Thr Arg Thr<br>385 390 395 400 | 1200 |
| atc ttg ttt ctt acc aaa gct ggc aca ttg aaa ccg att gct att gaa<br>Ile Leu Phe Leu Thr Lys Ala Gly Thr Leu Lys Pro Ile Ala Ile Glu<br>405 410 415 | 1248 |
| ctt agc ctt cct ccg agc aag gca ggc gag ccc cgg cca agc aag gtc<br>Leu Ser Leu Pro Pro Ser Lys Ala Gly Glu Pro Arg Pro Ser Lys Val<br>420 425 430 | 1296 |
| ctt act cct ccc gct gat gct acc tcc aat tgg cta tgg atg ctt gcc<br>Leu Thr Pro Pro Ala Asp Ala Thr Ser Asn Trp Leu Trp Met Leu Ala<br>435 440 445 | 1344 |
| aaa gct cat gtc agc tcc aac gac gcc ggt gtt cac cag ctc gtt aat<br>Lys Ala His Val Ser Ser Asn Asp Ala Gly Val His Gln Leu Val Asn<br>450 455 460 | 1392 |
| cac tgg ctg agg aca cat gct gta atg gag ccg ttc ata ttg gca gcg<br>His Trp Leu Arg Thr His Ala Val Met Glu Pro Phe Ile Leu Ala Ala<br>465 470 475 480 | 1440 |
| cat cgg cgt atg agc gca atg cac cca gtc ttc aag ctc ctg cac ccc<br>His Arg Arg Met Ser Ala Met His Pro Val Phe Lys Leu Leu His Pro<br>485 490 495 | 1488 |
| cac atg cgg tac acg ctg gag atc aat gcg ctt gca cgg cag agc ctg<br>His Met Arg Tyr Thr Leu Glu Ile Asn Ala Leu Ala Arg Gln Ser Leu<br>500 505 510 | 1536 |
| atc agc gcg gac ggt gtc atc gag tcg tgc ttc acc cct ggt ccc gtc<br>Ile Ser Ala Asp Gly Val Ile Glu Ser Cys Phe Thr Pro Gly Pro Val<br>515 520 525 | 1584 |
| tcc ttc gag atc agc gct gca tac tac cgc gac cac tgg cgg ttc gac<br>Ser Phe Glu Ile Ser Ala Ala Tyr Tyr Arg Asp His Trp Arg Phe Asp<br>530 535 540 | 1632 |
| cta gag ggc ctc cct tct gac ctc gtc cgc agg aga gtg gcc gtg gag<br>Leu Glu Gly Leu Pro Ser Asp Leu Val Arg Arg Arg Val Ala Val Glu<br>545 550 555 560 | 1680 |

-continued

```
gat gcg tcg cag cct cat ggc atc aga ctc ctc atc gag gac tac cct    1728
Asp Ala Ser Gln Pro His Gly Ile Arg Leu Leu Ile Glu Asp Tyr Pro
            565                 570                 575 tac gca aac gac ggg ctc ctg ctg tgg tcg gcc att cgc agc tgg gtg    1776
Tyr Ala Asn Asp Gly Leu Leu Leu Trp Ser Ala Ile Arg Ser Trp Val
        580                 585                 590 gag tcg tat gtg cag ctc tac tac ccg gac gcc ggc acc gtt cag tcc    1824
Glu Ser Tyr Val Gln Leu Tyr Tyr Pro Asp Ala Gly Thr Val Gln Ser
    595                 600                 605 gac gac gag ctc caa ggg tgg tac cac gaa acg gtc cac gtc ggg cac    1872
Asp Asp Glu Leu Gln Gly Trp Tyr His Glu Thr Val His Val Gly His
610                 615                 620 gcc gac atc cgg cac gcg ccc tgg tgg ccc tcg ctc tcc acg ccg ggg    1920
Ala Asp Ile Arg His Ala Pro Trp Trp Pro Ser Leu Ser Thr Pro Gly
625                 630                 635                 640 gac ctc gcg tcc atc ctg acc acg ctc gtc tgg ctc gcg tcg gcg cag    1968
Asp Leu Ala Ser Ile Leu Thr Thr Leu Val Trp Leu Ala Ser Ala Gln
            645                 650                 655 cac gcg gcg ctc aac ttc ggg cag tac ccg ctg ggc ggg tac gtc ccg    2016
His Ala Ala Leu Asn Phe Gly Gln Tyr Pro Leu Gly Gly Tyr Val Pro
        660                 665                 670 aac cgc ccg ccg ctg atg cgc cgg ctg cta ccg gac ccg gag cgc gac    2064
Asn Arg Pro Pro Leu Met Arg Arg Leu Leu Pro Asp Pro Glu Arg Asp
    675                 680                 685 gcc gcc gag tac gcg acg ttc atg gcg gac ccg cac cgg ttc ttc ctg    2112
Ala Ala Glu Tyr Ala Thr Phe Met Ala Asp Pro His Arg Phe Phe Leu
690                 695                 700 aac gcg atg ccc ggg gtg ctg gag gcc acc aag ttc atg gct gtg gtg    2160
Asn Ala Met Pro Gly Val Leu Glu Ala Thr Lys Phe Met Ala Val Val
705                 710                 715                 720 gac acg ctg tcg acg cac tcc ccc gac gag gag tac ctc ggc gag gag    2208
Asp Thr Leu Ser Thr His Ser Pro Asp Glu Glu Tyr Leu Gly Glu Glu
            725                 730                 735 cgc gac gag ccg tgg acg ggc gac gct gcc gcc gtg gcg gcg cac gac    2256
Arg Asp Glu Pro Trp Thr Gly Asp Ala Ala Ala Val Ala Ala His Asp
        740                 745                 750 atg ttc acg gcc gac gtg cgc cgc gcc gag gaa gcc atc gat agt cga    2304
Met Phe Thr Ala Asp Val Arg Arg Ala Glu Glu Ala Ile Asp Ser Arg
    755                 760                 765 aac gcg gac cag cgc agg aag aac cgg tgc ggc gcc ggg gtg ctg ccg    2352
Asn Ala Asp Gln Arg Arg Lys Asn Arg Cys Gly Ala Gly Val Leu Pro
770                 775                 780 tac gag ctg ctg gcg ccc agc tcg ccg ccg ggg gtc acg tgc cgc ggc    2400
Tyr Glu Leu Leu Ala Pro Ser Ser Pro Pro Gly Val Thr Cys Arg Gly
785                 790                 795                 800 gtg cct aac agc atc tcc ata tga                                    2424
Val Pro Asn Ser Ile Ser Ile *
            805
```

<210> SEQ ID NO 44
<211> LENGTH: 807
<212> TYPE: PRT
<213> ORGANISM: Zea mays

<400> SEQUENCE: 44

```
Met Val Gly Arg Ser Val Ala Leu Glu Leu Ile Ser Thr Lys Ile His
 1               5                  10                  15

Pro Arg Thr Lys Lys Pro Leu His Ser Gly Gln Ala Ser Ile Lys Asp
            20                  25                  30
```

```
Trp Cys Gln Lys Arg Gly Val Lys Gly Glu His Val Val Tyr Thr Ala
        35                  40                  45
Glu Phe Met Val Asp Ser Asp Phe Gly Glu Pro Gly Ala Ile Thr Val
 50                  55                  60
Ala Asn Arg His His Arg Glu Phe Phe Leu Glu Ser Ile Val Val Glu
 65                  70                  75                  80
Gly Gly Leu Pro Cys Gly Pro Val His Phe Ala Cys Asn Ser Trp Val
                 85                  90                  95
Gln Ser Thr Arg Glu Leu Pro Gly Lys Arg Val Phe Phe Ser Asn Lys
            100                 105                 110
Pro Tyr Leu Pro Ser Glu Thr Pro Gly Leu Arg Glu Leu Arg Asp
            115                 120                 125
Lys Glu Leu Lys Asp Leu Arg Gly Asp Gly Thr Gly Val Arg Lys Leu
130                 135                 140
Ser Asp Arg Ile Tyr Asp Tyr Ala Thr Tyr Asn Asp Leu Gly Asn Pro
145                 150                 155                 160
Asp Arg Gly Lys Glu Phe Ile Arg Pro Ile Leu Gly Gly Asp Asn Ile
                165                 170                 175
Pro Tyr Pro Arg Arg Cys Arg Thr Gly Arg Pro Pro Thr Asp Thr Asn
            180                 185                 190
Met Leu Ala Glu Ser Arg Val Glu Lys Pro His Arg Ile Tyr Val Pro
            195                 200                 205
Arg Asp Glu Ala Phe Glu Glu Leu Lys Gln Gly Ala Phe Ser Ser Gly
            210                 215                 220
Arg Leu Arg Ala Val Leu His Thr Leu Ile Pro Ser Met Ile Ala Thr
225                 230                 235                 240
Ile Ser Ala Glu Thr His Ser Phe Gln Gly Phe His His Val Asp Asn
                245                 250                 255
Leu Tyr Lys Glu Gly Leu Arg Leu Lys Leu Gly Leu Gln Glu His Leu
            260                 265                 270
Phe Gln Lys Ile Pro Leu Val Gln Lys Ile Gln Glu Ser Ser Glu Gly
    275                 280                 285
Met Leu Arg Tyr Asp Thr Pro Arg Ile Leu Ser Lys Asp Lys Phe Ala
    290                 295                 300
Trp Leu Arg Asp Asp Glu Phe Ala Arg Gln Thr Val Ala Gly Ile Asn
305                 310                 315                 320
Pro Val Ser Ile Thr Arg Leu Thr Val Phe Pro Pro Val Ser Lys Met
                325                 330                 335
Asp Pro Ala Ile Tyr Gly Pro Pro Glu Ser Ser Ile Thr Glu Ala His
            340                 345                 350
Ile Thr Gly Gln Leu Asn Gly Leu Thr Val Gln Gln Ala Val Asp Glu
            355                 360                 365
Ala Lys Leu Phe Ile Leu Asp Tyr His Asp Val Tyr Met Pro Phe Leu
            370                 375                 380
Asp Arg Ile Asn Ala Ile Glu Gly Arg Lys Ala Tyr Ala Thr Arg Thr
385                 390                 395                 400
Ile Leu Phe Leu Thr Lys Ala Gly Thr Leu Lys Pro Ile Ala Ile Glu
                405                 410                 415
Leu Ser Leu Pro Pro Ser Lys Ala Gly Glu Pro Arg Pro Ser Lys Val
            420                 425                 430
Leu Thr Pro Pro Ala Asp Ala Thr Ser Asn Trp Leu Trp Met Leu Ala
            435                 440                 445
Lys Ala His Val Ser Ser Asn Asp Ala Gly Val His Gln Leu Val Asn
```

```
                    450                 455                 460
His Trp Leu Arg Thr His Ala Val Met Glu Pro Phe Ile Leu Ala Ala
465                 470                 475                 480

His Arg Arg Met Ser Ala Met His Pro Val Phe Lys Leu Leu His Pro
                485                 490                 495

His Met Arg Tyr Thr Leu Glu Ile Asn Ala Leu Ala Arg Gln Ser Leu
            500                 505                 510

Ile Ser Ala Asp Gly Val Ile Glu Ser Cys Phe Thr Pro Gly Pro Val
        515                 520                 525

Ser Phe Glu Ile Ser Ala Ala Tyr Tyr Arg Asp His Trp Arg Phe Asp
530                 535                 540

Leu Glu Gly Leu Pro Ser Asp Leu Val Arg Arg Val Ala Val Ala Glu
545                 550                 555                 560

Asp Ala Ser Gln Pro His Gly Ile Arg Leu Leu Ile Glu Asp Tyr Pro
                565                 570                 575

Tyr Ala Asn Asp Gly Leu Leu Leu Trp Ser Ala Ile Arg Ser Trp Val
            580                 585                 590

Glu Ser Tyr Val Gln Leu Tyr Tyr Pro Asp Ala Gly Thr Val Gln Ser
        595                 600                 605

Asp Asp Glu Leu Gln Gly Trp Tyr His Glu Thr Val His Val Gly His
610                 615                 620

Ala Asp Ile Arg His Ala Pro Trp Trp Pro Ser Leu Ser Thr Pro Gly
625                 630                 635                 640

Asp Leu Ala Ser Ile Leu Thr Thr Leu Val Trp Leu Ala Ser Ala Gln
                645                 650                 655

His Ala Ala Leu Asn Phe Gly Gln Tyr Pro Leu Gly Gly Tyr Val Pro
            660                 665                 670

Asn Arg Pro Pro Leu Met Arg Arg Leu Leu Pro Asp Pro Glu Arg Asp
        675                 680                 685

Ala Ala Glu Tyr Ala Thr Phe Met Ala Asp Pro His Arg Phe Phe Leu
            690                 695                 700

Asn Ala Met Pro Gly Val Leu Glu Ala Thr Lys Phe Met Ala Val Val
705                 710                 715                 720

Asp Thr Leu Ser Thr His Ser Pro Asp Glu Glu Tyr Leu Gly Glu Glu
                725                 730                 735

Arg Asp Glu Pro Trp Thr Gly Asp Ala Ala Val Ala Ala His Asp
            740                 745                 750

Met Phe Thr Ala Asp Val Arg Arg Ala Glu Glu Ala Ile Asp Ser Arg
        755                 760                 765

Asn Ala Asp Gln Arg Arg Lys Asn Arg Cys Gly Ala Gly Val Leu Pro
770                 775                 780

Tyr Glu Leu Leu Ala Pro Ser Ser Pro Pro Gly Val Thr Cys Arg Gly
785                 790                 795                 800

Val Pro Asn Ser Ile Ser Ile
                805
```

<210> SEQ ID NO 45
<211> LENGTH: 3074
<212> TYPE: DNA
<213> ORGANISM: Zea mays
<220> FEATURE:
<221> NAME/KEY: CDS
<222> LOCATION: (183)...(2900)
<223> OTHER INFORMATION: LOX11

<400> SEQUENCE: 45

-continued

```
ccacgcgtcc gggtgctcag cggaacagct agctatagcc tgtagctagc agctagcttc      60
agtcacaggc cggacggtcg gctcacacac agctagccgc cgccgccgct agcttagcca     120
ccagtagtcc gatctgatct acaggcaagg ggcaactagc tagctagccg cgcgccggcg     180 cc atg atg aac ctg aac ctg aag cag cct ctg gtg ctg ccc gcg cac       227
   Met Met Asn Leu Asn Leu Lys Gln Pro Leu Val Leu Pro Ala His
    1               5                  10                  15 cac agc aat gtc gtc ggc tcg cgc ctg tcg tcg tcg tcg ccc tcg gca       275
His Ser Asn Val Val Gly Ser Arg Leu Ser Ser Ser Ser Pro Ser Ala
                 20                  25                  30 gcc gcc gcc agc agg agg acc ggc ggc ggc gtg tcc tcc cgg tcc ggc       323
Ala Ala Ala Ser Arg Arg Thr Gly Gly Gly Val Ser Ser Arg Ser Gly
             35                  40                  45 tcc cgg cgg cac gtg cgg ctg ccg agg atc agc tgc agc gcc acc gag       371
Ser Arg Arg His Val Arg Leu Pro Arg Ile Ser Cys Ser Ala Thr Glu
         50                  55                  60 gag gtc agc ggc gcc gtg tcg tcc gtc acc gtg gag agg atg ctc acg       419
Glu Val Ser Gly Ala Val Ser Ser Val Thr Val Glu Arg Met Leu Thr
 65                  70                  75 gtg acg gcg tcg gtg gag gcg tcg ccg gcc atc ggg cag atg tac ttc       467
Val Thr Ala Ser Val Glu Ala Ser Pro Ala Ile Gly Gln Met Tyr Phe
 80                  85                  90                  95 cag cgc gcc gtc gac gac atc ggc gac ctc ctc ggc aag acg ctg ctg       515
Gln Arg Ala Val Asp Asp Ile Gly Asp Leu Leu Gly Lys Thr Leu Leu
                100                 105                 110 ctc gag ctc gtc agc tcc gag ctc gac gca aag tcg ggc gtg gag aag       563
Leu Glu Leu Val Ser Ser Glu Leu Asp Ala Lys Ser Gly Val Glu Lys
            115                 120                 125 acg cgg gtg acg gcg tac gcg cac aag acg ctg cgg gag ggc cac tac       611
Thr Arg Val Thr Ala Tyr Ala His Lys Thr Leu Arg Glu Gly His Tyr
        130                 135                 140 gag gcg gag ttc aag gtg ccg gcg tcg ttc ggg ccg gtg ggc gcg gtg       659
Glu Ala Glu Phe Lys Val Pro Ala Ser Phe Gly Pro Val Gly Ala Val
145                 150                 155 ctg gtg gag aac gag cac cac aag gag gtc ttc atc aag gag atc aag       707
Leu Val Glu Asn Glu His His Lys Glu Val Phe Ile Lys Glu Ile Lys
160                 165                 170                 175 ctc gtc acc ggc ggc gac agc agc acc gcc gtc acc ttc gac tgc aac       755
Leu Val Thr Gly Gly Asp Ser Ser Thr Ala Val Thr Phe Asp Cys Asn
                180                 185                 190 tcc tgg gtg cac tcc aag ttc gac aac ccg gag aag cgc atc ttc ttc       803
Ser Trp Val His Ser Lys Phe Asp Asn Pro Glu Lys Arg Ile Phe Phe
            195                 200                 205 acc ctc aag tca tac ctg ccg tcc gac acg ccc aag ggg ctg gag gac       851
Thr Leu Lys Ser Tyr Leu Pro Ser Asp Thr Pro Lys Gly Leu Glu Asp
        210                 215                 220 ctg agg aag aag gac ctg cag gcg ctg cgc ggc gac ggg cac ggc gag       899
Leu Arg Lys Lys Asp Leu Gln Ala Leu Arg Gly Asp Gly His Gly Glu
225                 230                 235 cgc aag gtg ttc gag cgc gtc tac gac tac gac gtg tac aac gac ctg       947
Arg Lys Val Phe Glu Arg Val Tyr Asp Tyr Asp Val Tyr Asn Asp Leu
240                 245                 250                 255 ggc gac ccg gac aag aac ccg gcc cac cag cgg ccc gtg ctg ggc ggc       995
Gly Asp Pro Asp Lys Asn Pro Ala His Gln Arg Pro Val Leu Gly Gly
                260                 265                 270 aac aag cag tac cca tac ccg cgc cgc tgc cgc acc ggc cgc ccc agg      1043
Asn Lys Gln Tyr Pro Tyr Pro Arg Arg Cys Arg Thr Gly Arg Pro Arg
            275                 280                 285
```

```
acc aag aag gac ccc gag acg gag atg cgc gag ggc cac aac tac gtg        1091
Thr Lys Lys Asp Pro Glu Thr Glu Met Arg Glu Gly His Asn Tyr Val
        290                 295                 300 ccc cgc gac gag cag ttc tcg gag gtg aag cag ctc acg ttc ggg gcc        1139
Pro Arg Asp Glu Gln Phe Ser Glu Val Lys Gln Leu Thr Phe Gly Ala
305                 310                 315 acc acg ctg cgc tcc ggc ctg cac gcg ctg ctg ccg gcg ctc cgc ccg        1187
Thr Thr Leu Arg Ser Gly Leu His Ala Leu Leu Pro Ala Leu Arg Pro
320                 325                 330                 335 ctg ctc atc aac aag aag gat ctg cgc ttc ccg cac ttc ccc gcc atc        1235
Leu Leu Ile Asn Lys Lys Asp Leu Arg Phe Pro His Phe Pro Ala Ile
            340                 345                 350 gac gac ctc ttc agc gac ggc atc ccg ctg ccg gcg cag acc ggg ttc        1283
Asp Asp Leu Phe Ser Asp Gly Ile Pro Leu Pro Ala Gln Thr Gly Phe
                355                 360                 365 gac gcc ttc cgc acc gtc gtc ccg cgc atg gtc aag ctg gtg gag gac        1331
Asp Ala Phe Arg Thr Val Val Pro Arg Met Val Lys Leu Val Glu Asp
                370                 375                 380 acc acc gac cac gtc ctc cgc ttc gag gtg ccg gag atg ata gag agg        1379
Thr Thr Asp His Val Leu Arg Phe Glu Val Pro Glu Met Ile Glu Arg
385                 390                 395 gac cgg ttc tcg tgg ttc aag gac gag gag ttc gcg agg cag acg atc        1427
Asp Arg Phe Ser Trp Phe Lys Asp Glu Glu Phe Ala Arg Gln Thr Ile
400                 405                 410                 415 gcg ggg ctc aac ccg ctg tgc atc cag ctg ctg act gag ttc ccc atc        1475
Ala Gly Leu Asn Pro Leu Cys Ile Gln Leu Leu Thr Glu Phe Pro Ile
            420                 425                 430 aag agc aag ctg gac ccg gag gtg tac ggg cca gcg gag tcc gcc atc        1523
Lys Ser Lys Leu Asp Pro Glu Val Tyr Gly Pro Ala Glu Ser Ala Ile
                435                 440                 445 acc aag gag atc ctg gag aag cag atg aac ggc gcg ctg acc gtg gag        1571
Thr Lys Glu Ile Leu Glu Lys Gln Met Asn Gly Ala Leu Thr Val Glu
                450                 455                 460 cag gcg ctg gcg gcg aag cgg ctg ttc atc ctg gac tac cac gac gtg        1619
Gln Ala Leu Ala Ala Lys Arg Leu Phe Ile Leu Asp Tyr His Asp Val
465                 470                 475 ttc ctg ccc tac gtg cac aag gtg cgg gag ctg cag gac gcg acg ctc        1667
Phe Leu Pro Tyr Val His Lys Val Arg Glu Leu Gln Asp Ala Thr Leu
480                 485                 490                 495 tac gcc tcg cgc acc atc ttc ttc ctg acg gac ctg ggc acg ctg atg        1715
Tyr Ala Ser Arg Thr Ile Phe Phe Leu Thr Asp Leu Gly Thr Leu Met
                500                 505                 510 ccg ctg gcc atc gag ctg acg cgg ccc aag tcg ccg acg cgg ccg cag        1763
Pro Leu Ala Ile Glu Leu Thr Arg Pro Lys Ser Pro Thr Arg Pro Gln
                515                 520                 525 tgg aag cgg gcg ttc acg cac ggg ccc gac gcc acc gac gcc tgg ctg        1811
Trp Lys Arg Ala Phe Thr His Gly Pro Asp Ala Thr Asp Ala Trp Leu
            530                 535                 540 tgg aag ctg gcc aag gcg cac gtg ctg acc cac gac acg ggg tac cac        1859
Trp Lys Leu Ala Lys Ala His Val Leu Thr His Asp Thr Gly Tyr His
545                 550                 555 cag ctg gtg agc cac tgg ctg cgc acg cac tgc tgc gtg gag ccc tac        1907
Gln Leu Val Ser His Trp Leu Arg Thr His Cys Cys Val Glu Pro Tyr
560                 565                 570                 575 atc atc gcc gcc aac cgg cag ctg agc cgg ctg cac ccg gtg tac cgc        1955
Ile Ile Ala Ala Asn Arg Gln Leu Ser Arg Leu His Pro Val Tyr Arg
                580                 585                 590 ctg ctg cac ccg cac ttc cgc tac acc atg gag atc aac gcg ctg gcc        2003
Leu Leu His Pro His Phe Arg Tyr Thr Met Glu Ile Asn Ala Leu Ala
                595                 600                 605
```

```
agg gag gcg ctc atc aac gcc gac ggc atc atc gag gag tcc ttc tgg      2051
Arg Glu Ala Leu Ile Asn Ala Asp Gly Ile Ile Glu Glu Ser Phe Trp
        610                 615                 620 ccg ggc aag tac gcc gtc gag ctc agc tcc gtg gcg tac ggc gcg acg      2099
Pro Gly Lys Tyr Ala Val Glu Leu Ser Ser Val Ala Tyr Gly Ala Thr
    625                 630                 635 tgg cag ttc gac acg gag gcg ctg ccc aac gac ctc atc aag cgc ggg      2147
Trp Gln Phe Asp Thr Glu Ala Leu Pro Asn Asp Leu Ile Lys Arg Gly
640                 645                 650                 655 ctg gcc gtg cgc ggg gag gac ggg gag ctg gag ctc acc atc aag gac      2195
Leu Ala Val Arg Gly Glu Asp Gly Glu Leu Glu Leu Thr Ile Lys Asp
                660                 665                 670 tac ccc tac gcc cac gac ggg ctc ctg gtc tgg gac tcc atc agg cag      2243
Tyr Pro Tyr Ala His Asp Gly Leu Leu Val Trp Asp Ser Ile Arg Gln
            675                 680                 685 tgg gcg tcc gag tac gtc aac gtc tac tac aag tcc gac gag gcc gtg      2291
Trp Ala Ser Glu Tyr Val Asn Val Tyr Tyr Lys Ser Asp Glu Ala Val
        690                 695                 700 gcc gcc gac ccc gag ctg agg gcg ttc tgg gac gag gtg cgc aac gtg      2339
Ala Ala Asp Pro Glu Leu Arg Ala Phe Trp Asp Glu Val Arg Asn Val
    705                 710                 715 ggg cac ggc gac aag aag gac gag ccg tgg tgg ccc gtg ctg gac acc      2387
Gly His Gly Asp Lys Lys Asp Glu Pro Trp Trp Pro Val Leu Asp Thr
720                 725                 730                 735 cgc gac agc ctg gtg gag acg ctg acc acc atc atg tgg gtc acc tcc      2435
Arg Asp Ser Leu Val Glu Thr Leu Thr Thr Ile Met Trp Val Thr Ser
                740                 745                 750 ggc cac cac tcg gcc gtc aac ttc ggc cag tac cac ttc gcc ggc tac      2483
Gly His His Ser Ala Val Asn Phe Gly Gln Tyr His Phe Ala Gly Tyr
            755                 760                 765 ttc ccc aac cgg ccg acc acc atc cgg aag aac atg ccg gtg gag gag      2531
Phe Pro Asn Arg Pro Thr Thr Ile Arg Lys Asn Met Pro Val Glu Glu
        770                 775                 780 ggc ggg ccg ggc gag gag atg gag aag ttc ctc aag cag ccg gag acg      2579
Gly Gly Pro Gly Glu Glu Met Glu Lys Phe Leu Lys Gln Pro Glu Thr
    785                 790                 795 acg ctg ctg gac atg ctg ccc acg cag atg cag gcc atc aag gtc atg      2627
Thr Leu Leu Asp Met Leu Pro Thr Gln Met Gln Ala Ile Lys Val Met
800                 805                 810                 815 acg acg ctg gac atc ctc tcg tcg cac tcg ccc gac gag gag tac atg      2675
Thr Thr Leu Asp Ile Leu Ser Ser His Ser Pro Asp Glu Glu Tyr Met
                820                 825                 830 ggg gag ttc gcg gag ccg tcg tgg ctg gcg gag ccc atg gtg aag gcg      2723
Gly Glu Phe Ala Glu Pro Ser Trp Leu Ala Glu Pro Met Val Lys Ala
            835                 840                 845 gcg ttc gag aag ttc ggc ggc agg atg aag gag atc gag ggg ttc atc      2771
Ala Phe Glu Lys Phe Gly Gly Arg Met Lys Glu Ile Glu Gly Phe Ile
        850                 855                 860 gac gag tgc aac aac aac ctg gac ctc aag aac cgc tgc ggc gcc ggg      2819
Asp Glu Cys Asn Asn Asn Leu Asp Leu Lys Asn Arg Cys Gly Ala Gly
    865                 870                 875 atc gtg ccg tac gag ctg ctc aag ccc ttc tcc aag ccg gga gtc acc      2867
Ile Val Pro Tyr Glu Leu Leu Lys Pro Phe Ser Lys Pro Gly Val Thr
880                 885                 890                 895 ggg agg ggc atc ccc agc agc atc tcc atc tga tccatcctca gcatgcatta   2920
Gly Arg Gly Ile Pro Ser Ser Ile Ser Ile  *
                900                 905 gtccaattaa atcgggggt gtactattat tgcatgcaga ggctgcttgt cgaataaaac    2980
```

-continued

```
gtactatatg tacgattgta ttgtacatgt gtgtcaatgc aacaagaggc acgtttgaga    3040
ctttgagttt aaaaaaaaaa aaaaaaaaaa aaaa                                3074
```

<210> SEQ ID NO 46
<211> LENGTH: 905
<212> TYPE: PRT
<213> ORGANISM: Zea mays

<400> SEQUENCE: 46

```
Met Met Asn Leu Asn Leu Lys Gln Pro Leu Val Leu Pro Ala His His
 1               5                  10                  15

Ser Asn Val Val Gly Ser Arg Leu Ser Ser Ser Pro Ser Ala Ala
            20                  25                  30

Ala Ala Ser Arg Arg Thr Gly Gly Val Ser Arg Ser Gly Ser
        35                  40                  45

Arg Arg His Val Arg Leu Pro Arg Ile Ser Cys Ser Ala Thr Glu Glu
 50                  55                  60

Val Ser Gly Ala Val Ser Ser Val Thr Val Glu Arg Met Leu Thr Val
 65                  70                  75                  80

Thr Ala Ser Val Glu Ala Ser Pro Ala Ile Gly Gln Met Tyr Phe Gln
                85                  90                  95

Arg Ala Val Asp Asp Ile Gly Asp Leu Leu Gly Lys Thr Leu Leu Leu
            100                 105                 110

Glu Leu Val Ser Ser Glu Leu Asp Ala Lys Ser Gly Val Glu Lys Thr
        115                 120                 125

Arg Val Thr Ala Tyr Ala His Lys Thr Leu Arg Glu Gly His Tyr Glu
130                 135                 140

Ala Glu Phe Lys Val Pro Ala Ser Phe Gly Pro Val Gly Ala Val Leu
145                 150                 155                 160

Val Glu Asn Glu His His Lys Glu Val Phe Ile Lys Glu Ile Lys Leu
                165                 170                 175

Val Thr Gly Gly Asp Ser Ser Thr Ala Val Thr Phe Asp Cys Asn Ser
            180                 185                 190

Trp Val His Ser Lys Phe Asp Asn Pro Glu Lys Arg Ile Phe Phe Thr
        195                 200                 205

Leu Lys Ser Tyr Leu Pro Ser Asp Thr Pro Lys Gly Leu Glu Asp Leu
210                 215                 220

Arg Lys Lys Asp Leu Gln Ala Leu Arg Gly Asp Gly His Gly Glu Arg
225                 230                 235                 240

Lys Val Phe Glu Arg Val Tyr Asp Tyr Asp Val Tyr Asn Asp Leu Gly
                245                 250                 255

Asp Pro Asp Lys Asn Pro Ala His Gln Arg Pro Val Leu Gly Gly Asn
            260                 265                 270

Lys Gln Tyr Pro Tyr Pro Arg Cys Arg Thr Gly Arg Pro Arg Thr
        275                 280                 285

Lys Lys Asp Pro Glu Thr Glu Met Arg Glu Gly His Asn Tyr Val Pro
290                 295                 300

Arg Asp Glu Gln Phe Ser Glu Val Lys Gln Leu Thr Phe Gly Ala Thr
305                 310                 315                 320

Thr Leu Arg Ser Gly Leu His Ala Leu Leu Pro Ala Leu Arg Pro Leu
                325                 330                 335

Leu Ile Asn Lys Lys Asp Leu Arg Phe Pro His Phe Pro Ala Ile Asp
            340                 345                 350

Asp Leu Phe Ser Asp Gly Ile Pro Leu Pro Ala Gln Thr Gly Phe Asp
```

```
                355                 360                 365
Ala Phe Arg Thr Val Val Pro Arg Met Val Lys Leu Val Glu Asp Thr
370                 375                 380

Thr Asp His Val Leu Arg Phe Glu Val Pro Glu Met Ile Glu Arg Asp
385                 390                 395                 400

Arg Phe Ser Trp Phe Lys Asp Glu Glu Phe Ala Arg Gln Thr Ile Ala
                405                 410                 415

Gly Leu Asn Pro Leu Cys Ile Gln Leu Leu Thr Glu Phe Pro Ile Lys
                420                 425                 430

Ser Lys Leu Asp Pro Glu Val Tyr Gly Pro Ala Glu Ser Ala Ile Thr
                435                 440                 445

Lys Glu Ile Leu Glu Lys Gln Met Asn Gly Ala Leu Thr Val Glu Gln
450                 455                 460

Ala Leu Ala Ala Lys Arg Leu Phe Ile Leu Asp Tyr His Asp Val Phe
465                 470                 475                 480

Leu Pro Tyr Val His Lys Val Arg Glu Leu Gln Asp Ala Thr Leu Tyr
                485                 490                 495

Ala Ser Arg Thr Ile Phe Phe Leu Thr Asp Leu Gly Thr Leu Met Pro
                500                 505                 510

Leu Ala Ile Glu Leu Thr Arg Pro Lys Ser Pro Thr Arg Pro Gln Trp
                515                 520                 525

Lys Arg Ala Phe Thr His Gly Pro Asp Ala Thr Asp Ala Trp Leu Trp
530                 535                 540

Lys Leu Ala Lys Ala His Val Leu Thr His Asp Thr Gly Tyr His Gln
545                 550                 555                 560

Leu Val Ser His Trp Leu Arg Thr His Cys Cys Val Glu Pro Tyr Ile
                565                 570                 575

Ile Ala Ala Asn Arg Gln Leu Ser Arg Leu His Pro Val Tyr Arg Leu
                580                 585                 590

Leu His Pro His Phe Arg Tyr Thr Met Glu Ile Asn Ala Leu Ala Arg
                595                 600                 605

Glu Ala Leu Ile Asn Ala Asp Gly Ile Ile Glu Glu Ser Phe Trp Pro
610                 615                 620

Gly Lys Tyr Ala Val Glu Leu Ser Ser Val Ala Tyr Gly Ala Thr Trp
625                 630                 635                 640

Gln Phe Asp Thr Glu Ala Leu Pro Asn Asp Leu Ile Lys Arg Gly Leu
                645                 650                 655

Ala Val Arg Gly Glu Asp Gly Glu Leu Glu Leu Thr Ile Lys Asp Tyr
                660                 665                 670

Pro Tyr Ala His Asp Gly Leu Leu Val Trp Asp Ser Ile Arg Gln Trp
                675                 680                 685

Ala Ser Glu Tyr Val Asn Val Tyr Tyr Lys Ser Asp Glu Ala Val Ala
                690                 695                 700

Ala Asp Pro Glu Leu Arg Ala Phe Trp Asp Glu Val Arg Asn Val Gly
705                 710                 715                 720

His Gly Asp Lys Lys Asp Glu Pro Trp Trp Pro Val Leu Asp Thr Arg
                725                 730                 735

Asp Ser Leu Val Glu Thr Leu Thr Thr Ile Met Trp Val Thr Ser Gly
                740                 745                 750

His His Ser Ala Val Asn Phe Gly Gln Tyr His Phe Ala Gly Tyr Phe
                755                 760                 765

Pro Asn Arg Pro Thr Thr Ile Arg Lys Asn Met Pro Val Glu Glu Gly
770                 775                 780
```

```
Gly Pro Gly Glu Glu Met Glu Lys Phe Leu Lys Gln Pro Glu Thr Thr
785                 790                 795                 800

Leu Leu Asp Met Leu Pro Thr Gln Met Gln Ala Ile Lys Val Met Thr
                805                 810                 815

Thr Leu Asp Ile Leu Ser Ser His Ser Pro Asp Glu Glu Tyr Met Gly
            820                 825                 830

Glu Phe Ala Glu Pro Ser Trp Leu Ala Glu Pro Met Val Lys Ala Ala
        835                 840                 845

Phe Glu Lys Phe Gly Arg Met Lys Glu Ile Glu Gly Phe Ile Asp
    850                 855                 860

Glu Cys Asn Asn Leu Asp Leu Lys Asn Arg Cys Gly Ala Gly Ile
865                 870                 875                 880

Val Pro Tyr Glu Leu Leu Lys Pro Phe Ser Lys Pro Gly Val Thr Gly
                885                 890                 895

Arg Gly Ile Pro Ser Ser Ile Ser Ile
            900                 905

<210> SEQ ID NO 47
<211> LENGTH: 2718
<212> TYPE: DNA
<213> ORGANISM: Zea mays
<220> FEATURE:
<221> NAME/KEY: CDS
<222> LOCATION: (1)...(2718)

<400> SEQUENCE: 47 atg atg aac ctg aac ctg aag cag cct ctg gtg ctg ccc gcg cac cac     48
Met Met Asn Leu Asn Leu Lys Gln Pro Leu Val Leu Pro Ala His His
1               5                  10                  15 agc aat gtc gtc ggc tcg cgc ctg tcg tcg tcg tcg ccc tcg gca gcc     96
Ser Asn Val Val Gly Ser Arg Leu Ser Ser Ser Ser Pro Ser Ala Ala
            20                  25                  30 gcc gcc agc agg agg acc ggc ggc ggc gtg tcc tcc cgg tcc ggc tcc    144
Ala Ala Ser Arg Arg Thr Gly Gly Gly Val Ser Ser Arg Ser Gly Ser
        35                  40                  45 cgg cgg cac gtg cgg ctg ccg agg atc agc tgc agc gcc acc gag gag    192
Arg Arg His Val Arg Leu Pro Arg Ile Ser Cys Ser Ala Thr Glu Glu
    50                  55                  60 gtc agc ggc gcc gtg tcg tcc gtc acc gtg gag agg atg ctc acg gtg    240
Val Ser Gly Ala Val Ser Ser Val Thr Val Glu Arg Met Leu Thr Val
65                  70                  75                  80 acg gcg tcg gtg gag gcg tcg ccg gcc atc ggg cag atg tac ttc cag    288
Thr Ala Ser Val Glu Ala Ser Pro Ala Ile Gly Gln Met Tyr Phe Gln
                85                  90                  95 cgc gcc gtc gac gac atc ggc gac ctc ctc ggc aag acg ctg ctg ctc    336
Arg Ala Val Asp Asp Ile Gly Asp Leu Leu Gly Lys Thr Leu Leu Leu
            100                 105                 110 gag ctc gtc agc tcc gag ctc gac gca aag tcg ggc gtg gag aag acg    384
Glu Leu Val Ser Ser Glu Leu Asp Ala Lys Ser Gly Val Glu Lys Thr
        115                 120                 125 cgg gtg acg gcg tac gcg cac aag acg ctg cgg gag ggc cac tac gag    432
Arg Val Thr Ala Tyr Ala His Lys Thr Leu Arg Glu Gly His Tyr Glu
    130                 135                 140 gcg gag ttc aag gtg ccg gcg tcg ttc ggg ccg gtg ggc gcg gtg ctg    480
Ala Glu Phe Lys Val Pro Ala Ser Phe Gly Pro Val Gly Ala Val Leu
145                 150                 155                 160 gtg gag aac gag cac cac aag gag gtc ttc atc aag gag atc aag ctc    528
Val Glu Asn Glu His His Lys Glu Val Phe Ile Lys Glu Ile Lys Leu
                165                 170                 175
```

```
                                                     -continued gtc acc ggc ggc gac agc agc acc gcc gtc acc ttc gac tgc aac tcc      576
Val Thr Gly Gly Asp Ser Ser Thr Ala Val Thr Phe Asp Cys Asn Ser
            180                 185                 190 tgg gtg cac tcc aag ttc gac aac ccg gag aag cgc atc ttc ttc acc      624
Trp Val His Ser Lys Phe Asp Asn Pro Glu Lys Arg Ile Phe Phe Thr
                195                 200                 205 ctc aag tca tac ctg ccg tcc gac acg ccc aag ggg ctg gag gac ctg      672
Leu Lys Ser Tyr Leu Pro Ser Asp Thr Pro Lys Gly Leu Glu Asp Leu
    210                 215                 220 agg aag aag gac ctg cag gcg ctg cgc ggc gac ggg cac ggc gag cgc      720
Arg Lys Lys Asp Leu Gln Ala Leu Arg Gly Asp Gly His Gly Glu Arg
225                 230                 235                 240 aag gtg ttc gag cgc gtc tac gac tac gac gtg tac aac gac ctg ggc      768
Lys Val Phe Glu Arg Val Tyr Asp Tyr Asp Val Tyr Asn Asp Leu Gly
                245                 250                 255 gac ccg gac aag aac ccg gcc cac cag cgg ccc gtg ctg ggc ggc aac      816
Asp Pro Asp Lys Asn Pro Ala His Gln Arg Pro Val Leu Gly Gly Asn
            260                 265                 270 aag cag tac cca tac ccg cgc cgc tgc cgc acc ggc cgc ccc agg acc      864
Lys Gln Tyr Pro Tyr Pro Arg Arg Cys Arg Thr Gly Arg Pro Arg Thr
        275                 280                 285 aag aag gac ccc gag acg gag atg cgc gag ggc cac aac tac gtg ccc      912
Lys Lys Asp Pro Glu Thr Glu Met Arg Glu Gly His Asn Tyr Val Pro
    290                 295                 300 cgc gac gag cag ttc tcg gag gtg aag cag ctc acg ttc ggg gcc acc      960
Arg Asp Glu Gln Phe Ser Glu Val Lys Gln Leu Thr Phe Gly Ala Thr
305                 310                 315                 320 acg ctg cgc tcc ggc ctg cac gcg ctg ctg ccg gcg ctc cgc ccg ctg     1008
Thr Leu Arg Ser Gly Leu His Ala Leu Leu Pro Ala Leu Arg Pro Leu
                325                 330                 335 ctc atc aac aag aag gat ctg cgc ttc ccg cac ttc ccc gcc atc gac     1056
Leu Ile Asn Lys Lys Asp Leu Arg Phe Pro His Phe Pro Ala Ile Asp
            340                 345                 350 gac ctc ttc agc gac ggc atc ccg ctg ccg gcg cag acc ggg ttc gac     1104
Asp Leu Phe Ser Asp Gly Ile Pro Leu Pro Ala Gln Thr Gly Phe Asp
        355                 360                 365 gcc ttc cgc acc gtc gtc ccg cgc atg gtc aag ctg gtg gag gac acc     1152
Ala Phe Arg Thr Val Val Pro Arg Met Val Lys Leu Val Glu Asp Thr
    370                 375                 380 acc gac cac gtc ctc cgc ttc gag gtg ccg gag atg ata gag agg gac     1200
Thr Asp His Val Leu Arg Phe Glu Val Pro Glu Met Ile Glu Arg Asp
385                 390                 395                 400 cgg ttc tcg tgg ttc aag gac gag gag ttc gcg agg cag acg atc gcg     1248
Arg Phe Ser Trp Phe Lys Asp Glu Glu Phe Ala Arg Gln Thr Ile Ala
                405                 410                 415 ggg ctc aac ccg ctg tgc atc cag ctg ctg act gag ttc ccc atc aag     1296
Gly Leu Asn Pro Leu Cys Ile Gln Leu Leu Thr Glu Phe Pro Ile Lys
            420                 425                 430 agc aag ctg gac ccg gag gtg tac ggg cca gcg gag tcc gcc atc acc     1344
Ser Lys Leu Asp Pro Glu Val Tyr Gly Pro Ala Glu Ser Ala Ile Thr
        435                 440                 445 aag gag atc ctg gag aag cag atg aac ggc gcg ctg acc gtg gag cag     1392
Lys Glu Ile Leu Glu Lys Gln Met Asn Gly Ala Leu Thr Val Glu Gln
    450                 455                 460 gcg ctg gcg gcg aag cgg ctg ttc atc ctg gac tac cac gac gtg ttc     1440
Ala Leu Ala Ala Lys Arg Leu Phe Ile Leu Asp Tyr His Asp Val Phe
465                 470                 475                 480 ctg ccc tac gtg cac aag gtg cgg gag ctg cag gac gcg acg ctc tac     1488
Leu Pro Tyr Val His Lys Val Arg Glu Leu Gln Asp Ala Thr Leu Tyr
```

-continued

```
                485                 490                 495
gcc tcg cgc acc atc ttc ttc ctg acg gac ctg ggc acg ctg atg ccg    1536
Ala Ser Arg Thr Ile Phe Phe Leu Thr Asp Leu Gly Thr Leu Met Pro
            500                 505                 510 ctg gcc atc gag ctg acg cgg ccc aag tcg ccg acg cgg ccg cag tgg    1584
Leu Ala Ile Glu Leu Thr Arg Pro Lys Ser Pro Thr Arg Pro Gln Trp
        515                 520                 525 aag cgg gcg ttc acg cac ggg ccc gac gcc acc gac gcc tgg ctg tgg    1632
Lys Arg Ala Phe Thr His Gly Pro Asp Ala Thr Asp Ala Trp Leu Trp
    530                 535                 540 aag ctg gcc aag gcg cac gtg ctg acc cac gac acg ggg tac cac cag    1680
Lys Leu Ala Lys Ala His Val Leu Thr His Asp Thr Gly Tyr His Gln
545                 550                 555                 560 ctg gtg agc cac tgg ctg cgc acg cac tgc tgc gtg gag ccc tac atc    1728
Leu Val Ser His Trp Leu Arg Thr His Cys Cys Val Glu Pro Tyr Ile
                565                 570                 575 atc gcc gcc aac cgg cag ctg agc cgg ctg cac ccg gtg tac cgc ctg    1776
Ile Ala Ala Asn Arg Gln Leu Ser Arg Leu His Pro Val Tyr Arg Leu
            580                 585                 590 ctg cac ccg cac ttc cgc tac acc atg gag atc aac gcg ctg gcc agg    1824
Leu His Pro His Phe Arg Tyr Thr Met Glu Ile Asn Ala Leu Ala Arg
        595                 600                 605 gag gcg ctc atc aac gcc gac ggc atc atc gag gag tcc ttc tgg ccg    1872
Glu Ala Leu Ile Asn Ala Asp Gly Ile Ile Glu Glu Ser Phe Trp Pro
    610                 615                 620 ggc aag tac gcc gtc gag ctc agc tcc gtg gcg tac ggc gcg acg tgg    1920
Gly Lys Tyr Ala Val Glu Leu Ser Ser Val Ala Tyr Gly Ala Thr Trp
625                 630                 635                 640 cag ttc gac acg gag gcg ctg ccc aac gac ctc atc aag cgc ggg ctg    1968
Gln Phe Asp Thr Glu Ala Leu Pro Asn Asp Leu Ile Lys Arg Gly Leu
                645                 650                 655 gcc gtg cgc ggg gag gac ggg gag ctg gag ctc acc atc aag gac tac    2016
Ala Val Arg Gly Glu Asp Gly Glu Leu Glu Leu Thr Ile Lys Asp Tyr
            660                 665                 670 ccc tac gcc cac gac ggg ctc ctg gtc tgg gac tcc atc agg cag tgg    2064
Pro Tyr Ala His Asp Gly Leu Leu Val Trp Asp Ser Ile Arg Gln Trp
        675                 680                 685 gcg tcc gag tac gtc aac gtc tac tac aag tcc gac gag gcc gtg gcc    2112
Ala Ser Glu Tyr Val Asn Val Tyr Tyr Lys Ser Asp Glu Ala Val Ala
    690                 695                 700 gcc gac ccc gag ctg agg gcg ttc tgg gac gag gtg cgc aac gtg ggg    2160
Ala Asp Pro Glu Leu Arg Ala Phe Trp Asp Glu Val Arg Asn Val Gly
705                 710                 715                 720 cac ggc gac aag aag gac gag ccg tgg tgg ccc gtg ctg gac acc cgc    2208
His Gly Asp Lys Lys Asp Glu Pro Trp Trp Pro Val Leu Asp Thr Arg
                725                 730                 735 gac agc ctg gtg gag acg ctg acc acc atc atg tgg gtc acc tcc ggc    2256
Asp Ser Leu Val Glu Thr Leu Thr Thr Ile Met Trp Val Thr Ser Gly
            740                 745                 750 cac cac tcg gcc gtc aac ttc ggc cag tac cac ttc gcc ggc tac ttc    2304
His His Ser Ala Val Asn Phe Gly Gln Tyr His Phe Ala Gly Tyr Phe
        755                 760                 765 ccc aac cgg ccg acc acc atc cgg aag aac atg ccg gtg gag gag ggc    2352
Pro Asn Arg Pro Thr Thr Ile Arg Lys Asn Met Pro Val Glu Glu Gly
    770                 775                 780 ggg ccg ggc gag gag atg gag aag ttc ctc aag cag ccg gag acg acg    2400
Gly Pro Gly Glu Glu Met Glu Lys Phe Leu Lys Gln Pro Glu Thr Thr
785                 790                 795                 800 ctg ctg gac atg ctg ccc acg cag atg cag gcc atc aag gtc atg acg    2448
```

```
Leu Leu Asp Met Leu Pro Thr Gln Met Gln Ala Ile Lys Val Met Thr
            805                 810                 815
acg ctg gac atc ctc tcg tcg cac tcg ccc gac gag gag tac atg ggg      2496
Thr Leu Asp Ile Leu Ser Ser His Ser Pro Asp Glu Glu Tyr Met Gly
            820                 825                 830 gag ttc gcg gag ccg tcg tgg ctg gcg gag ccc atg gtg aag gcg gcg      2544
Glu Phe Ala Glu Pro Ser Trp Leu Ala Glu Pro Met Val Lys Ala Ala
            835                 840                 845 ttc gag aag ttc ggc ggc agg atg aag gag atc gag ggg ttc atc gac      2592
Phe Glu Lys Phe Gly Gly Arg Met Lys Glu Ile Glu Gly Phe Ile Asp
        850                 855                 860 gag tgc aac aac aac ctg gac ctc aag aac cgc tgc ggc gcc ggg atc      2640
Glu Cys Asn Asn Asn Leu Asp Leu Lys Asn Arg Cys Gly Ala Gly Ile
865                 870                 875                 880 gtg ccg tac gag ctg ctc aag ccc ttc tcc aag ccg gga gtc acc ggg      2688
Val Pro Tyr Glu Leu Leu Lys Pro Phe Ser Lys Pro Gly Val Thr Gly
                885                 890                 895 agg ggc atc ccc agc agc atc tcc atc tga                              2718
Arg Gly Ile Pro Ser Ser Ile Ser Ile *
            900                 905
```

<210> SEQ ID NO 48
<211> LENGTH: 905
<212> TYPE: PRT
<213> ORGANISM: Zea mays

<400> SEQUENCE: 48

```
Met Met Asn Leu Asn Leu Lys Gln Pro Leu Val Leu Pro Ala His His
  1               5                  10                  15

Ser Asn Val Val Gly Ser Arg Leu Ser Ser Ser Ser Pro Ser Ala Ala
             20                  25                  30

Ala Ala Ser Arg Arg Thr Gly Gly Gly Val Ser Ser Arg Ser Gly Ser
         35                  40                  45

Arg Arg His Val Arg Leu Pro Arg Ile Ser Cys Ser Ala Thr Glu Glu
 50                  55                  60

Val Ser Gly Ala Val Ser Ser Val Thr Val Glu Arg Met Leu Thr Val
 65                  70                  75                  80

Thr Ala Ser Val Glu Ala Ser Pro Ala Ile Gly Gln Met Tyr Phe Gln
                 85                  90                  95

Arg Ala Val Asp Asp Ile Gly Asp Leu Leu Gly Lys Thr Leu Leu Leu
            100                 105                 110

Glu Leu Val Ser Ser Glu Leu Asp Ala Lys Ser Gly Val Glu Lys Thr
        115                 120                 125

Arg Val Thr Ala Tyr Ala His Lys Thr Leu Arg Glu Gly His Tyr Glu
    130                 135                 140

Ala Glu Phe Lys Val Pro Ala Ser Phe Gly Pro Val Gly Ala Val Leu
145                 150                 155                 160

Val Glu Asn Glu His His Lys Glu Val Phe Ile Lys Glu Ile Lys Leu
                165                 170                 175

Val Thr Gly Gly Asp Ser Ser Thr Ala Val Thr Phe Asp Cys Asn Ser
            180                 185                 190

Trp Val His Ser Lys Phe Asp Asn Pro Glu Lys Arg Ile Phe Phe Thr
        195                 200                 205

Leu Lys Ser Tyr Leu Pro Ser Asp Thr Pro Lys Gly Leu Glu Asp Leu
    210                 215                 220

Arg Lys Lys Asp Leu Gln Ala Leu Arg Gly Asp Gly His Gly Glu Arg
225                 230                 235                 240
```

```
Lys Val Phe Glu Arg Val Tyr Asp Tyr Asp Val Tyr Asn Asp Leu Gly
                245                 250                 255
Asp Pro Asp Lys Asn Pro Ala His Gln Arg Pro Val Leu Gly Gly Asn
            260                 265                 270
Lys Gln Tyr Pro Tyr Pro Arg Arg Cys Arg Thr Gly Arg Pro Arg Thr
            275                 280                 285
Lys Lys Asp Pro Glu Thr Glu Met Arg Glu Gly His Asn Tyr Val Pro
290                 295                 300
Arg Asp Glu Gln Phe Ser Glu Val Lys Gln Leu Thr Phe Gly Ala Thr
305                 310                 315                 320
Thr Leu Arg Ser Gly Leu His Ala Leu Leu Pro Ala Leu Arg Pro Leu
                325                 330                 335
Leu Ile Asn Lys Lys Asp Leu Arg Phe Pro His Phe Pro Ala Ile Asp
                340                 345                 350
Asp Leu Phe Ser Asp Gly Ile Pro Leu Pro Ala Gln Thr Gly Phe Asp
            355                 360                 365
Ala Phe Arg Thr Val Val Pro Arg Met Val Lys Leu Val Glu Asp Thr
370                 375                 380
Thr Asp His Val Leu Arg Phe Glu Val Pro Glu Met Ile Glu Arg Asp
385                 390                 395                 400
Arg Phe Ser Trp Phe Lys Asp Glu Glu Phe Ala Arg Gln Thr Ile Ala
                405                 410                 415
Gly Leu Asn Pro Leu Cys Ile Gln Leu Leu Thr Glu Phe Pro Ile Lys
            420                 425                 430
Ser Lys Leu Asp Pro Glu Val Tyr Gly Pro Ala Glu Ser Ala Ile Thr
            435                 440                 445
Lys Glu Ile Leu Glu Lys Gln Met Asn Gly Ala Leu Thr Val Glu Gln
            450                 455                 460
Ala Leu Ala Ala Lys Arg Leu Phe Ile Leu Asp Tyr His Asp Val Phe
465                 470                 475                 480
Leu Pro Tyr Val His Lys Val Arg Glu Leu Gln Asp Ala Thr Leu Tyr
                485                 490                 495
Ala Ser Arg Thr Ile Phe Phe Leu Thr Asp Leu Gly Thr Leu Met Pro
            500                 505                 510
Leu Ala Ile Glu Leu Thr Arg Pro Lys Ser Pro Thr Arg Pro Gln Trp
            515                 520                 525
Lys Arg Ala Phe Thr His Gly Pro Asp Ala Thr Asp Ala Trp Leu Trp
530                 535                 540
Lys Leu Ala Lys Ala His Val Leu Thr His Asp Thr Gly Tyr His Gln
545                 550                 555                 560
Leu Val Ser His Trp Leu Arg Thr His Cys Cys Val Glu Pro Tyr Ile
                565                 570                 575
Ile Ala Ala Asn Arg Gln Leu Ser Arg Leu His Pro Val Tyr Arg Leu
            580                 585                 590
Leu His Pro His Phe Arg Tyr Thr Met Glu Ile Asn Ala Leu Ala Arg
            595                 600                 605
Glu Ala Leu Ile Asn Ala Asp Gly Ile Ile Glu Ser Phe Trp Pro
610                 615                 620
Gly Lys Tyr Ala Val Glu Leu Ser Ser Val Ala Tyr Gly Ala Thr Trp
625                 630                 635                 640
Gln Phe Asp Thr Glu Ala Leu Pro Asn Asp Leu Ile Lys Arg Gly Leu
                645                 650                 655
```

```
Ala Val Arg Gly Glu Asp Gly Glu Leu Glu Leu Thr Ile Lys Asp Tyr
            660                 665                 670

Pro Tyr Ala His Asp Gly Leu Leu Val Trp Asp Ser Ile Arg Gln Trp
            675                 680                 685

Ala Ser Glu Tyr Val Asn Val Tyr Tyr Lys Ser Asp Glu Ala Val Ala
            690                 695                 700

Ala Asp Pro Glu Leu Arg Ala Phe Trp Asp Glu Val Arg Asn Val Gly
705                 710                 715                 720

His Gly Asp Lys Lys Asp Glu Pro Trp Trp Pro Val Leu Asp Thr Arg
                725                 730                 735

Asp Ser Leu Val Glu Thr Leu Thr Thr Ile Met Trp Val Thr Ser Gly
            740                 745                 750

His His Ser Ala Val Asn Phe Gly Gln Tyr His Phe Ala Gly Tyr Phe
            755                 760                 765

Pro Asn Arg Pro Thr Thr Ile Arg Lys Asn Met Pro Val Glu Glu Gly
            770                 775                 780

Gly Pro Gly Glu Glu Met Glu Lys Phe Leu Lys Gln Pro Glu Thr Thr
785                 790                 795                 800

Leu Leu Asp Met Leu Pro Thr Gln Met Gln Ala Ile Lys Val Met Thr
                805                 810                 815

Thr Leu Asp Ile Leu Ser Ser His Ser Pro Asp Glu Glu Tyr Met Gly
            820                 825                 830

Glu Phe Ala Glu Pro Ser Trp Leu Ala Glu Pro Met Val Lys Ala Ala
            835                 840                 845

Phe Glu Lys Phe Gly Gly Arg Met Lys Glu Ile Glu Gly Phe Ile Asp
850                 855                 860

Glu Cys Asn Asn Asn Leu Asp Leu Lys Asn Arg Cys Gly Ala Gly Ile
865                 870                 875                 880

Val Pro Tyr Glu Leu Leu Lys Pro Phe Ser Lys Pro Gly Val Thr Gly
                885                 890                 895

Arg Gly Ile Pro Ser Ser Ile Ser Ile
                900                 905

<210> SEQ ID NO 49
<211> LENGTH: 2689
<212> TYPE: DNA
<213> ORGANISM: Zea mays
<220> FEATURE:
<221> NAME/KEY: CDS
<222> LOCATION: (1)...(2529)
<223> OTHER INFORMATION: LOX12

<400> SEQUENCE: 49 ctg aac ctg tgg gac cgg agc ccg gct cat gcg cct gag aac cac atc      48
Leu Asn Leu Trp Asp Arg Ser Pro Ala His Ala Pro Glu Asn His Ile
1               5                   10                  15 gcc atc gat ggc acg gtg gtc gtg tct tgc cac ttt ggc ctg tcg ttg      96
Ala Ile Asp Gly Thr Val Val Val Ser Cys His Phe Gly Leu Ser Leu
                20                  25                  30 ccg ggg aag act acc acg ctt cgc ctc ttc agc agc acg cag atg gat     144
Pro Gly Lys Thr Thr Thr Leu Arg Leu Phe Ser Ser Thr Gln Met Asp
            35                  40                  45 cca aac acg ggc aag ggg aag ctg agc gcg gag gcg ccg ctg agg ggc     192
Pro Asn Thr Gly Lys Gly Lys Leu Ser Ala Glu Ala Pro Leu Arg Gly
    50                  55                  60 ggc aag aag acg aag cag cag ggg agg aag acg agc acg atg gcg tac     240
Gly Lys Lys Thr Lys Gln Gln Gly Arg Lys Thr Ser Thr Met Ala Tyr
65                  70                  75                  80
```

-continued

| | |
|---|---|
| cag gtg acc ttc ttc gtg gac gcc gag ttc ggc acg ccg ggc gcc gtc<br>Gln Val Thr Phe Phe Val Asp Ala Glu Phe Gly Thr Pro Gly Ala Val<br>        85          90          95 | 288 |
| gtc gtc aag aac ggg ctg agg aac gac cag ttc ttc ctc cgc cac gtg<br>Val Val Lys Asn Gly Leu Arg Asn Asp Gln Phe Phe Leu Arg His Val<br>     100          105          110 | 336 |
| cag ctg aac ctg ccc gag gac ggc cgg agc gtc cac ttc gag tgc aac<br>Gln Leu Asn Leu Pro Glu Asp Gly Arg Ser Val His Phe Glu Cys Asn<br>       115          120         125 | 384 |
| tcc tgg gtc tac ccc tac aag aag acc aac gcc gac cgc gtc ttc ttc<br>Ser Trp Val Tyr Pro Tyr Lys Lys Thr Asn Ala Asp Arg Val Phe Phe<br>130         135          140 | 432 |
| atc aac acg agc tac ctg ccc gac agg acg ccc cag gct ctg cgc ctg<br>Ile Asn Thr Ser Tyr Leu Pro Asp Arg Thr Pro Gln Ala Leu Arg Leu<br>145         150         155         160 | 480 |
| ctg cga gac gag gag ctg cgg agc ctc cgg ggc aac ggc cgc ggc gag<br>Leu Arg Asp Glu Glu Leu Arg Ser Leu Arg Gly Asn Gly Arg Gly Glu<br>         165          170         175 | 528 |
| cgc aag gac tgg gag cgc gtc tac gac tac gac ctg tac aac gac ctg<br>Arg Lys Asp Trp Glu Arg Val Tyr Asp Tyr Asp Leu Tyr Asn Asp Leu<br>       180          185         190 | 576 |
| ggc gac ccg gac aag gag gac cgc gcc cgc ccg gcg ctc ggc ggc acc<br>Gly Asp Pro Asp Lys Glu Asp Arg Ala Arg Pro Ala Leu Gly Gly Thr<br>     195          200          205 | 624 |
| gcc acg cac ccg tac ccg cgc cgc tgc cgc acc ggc cgc cct ctc ttc<br>Ala Thr His Pro Tyr Pro Arg Arg Cys Arg Thr Gly Arg Pro Leu Phe<br>210         215         220 | 672 |
| aag aca gac ggc gtg acg gag acg cgg aag cac ctc atc aac ctc gac<br>Lys Thr Asp Gly Val Thr Glu Thr Arg Lys His Leu Ile Asn Leu Asp<br>225         230         235         240 | 720 |
| ttc tac atc ccg ccg gac gag cgc ttc agc ccg acc aag ctg gcg gag<br>Phe Tyr Ile Pro Pro Asp Glu Arg Phe Ser Pro Thr Lys Leu Ala Glu<br>         245          250         255 | 768 |
| gtg ctg gcg ctg gcg gtg cag gcc gtg acg cac ttc gtg gtg cca gag<br>Val Leu Ala Leu Ala Val Gln Ala Val Thr His Phe Val Val Pro Glu<br>     260          265          270 | 816 |
| tcc aac gcg ctg ttc cac ggc aac gtc aac agc ttc cgc tcg ttt gat<br>Ser Asn Ala Leu Phe His Gly Asn Val Asn Ser Phe Arg Ser Phe Asp<br>       275          280         285 | 864 |
| cag ctc aag gac gac ctg tac ggc agg aga ccg ccg gtc gcc gtg gat<br>Gln Leu Lys Asp Asp Leu Tyr Gly Arg Arg Pro Pro Val Ala Val Asp<br>290         295         300 | 912 |
| ggg cag gtg atg gac aag ctc aag acg tcg gtg ccg tcg cac aag acc<br>Gly Gln Val Met Asp Lys Leu Lys Thr Ser Val Pro Ser His Lys Thr<br>305         310         315         320 | 960 |
| tac aag cag gtg tcc aag atg gtc aag gag acg ccc gtc aag ttc ccc<br>Tyr Lys Gln Val Ser Lys Met Val Lys Glu Thr Pro Val Lys Phe Pro<br>         325          330         335 | 1008 |
| atc cct caa gtc atc gag cat gat cag gag gcg tgg cgt agc gac gag<br>Ile Pro Gln Val Ile Glu His Asp Gln Glu Ala Trp Arg Ser Asp Glu<br>     340          345         350 | 1056 |
| gag ttc gct agg gag atg ctg gcg ggg ctc aac ccg gtg gtg atc agt<br>Glu Phe Ala Arg Glu Met Leu Ala Gly Leu Asn Pro Val Val Ile Ser<br>       355          360         365 | 1104 |
| aga cta gag gtg ttc ccg ccg gtg agc aga gga ggg aag aag agc tcc<br>Arg Leu Glu Val Phe Pro Pro Val Ser Arg Gly Gly Lys Lys Ser Ser<br>370         375         380 | 1152 |
| att acg gaa gcg cac atc gag agc cag ctc caa gga cga act gtg caa<br>Ile Thr Glu Ala His Ile Glu Ser Gln Leu Gln Gly Arg Thr Val Gln | 1200 |

```
                    -continued 385              390              395              400 aag gca cta gat gac aag agg ctg tat ctt ctt gac cac cat gac tac   1248
Lys Ala Leu Asp Asp Lys Arg Leu Tyr Leu Leu Asp His His Asp Tyr
                405              410              415 ctg atg cca tac ctg cgg cgc atc aac acg caa caa ggg gtg tgc gtc   1296
Leu Met Pro Tyr Leu Arg Arg Ile Asn Thr Gln Gln Gly Val Cys Val
                420              425              430 tac gcg tcg cgc acg ctg ctc ttc ctc agg gac gac ggc gcc ctc aag   1344
Tyr Ala Ser Arg Thr Leu Leu Phe Leu Arg Asp Asp Gly Ala Leu Lys
                435              440              445 cct ctt gcc ata gag ctc agc ctg ccc ggt gac ggc gcc gag gtc agc   1392
Pro Leu Ala Ile Glu Leu Ser Leu Pro Gly Asp Gly Ala Glu Val Ser
450              455              460 agc agg gtc atc ctc cct gcg acc cca ggg acg acc gat gga cac ctg   1440
Ser Arg Val Ile Leu Pro Ala Thr Pro Gly Thr Thr Asp Gly His Leu
465              470              475              480 tgg tgg ctt gct aag gct cat gtc tcc gtc aat gat tca ggc tac cat   1488
Trp Trp Leu Ala Lys Ala His Val Ser Val Asn Asp Ser Gly Tyr His
                485              490              495 cag ctc atc agc cac tgg ctg ttc acg cac gcg acg gtg gag ccg ttc   1536
Gln Leu Ile Ser His Trp Leu Phe Thr His Ala Thr Val Glu Pro Phe
                500              505              510 atc atc gcc acc aag agg cag atg agc gcc atg cac ccg atc cac aag   1584
Ile Ile Ala Thr Lys Arg Gln Met Ser Ala Met His Pro Ile His Lys
                515              520              525 ctg ctg gag ccg cac ttc aag gac aac atg cag atc aac acg ctg gcc   1632
Leu Leu Glu Pro His Phe Lys Asp Asn Met Gln Ile Asn Thr Leu Ala
530              535              540 agg agc atc ctg ctg agc gcg ggc ggc atc ctg gag agg acc atg tac   1680
Arg Ser Ile Leu Leu Ser Ala Gly Gly Ile Leu Glu Arg Thr Met Tyr
545              550              555              560 ccg ggg aag tac gcc atg gag atg tcc tcg gcc atc tac tcc gag tgg   1728
Pro Gly Lys Tyr Ala Met Glu Met Ser Ser Ala Ile Tyr Ser Glu Trp
                565              570              575 agg ttc acg gag cag tcc ctg ccc aac gag ctc gtc aag agg ggc atg   1776
Arg Phe Thr Glu Gln Ser Leu Pro Asn Glu Leu Val Lys Arg Gly Met
                580              585              590 gcg tcc aag atg ggc ggc ggc gcc atc gcc ctg cac gtg gag gac tac   1824
Ala Ser Lys Met Gly Gly Gly Ala Ile Ala Leu His Val Glu Asp Tyr
                595              600              605 ccg tac gcg gtg gac ggc atg gac gtg tgg cgc gcc atc gag ggc tgg   1872
Pro Tyr Ala Val Asp Gly Met Asp Val Trp Arg Ala Ile Glu Gly Trp
610              615              620 gtc agg acc tac tgc gcc cac ttc tac cac tcc gac gcc gcg gtg gcc   1920
Val Arg Thr Tyr Cys Ala His Phe Tyr His Ser Asp Ala Ala Val Ala
625              630              635              640 gcc gac gcg gag ctg cag gcg tgg tgg gac gac gtc cgc cgc gtc ggc   1968
Ala Asp Ala Glu Leu Gln Ala Trp Trp Asp Asp Val Arg Arg Val Gly
                645              650              655 cac ggc gac cgc cag cgc gac ccg gcg tgc tgg ctg gac ctc gac tcc   2016
His Gly Asp Arg Gln Arg Asp Pro Ala Cys Trp Leu Asp Leu Asp Ser
                660              665              670 gtg gcc aac ctc gcc gag tcg ctg tcc acg ctc atc tgg atc gcc tcc   2064
Val Ala Asn Leu Ala Glu Ser Leu Ser Thr Leu Ile Trp Ile Ala Ser
                675              680              685 gcg ctg cac gcc gcc gtc aac ttc ggc cag tac ggc tac gcc ggg tac   2112
Ala Leu His Ala Ala Val Asn Phe Gly Gln Tyr Gly Tyr Ala Gly Tyr
690              695              700 atg ccc aac cgc ccc acc cgg tgc cgc cgc ttc gtg ccg ctg ccg gac   2160
```

-continued

| | | |
|---|---|---|
| Met Pro Asn Arg Pro Thr Arg Cys Arg Arg Phe Val Pro Leu Pro Asp<br>705                       710                       715                       720 | | |
| tcc ccg gag atg gcg cag ctg gag gcc gac ccg gac agg ttc ttc ctc<br>Ser Pro Glu Met Ala Gln Leu Glu Ala Asp Pro Asp Arg Phe Phe Leu<br>                      725                       730                       735 | 2208 | |
| gac acg gtg ccc gac cgc ttc acc gcc acg ctc ggg ctc acg ctc atc<br>Asp Thr Val Pro Asp Arg Phe Thr Ala Thr Leu Gly Leu Thr Leu Ile<br>                      740                       745                       750 | 2256 | |
| gag gtg ctc tcc aac cac acc tcc gac gag ctc tac ctg ggc cag cgc<br>Glu Val Leu Ser Asn His Thr Ser Asp Glu Leu Tyr Leu Gly Gln Arg<br>                      755                       760                       765 | 2304 | |
| gcc acc gcg gcg tgg acc gac gat ggg gag gtg ctg cag ctg ctc gac<br>Ala Thr Ala Ala Trp Thr Asp Asp Gly Glu Val Leu Gln Leu Leu Asp<br>770                       775                       780 | 2352 | |
| agg ttc cgg gag gag ctc cgc cgg gtg gag aag cgg att acg gag agg<br>Arg Phe Arg Glu Glu Leu Arg Arg Val Glu Lys Arg Ile Thr Glu Arg<br>785                       790                       795                       800 | 2400 | |
| aac agg gac ccg cga ctc aag aac cgg aag gga ccc gcc aag gtg ccg<br>Asn Arg Asp Pro Arg Leu Lys Asn Arg Lys Gly Pro Ala Lys Val Pro<br>                      805                       810                       815 | 2448 | |
| tac acg ctg ctg ttc ccg gac gtc ggc ggc aag gag aag ggg atc acc<br>Tyr Thr Leu Leu Phe Pro Asp Val Gly Gly Lys Glu Lys Gly Ile Thr<br>                      820                       825                       830 | 2496 | |
| ggc aaa ggg ata ccc aac agc gtc tcc ata tga caattgacaa gctcgctcct<br>Gly Lys Gly Ile Pro Asn Ser Val Ser Ile *<br>                      835                       840 | 2549 | |
| tttttttttta ttgttttgtt gcagaggatc tgattatggt tgtcggttta atttcgttgt | 2609 | |
| gagcatcatt gtgttaatat gttttattgc gatgattggt ttggaattta aaaaaaaaaa | 2669 | |
| aaaaaaaaaa aaaaaaaaaa | 2689 | |

<210> SEQ ID NO 50
<211> LENGTH: 842
<212> TYPE: PRT
<213> ORGANISM: Zea mays

<400> SEQUENCE: 50

Leu Asn Leu Trp Asp Arg Ser Pro Ala His Ala Pro Glu Asn His Ile
1               5                   10                  15

Ala Ile Asp Gly Thr Val Val Ser Cys His Phe Gly Leu Ser Leu
            20                  25                  30

Pro Gly Lys Thr Thr Thr Leu Arg Leu Phe Ser Ser Thr Gln Met Asp
        35                  40                  45

Pro Asn Thr Gly Lys Gly Lys Leu Ser Ala Glu Ala Pro Leu Arg Gly
    50                  55                  60

Gly Lys Lys Thr Lys Gln Gln Gly Arg Lys Thr Ser Thr Met Ala Tyr
65                  70                  75                  80

Gln Val Thr Phe Phe Val Asp Ala Glu Phe Gly Thr Pro Gly Ala Val
                85                  90                  95

Val Val Lys Asn Gly Leu Arg Asn Asp Gln Phe Phe Leu Arg His Val
            100                 105                 110

Gln Leu Asn Leu Pro Glu Asp Gly Arg Ser Val His Phe Glu Cys Asn
        115                 120                 125

Ser Trp Val Tyr Pro Tyr Lys Lys Thr Asn Ala Asp Arg Val Phe Phe
    130                 135                 140

Ile Asn Thr Ser Tyr Leu Pro Asp Arg Thr Pro Gln Ala Leu Arg Leu
145                 150                 155                 160

-continued

```
Leu Arg Asp Glu Glu Leu Arg Ser Leu Arg Gly Asn Gly Arg Gly Glu
                165                 170                 175

Arg Lys Asp Trp Glu Arg Val Tyr Asp Tyr Asp Leu Tyr Asn Asp Leu
            180                 185                 190

Gly Asp Pro Asp Lys Glu Asp Arg Ala Arg Pro Ala Leu Gly Gly Thr
        195                 200                 205

Ala Thr His Pro Tyr Pro Arg Arg Cys Arg Thr Gly Arg Pro Leu Phe
    210                 215                 220

Lys Thr Asp Gly Val Thr Glu Thr Arg Lys His Leu Ile Asn Leu Asp
225                 230                 235                 240

Phe Tyr Ile Pro Pro Asp Glu Arg Phe Ser Pro Thr Lys Leu Ala Glu
                245                 250                 255

Val Leu Ala Leu Ala Val Gln Ala Val Thr His Phe Val Val Pro Glu
            260                 265                 270

Ser Asn Ala Leu Phe His Gly Asn Val Asn Ser Phe Arg Ser Phe Asp
        275                 280                 285

Gln Leu Lys Asp Asp Leu Tyr Gly Arg Arg Pro Val Ala Val Asp
    290                 295                 300

Gly Gln Val Met Asp Lys Leu Lys Thr Ser Val Pro Ser His Lys Thr
305                 310                 315                 320

Tyr Lys Gln Val Ser Lys Met Val Lys Glu Thr Pro Val Lys Phe Pro
                325                 330                 335

Ile Pro Gln Val Ile Glu His Asp Gln Glu Ala Trp Arg Ser Asp Glu
            340                 345                 350

Glu Phe Ala Arg Glu Met Leu Ala Gly Leu Asn Pro Val Ile Ser
        355                 360                 365

Arg Leu Glu Val Phe Pro Pro Val Ser Arg Gly Gly Lys Lys Ser Ser
    370                 375                 380

Ile Thr Glu Ala His Ile Glu Ser Gln Leu Gln Gly Arg Thr Val Gln
385                 390                 395                 400

Lys Ala Leu Asp Asp Lys Arg Leu Tyr Leu Leu Asp His His Asp Tyr
                405                 410                 415

Leu Met Pro Tyr Leu Arg Arg Ile Asn Thr Gln Gln Gly Val Cys Val
            420                 425                 430

Tyr Ala Ser Arg Thr Leu Leu Phe Leu Arg Asp Asp Gly Ala Leu Lys
        435                 440                 445

Pro Leu Ala Ile Glu Leu Ser Leu Pro Gly Asp Gly Ala Glu Val Ser
    450                 455                 460

Ser Arg Val Ile Leu Pro Ala Thr Pro Gly Thr Thr Asp Gly His Leu
465                 470                 475                 480

Trp Trp Leu Ala Lys Ala His Val Ser Val Asn Asp Ser Gly Tyr His
                485                 490                 495

Gln Leu Ile Ser His Trp Leu Phe Thr His Ala Thr Val Glu Pro Phe
            500                 505                 510

Ile Ile Ala Thr Lys Arg Gln Met Ser Ala Met His Pro Ile His Lys
        515                 520                 525

Leu Leu Glu Pro His Phe Lys Asp Asn Met Gln Ile Asn Thr Leu Ala
    530                 535                 540

Arg Ser Ile Leu Leu Ser Ala Gly Gly Ile Leu Glu Arg Thr Met Tyr
545                 550                 555                 560

Pro Gly Lys Tyr Ala Met Glu Met Ser Ser Ala Ile Tyr Ser Glu Trp
                565                 570                 575

Arg Phe Thr Glu Gln Ser Leu Pro Asn Glu Leu Val Lys Arg Gly Met
```

-continued

```
                580             585             590
Ala Ser Lys Met Gly Gly Ala Ile Ala Leu His Val Glu Asp Tyr
        595             600             605

Pro Tyr Ala Val Asp Gly Met Asp Val Trp Arg Ala Ile Glu Gly Trp
    610             615             620

Val Arg Thr Tyr Cys Ala His Phe Tyr His Ser Asp Ala Ala Val Ala
625             630             635             640

Ala Asp Ala Glu Leu Gln Ala Trp Trp Asp Val Arg Arg Val Gly
            645             650             655

His Gly Asp Arg Gln Arg Asp Pro Ala Cys Trp Leu Asp Leu Asp Ser
            660             665             670

Val Ala Asn Leu Ala Glu Ser Leu Ser Thr Leu Ile Trp Ile Ala Ser
    675             680             685

Ala Leu His Ala Ala Val Asn Phe Gly Gln Tyr Gly Tyr Ala Gly Tyr
    690             695             700

Met Pro Asn Arg Pro Thr Arg Cys Arg Arg Phe Val Pro Leu Pro Asp
705             710             715             720

Ser Pro Glu Met Ala Gln Leu Glu Ala Asp Pro Asp Arg Phe Phe Leu
            725             730             735

Asp Thr Val Pro Asp Arg Phe Thr Ala Thr Leu Gly Leu Thr Leu Ile
            740             745             750

Glu Val Leu Ser Asn His Thr Ser Asp Glu Leu Tyr Leu Gly Gln Arg
    755             760             765

Ala Thr Ala Ala Trp Thr Asp Asp Gly Glu Val Leu Gln Leu Leu Asp
    770             775             780

Arg Phe Arg Glu Glu Leu Arg Arg Val Glu Lys Arg Ile Thr Glu Arg
785             790             795             800

Asn Arg Asp Pro Arg Leu Lys Asn Arg Lys Gly Pro Ala Lys Val Pro
            805             810             815

Tyr Thr Leu Leu Phe Pro Asp Val Gly Gly Lys Glu Lys Gly Ile Thr
            820             825             830

Gly Lys Gly Ile Pro Asn Ser Val Ser Ile
            835             840
```

<210> SEQ ID NO 51
<211> LENGTH: 2529
<212> TYPE: DNA
<213> ORGANISM: Zea mays
<220> FEATURE:
<221> NAME/KEY: CDS
<222> LOCATION: (1)...(2529)

<400> SEQUENCE: 51

```
ctg aac ctg tgg gac cgg agc ccg gct cat gcg cct gag aac cac atc     48
Leu Asn Leu Trp Asp Arg Ser Pro Ala His Ala Pro Glu Asn His Ile
1               5                   10                  15 gcc atc gat ggc acg gtg gtc gtg tct tgc cac ttt ggc ctg tcg ttg     96
Ala Ile Asp Gly Thr Val Val Val Ser Cys His Phe Gly Leu Ser Leu
            20                  25                  30 ccg ggg aag act acc acg ctt cgc ctc ttc agc agc acg cag atg gat    144
Pro Gly Lys Thr Thr Thr Leu Arg Leu Phe Ser Ser Thr Gln Met Asp
        35                  40                  45 cca aac acg ggc aag ggg aag ctg agc gcg gag gcg ccg ctg agg ggc    192
Pro Asn Thr Gly Lys Gly Lys Leu Ser Ala Glu Ala Pro Leu Arg Gly
    50                  55                  60 ggc aag aag acg aag cag cag ggg agg aag acg agc acg atg gcg tac    240
Gly Lys Lys Thr Lys Gln Gln Gly Arg Lys Thr Ser Thr Met Ala Tyr
```

-continued

```
           65                  70                  75                  80
cag gtg acc ttc ttc gtg gac gcc gag ttc ggc acg ccg ggc gcc gtc    288
Gln Val Thr Phe Phe Val Asp Ala Glu Phe Gly Thr Pro Gly Ala Val
                85                  90                  95 gtc gtc aag aac ggg ctg agg aac gac cag ttc ttc ctc cgc cac gtg    336
Val Val Lys Asn Gly Leu Arg Asn Asp Gln Phe Phe Leu Arg His Val
            100                 105                 110 cag ctg aac ctg ccc gag gac ggc cgg agc gtc cac ttc gag tgc aac    384
Gln Leu Asn Leu Pro Glu Asp Gly Arg Ser Val His Phe Glu Cys Asn
        115                 120                 125 tcc tgg gtc tac ccc tac aag aag acc aac gcc gac cgc gtc ttc ttc    432
Ser Trp Val Tyr Pro Tyr Lys Lys Thr Asn Ala Asp Arg Val Phe Phe
    130                 135                 140 atc aac acg agc tac ctg ccc gac agg acg ccc cag gct ctg cgc ctg    480
Ile Asn Thr Ser Tyr Leu Pro Asp Arg Thr Pro Gln Ala Leu Arg Leu
145                 150                 155                 160 ctg cga gac gag gag ctg cgg agc ctc cgg ggc aac ggc cgc ggc gag    528
Leu Arg Asp Glu Glu Leu Arg Ser Leu Arg Gly Asn Gly Arg Gly Glu
                165                 170                 175 cgc aag gac tgg gag cgc gtc tac gac tac gac ctg tac aac gac ctg    576
Arg Lys Asp Trp Glu Arg Val Tyr Asp Tyr Asp Leu Tyr Asn Asp Leu
            180                 185                 190 ggc gac ccg gac aag gag gac cgc gcc cgc ccg gcg ctc ggc ggc acc    624
Gly Asp Pro Asp Lys Glu Asp Arg Ala Arg Pro Ala Leu Gly Gly Thr
        195                 200                 205 gcc acg cac ccg tac ccg cgc cgc tgc cgc acc ggc cgc cct ctc ttc    672
Ala Thr His Pro Tyr Pro Arg Arg Cys Arg Thr Gly Arg Pro Leu Phe
    210                 215                 220 aag aca gac ggc gtg acg gag acg cgg aag cac ctc atc aac ctc gac    720
Lys Thr Asp Gly Val Thr Glu Thr Arg Lys His Leu Ile Asn Leu Asp
225                 230                 235                 240 ttc tac atc ccg ccg gac gag cgc ttc agc ccg acc aag ctg gcg gag    768
Phe Tyr Ile Pro Pro Asp Glu Arg Phe Ser Pro Thr Lys Leu Ala Glu
                245                 250                 255 gtg ctg gcg ctg gcg gtg cag gcc gtg acg cac ttc gtg gtg cca gag    816
Val Leu Ala Leu Ala Val Gln Ala Val Thr His Phe Val Val Pro Glu
            260                 265                 270 tcc aac gcg ctg ttc cac ggc aac gtc aac agc ttc cgc tcg ttt gat    864
Ser Asn Ala Leu Phe His Gly Asn Val Asn Ser Phe Arg Ser Phe Asp
        275                 280                 285 cag ctc aag gac gac ctg tac ggc agg aga ccg ccg gtc gcc gtg gat    912
Gln Leu Lys Asp Asp Leu Tyr Gly Arg Arg Pro Pro Val Ala Val Asp
    290                 295                 300 ggg cag gtg atg gac aag ctc aag acg tcg gtg ccg tcg cac aag acc    960
Gly Gln Val Met Asp Lys Leu Lys Thr Ser Val Pro Ser His Lys Thr
305                 310                 315                 320 tac aag cag gtg tcc aag atg gtc aag gag acg ccc gtc aag ttc ccc   1008
Tyr Lys Gln Val Ser Lys Met Val Lys Glu Thr Pro Val Lys Phe Pro
                325                 330                 335 atc cct caa gtc atc gag cat gat cag gag gcg tgg cgt agc gac gag   1056
Ile Pro Gln Val Ile Glu His Asp Gln Glu Ala Trp Arg Ser Asp Glu
            340                 345                 350 gag ttc gct agg gag atg ctg gcg ggg ctc aac ccg gtg gtg atc agt   1104
Glu Phe Ala Arg Glu Met Leu Ala Gly Leu Asn Pro Val Val Ile Ser
        355                 360                 365 aga cta gag gtg ttc ccg ccg gtg agc aga gga ggg aag aag agc tcc   1152
Arg Leu Glu Val Phe Pro Pro Val Ser Arg Gly Gly Lys Lys Ser Ser
    370                 375                 380 att acg gaa gcg cac atc gag agc cag ctc caa gga cga act gtg caa   1200
```

-continued

| | | |
|---|---|---|
| Ile Thr Glu Ala His Ile Glu Ser Gln Leu Gln Gly Arg Thr Val Gln<br>385                        390                    395                    400 | | |
| aag gca cta gat gac aag agg ctg tat ctt ctt gac cac cat gac tac<br>Lys Ala Leu Asp Asp Lys Arg Leu Tyr Leu Leu Asp His His Asp Tyr<br>                      405                    410                    415 | 1248 | |
| ctg atg cca tac ctg cgg cgc atc aac acg caa caa ggg gtg tgc gtc<br>Leu Met Pro Tyr Leu Arg Arg Ile Asn Thr Gln Gln Gly Val Cys Val<br>                    420                    425                    430 | 1296 | |
| tac gcg tcg cgc acg ctg ctc ttc ctc agg gac gac ggc gcc ctc aag<br>Tyr Ala Ser Arg Thr Leu Leu Phe Leu Arg Asp Asp Gly Ala Leu Lys<br>            435                    440                    445 | 1344 | |
| cct ctt gcc ata gag ctc agc ctg ccc ggt gac ggc gcc gag gtc agc<br>Pro Leu Ala Ile Glu Leu Ser Leu Pro Gly Asp Gly Ala Glu Val Ser<br>      450                    455                    460 | 1392 | |
| agc agg gtc atc ctc cct gcg acc cca ggg acg acc gat gga cac ctg<br>Ser Arg Val Ile Leu Pro Ala Thr Pro Gly Thr Thr Asp Gly His Leu<br>465                        470                    475                    480 | 1440 | |
| tgg tgg ctt gct aag gct cat gtc tcc gtc aat gat tca ggc tac cat<br>Trp Trp Leu Ala Lys Ala His Val Ser Val Asn Asp Ser Gly Tyr His<br>                        485                    490                    495 | 1488 | |
| cag ctc atc agc cac tgg ctg ttc acg cac gcg acg gtg gag ccg ttc<br>Gln Leu Ile Ser His Trp Leu Phe Thr His Ala Thr Val Glu Pro Phe<br>            500                    505                    510 | 1536 | |
| atc atc gcc acc aag agg cag atg agc gcc atg cac ccg atc cac aag<br>Ile Ile Ala Thr Lys Arg Gln Met Ser Ala Met His Pro Ile His Lys<br>      515                    520                    525 | 1584 | |
| ctg ctg gag ccg cac ttc aag gac aac atg cag atc aac acg ctg gcc<br>Leu Leu Glu Pro His Phe Lys Asp Asn Met Gln Ile Asn Thr Leu Ala<br>530                        535                    540 | 1632 | |
| agg agc atc ctg ctg agc gcg ggc ggc atc ctg gag agg acc atg tac<br>Arg Ser Ile Leu Leu Ser Ala Gly Gly Ile Leu Glu Arg Thr Met Tyr<br>545                        550                    555                    560 | 1680 | |
| ccg ggg aag tac gcc atg gag atg tcc tcg gcc atc tac tcc gag tgg<br>Pro Gly Lys Tyr Ala Met Glu Met Ser Ser Ala Ile Tyr Ser Glu Trp<br>                        565                    570                    575 | 1728 | |
| agg ttc acg gag cag tcc ctg ccc aac gag ctc gtc aag agg ggc atg<br>Arg Phe Thr Glu Gln Ser Leu Pro Asn Glu Leu Val Lys Arg Gly Met<br>            580                    585                    590 | 1776 | |
| gcg tcc aag atg ggc ggc ggc gcc atc gcc ctg cac gtg gag gac tac<br>Ala Ser Lys Met Gly Gly Gly Ala Ile Ala Leu His Val Glu Asp Tyr<br>      595                    600                    605 | 1824 | |
| ccg tac gcg gtg gac ggc atg gac gtg tgg cgc gcc atc gag ggc tgg<br>Pro Tyr Ala Val Asp Gly Met Asp Val Trp Arg Ala Ile Glu Gly Trp<br>610                        615                    620 | 1872 | |
| gtc agg acc tac tgc gcc cac ttc tac cac tcc gac gcc gcg gtg gcc<br>Val Arg Thr Tyr Cys Ala His Phe Tyr His Ser Asp Ala Ala Val Ala<br>625                        630                    635                    640 | 1920 | |
| gcc gac gcg gag ctg cag gcg tgg tgg gac gac gtc cgc cgc gtc ggc<br>Ala Asp Ala Glu Leu Gln Ala Trp Trp Asp Asp Val Arg Arg Val Gly<br>                        645                    650                    655 | 1968 | |
| cac ggc gac cgc cag cgc gac ccg gcg tgc tgg ctg gac ctc gac tcc<br>His Gly Asp Arg Gln Arg Asp Pro Ala Cys Trp Leu Asp Leu Asp Ser<br>            660                    665                    670 | 2016 | |
| gtg gcc aac ctc gcc gag tcg ctg tcc acg ctc atc tgg atc gcc tcc<br>Val Ala Asn Leu Ala Glu Ser Leu Ser Thr Leu Ile Trp Ile Ala Ser<br>      675                    680                    685 | 2064 | |
| gcg ctg cac gcc gcc gtc aac ttc ggc cag tac ggc tac gcc ggg tac<br>Ala Leu His Ala Ala Val Asn Phe Gly Gln Tyr Gly Tyr Ala Gly Tyr<br>      690                    695                    700 | 2112 | |

-continued

| | |
|---|---|
| atg ccc aac cgc ccc acc cgg tgc cgc cgc ttc gtg ccg ctg ccg gac<br>Met Pro Asn Arg Pro Thr Arg Cys Arg Arg Phe Val Pro Leu Pro Asp<br>705                    710                    715                    720 | 2160 |
| tcc ccg gag atg gcg cag ctg gag gcc gac ccg gac agg ttc ttc ctc<br>Ser Pro Glu Met Ala Gln Leu Glu Ala Asp Pro Asp Arg Phe Phe Leu<br>                    725                    730                    735 | 2208 |
| gac acg gtg ccc gac cgc ttc acc gcc acg ctc ggg ctc acg ctc atc<br>Asp Thr Val Pro Asp Arg Phe Thr Ala Thr Leu Gly Leu Thr Leu Ile<br>740                    745                    750 | 2256 |
| gag gtc ctc tcc aac cac acc tcc gac gag ctc tac ctg ggc cag cgc<br>Glu Val Leu Ser Asn His Thr Ser Asp Glu Leu Tyr Leu Gly Gln Arg<br>                    755                    760                    765 | 2304 |
| gcc acc gcg gcg tgg acc gac gat ggg gag gtg ctg cag ctg ctc gac<br>Ala Thr Ala Ala Trp Thr Asp Asp Gly Glu Val Leu Gln Leu Leu Asp<br>770                    775                    780 | 2352 |
| agg ttc cgg gag gag ctc cgc cgg gtg gag aag cgg att acg gag agg<br>Arg Phe Arg Glu Glu Leu Arg Arg Val Glu Lys Arg Ile Thr Glu Arg<br>785                    790                    795                    800 | 2400 |
| aac agg gac ccg cga ctc aag aac cgg aag gga ccc gcc aag gtg ccg<br>Asn Arg Asp Pro Arg Leu Lys Asn Arg Lys Gly Pro Ala Lys Val Pro<br>                    805                    810                    815 | 2448 |
| tac acg ctg ctg ttc ccg gac gtc ggc ggc aag gag aag ggg atc acc<br>Tyr Thr Leu Leu Phe Pro Asp Val Gly Gly Lys Glu Lys Gly Ile Thr<br>820                    825                    830 | 2496 |
| ggc aaa ggg ata ccc aac agc gtc tcc ata tga<br>Gly Lys Gly Ile Pro Asn Ser Val Ser Ile *<br>           835                    840 | 2529 |

<210> SEQ ID NO 52
<211> LENGTH: 842
<212> TYPE: PRT
<213> ORGANISM: Zea mays

<400> SEQUENCE: 52

Leu Asn Leu Trp Asp Arg Ser Pro Ala His Ala Pro Glu Asn His Ile
1                 5                      10                  15

Ala Ile Asp Gly Thr Val Val Ser Cys His Phe Gly Leu Ser Leu
                20                    25                    30

Pro Gly Lys Thr Thr Thr Leu Arg Leu Phe Ser Ser Thr Gln Met Asp
                35                    40                    45

Pro Asn Thr Gly Lys Gly Lys Leu Ser Ala Glu Ala Pro Leu Arg Gly
        50                    55                    60

Gly Lys Lys Thr Lys Gln Gln Gly Arg Lys Thr Ser Thr Met Ala Tyr
65                    70                    75                    80

Gln Val Thr Phe Phe Val Asp Ala Glu Phe Gly Thr Pro Gly Ala Val
                85                    90                    95

Val Val Lys Asn Gly Leu Arg Asn Asp Gln Phe Phe Leu Arg His Val
                100                   105                  110

Gln Leu Asn Leu Pro Glu Asp Gly Arg Ser Val His Phe Glu Cys Asn
           115                    120                    125

Ser Trp Val Tyr Pro Tyr Lys Lys Thr Asn Ala Asp Arg Val Phe Phe
    130                    135                    140

Ile Asn Thr Ser Tyr Leu Pro Asp Arg Thr Pro Gln Ala Leu Arg Leu
145                  150                   155                  160

Leu Arg Asp Glu Glu Leu Arg Ser Leu Arg Gly Asn Gly Arg Gly Glu
                165                   170                  175

Arg Lys Asp Trp Glu Arg Val Tyr Asp Tyr Asp Leu Tyr Asn Asp Leu
           180                    185                  190

-continued

```
Gly Asp Pro Asp Lys Glu Asp Arg Ala Arg Pro Ala Leu Gly Gly Thr
            195                 200                 205
Ala Thr His Pro Tyr Pro Arg Arg Cys Arg Thr Gly Arg Pro Leu Phe
            210                 215                 220
Lys Thr Asp Gly Val Thr Glu Thr Arg Lys His Leu Ile Asn Leu Asp
225                 230                 235                 240
Phe Tyr Ile Pro Pro Asp Glu Arg Phe Ser Pro Thr Lys Leu Ala Glu
                245                 250                 255
Val Leu Ala Leu Ala Val Gln Ala Val Thr His Phe Val Val Pro Glu
            260                 265                 270
Ser Asn Ala Leu Phe His Gly Asn Val Asn Ser Phe Arg Ser Phe Asp
            275                 280                 285
Gln Leu Lys Asp Asp Leu Tyr Gly Arg Arg Pro Pro Val Ala Val Asp
            290                 295                 300
Gly Gln Val Met Asp Lys Leu Lys Thr Ser Val Pro Ser His Lys Thr
305                 310                 315                 320
Tyr Lys Gln Val Ser Lys Met Val Lys Glu Thr Pro Val Lys Phe Pro
                325                 330                 335
Ile Pro Gln Val Ile Glu His Asp Gln Glu Ala Trp Arg Ser Asp Glu
            340                 345                 350
Glu Phe Ala Arg Glu Met Leu Ala Gly Leu Asn Pro Val Val Ile Ser
            355                 360                 365
Arg Leu Glu Val Phe Pro Pro Val Ser Arg Gly Gly Lys Lys Ser Ser
            370                 375                 380
Ile Thr Glu Ala His Ile Glu Ser Gln Leu Gln Gly Arg Thr Val Gln
385                 390                 395                 400
Lys Ala Leu Asp Asp Lys Arg Leu Tyr Leu Leu Asp His His Asp Tyr
                405                 410                 415
Leu Met Pro Tyr Leu Arg Arg Ile Asn Thr Gln Gln Gly Val Cys Val
            420                 425                 430
Tyr Ala Ser Arg Thr Leu Leu Phe Leu Arg Asp Asp Gly Ala Leu Lys
            435                 440                 445
Pro Leu Ala Ile Glu Leu Ser Leu Pro Gly Asp Gly Ala Glu Val Ser
450                 455                 460
Ser Arg Val Ile Leu Pro Ala Thr Pro Gly Thr Thr Asp Gly His Leu
465                 470                 475                 480
Trp Trp Leu Ala Lys Ala His Val Ser Val Asn Asp Ser Gly Tyr His
                485                 490                 495
Gln Leu Ile Ser His Trp Leu Phe Thr His Ala Thr Val Glu Pro Phe
            500                 505                 510
Ile Ile Ala Thr Lys Arg Gln Met Ser Ala Met His Pro Ile His Lys
            515                 520                 525
Leu Leu Glu Pro His Phe Lys Asp Asn Met Gln Ile Asn Thr Leu Ala
            530                 535                 540
Arg Ser Ile Leu Leu Ser Ala Gly Gly Ile Leu Glu Arg Thr Met Tyr
545                 550                 555                 560
Pro Gly Lys Tyr Ala Met Glu Met Ser Ser Ala Ile Tyr Ser Glu Trp
                565                 570                 575
Arg Phe Thr Glu Gln Ser Leu Pro Asn Glu Leu Val Lys Arg Gly Met
            580                 585                 590
Ala Ser Lys Met Gly Gly Gly Ala Ile Ala Leu His Val Glu Asp Tyr
            595                 600                 605
```

-continued

```
Pro Tyr Ala Val Asp Gly Met Asp Val Trp Arg Ala Ile Glu Gly Trp
    610                 615                 620
Val Arg Thr Tyr Cys Ala His Phe Tyr His Ser Asp Ala Ala Val Ala
625                 630                 635                 640
Ala Asp Ala Glu Leu Gln Ala Trp Trp Asp Asp Val Arg Arg Val Gly
                645                 650                 655
His Gly Asp Arg Gln Arg Asp Pro Ala Cys Trp Leu Asp Leu Asp Ser
            660                 665                 670
Val Ala Asn Leu Ala Glu Ser Leu Ser Thr Leu Ile Trp Ile Ala Ser
        675                 680                 685
Ala Leu His Ala Ala Val Asn Phe Gly Gln Tyr Gly Tyr Ala Gly Tyr
    690                 695                 700
Met Pro Asn Arg Pro Thr Arg Cys Arg Arg Phe Val Pro Leu Pro Asp
705                 710                 715                 720
Ser Pro Glu Met Ala Gln Leu Glu Ala Asp Pro Asp Arg Phe Phe Leu
                725                 730                 735
Asp Thr Val Pro Asp Arg Phe Thr Ala Thr Leu Gly Leu Thr Leu Ile
            740                 745                 750
Glu Val Leu Ser Asn His Thr Ser Asp Glu Leu Tyr Leu Gly Gln Arg
        755                 760                 765
Ala Thr Ala Ala Trp Thr Asp Asp Gly Glu Val Leu Gln Leu Leu Asp
    770                 775                 780
Arg Phe Arg Glu Glu Leu Arg Arg Val Glu Lys Arg Ile Thr Glu Arg
785                 790                 795                 800
Asn Arg Asp Pro Arg Leu Lys Asn Arg Lys Gly Pro Ala Lys Val Pro
                805                 810                 815
Tyr Thr Leu Leu Phe Pro Asp Val Gly Gly Lys Glu Lys Gly Ile Thr
            820                 825                 830
Gly Lys Gly Ile Pro Asn Ser Val Ser Ile
        835                 840

<210> SEQ ID NO 53
<211> LENGTH: 7492
<212> TYPE: DNA
<213> ORGANISM: Zea mays
<220> FEATURE:
<221> NAME/KEY: promoter
<222> LOCATION: (1)...(2086)
<220> FEATURE:
<221> NAME/KEY: TATA_signal
<222> LOCATION: (1548)...(1555)
<220> FEATURE:
<221> NAME/KEY: 5'UTR
<222> LOCATION: (1864)...(2086)
<220> FEATURE:
<221> NAME/KEY: misc_feature
<222> LOCATION: (28)...(31)
<223> OTHER INFORMATION: W box
<220> FEATURE:
<221> NAME/KEY: misc_feature
<222> LOCATION: (86)...(89)
<223> OTHER INFORMATION: W box
<220> FEATURE:
<221> NAME/KEY: misc_feature
<222> LOCATION: (345)...(348)
<223> OTHER INFORMATION: W box
<220> FEATURE:
<221> NAME/KEY: misc_feature
<222> LOCATION: (414)...(417)
<223> OTHER INFORMATION: W box
<220> FEATURE:
<221> NAME/KEY: misc_feature
<222> LOCATION: (733)...(736)
<223> OTHER INFORMATION: W box
```

```
<220> FEATURE:
<221> NAME/KEY: misc_feature
<222> LOCATION: (928)...(931)
<223> OTHER INFORMATION: W box
<220> FEATURE:
<221> NAME/KEY: misc_feature
<222> LOCATION: (1022)...(1025)
<223> OTHER INFORMATION: W box
<220> FEATURE:
<221> NAME/KEY: misc_feature
<222> LOCATION: (260)...(266)
<223> OTHER INFORMATION: MRE-like element
<220> FEATURE:
<221> NAME/KEY: misc_feature
<222> LOCATION: (167)...(172)
<223> OTHER INFORMATION: H box
<220> FEATURE:
<221> NAME/KEY: misc_feature
<222> LOCATION: (1446)...(1552)
<223> OTHER INFORMATION: C2H2 response element
<220> FEATURE:
<221> NAME/KEY: 3'UTR
<222> LOCATION: (6569)...(6767)

<400> SEQUENCE: 53
```

| | | | |
|---|---|---|---|
| gaattcggat cgttggatag gagagtatga cacaagggag tgcgtatcta tacagaggta | 60 |
| cgcgtataca gcatagcgtt aagccgtcaa tgaaaaacaa aatctagggt tggtttgttt | 120 |
| tagattacaa tataactaaa atatataatc caagttattt taaaataaca cttaatttaa | 180 |
| aataatttag attatataat ctaagtagat ttataatccg aaacaaaccg ctacacagtg | 240 |
| aaacagctag ctaagagatg tttggttttt atagactaaa ttttactcta tctattttat | 300 |
| tttatcttag tctctaaatt gctaaatatt tagtttctat atttgtcaat ttaaaaacta | 360 |
| aaaaagaaca aagagattaa aaattagtct ctataaacgt aacacgccta gtgtgaccag | 420 |
| accaccaatc ttccatctgg aaaaaccgct gtcgccttct tgcattccat cctgagcttg | 480 |
| gtttacaagc aaagcaaaga cgaatgatct ttctcgaccc gagagacttg tctgggccaa | 540 |
| aaacaatctg gaggagaaat ttattgctcc tctattttc gaaggctcgc cttcaccgta | 600 |
| ccaaatggcg tccggaattg tttagtcctg tagtatatat gtacgcggaa tcggtcgctc | 660 |
| gtacgatccg ccatcggtta gcacgagaag ctagcgcctg gtgcagatct tctcggggta | 720 |
| gtttttagtg ttgtcaacta ttattataaa caattattta gaaagtgagt ctaacttcat | 780 |
| tggttatgat atgaagaaag ttgagctaca cagccatgtc catcggtgtc ggcgaaacgt | 840 |
| gcagcaactg aaaccgaaac cgcggccttt ctcttcgttc gagttttaca cggtgtctat | 900 |
| tccgtggccc cggcggatgc cttgccatga ccggggccgg gaccgggagg atcaacacta | 960 |
| cgcacctcct cagctacgta atttactact aacacaagcc aggcgcaatt aagaccggcc | 1020 |
| ggtcaatgtc cagtccctgt ttccctgttc tgcttgcagg gcggaccacc gagaggaaac | 1080 |
| aacgttgagg acggcacgcg accgtcacga cgcgcggccc tcacggccac tgtacatgat | 1140 |
| cgtcgtcgac ggcagcagct ccgtaggacg actcagcgct ggagcctagt gaagggtctg | 1200 |
| cagtgcactc gcgacgacgt gtctcgtgtg tgtcgtcgcc ctcggagtcg atgtgggatg | 1260 |
| cgcatggcac cgcagcccgt ttccgccgcg gtttcggtct cggcgctatg gacacagtca | 1320 |
| gctcggcctc tggcctctgg gctcgtccgt gctcgcttgc aggttgcaat tacacacctg | 1380 |
| cgccgttgct ggctccgccg gcgtggacca gctggagccg gagaaaccgc gcatgtgccc | 1440 |
| ggggcagccg ccagccggct cccagcctga tggctttctg atctcgtttt tcgtttgtgt | 1500 |
| cggattggtg ggtcggaacg attcttagcc ggattgcttc tctaatttat ataaacttta | 1560 |
| atcaactgga acgattccgg gtgcaatccg acgtaaacga acaaggcctt accgggatca | 1620 |

```
ccattaccat aagccgcacg gtccccaaac ccgtgacgcc gacgtatacc ataccatacc    1680
atactatgta atacgtacta tccaatctta atccccgcat tttttaaact agtttctcat    1740
catcatcgtc ctcgtcgtca tcttcttctt cacccttttcc ttatcgtgta gtagtacatg    1800
tcgttgtcgc ctacatcact ggctggcaga gcagtaagca gtaaagagta ggcgcagcat    1860
aaagccgagg cgagcagccg tcgccgccta tatatcgcgg cgcagggcag caggagttcc    1920
acacttccat acacgcctgc cttgtgcctt cccttcccctt gccttgcttc gcttattgcc    1980
ggcacatcac atcggcaggc gagggacgga gcgagcaggg aagcccatcc accagccagc    2040
caccgcgttc ctgagaagcg aggagcgaga aaagcgaaga gcggccatgt tctggcacgg    2100
ggtcgcggac cggctgacgg gaaagaacaa ggaggcgtgg agcgagggca agatccgcgg    2160
cacggtgagg ctggtcaaga aggaggtgct ggacgtcggc gacttcaacg cctcgctcct    2220
cgacggcgtc cacaggatcc tcggctggga cgacggcgtc gccttccagc tcgtcagcgc    2280
caccgcggcc gaccccagta agcgagcccc tgccccacgc cacctatctg aacacgcccg    2340 ctcccgtgg ccacggggcc gtgacgtgac gccgggccgc gctcgctcgc cggctcgccg    2400
cccgtggccg gaccggaacg cacgggcatg cggccaccgc gcgtttcgcc gtccatttcg    2460
gtttctacgt ttcgtctctt cctgcctgta ctggactggt cacccgtccg gcatggcaag    2520
cacacagtca gacggacagg agcgacaccg cgcgacccgg gagagttggt cgctggtcca    2580
tggtccgttg cacccgcggt ggctgggtcc gtgtctctgc gacgaactca tgattgcggt    2640
taagaaactt gcttgcctgc tctgcttcca tggacacgga cagacagtga gacagggatg    2700
tatttttttt tggaattttc tccgggctgg aacagttgtt gtgtgtgggt ggtgtggcat    2760
tctgaatctc gaacgcgact gcggtttcat gttcgctatc gcttccacgg caacgctcca    2820
gctagcgtca tctgattgca tgcaggcgtt taggacccgg ccggccgtac tgtaatctcc    2880
gctgaaatgt cgtatagtaa accttgttta ttagtactat ttttgtgtgt gtgtgtgtgg    2940
agctaataat gtgcttaaac gaaacctcgc cgtcatgctg tcatggtttg gtggatccca    3000
ggcaacgggg gccgtggcaa ggtggggaag gcggcgcacc tggaggaggc ggtggtgtcg    3060
ctcaagtcca cggcggacgg ggagaccgtg taccgggtga gcttcgagtg ggacgagtcg    3120
cagggcatcc cggcgccgt cctggtcagg aacctgcagc acgccgagtt cttcctcaag    3180
acgctcaccc tcgagggcgt cccaggcaag ggcaccgtcg tcttcgtcgc caactcgtgg    3240
gtctacccgc acaagctcta ctcccaggaa cgcatcttct tcgccaacga cgtgagtatt    3300
aatctttctg atgcatgtca cgattttttt ttttgaaaag cgaccagcag gaggagatct    3360
accgggcata tattaacaga gaaggagttt taaaaaacta attacaaaaa ttgaggttac    3420
tttttttttt gctgctagaa gcaaaaatat ggacaagaca aggacaatca ttgctatatg    3480
tatctgtata ctcctacaca acacgtacta cccaaacaac cgcatccaca cactcatcac    3540
ttcgtattat tgttagggct ctctactgca tttacgtagc atatgactaa attaacgcaa    3600
agtagtgctg cttaattagg tttgtggaaa ggatccatca gggcatattc attatgctcg    3660
tttgttgacc cagaaggcca gaactggttg atccatcacg gcatattcat cctacgtttt    3720
acttctgcca gcactatatt actccgtggc tatatataga aaaaaacagg ccagtctcac    3780
tctaatcctg tgttgcttgc agacctatct gccgagcaaa atgccggcgg cgttggtgcc    3840
ttatcggcaa gatgagctca agattctccg tggcgacgat aatcctggac ataccagga    3900 gcatgatcgc gtctaccgtt acgactacta caatgacctt ggtgatcccg acaagggcga    3960
```

```
agagcacgct cggccgatcc tcggtggcag ccaagaacac ccgtatcccc gtcgctgcag    4020
aactggccgg cacccaacaa agaaaggtac tagctcaagt cagctagtgc tagtccatac    4080
catacaggat gccagaaatt tggctgaaat ccttgctgag ttaaccttt tacgcagacc     4140 caaattcgga gagcaggctt ttcctgctga acctgaacat ctacgtcccg cgtgacgaac    4200
gctttgggca tctcaagatg tcggacttcc ttgggtactc gctgaagacg atcatcgagg    4260
ctgttcttcc aacactgggg actttcgtcg atgcacgcc caaggagttc gattcgtttg     4320
aggatatcct cgggctctac gagctgggcc cagaggcacc caacaaccca ctgatagcag    4380
agatcaggaa gaagatcccc agcgagttcc ttcgaagcat tctgccgaac ggtagccatg    4440
accacccgct aaagatgccc cttccaaatg tcatcaaatc aggtaaaccc aaatttcttt    4500 ttttttttgga atctttctat gttaaacggc cggtgcctga actagaaaaa aatttaccat   4560
ggctaaggct gaatcttggt tggtataaaa ccagatgtgt tgaaaaggc tccggagttt    4620 aagtttggct ggaggactga cgaagagttc gcgagagaga cacttgcagg cgtgaaccca    4680
gtaatcatca aacgtctgac ggttagcgtt cttgcatcat ttggatcggc aaaaatacac    4740
cttgccccat atattaactg agtacagagc cttaaaggcc ttttttttata tatatatttc    4800 gtatctcagg agttccccgc taaaagcacc ctggacccaa ggcagtacgg agaccacacc    4860
agcaagatca ctgaagctca catccggcat aacatgggag cctgtcggt gcagaacgta     4920 tgctggactg catgaacgca cgcacgtaca accgaaagcc gcttaaaacc atcgactgat    4980
ctgatttccg cgtaacgaac cctgtgcagg cactgaggaa caagaggctc ttcatcctag    5040
accaccatga ccatttcatg ccgtacctcg acgagatcaa cgagctggag gggaacttca    5100
tctacgccag caggaccta ctgttcctga aggacgatgg cacgctgaag cccctggcca    5160
tcgagctgag cctgccccac cctgacggcc agcagcgcgg cgcggtcagc aaggtgtaca    5220
ccccggctca caccgcgtc gagggccacg tctggcagct cgccaaggct tatgcctgcg     5280
taaacgactc tgcctggcat cagctgatca gccactggta taagaaatgt ttctggtgcc    5340
tttttctctt tttttttcct tttaattaat taatgtacat agataactga agcactaatc    5400
ttaattgtgt ggcttgcatt gcattgcagg ctgaacacgc acgcggtgat cgagccgttc    5460
gtaatcgcga caaaccggca gctcagcgtg gtgcatcccg tgcacaagct gctgagcccg    5520
cactaccgtg acacgctgaa catcaacgcc ctggcacgcc agacactcat caacgccggc    5580
ggcgtcttcg agcgcaccgt gttccctgca aagtacgcgc tggggatgtc ggcagacgtg    5640
tacaagagct ggaatttcaa cgagcaggct ctcccagcag atctcgtcaa gaggtacgta    5700
gacaatacac tgaggtgagc agcactaaac gcctatagaa aactgttcgg ttcttgacgt    5760
ggttgtggtt gcgtgcgttc agaggtgtgg ctgtgccgga ccagtcaagc ccatatggtg    5820
tccgactgct gatcaaggac taccctatg ccgttgacgg gctcgtcatc tggtgggcga     5880
tcgagcggtg ggtcaaggag tacctggaca tctactaccc taacgacggc gagctccagc    5940
gtgacgtgga gctgcaggcg tggtggaagg aggtgcgtga ggaggcgcac ggcgacctca    6000
aggaccgaga ctggtggccc aggatggaca ccgtccagca gctggctagg gcgtgcacga    6060
ccatcatctg ggtggcatcc gcgctgcacg cggctgtcaa cttgggcag tacccatacg     6120 ccgggtacct cccgaaccgg ccgacggcca gccggcgccc gatgccggag ccaggcagcc    6180
acgactacaa gaagctggga gcggggcaga aggaggcgga catggtgttc atccgcacca    6240
tcaccagcca gttccagacc atcctgggca tctcgctcat cgagatcctc tccaagcact    6300
cctccgacga ggtgtacctc ggccagcgtg acgagcctga tcgctggacg tcagacgcca    6360
```

-continued

```
aggcgctgga tgcgttcaaa agattcggga gccggctggt gcagattgag aatcggatca    6420
agacgatgaa cgacagtccg gacttgaaga accggaaggg gcctgtggaa atgccgtaca    6480
tgctgctgta ccccaacacg tcggacgtta ccggcgagaa ggccgagggg cttactgcca    6540
tgggcattcc caacagcatc tccatatgag cctgggcaga ttgtgtctcg tagtaaattg    6600
ttgtgctgcg ccgtgcgatg tgtttcttca ttggttttgt cagtctcagg gtaggggatg    6660
gagatcatac catgatcttt gtagggttga gagaggagtc cacgcttgaa tattgttgtc    6720
atgtatgtaa ttcttggtta ataataaagt tcgtcagttc atttcttagc ctatcagtct    6780
ccagccaaaa cttatacttc aaaaaaaagt aataggcatt tgattccaat atgataataa    6840
aataggacta cttttttccgt ccgttcacgc atgtgagtgt tgccggttcc gaagacgatg    6900
acacgggtat tcgttttgt cccgggctta ttcctttatg ctggattggt gggtcgaaac    6960
gatttctaac cggattgctt atctaatttg tataaatttt tattagctca aacgattccg    7020
gacgcaatcc aatacaaacg aacaagccgt caggtgtcat ggagtactgt actcatgtgt    7080
actgtattcc tgatgccgcc gcccgccgac tttggcggtt tgccggccct gcgaatgcca    7140
ccgctcttcc tagctggggt cgtacactct ccacgcctcc cacgtcttac tgctcaccgc    7200 caccacccccg ccgcctctat ctcggtctgc gacgcgttgg cccatccctg ctccccgcca    7260
tggtctctcg cccaccgagg tatgttcgag gagcaaataa gatgaggagc cagttttctt    7320
cttccgttct tctctcgcat tagccaagga aggcaccgta gaaagatccc caaagctttc    7380
cagaaatccg ctttcacgat cagtagggct cgcagttttt ttttctttcc tacagcgcat    7440
ttctcggtct tcacctcgct cctgttgtag agttctcgtg gcaggggaat tc            7492
```

<210> SEQ ID NO 54
<211> LENGTH: 2086
<212> TYPE: DNA
<213> ORGANISM: Zea mays
<220> FEATURE:
<221> NAME/KEY: promoter
<222> LOCATION: (1)...(2086)
<223> OTHER INFORMATION: LOX5 promoter

<400> SEQUENCE: 54

```
gaattcggat cgttggatag gagagtatga cacaagggag tgcgtatcta tacagaggta      60
cgcgtataca gcatagcgtt aagccgtcaa tgaaaacaa atctagggt tggtttgttt      120 tagattacaa tataactaaa atatataatc caagttattt taaataaca cttaatttaa      180 aataatttag attatataat ctaagtagat ttataatccg aaacaaaccg ctacacagtg      240
aaacagctag ctaagagatg tttggttttt atagactaaa ttttactcta tctattttat      300
tttatcttag tctctaaatt gctaaatatt tagtttctat atttgtcaat ttaaaaacta      360
aaaaagaaca aagagattaa aaattagtct ctataaacgt aacacgccta gtgtgaccag      420
accaccaatc ttccatctgg aaaaccgct gtcgccttct tgcattccat cctgagcttg      480
gtttacaagc aaagcaaaga cgaatgatct ttctcgaccc gagagacttg tctgggccaa      540
aaacaatctg gaggagaaat ttattgctcc tctatttttc gaaggctcgc cttcaccgta      600
ccaaatggcg tccggaattg tttagtcctg tagtatatat gtacgcggaa tcggtcgctc      660
gtacgatccg ccatcggtta gcacgagaag ctagcgcctg gtgcagatct tctcgggta      720 gtttttagtg ttgtcaacta ttattataaa caattattta gaaagtgagt ctaacttcat      780
tggttatgat atgaagaaag ttgagctaca cagccatgtc catcggtgtc ggcgaaacgt      840
```

```
gcagcaactg aaaccgaaac cgcggccttt ctcttcgttc gagttttaca cggtgtctat    900
tccgtggccc cggcggatgc cttgccatga ccggggccgg gaccgggagg atcaacacta    960
cgcacctcct cagctacgta atttactact aacacaagcc aggcgcaatt aagaccggcc   1020
ggtcaatgtc cagtccctgt ttccctgttc tgcttgcagg gcggaccacc gagaggaaac   1080
aacgttgagg acggcacgcg accgtcacga cgcgcggccc tcacggccac tgtacatgat   1140
cgtcgtcgac ggcagcagct ccgtaggacg actcagcgct ggagcctagt gaagggtctg   1200
cagtgcactc gcgacgacgt gtctcgtgtg tgtcgtcgcc ctcggagtcg atgtgggatg   1260
cgcatggcac cgcagcccgt ttccgccgcg gtttcggtct cggcgctatg gacacagtca   1320
gctcggcctc tggcctctgg gctcgtccgt gctcgcttgc aggttgcaat tacacacctg   1380
cgccgttgct ggctccgccg gcgtggacca gctggagccg gagaaaccgc gcatgtgccc   1440
ggggcagccg ccagccggct cccagcctga tggctttctg atctcgtttt cgtttgtgt    1500 cggattggtg ggtcggaacg attcttagcc ggattgcttc tctaatttat ataaacttta   1560
atcaactgga acgattccgg gtgcaatccg acgtaaacga acaaggcctt accgggatca   1620
ccattaccat aagccgcacg gtccccaaac ccgtgacgcc gacgtatacc ataccatacc   1680
atactatgta atacgtacta tccaatctta atccccgcat ttttaaact agtttctcat    1740 catcatcgtc ctcgtcgtca tcttcttctt cacccttttcc ttatcgtgta gtagtacatg   1800
tcgttgtcgc ctacatcact ggctggcaga gcagtaagca gtaaagagta ggcgcagcat   1860
aaagccgagg cgagcagccg tcgccgccta tatcgcgg cgcagggcag caggagttcc    1920
acacttccat acacgcctgc cttgtgcctt cccttccctt gccttgcttc gcttattgcc   1980
ggcacatcac atcggcaggc gagggacgga gcgagcaggg aagcccatcc accagccagc   2040
caccgcgttc ctgagaagcg aggagcgaga aaagcgaaga gcggcc              2086

<210> SEQ ID NO 55
<211> LENGTH: 198
<212> TYPE: DNA
<213> ORGANISM: Zea mays
<220> FEATURE:
<221> NAME/KEY: 3'UTR
<222> LOCATION: (1)...(198)
<223> OTHER INFORMATION: LOX5 3'UTR

<400> SEQUENCE: 55
gcctgggcag attgtgtctc gtagtaaatt gttgtgctgc gccgtgcgat gtgtttcttc     60
attggttttg tcagtctcag ggtaggggat ggagatcata ccatgatctt tgtagggttg    120
agagaggagt ccacgcttga atattgttgt catgtatgta attcttggtt aataataaag    180
ttcgtcagtt catttctt                                                  198

<210> SEQ ID NO 56
<211> LENGTH: 4483
<212> TYPE: DNA
<213> ORGANISM: Zea mays
<220> FEATURE:
<221> NAME/KEY: exon
<222> LOCATION: (1)...(211)
<223> OTHER INFORMATION: LOX5
<220> FEATURE:
<221> NAME/KEY: intron
<222> LOCATION: (212)...(915)
<220> FEATURE:
<221> NAME/KEY: exon
<222> LOCATION: (916)...(1205)
<220> FEATURE:
<221> NAME/KEY: intron
```

```
<222> LOCATION: (1206)...(1716)
<220> FEATURE:
<221> NAME/KEY: exon
<222> LOCATION: (1717)...(1960)
<220> FEATURE:
<221> NAME/KEY: intron
<222> LOCATION: (1961)...(2051)
<220> FEATURE:
<221> NAME/KEY: exon
<222> LOCATION: (2052)...(2396)
<220> FEATURE:
<221> NAME/KEY: intron
<222> LOCATION: (2397)...(2508)
<220> FEATURE:
<221> NAME/KEY: exon
<222> LOCATION: (2509)...(2615)
<220> FEATURE:
<221> NAME/KEY: intron
<222> LOCATION: (2616)...(2723)
<220> FEATURE:
<221> NAME/KEY: exon
<222> LOCATION: (2724)...(2831)
<220> FEATURE:
<221> NAME/KEY: intron
<222> LOCATION: (2832)...(2923)
<220> FEATURE:
<221> NAME/KEY: exon
<222> LOCATION: (2924)...(3231)
<220> FEATURE:
<221> NAME/KEY: intron
<222> LOCATION: (3232)...(3343)
<220> FEATURE:
<221> NAME/KEY: exon
<222> LOCATION: (3344)...(3608)
<220> FEATURE:
<221> NAME/KEY: intron
<222> LOCATION: (3609)...(3696)
<220> FEATURE:
<221> NAME/KEY: exon
<222> LOCATION: (3697)...(4483)

<400> SEQUENCE: 56
atgttctggc acgggtcgc ggaccggctg acgggaaaga acaaggaggc gtggagcgag      60
ggcaagatcc gcggcacggt gaggctggtc aagaaggagg tgctggacgt cggcgacttc     120
aacgcctcgc tcctcgacgg cgtccacagg atcctcggct gggacgacgg cgtcgccttc     180
cagctcgtca gcgccaccgc ggccgacccc agtaagcgag ccctgcccc acgccaccta     240 tctgaacacg cccgctcccg gtggccacgg ggccgtgacg tgacgccggg ccgcgctcgc     300
tcgccggctc gccgcccgtg gccggaccgg aacgcacggg catgcggcca ccgcgcgttt     360
cgccgtccat ttcggttct acgttcgtc tcttcctgcc tgtactggac tggtcacccg      420
tccggcatgg caagcacaca gtcagacgga caggagcgac accgcgcgac ccgtgagagt     480
tggtcgctgg tccatggtcc gttgcacccg cggtggctgg gtccgtgtct ctgcgacgaa     540
ctcatgattg cggttaagaa acttgcttgc ctgctctgct tccatggaca cggacagaca     600
gtgagacagg gatgtatttt tttttggaat tttctccggg ctggaacagt tgttgtgtgt     660
gggtggtgtg gcattctgaa tctcgaacgc gactgcggtt tcatgttcgc tatcgcttcc     720
acggcaacgc tccagctagc gtcatctgat tgcatgcagg cgtttaggac ccggccggcc     780
gtactgtaat ctccgctgaa atgtcgtata gtaaaccttg tttattagta ctattttgt     840 gtgtgtgtgt gtggagctaa taatgtgctt aaacgaaacc tcgccgtcat gctgtcatgg     900
gttggtggat cccaggcaac gggggccgtg gcaaggtggg gaaggcggcg cacctggagg     960
aggcggtggt gtcgctcaag tccacggcgc acgggagac cgtgtaccgg gtgagcttcg    1020
agtgggacga gtcgcagggc atcccggcg ccgtcctggt caggaacctg cagcacgccg    1080
```

```
agttcttcct caagacgctc accctcgagg gcgtcccagg caagggcacc gtcgtcttcg   1140
tcgccaactc gtgggtctac ccgcacaagc tctactccca ggaacgcatc ttcttcgcca   1200
acgacgtgag tattaatctt tctgatgcat gtcacgattt ttttttttga aaagcgacca   1260
gcaggaggag atctaccggg catatattaa cagagaagga gttttaaaaa actaattaca   1320
aaaattgagg ttacttttt ttttgctgct agaagcaaaa atatggacaa gacaaggaca   1380
atcattgcta tatgtatctg tatactccta cacaacacgt actacccaaa caaccgcatc   1440
cacacactca tcacttcgta ttattgttag ggctctctac tgcatttacg tagcatatga   1500
ctaaattaac gcaaagtagt gctgcttaat taggtttgtg gaaggatcc atcagggcat    1560 attcattatg ctcgtttgtt gacccagaag gccagaactg gttgatccat cacggcatat   1620
tcatcctacg ttttacttct gccagcacta tattactccg tggctatata tagaaaaaaa   1680
caggccagtc tcactctaat cctgtgttgc ttgcagacct atctgccgag caaaatgccg   1740
gcggcgttgg tgccttatcg gcaagatgag ctcaagattc tccgtggcga cgataatcct   1800
ggaccatacc aggagcatga tcgcgtctac cgttacgact actacaatga ccttggtgat   1860
cccgacaagg gcgaagagca cgctcggccg atcctcggtg gcagccaaga acacccgtat   1920
ccccgtcgct gcagaactgg ccggcaccca acaaagaaag gtactagctc aagtcagcta   1980
gtgctagtcc ataccataca ggatgccaga aatttggctg aaatccttgc tgagttaacc   2040 ttttttacgca gacccaaatt cggagagcag gcttttcctg ctgaacctga acatctacgt   2100
cccgcgtgac gaacgctttg gcatctcaa gatgtcggac ttccttgggt actcgctgaa    2160
gacgatcatc gaggctgttc ttccaacact ggggactttc gtcgatgaca cgcccaagga   2220
gttcgattcg tttgaggata tcctcgggct ctacgagctg ggcccagagg cacccaacaa   2280
cccactgata gcagagatca ggaagaagat ccccagcgag ttccttcgaa gcattctgcc   2340
gaacggtagc catgaccacc cgctaaagat gccccttcca aatgtcatca aatcaggtaa   2400
acccaaattt ctttttttt tggaatcttt ctatgttaaa cggccggtgc ctgaactaga    2460
aaaaaattta ccatggctaa ggctgaatct tggttggtat aaaaccagat gtgttgaaaa   2520
aggctccgga gtttaagttt ggctggagga ctgacgaaga gttcgcgaga gagacacttg   2580
caggcgtgaa cccagtaatc atcaaacgtc tgacggttag cgttcttgca tcatttggat   2640
cggcaaaaat acaccttgcc ccatatatta actgagtaca gagccttaaa ggccttttt    2700 tatatatata tttcgtatct caggagttcc ccgctaaaag caccctggac ccaaggcagt   2760
acggagacca caccagcaag atcactgaag ctcacatccg gcataacatg ggaggcctgt   2820
cggtgcagaa cgtatgctgg actgcatgaa cgcacgcacg tacaaccgaa agccgcttaa   2880
aaccatcgac tgatctgatt tccgcgtaac gaaccctgtg caggcactga ggaacaagag   2940
gctcttcatc ctagaccacc atgaccattt catgccgtac ctcgacgaga tcaacgagct   3000 ggagggaac ttcatctacg ccagcaggac cctactgttc ctgaaggacg atggcacgct    3060
gaagcccctg gccatcgagc tgagcctgcc ccaccctgac ggccagcagc gcggcgcggt   3120
cagcaaggtg tacacccccgg ctcacaccgg cgtcgagggc cacgtctggc agctcgccaa   3180
ggcttatgcc tgcgtaaacg actctgcctg gcatcagctg atcagccact ggtataagaa   3240
atgtttctgg tgccttttc tcttttttt tcctttaat taattaatgt acatagataa       3300
ctgaagcact aatcttaatt gtgtggcttg cattgcattg caggctgaac acgcacgcgg   3360
tgatcgagcc gttcgtaatc gcgacaaacc ggcagtcag cgtggtgcat cccgtgcaca    3420
agctgctgag cccgcactac cgtgacacgc tgaacatcaa cgccctggca cgccagacac   3480
```

```
tcatcaacgc cggcggcgtc ttcgagcgca ccgtgttccc tgcaaagtac gcgctgggga      3540
tgtcggcaga cgtgtacaag agctggaatt tcaacgagca ggctctccca gcagatctcg      3600
tcaagaggta cgtagacaat acactgaggt gagcagcact aaacgcctat agaaaactgt      3660
tcggttcttg acgtggttgt ggttgcgtgc gttcagaggt gtggctgtgc cggaccagtc      3720
aagcccatat ggtgtccgac tgctgatcaa ggactacccc tatgccgttg acgggctcgt      3780
catctggtgg gcgatcgagc ggtgggtcaa ggagtacctg gacatctact accctaacga      3840
cggcgagctc cagcgtgacg tggagctgca ggcgtggtgg aaggaggtgc gtgaggaggc      3900
gcacggcgac ctcaaggacc gagactggtg gcccaggatg gacaccgtcc agcagctggc      3960
tagggcgtgc acgaccatca tctgggtggc atccgcgctg cacgcggctg tcaactttgg      4020
gcagtaccca tacgccgggt acctcccgaa ccggccgacg gccagccggc gcccgatgcc      4080
ggagccaggc agccacgact acaagaagct gggagcgggg cagaaggagg cggacatggt      4140
gttcatccgc accatcacca gccagttcca gaccatcctg ggcatctcgc tcatcgagat      4200
cctctccaag cactcctccg acgaggtgta cctcggccag cgtgacgagc ctgatcgctg      4260
gacgtcagac gccaaggcgc tggatgcgtt caaaagattc gggagccggc tggtgcagat      4320
tgagaatcgg atcaagacga tgaacgacag tccggacttg aagaaccgga aggggcctgt      4380
ggaaatgccg tacatgctgc tgtaccccaa cacgtcggac gttaccggcg agaaggccga      4440
ggggcttact gccatgggca ttcccaacag catctccata tga                        4483
```

LIPOXYGENASE POLYNUCLEOTIDES AND METHODS OF USE

CROSS-REFERENCE TO RELATED APPLICATIONS

This application is related to U.S. Provisional Application No. 60/286,889 filed Apr. 27, 2001, and U.S. Provisional Application No. 60/305,366 filed Jul. 13, 2001, both of which are hereby incorporated herein in their entirety by reference.

FIELD OF INVENTION

The invention relates to the field of the genetic manipulation of plants, particularly the modulation of gene activity and development in plants and increased disease resistance.

BACKGROUND OF THE INVENTION

*Aspergillus* spp. are seed deteriorating fungi known for their ability to produce mycotoxins in crops. Typically, the mycotoxins produced by *Aspergillus* spp. during colonization are aflatoxin and sterigmatocystin. Both aflatoxin and sterigmatocystin are derived from polyketides, which are bioreactive secondary metabolites that are synthesized like fatty acids.

Infection of crops by *Aspergillus* spp. is highly undesirable since aflatoxin and the related mycotoxin sterigmatocystin are human carcinogens. In certain years, environmental conditions heavily favor the production of mycotoxins. Thus, it is necessary to survey food products and feeds for such contamination of mycotoxins. Contaminated supplies in the United States are typically destroyed. In developing countries, where governments cannot afford to screen and destroy contaminated food, high liver cancer rates are associated with mycotoxin contamination. Thus, methods are needed to control mycotoxin contamination in foods.

In addition to fungi, diseases in plants are caused by viruses, bacteria, and nematodes. Phytopathogenic fungi cause significant annual crop yield losses as well as devastating epidemics. Plant disease outbreaks have resulted in catastrophic crop failures that have triggered famines and caused major social change. Pathogenic fungi attack all of the approximately 300,000 species of flowering plants; however, a single plant species can be host to only a few fungal species, and similarly, most fungi usually have a limited host range. Generally, the best strategy for plant disease control is to use resistant cultivars selected or developed by plant breeders for this purpose. However, the potential for serious crop disease epidemics persists today, as evidenced by outbreaks of the Victoria blight of oats and southern corn leaf blight. Molecular methods of crop protection have the potential to implement novel mechanisms for disease resistance and can also be implemented more quickly than traditional breeding methods. Accordingly, molecular methods are needed to supplement traditional breeding methods to protect plants from pathogen attack.

A host of cellular processes enable plants to defend themselves against disease caused by pathogenic agents. These defense mechanisms are activated by initial pathogen infection in a process known as elicitation. In elicitation, the host plant recognizes a pathogen-derived compound known as an elicitor; the plant then activates disease gene expression to limit further spread of the invading microorganism. It is generally believed that to overcome these plant defense mechanisms, plant pathogens must find a way to suppress elicitation as well as to overcome more physically-based barriers to infection, such as reinforcement and/or rearrangement of the actin filament networks near the cell's plasma membrane.

Thus, the present invention solves needs for enhancement of the plant's defensive elicitation response via a molecularly based mechanism that can be quickly incorporated into commercial crops.

SUMMARY OF THE INVENTION

The present invention provides nucleotide sequences that find use in modulating the plant pathogen defense system. Particularly, nucleotide and amino acid sequences for maize lipoxygenase (LOX) genes and a promoter region derived from a *Zea mays* LOX5 gene are provided.

The methods and compositions can be used to modulate plant development, to promote healing of damaged tissues, and to enhance resistance to plant pathogens including fungal pathogens, plant viruses, and the like. The method involves stably transforming a plant with a nucleotide sequence capable of modulating the plant pathogen defense system operably linked with a promoter capable of driving expression of a gene in a plant cell. The disease resistance genes of the present invention additionally find use in manipulating these processes in transformed plants and plant cells.

Transformed plants, plant cells, and seeds, as well as methods for making such plants, plant cells, and seeds are additionally provided. It is recognized that a variety of promoters will be useful in the invention, the choice of which will depend, in part, upon the desired level of expression of the disclosed nucleotide sequences. It is recognized that the levels of expression can be controlled to modulate the levels of expression in the plant cell.

BRIEF DESCRIPTION OF THE DRAWING

FIGS. 1(A and B) sets forth the nucleotide sequence of the genomic *Zea mays* LOX5 gene (SEQ ID NO:53). SEQ ID NO:54 corresponds to nucleotide residues 1 through 2086 of SEQ ID NO:53 and represents the LOX5 gene promoter region. The 5' UTR (untranslated region) is indicated with an underline. Putative TATA-box, GCC-box, W-boxes, H-box, $C_2H_2$ response element, and MRE-like elements are indicated by bold type and underlining. Intron sequences are indicated with lower case letters.

DETAILED DESCRIPTION OF THE INVENTION

Overview

The present invention provides, inter alia, compositions and methods for modulating the total level of proteins of the present invention and/or altering their ratios in a plant. By "modulation" is intended an increase or a decrease in a particular character, quality, substance, or response.

The compositions comprise maize nucleic acid and amino acid sequences. Particularly, the nucleotide and amino acid sequences for maize lipoxygenases (LOXs) are provided. As discussed in more detail below, the sequences of the invention are involved in basic biochemical pathways that regulate plant growth, development, and pathogen resistance. Methods are provided for the expression of these sequences in a host plant to modulate plant development, developmental pathways, and defense responses. The method involves stably transforming a plant with a nucleotide sequence capable of modulating the plant pathogen defense system operably linked with a promoter capable of driving expression of the nucleotide sequence in a plant cell.

Lipoxygenases (LOX's) (linoleate: oxygen oxidoreductase, EC 1.13.11.12) are a family of nonheme, iron-containing enzymes that catalyze the oxygenation of polyunsaturated fatty acids or their esters containing a cis, cis-1, 4-pentadiene-system. The most common substrates of lipoxygenases in higher plants are linolenic and linoleic acids, fatty acids most likely derived from membrane phospholipids (Conconi et al. (1996) *Plant Physiol.* 111:797–803; Siedow (1991) *Plant Mol. Biol.* 42:145–188). LOX-catalyzed incorporation of molecular oxygen into these fatty acids can occur either at position 9 or 13 of their carbon chains. As a result, two distinct fatty acid monohydroperoxides are formed, which feed into separate biosynthetic pathways to produce compounds with distinct physiological functions (Anderson (1989). Membrane derived fatty acids as precursors to second messengers. In *Second Messengers in Plant Growth and Development* (Boxx, W. F. and Moore, D. J., eds). New York: Alan R. Liss, pp. 181–212). Distinct LOX isozyme forms may catalyze the C-13 or the C-9 reaction preferentially ((1991) *Plant Mol. Biol.* 42:145–188), or they may add molecular oxygen exclusively into one or the other position of fatty acids (Doderer et al. (1992) *Biochim. Biophys. Acta* 1120:97–104); Peng et al. (1994) *J. Biol. Chem.* 269:3755–3761); Siedow (1991) *Plant Mol. Biol.* 42:145–188).

In plants, some LOX-derived fatty acid hydroperoxides are metabolized into biologically active molecules, such as traumatin, jasmonic acid (JA), and methyl jasmonate (MJ), which serve hormone-like regulatory roles (Anderson (1989). Membrane derived fatty acids as precursors to second messengers. In *Second Messengers in Plant Growth and Development* (Boxx, W. F. and Moore, D. J., eds). New York: Alan R. Liss, pp. 181–212); Koda (1992) *Int. Rev. Cytol.* 135:155–199; Creelman and Mullet (1997) *Annu. Rev. Plant Physiol. Plant Mol. Biol.* 48:355–381). Traumatin induces cell division, as a result it may promote healing of damaged tissues in response to wounding or insect chewing (Anderson (1989). Membrane derived fatty acids as precursors to second messengers. In *Second Messengers in Plant Growth and Development* (Boxx, W. F. and Moore, D. J., eds. New York: Alan R. Liss, pp. 181–212). JA and MJ are involved in a variety of physiological processes (Koda (1992) *Int. Rev. Cytol.* 135:155–199), and they appear to do so by regulating the expression of genes such as phenylalanine ammonia lyase (Gundlach et al. (1992) *Proc. Natl. Acad. Sci. USA* 89:2389–2393), protease inhibitors (Farmer and Ryan (1992) *Plant Cell* 4:129–134), vegetative storage proteins, chalcone synthase, PR1 (Reinbothe et al. (1994) *The Plant Cell* 6:1197–1209), proline-rich cell wall proteins (Creelman et al (1992) *Proc. Natl. Acad. Sci. USA* 89:4938–4941), and LOX's (Melan et al. (1994) *Plant Physiol.* 105:385–393: Kolomiets et al. (2000) *Plant Physiol.* 124:1121–1130). Another LOX-derived product, dihydrojasmonic acid, as well as its 18-carbon oxylipin precursors, 12-oxophytodienoic and 12-oxophytoenoic acid, can act as defense signals (Blechert et al. (1995) *Proc. Natl. Acad. Sci. USA* 92:4099–4105). In addition, the C-6 volatile compounds derived from lipoxygenase activities possess antimicrobial activities (Croft et al. (1993) *Plant Physiol.* 101:13–24). Other less known LOX-derived intermediate and/or final products that have antimicrobial activity include epoxides, epoxy alcohols, aldehydes, oxo-acids, α- and γ-ketols, and divinyl ether fatty acids (Blee (1998) *Prog. Lipid Res.* 37(1):33–72; Weber et al. (1999) *Plant Cell.* 11:485–493).

Multiple LOX isozyme forms exist in all plant species that have been studied, and their expression is dictated by strict developmental, organ/tissue-preferred, and stress-regulated controls (Heitz et. al. (1997) *Plant Physiol.* 114:1085–1093; Kausch and Handa (1997) *Plant Physiol.* 113:1041–1050); Kolomiets et al. (2000) *Plant Physiol.* 124:1121–1130; Melan et al. (1994) *Plant Physiol.* 105:385–393; Saravitz and Siedow (1995) *Plant Physiol.* 107–535–543; Royo et al. (1996) *J Biol. Chem.* 271:21012–21019. Because different LOX isozymes initiate production of functionally diverse final products, it is not surprising that LOXs were implicated in physiological processes as diverse as senescence, growth and development, and wound- and pathogen-induced responses (Siedow (1991) *Plant Mol. Biol.* 42–145–188). It is suggested that individual isozyme forms within a given organ, tissue, or cell type may have a distinct physiological role (Kolomiets et al. (2000) *Plant Physiol.* 124:1121–1130; Peng et al. (1994) *J Biol. Chem.* 269:3755–3761; Saravitz and Siedow (1995) *Plant Physiol* 107:535–543; Stephenson et al. (1998) *Plant Physiol.* 116–923–933). LOX multigene families likely serve as a means to carry on these diverse functions by elaborate regulation of their expression in specific tissues and cells in response to various developmental and environmental cues (Eiben and Slusarenko (1994) *Plant J.* 5:123–135; Fisher et al. (1999) *Plant Journal* 19(5): 543–554; Stephenson et al. (1998) *Plant Physiol.* 116:923–933).

Several lines of correlative evidence suggest that LOX may play an important role in plant growth and development. In many plant species including corn, it was observed that rapidly growing tissues have the greatest LOX activity. Furthermore, there is a positive correlation between LOX activity within an organ and its rate of elongation (Siedow (1991) *Plant Mol. Biol.* 42:145–188). LOX isozyme profiles change quantitatively and qualitatively during soybean leaf development (Saravitz and Siedow (1995) *Plant Physiol.* 107:535–543) and during seed germination in cucumbers and pea (Feussner et al. (1996) *Planta* 198:288–293; Chateigner et al. (1999) *Planta.* 208-606–613). In addition, many LOX genes are regulated differentially during *Arabidopsis* seedling development (Melan et al. (1994) *Plant Physiol.* 105:385–393), tomato fruit ripening (Ferrie et al. (1994) *Plant Physiol.* 106:109–118; Kausch and Handa (1997) *Plant Physiol.* 113:1041–1050) and pea carpel development (Rodriguez-Conception and Beltran (1995) *Plant Mol. Biol.* 27:887–899). One possible role of LOX during seed germination and seedling development is utilization of lipid reserves as a source of energy during active cell division and enlargement (Feussner et al. (1995) *Proc. Natl. Acad. Sci. USA* 92:11849–11853). LOX has also been implicated in plant development (Kolomiets et al. (2001) *Plant Cell.* 13(3): In press). In transgenic POTLX-1 potato plants in which expression of tuber-specific LOXs was suppressed by an antisense approach, significant decrease in tuber yield and size was seen, indicating that these genes are directly involved in the regulation of tuber growth and development. Pollen development and shedding are additional processes in which LOX may have an important role as mutants that are insensitive to or lack JA and MJ, produced by 13-LOXs, are male sterile (Xie et al. (1998) *Science* 280:1091–1094). Correlative evidence is accumulating that implicates LOXs in senescence primarily due to the role in lipid peroxidation and the production of jasmonates (Paliyath and Drillard (1992) *Plant Physiol. Biochem.* 30:789–812), which are strong inducers of senescence of leaf and other organs (Siedow (1991) *Plant Mol. Biol.* 42:145–188). Consistent with this result, senescence processes were retarded by application of LOX inhibitors and induced by exogenous application of linolenic acid (Hung and Kao (1996) *Plant Growth Reg.* 19(1):77–83).

While not bound by any particular mechanism of action, LOX involvement in defense responses most likely is due to LOX participation in the biosynthesis of JA, MJ, and the C-6 volatile compounds (Siedow (1991) *Plant Mol. Biol.* 42–145–188; Slusarenko (1996) "The Role of Lipoxygenase in Plant Resistance to Infection," in *Lipoxygenase and Lipoxygenase Pathway Enzymes*, ed. Piazza (Champaign, Ill.: AOCS Press), pp. 176–197; Vijayan et al. (1998) *Proc. Natl. Acad. Sci. USA* 95(12):7209–7214). The LOX gene may play an important role in cell division and defense signal transduction pathways that are regulated by the biosynthesis of traumatin and jasmonic acid. Biochemical studies indicated that LOX protein and activity levels are modulated in response to both biotic and abiotic stresses, such as mechanical wounding, insect chewing, and pathogen attack (Blee (1998) *Prog. Lipid Res.* 37(1):33–72). Increases in LOX activity in response to pathogen infection have been reported for a number of plant-pathogen systems (Siedow (1991) *Plant Mol. Biol.* 42:145–188; Blee (1998) *Prog. Lipid Res.* 37(1):33–72). LOX activity increased only upon infection by an avirulent pathogen (Ohta et al. (1991) *Plant Physiol.* 97:94–98) or it was induced rapidly by infection with an avirulent pathogen and slowly with the virulent strain (Kolomiets et al. (2000) *Plant Physiol.* 124:1121–1130). LOX activity also is induced by treatment of cell cultures or plants with elicitors. When potato tuber disks were treated with the fungal (*Phytophthora infestans*) elicitor arachidonic acid (AA), the activity of LOX increased almost 2-fold within half an hour to 3 hours after treatment (Bostock et al. (1992) *Plant Physiol.* 100:1448–1456). In addition, LOX genes are activated transcriptionally by wounding, pathogens, or their elicitors (Bell and Mullet (1991) *Mol. Gen. Genet.* 230:456–462; Bohland et al. (1997) *Plant Physiol.* 114:679–685; Kolomiets et al. (2000) *Plant Physiol.* 124:1121–1130; Melan et al. (1993) *Plant Physiol.* 101:441–450; Peng et al. (1994) *J. Biol. Chem.* 269:3755–3761). LOX plays a pivotal role in defense responses against herbivory, as transgenic plants expressing the potato H3 gene, a 13-LOX targeted to chloroplasts, in antisense orientation were more susceptible to insect feeding (Royo et al. (1999) *Proc. Natl. Acad. Sci. USA* 96:1146–1151).

LOX also plays a role in the wound- and pathogen-inducible lipid-based signal-transduction pathway that leads to the induction of defense responses. JA and MJ are two of the best-studied signaling molecules in this pathway. Mutant plants in which JA perception or biosynthesis is blocked are more susceptible to certain pathogens, suggesting JA involvement in disease resistance mechanisms (Thomma et al. (1998) *Proc. Natl. Acad. Sci. USA* 95–15107–15111; Xie et al. (1998) *Science* 280:1091–1094). Plants commonly confer resistance to pathogens via manifestation of an active defense mechanism known as the hypersensitive response (HR), a form of programmed cell death (Dangl et al. (1996) *Plant Cell* 8:1793–1807). This reaction limits pathogen spread and prevents further damage to the remainder of the plant organ. In soybean, potato, and tomato, occurrence of the HR is associated with increased activity of LOX (Slusarenko (1996), "The Role of Lipoxygenase in Plant Resistance to Infection," in *Lipoxygenase and Lipoxygenase Pathway Enzymes*, ed. Piazza (Chamapin, Ill.: AOCS Press), pp. 176–197). Peroxidation of membrane lipids has been postulated to be a causative factor in the localized cell death associated with the HR (Keppler and Novacky (1987) *Physiol. Mol. Plant Pathol.* 30:233–245).

The LOX gene has also been implicated in the regulation of coordinated gene activation in response to wounding. It is speculated that resistance to pathogen attack is the result of the coordinated accumulation of secondary metabolites and protein products. Some of these products, such as proteinase inhibitors, may directly interfere with digestibility of the injected tissue whereas others products may affect food intake. Therefore, the LOX sequences of the present invention may find use in an antifeedant strategy by regulating proteinase inhibitor levels in plants, and thereby controlling insect and nematode pathogens.

The LOX proteins of the invention are also useful for inhibiting the production of the mycotoxins of fungi such as aflatoxin and sterigmatocystin producing fungus in plants susceptible to contamination by such mycotoxins. Particular crops include maize, peanuts, treenuts, almonds, brazil nuts, pistachios, melon, pumpkin, sunflower seeds, corn, rice, and walnuts. The method involves introducing into a plant of interest a gene encoding an enzyme within the lipoxygenase pathway. The production of aflatoxin is influenced by high levels of oxidized fatty acids such as fatty acid hydroperoxides. Fatty acid hydroperoxides can be formed enzymatically by lipoxygenases. Lipoxygenases catalyze the addition of molecular oxygen to unsaturated fatty acids containing cis, cis-1, 4-pentadiene moieties.

Additionally, LOX-derived fatty acid hydroperoxides and free radical species are cytotoxic and are capable of damaging membranes, proteins, and DNA (Hildebrand et al. (1998) *Curr. Top. Plant Biochem. Physiol.* 7:201–219). Therefore, LOXs may play a role in membrane degradation observed during senescence, wounding, and the hypersensitive response to pathogen attack. Thus, the compositions of the invention have LOX-like activity. By "LOX-like" activity is intended one of the activities listed above for lipoxygenases, particularly modulating plant defense systems. Assays for activity can be performed as set forth in the above-listed references.

LOX proteins may also play an important role in plant growth and development. There is a positive correlation between LOX activity levels within an organ and its rate of elongation. The concomitant increase in LOXs and the enzymes involved in the metabolism of LOX-derived fatty hydroperoxides is consistent with a role for LOX in generating lipid-derived growth regulators. In plants, the LOX proteins may be involved in lipid turnover and fat mobilization. Thus, the compositions and methods of the invention find use in the turnover of lipids in the developing seedling.

Generally, the LOX sequences of the present invention may be used to modulate many important developmental processes, such as, cell division, seed germination, plant growth and senescence, and/or to enhance plant resistance to environmental stresses, such as, wounding and pathogen attacks.

A number of terms used herein are defined and clarified in the following section.

Definitions

By "nucleic acid molecule" is intended a molecule composed of nucleotides covalently bound to one another. Nucleotides include both ribonucleotides and deoxyribonucleotides. "Nucleic acid molecule" encompasses single-stranded and double stranded forms of both DNA and RNA. Nucleic acid molecules may be naturally occurring, synthetic, or a combination of both. The linear arrangement of nucleotides in a nucleic acid molecule is referred to as a "nucleotide sequence" and, unless specified otherwise, is presented herein from left to right corresponding to the 5'-to-3' direction.

By "pathogenic agent" or "pathogen" is intended any organism that has the potential to negatively impact a plant, typically, but not exclusively, by causing disease or inflicting physical damage. Such organisms include, but are not limited to, fungi, bacteria, nematodes, mycoplasmas, viruses, and insects.

By "promoter" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate.

By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein-coding regions in the same reading frame.

By "stably transformed" is intended that the nucleotide sequences introduced into a cell and/or plant using transformation methods described herein are stably incorporated into the genome of the cell and/or plant. Stably incorporated nucleotide sequences are heritable.

By "defense-inducible" is intended that transcription of a nucleotide sequence operably linked to the defense-inducible promoter is regulated when the plant is exposed to biotic and abiotic stress. By "regulate" is intended the repression or activation of transcription from a promoter region. The regulation of transcription by the promoter sequences of the present invention is defined herein as "inducible." By "inducible" is intended the ability of the promoter sequence to regulate expression of an operably linked nucleotide sequence in response to a stimulus.

By "stimulus" is intended an elemental or molecular species which either directly or indirectly regulates the activity (i.e., an increase in initiation or expression) of an inducible promoter.

By "direct action" is intended that the stimulus regulates transcription via a direct interaction between the stimulus and the DNA sequence. By "indirect action" is meant that the regulation occurs via an interaction between the stimulus and some other endogenous or exogenous component in the system, the ultimate result of the indirect action being regulation of the inducible promoter. The stimulus can result from a biotic or abiotic stress, including for example, tissue wounding (i.e., insect herbivory, wind, intentional abiotic infliction of tissue injury or wounding for the purpose of experimentation and/or expression analysis); wound-responsive chemicals (i.e., chemicals that result in the activation of wound-response signal transduction pathways, including, various hormones, jasmonic acid, abscissic acid, linolenic acid, ethylene, their chemical analogues, derivatives, precursors, and the like); pathogens (i.e, fungi, bacteria, nematodes, mycoplasmas, viruses, and insects and the like); and various environmental stresses (i.e., heat, drought, cold, reactive oxygen species and/or radiation). Hence, the promoter of the present invention can be used in combination with a nucleotide sequence that enhances disease resistance, and the compositions therefor find use in the defense of a plant against disease, pathogens, and the like.

Nucleotide and Amino Acid Sequence Compositions

Compositions of the invention include the polynucleotide sequences of the maize LOX genes. The polypeptides encoded by those sequences may be involved in various plant developmental processes, including the plant pathogen defense response.

Thirteen maize LOX nucleic acid and amino acid sequences are provided, as well as a genomic sequence of the Zea mays LOX5 gene which comprises a promoter sequence. The sequences are classified as lipoxygenases based on sequence similarity to known lipoxygenases. For each sequence, the full nucleotide sequence is assigned a SEQ ID NO., the translation product of the full sequence is assigned a SEQ ID NO., the coding region of the sequence is assigned a SEQ ID NO., and the predicted polypeptide is assigned a SEQ ID NO. LOX1 (SEQ ID NO:1–4), LOX2 (SEQ ID NO:9–12), LOX5 (SEQ ID NO:21–24, SEQ ID NO:56), and LOX11 (SEQ ID NO:45–48) are members of the lipoxygenase family that includes the nucleotide and amino acid sequences of the invention. The LOX1 sequence is publicly available in the GenBank database under the GenBank Accession No. AP27 1894. The Zm-LOXS polypeptide encoded by SEQ ID NO:21 and SEQ ID NO:56 shows 74% identity to a barley lipoxygenase. The Zm-LOX11 polypeptide encoded by SEQ ID NO:45 shows 62% identity to a potato lipoxygenase. The LOX1b (SEQ ID NOS:5 and 7), LOX3 (SEQ ID NOS:13 and 15), LOX4 (SEQ ID NOS:17 and 19), LOX6 (SEQ ID NO:25), LOX7 (SEQ ID NO:29 and 31), LOX8 (SEQ ID NOS:33 and 35), LOX9 (SEQ ID NOS:37 and 39), LOX10 (SEQ ID NOS:41 and 43), LOX12 (SEQ ID NOS:49 and 51) encode the polypeptides set forth in SEQ ID NOS:6, 14, 18, 26, 30, 34, 38, 42, and 50 respectively. SEQ ID NOS:8, 16, 20, 28, 32, 36, 40, 44, and 52 indicate the predicted amino acid sequences for LOX1b, LOX3, LOX4, LOX6, LOX7, LOX8, LOX9, LOX10, and LOX12, respectively. Additionally, protein domain analysis indicates that the sequences are lipoxygenases. The Zm-LOX2b polypeptide encoded by SEQ ID NO:9 shows 85% identity to a harley lipoxygenase (GenBank Accession No. P29114). The Zm-LOX3 polypeptide encoded by SEQ ID NO:13 shows 83% identity to a maize lipoxygenase (GenBank Accession No.271894). The Zm-LOX4 polypeptide encoded by SEQ ID NO:17 shows 74% identity to a barley lipoxygenase (GenBank Accession No.AAB60715). The Zm-LOX6 polypeptide encoded by SEQ ID NO:25 shows 49% identity to a tobacco lipoxygenase (GenBank Accession No. S57964). The Zm-LOX7 polypeptide encoded by SEQ ID NO:29 shows 64% identity to an Arabidopsis lipoxygenase (GenBank Accession No. AAF21176). The Zm-LOX12 polypeptide encoded by SEQ ID NO:37 shows 69% identity to an Arabidopsis lipoxygenase (GenBank Accession No.AAF79461.1). The Zm-LOX10 polypeptide encoded by SEQ ID NO:41 shows 68% identity to a potato lipoxygenase (GenBank Accession No.T07065). The Zm-LOX12 polypeptide encoded by SEQ ID NO:49 shows 51% identity to a potato lipoxygenase (GenBank Accession No.CAA64766.1). These identities were determined using the BLAST program for sequence analysis.

In particular, the present invention provides for isolated nucleic acid molecules comprising nucleotide sequences encoding the amino acid sequences shown in SEQ ID NOS: 6, 8, 14, 16, 18, 20, 26, 28, 30, 32, 34, 36, 38, 40, 42, 44, 50, and 52. Further provided are polypeptides having an amino acid sequence encoded by a nucleic acid molecule described herein, for example those set forth in SEQ ID NOS:5, 7, 13, 15, 17, 19, 25, 27, 29, 31, 33, 35, 37, 39, 41, 43, 45, 49, and 51.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, preferably culture medium represents less than about 30%, 20%, 10%, 5%, or 1% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence affect development, developmental pathways, and defense response by retaining LOX-like activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a LOX nucleotide sequence that encodes a biologically active portion of a LOX protein of the invention will encode at least 22, 30, 50, 100, 150, 200, or 232 contiguous amino acids for SEQ ID NO:6; at least 22, 30, 50, 100, 150, 200, or 226 contiguous amino acids for SEQ ID NO:8; at least 22, 30, 50, 100, 150, 200, 300, 400, 500, 600, 700, 800, or 871 contiguous amino acids for SEQ ID NOS:14 and 16; at least 22, 30, 50, 100, 150, 200, 300, 400, 500, 600, 700, 800, or 887 contiguous amino acids for SEQ ID NOS:18 and 20; at least 22, 30, 50, 100, 150, 200, 300, 400, 500, 600, 700, 800, or 892 contiguous amino acids for SEQ ID NOS:26 and 28; at least 22, 30, 50, 100, 150, 200, or 223 contiguous amino acids for SEQ ID NOS:30 and 32; at least 22, 30, 40 or 46 contiguous amino acids for SEQ ID NOS:34 and 36; at least 22, 30, 50, 100, 150, 200, 300, 400, 500 or 543 contiguous amino acids for SEQ ID NOS:38 and 40; at least 22, 30, 50, 100, 150, 200, 300, 400, 500, 600, 700, 800, or 807 contiguous amino acids for SEQ ID NOS:42 and 44; or at least 22, 30, 50, 100, 150, 200, 300, 400, 500, 600, 700, 800, or 842 contiguous amino acids for SEQ ID NOS:50 and 52. Fragments of a LOX nucleotide sequence that are useful as hybridization probes or PCR primers generally need not encode a biologically active portion of a LOX protein.

Thus, a fragment of a LOX nucleotide sequence may encode a biologically active portion of a LOX protein, or it may be a fragment that can be used as a hybridization probe or PCR primer using methods disclosed below. A biologically active portion of a LOX protein can be prepared by isolating a portion of one of the LOX nucleotide sequences of the invention, expressing the encoded portion of the LOX protein (e.g., by recombinant expression in vitro), and assessing the activity of the encoded portion of the LOX protein. Nucleic acid molecules that are fragments of a LOX nucleotide sequence comprise at least 16, 20, 50, 75, 100, 150, 200, 250, 300, 350, 400, 450, 500, 550, 600, 650, 700, 800, 900, or 911 nucleotides present in SEQ ID NO:5; at least 16, 20, 50, 75, 100, 150, 200, 250, 300, 350, 400, 450, 500, 550, 600, 650, 700, or 702 nucleotides present in SEQ ID NO:7; at least 16, 20, 50, 75, 100, 150, 200, 250, 300, 350, 400, 450, 500, 550, 600, 650, 700, 800, 900, 1000, 1100, 1200, 1300, 1400, 1500, 1600, 1700, 1800, 1900, 2000, 2100, 2200, 2300, 2400, 2500, 2600, 2700, 2800, 2900 or 2949 nucleotides present in SEQ ID NO:13; at least 16, 20, 50, 75, 100, 150, 200, 250, 300, 350, 400,450, 500, 550, 600, 650, 700, 800, 900, 1000, 1100, 1200, 1300, 1400, 1500, 1600, 1700, 1800, 1900, 2000, 2100, 2200, 2300, 2400, 2500, 2600, or 2616 nucleotides present in SEQ ID NO:15; at least 16, 20, 50, 75, 100, 150, 200, 250, 300, 350, 400, 450, 500, 550, 600, 650, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, or 3080 nucleotides present in SEQ ID NO:17; at least 16, 20, 50, 75, 100, 150, 200, 250, 300, 350, 400, 450, 500, 550, 600, 650, 700, 800, 900, 1000, 1100, 1200, 1300, 1400, 1500, 1600, 1700, 1800, 1900, 2000, 2100, 2200, 2300, 2400, 2500, 2600, or 2664 nucleotides present in SEQ ID NO:19; at least 16, 20, 50, 75, 100, 150, 200, 250, 300, 350, 400, 450, 500, 550, 600, 650, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 2919 nucleotides present in SEQ ID NO:25; at least 16, 20, 50, 75, 100, 150, 200, 250, 300, 350, 400, 450, 500, 550, 600, 650, 700, 800, 900, 1000, 1100, 1200, 1300, 1400, 1500, 1600, 1700, 1800, 1900, 2000, 2100, 2200, 2300, 2400, 2500, 2600, or 2664 nucleotides present in SEQ ID NO:27; at least 16, 20, 50, 75, 100, 150, 200, 250, 300, 350, 400, 450, 500, 550, 600, or 670 nucleotides present in SEQ ID NOS:29 and 31; at least 16, 20, 50, 75, 100, or 140 nucleotides present in SEQ ID NOS:33 and 35; at least 16, 20, 50, 75, 100, 150, 200, 250, 300, 350, 400, 450, 500, 550, 600, 650, 700, 800, 900, 1000, 1100, 1200, 1300, 1400, 1500, 1600, 1700, 1800, or 1803 nucleotides present in SEQ ID NO: 37; at least 16, 20, 50, 75, 100, 150, 200, 250, 300, 350, 400, 450, 500, 550, 600, 650, 700, 800, 900, 1000, 1100, 1200, 1300, 1400, 1500, 1600, or 1632 nucleotides present in SEQ ID NO:39; at least 16, 20, 50, 75, 100, 150, 200, 250, 300, 350, 400, 450, 500, 550, 600, 650, 700, 800, 900, 1000, 1100, 1200, 1300, 1400, 1500, 1600, 1700, 1800, 1900, 2000, 2100, 2200, 2300, 2400, 2500, 2600, 2700, 2800, or 2835 nucleotides present in SEQ ID NO:41; at least 16, 20, 50, 75, 100, 150, 200, 250, 300, 350, 400, 450, 500, 550, 600, 650, 700, 800, 900, 1000, 1100, 1200, 1300, 1400, 1500, 1600, 1700, 1800, 1900, 2000, 2100, 2200, 2300, 2400, or 2424 nucleotides present in SEQ ID NO: 43; at least 16, 20, 50, 75, 100, 150, 200, 250, 300, 350, 400, 450, 500, 550, 600, 650, 700, 800, 900, 1000, 1100, 1200, 1300, 1400, 1500, 1600, 1700, 1800, 1900, 2000, 2100, 2200, 2300, 2400, 2500, 2600, or 2689 nucleotides present in SEQ ID NO:49; or at least 16, 20, 50, 75, 100, 150, 200, 250, 300, 350, 400, 450, 500, 550, 600, 650, 700, 800, 900, 1000, 1100, 1200, 1300, 1400, 1500, 1600, 1700, 1800, 1900, 2000, 2100, 2200, 2300, 2400, 2500, or 2529 nucleotides present in SEQ ID NO:51.

By "variants" is intended substantially similar sequences. For nucleotide sequences, conservative variants include those sequences that, because of the degeneracy of the genetic code, encode the amino acid sequence of one of the LOX polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a LOX protein of the invention. Generally, variants of a particular nucleotide sequence of the invention will have at least 40%, 50%, 51%, 52%, 53%, 54%, 55%, 56%, 57%, 58%, 59%, 60%, 65%, 66%, 67%, 68%, 69%, 70%, generally at least 75%, 80%, 81%, 83%, 84%, 85%, preferably about 90%, 91%, 92%, 93%, 94%, 95%, 96%, 97%, and more preferably about 98%, 99%, or more sequence identity to that particular nucleotide sequence as determined by sequence alignment programs described elsewhere herein using default parameters.

By "variant protein" is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, hence they will continue to possess LOX activity. Such variants may result from, for example, genetic polymorphism or from human manipulation. Biologically active variants of a native LOX protein of the invention will have at least 40%, 50%, 52%, 55%, 60%, 63%, 64%, 65%, 66%, 67%, 68%, 69%, 70%, generally at least 75%, 76%, 77%, 78%, 79%, 80%, 81%, 82%, 83%, 84%, 85%, 86%, 87%, 88%, 89%, preferably about 90%, 91%, 92%, 93%, 94%, 95%, 96%, 97%, 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

Biological activity of the LOX polypeptides can be assayed by any method known in the art. Assays to measure the developmental pathways and defense responses that are influenced by the LOX polypeptides having LOX-like activity are well known in the art. Assays to detect LOX-like activity include, for example, assays to measure LOX enzymatic activity (Maach et al. (1997) *Plant Physiol.* 114:1561–1566, Royo et al. (1996) *J. Biol. Chem.* 35:21012–21019 and Voros et al. (1998) *FEBS Letters* 251:36–44).

The proteins of the invention may be altered in various ways including amino acid substitutions, deletions, truncations, and insertions. Methods for such manipulations are generally known in the art. For example, amino acid sequence variants of the LOX proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired LOX-like activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by either an enhanced resistance to pathogens, or a modulation in a plant developmental process when expression of the protein sequence is altered.

Variant nucleotide sequences and proteins also encompass sequences and proteins derived from a mutagenic and recombinogenic procedure such as DNA shuffling. With such a procedure, one or more different LOX coding sequences can be manipulated to create a new LOX possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

For example, using a recombinogenic procedure, sequence motifs encoding a domain of interest may be shuffled between the LOX gene of the invention and other known LOX genes to obtain a new gene coding for a protein with an improved property of interest, such as an increased $K_m$ in the case of an enzyme. Likewise, sequences corresponding to regulatory motifs, such as specific cis-acting elements within the promoters of the invention may be shuffled creating improved regulatory functions, such as increased pathogen inducibility or an increased expression. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The invention also encompasses the 5' regulatory regions of the LOX5 gene (shown in FIG. 1; SEQ ID NO:53) disclosed herein. The nucleotide sequence of the native 5' untranslated region (i.e., the promoter region) encompassing nucleotide residues 1 through 2086 of SEQ ID NO:53 is provided in SEQ ID NO:54. It is recognized that having identified the nucleotide sequences for the promoter regions disclosed herein, it is within the state of the art to isolate and identify further regulatory elements in the 5' untranslated region upstream from the particular promoter regions identified herein. Thus, for example, the promoter regions disclosed herein may further comprise upstream regulatory elements that confer tissue-specific and/or tissue-preferred expression of any heterologous nucleotide sequence operably linked to one of the disclosed promoter sequences. See particularly Australian Patent No. AU-A-77751/94 and U.S. Pat. Nos. 5,466,785 and 5,635,618. Likewise, promoter regions having homology to the promoters of the invention can be isolated by hybridization under stringent conditions, as described elsewhere herein. Alternatively, the 5' regions upstream of the coding sequences can be isolated and the promoter region identified.

Pathogen-responsive cis-acting elements have been identified within these promoter regions, such as a GCC box, W-box, H-box and MRE-like elements. It is known that GCC boxes are found in the promoters of many basic PR protein genes, for example basic PR-1s, beta-glucanases, chitinases and osmotin. W-boxes have been implicated in parsley PR1-1, maize PRms, and tobacco class 1-chitinase promoters in fungal elicitor-inducible DNA-binding activity. H boxes, which are found in many promoters of genes involved in flavonoid biosynthesis and which often function in association with G-boxes have been implicated in ABA, light, UV wounding and pathogen responses. Thus, where gene expression in response to a stimulus is desired, an inducible promoter of the invention is the regulatory element of choice. When using an inducible promoter, expression of the nucleotide sequence is initiated in cells in response to a stimulus are described elsewhere herein.

The promoter sequences of the invention include both the naturally occurring sequences as well as mutant forms. Such variant promoter regions can be derived from a mutagenic and recombinogenic procedure such as DNA shuffling. With such a procedure, one or more different promoter sequences can be manipulated to create new sequences possessing the desired properties. In this manner, libraries of recombinant polynucleotides are generated from a population of related sequence polynucleotides comprising sequence regions that have substantial sequence identity and can be homologously recombined in vitro or in vivo. For example, sequences corresponding to regulatory motifs, such as specific cis-acting elements within the promoters of the invention, may be shuffled, creating improved regulatory functions, such as increased pathogen inducibility. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotechnology* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

Fragments and variants of the promoter nucleotide sequences disclosed herein are also encompassed by the present invention. A fragment of a LOX promoter nucleotide sequence comprises at least 15, 20, 25, 30, 35, 40, 45, 50, 75, 100, 325, 350, 375, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, or 2080 nucleotides, or up to the number of nucleotides present in a full-length promoter nucleotide sequence disclosed herein (for example, 2086 nucleotides of SEQ ID NO:53 or the nucleotide sequence of SEQ ID NO:54). Generally, fragments of a promoter sequence that retain their biological activity (i.e., regulate transcription) comprise at least 30, 35, 40 contiguous nucleotides, preferably at least 50 contiguous nucleotides, more preferably at least 75 contiguous nucleotides, still more preferably at least 100 contiguous nucleotides of the particular promoter nucleotide sequence disclosed herein. Preferred fragment lengths depend upon the objective and will also vary depending upon the particular promoter sequence.

The nucleotides of such fragments will usually comprise the TATA recognition sequence of the particular promoter sequence. Such fragments may be obtained by use of restriction enzymes to cleave the naturally occurring promoter nucleotide sequence disclosed herein, by synthesizing a nucleotide sequence from the naturally occurring sequence of the promoter DNA sequence, or may be obtained through the use of PCR technology. See particularly, Mullis et al. (1987) *Methods Enzymol.* 155:335–350, and Erlich, ed. (1989) *PCR Technology* (Stockton Press, New York). Variants of these promoter fragments, such as those resulting from site-directed mutagenesis, are encompassed by the compositions of the present invention.

The nucleotide sequences of the invention, coding and promoter sequences, can be used to isolate corresponding sequences from other organisms, particularly other plants. In this manner, methods such as PCR, hybridization, and the like can be used to identify such sequences based on their sequence homology to the sequences set forth herein. It is to be understood that sequences isolated based on their sequence identity to an entire LOX gene or to the LOX5 gene promoter sequences of the present invention, or to fragments thereof are considered to be encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated nucleotide sequences that either encode a LOX polypeptide or, represent a LOX gene promoter, and which hybridize under stringent conditions to the corresponding LOX sequence disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications*

(Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the disease resistant sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire nucleotide sequence disclosed herein that is derived from either the coding sequence or the putative promoter sequence of the LOX5 gene provided in SEQ ID NO:54, or one or more portions thereof, may be used as a probe capable of specifically hybridizing to the corresponding LOX sequences and messenger RNAs. To achieve specific hybridization under a variety of conditions, such probes include sequences that are unique among disease resistant sequences and are preferably at least about 10 nucleotides in length, and most preferably at least about 20 nucleotides in length. Such probes may be used to amplify corresponding sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plain View, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m = 81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

In general, sequences that encode a LOX polypeptide and which hybridize under stringent conditions to the LOX sequences disclosed herein, or to fragments thereof, are encompassed by the present invention. Similarly, isolated nucleotide sequences which hybridize under stringent conditions to the *Zea mays* LOX5 promoter sequence disclosed herein (SEQ ID NO:54) and have promoter activity, or isolated sequences that hybridize to fragments of SEQ ID NO:54 that are capable of directing the expression of an coding sequence operably linked thereto, are encompassed by the present invention. The LOX5 gene promoter was isolated from the 5' untranslated region flanking its transcription initiation site. Methods for isolation of promoter regions are well known in the art. A promoter may additionally comprise other recognition sequences generally positioned upstream or 5' to the TATA box, referred to as upstream promoter elements or cis-acting elements, which influence the transcription initiation rate.

It is to be understood that the scope of the invention disclosed herein encompasses fragments of the LOX5 promoter sequence disclosed herein that operate to promote the expression of an operably linked heterologous nucleotide sequence. These fragments will comprise at least about 40 consecutive nucleotides, preferably at least about 50 consecutive nucleotides, more preferably at least about 75 consecutive nucleotides of the particular promoter nucleotide sequence disclosed herein.

The nucleotides of the fragments encompassed by the invention will usually comprise the TATA recognition sequence of the particular promoter sequence. Such fragments may be obtained by use of restriction enzymes to cleave the naturally occurring promoter nucleotide sequence disclosed herein; by synthesizing a nucleotide sequence from the naturally occurring sequence of the promoter DNA sequence; or may be obtained through the use of PCR technology. See particularly, Mullis et al. (1987) *Methods Enzymol.* 155:335–350, and Erlich, ed. (1989) *PCR Technology* (Stockton Press, New York). Variants of these promoter fragments, such as those resulting from site-directed mutagenesis, are also encompassed by the compositions of the present invention.

Nucleic acid molecules that are represent a fragment of the *Zea mays* LOX5 promoter disclosed herein may comprise at least 15, 20, 25, 30, 35, 40, 45, 50, 75, 100, 325, 350, 375, 400, 425, 450, 500, 550, 600, 650, 700, 800 or 900 nucleotides, or up to the number of nucleotides present in the full-length promoter nucleotide sequence disclosed herein (i.e. 2086 nucleotides or base pairs). Fragments of a promoter sequence that retain their regulatory activity comprise at least 30, 35, 40 contiguous nucleotides, preferably at least 50 contiguous nucleotides, more preferably at least 75 contiguous nucleotides, still more preferably at least 100 contiguous nucleotides of the particular promoter nucleotide sequence disclosed herein. Preferred fragment lengths depend upon the objective and will also vary depending upon the particular promoter sequence.

It is recognized that the nucleotide sequence of the LOX5 promoter disclosed in the present invention, as well as variants and fragments thereof, are useful in the genetic manipulation of any plant when operably linked with a heterologous nucleotide sequence whose expression is to be induced by a particular stimulus to achieve a desired phenotypic response.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, PASTA, and TFASTA in the Wisconsin Genetics Software Package, Version 8 (available from Genetics Computer Group (GCG), 575 Science Drive, Madison, Wis. USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16;10881–90; Huang et al. (1992) *CABIOS* 8:155–65; and Pearson et al. (1994) *Meth. Mol. Rio.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.hlm.nih.gov. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48:443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

For purposes of the present invention, comparison of nucleotide or protein sequences for determination of percent sequence identity to the LOX sequences disclosed herein is preferably made using the ClustalW program (Version 1.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, 91%, 92%, 93%, 94%, 95%, 96%, 97%, 98%, 99% or more compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, 91%, 92%, 93%, 94%, 95%, 96%, 97%, 98%, 99% or more.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90%, 91%, 92%, 93%, 94%, 95%, 96%, 97%, 98%, 99% or more sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Pathogens and Pests

Compositions and methods for controlling pathogenic agents are provided. The antipathogenic compositions comprise nucleotide and polypeptide sequences. Particularly, maize LOX nucleic acid and amino acid sequences are provided. Accordingly, the compositions and methods are useful in protecting plants against fungal pathogens, viruses, nematodes, insects, and the like.

By "disease resistance" or "pathogen resistance" is intended that the plants avoid the disease symptoms which are the outcome of plant-pathogen interactions. That is, pathogens are prevented from causing plant diseases and the associated disease symptoms, or alternatively, the disease symptoms caused by the pathogen is minimized or lessened. The methods of the invention can be utilized to protect plants from disease, particularly those diseases that are caused by plant pathogens.

By "antipathogenic compositions" is intended that the compositions of the invention have antipathogenic activity and thus are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888–1892, herein incorporated by reference). Additionally, microspectrophotometrical analysis can be used to measure the in vitro antipathogenic properties of a composition (Hu et al. (1997) *Plant Mol. Biol.* 34:949–959 and Cammue et al. (1992) *J. Biol. Chem.* 267: 2228–2233, both of which are herein incorporated by reference).

Methods for increasing pathogen resistance in a plant are provided. The methods involve stably transforming a plant with a DNA construct comprising an antipathogenic nucleotide sequence of the invention operably linked to promoter that drives expression in a plant. Such methods may find use in agriculture particularly in limiting the impact of plant pathogens on crop plants. The antipathogenic nucleotide sequences comprise the maize LOX nucleic acid molecules and fragments and variants thereof. While the choice of promoter will depend on the desired timing and location of expression of the antipathogenic nucleotide sequences, preferred promoters include constitutive and pathogen-inducible promoters.

Additionally, the compositions can be used in formulation use for their disease resistance activities. The proteins of the invention can be formulated with an acceptable carrier into a pesticidal composition(s) that is for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Additionally, transformed plants, plant cells, plant tissues and seeds thereof are provided.

It is understood in the art that plant DNA viruses and fungal pathogens remodel the control of the host replication and gene expression machinery to accomplish their own replication and effective infection. The present invention may be useful in preventing such corruption of the cell.

As discussed above, the sequences encoding the sunflower LOX are involved in many basic biochemical pathways and cellular functions that influence the plant defense response. Hence, the sequences of the invention may find use in disrupting cellular function of plant pathogens or insect pests as well as altering the defense mechanisms of a host plant to enhance resistance to disease or insect pests. While the invention is not bound by any particular mechanism of action, the gene products, probably proteins or polypeptides, function to inhibit or prevent plant diseases in a plant. Such gene products may be antipathogenic. It is recognized that the present invention is not dependent upon a particular mechanism of defense. Rather, the genes and methods of the invention work to increase resistance of the plant to pathogens independent of how that resistance is increased or achieved.

The methods of the invention can be used with other methods available in the art for enhancing disease resistance in plants. Similarly, the plant defense mechanisms described herein may be used alone or in combination with other proteins or agents to protect against plant diseases and pathogens. Although any one of a variety of second nucleotide sequences may be utilized, specific embodiments of the invention encompass those second nucleotide sequences that, when expressed in a plant, help to increase the resistance of a plant to pathogens. It is recognized that such second nucleotide sequences may be used in either the sense or antisense orientation depending on the desired outcome. Other plant defense proteins include those described in WO 99/43823 and WO 99/43821, all of which are herein incorporated by reference.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* f.sp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthephaseolorum* var. *caulivora, Sclerotium roltsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines Fusarium solani*; Canola:*Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: Orobanche, *Plasmophora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride*, Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora*, Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

Nematodes include parasitic nematodes such as root-knot, cyst, and lesion nematodes, including *Heterodera* and *Globodera* spp; particularly *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; Melanotus spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplusfemurrubrum*, redlegged grasshopper; *Melanoplus sanguinipes*, migratory grasshopper; *Hylemya platura*, seedcorn maggot; *Agromyza parvicornis*, corn blot leafmniner; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Franklinniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carnine spider mite; *Tetranychus urticae*, twospotted spider mite; Rice: *Diatraea saccharalis*, sugarcane borer; *Spodoptera frugiperda*, fall arrnyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Expression of Sequences

The nucleic acid sequences of the present invention can be expressed in a host cell such as bacteria, yeast, insect, mammalian, or preferably plant cells. It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species, or, if from the same species, is substantially modified from its original form by deliberate human intervention.

By "host cell" is meant a cell, which comprises a heterologous nucleic acid sequence of the invention. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The disease resistant sequences of the invention are provided in expression cassettes or DNA constructs for expression in the plant of interest. The cassette will include 5' and 3' regulatory sequences operably linked to a LOX sequence of the invention. For example, SEQ ID NO:53 provides the nucleotide sequence of a genomic clone for the *Zea mays* LOX5 gene, which encompasses both a 2086 base pair promoter sequence (SEQ ID NO:54) as well as sequence downstream from the 3' UTR (SEQ ID NO: 55). Alternatively, an expression cassette according to then invention could comprise suitable heterologous promoter capable of directing expression of a LOX gene coding sequence. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. Thus as used herein the term "operably linked" indicates the transcription or translation of a heterologous nucleotide sequence is under the influence of the promoter sequence. In this manner, the nucleotide sequences for the promoters of the invention are provided in expression cassettes along with heterologous nucleotide sequences for expression in the plant of interest.

Expression cassettes of the invention may additionally contain at least one additional gene to be cotransformed into the organism. Alternatively, the additional gene(s) can be provided on multiple expression cassettes. Such an expression cassette is provided with a plurality of restriction sites for insertion of the disease resistant sequence to be under the transcriptional regulation of the regulatory regions. The expression cassette may additionally contain selectable marker genes.

The expression cassette will include in the 5'-3' direction of transcription, a transcriptional and translational initiation region, a disease resistant DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" or "heterologous" is intended that the transcriptional initiation region is either not found in the native plant, into which the transcriptional initiation region is introduced; or not found naturally found in association with the coding sequence to which it is operably linked. By "homologous" is intended that the transcription initiation region or promoter is found in the native plant into which the transcription initiation region is introduced; or is naturally found in association with the coding sequence to which it is operably linked. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of the disease resistant RNA/protein in the plant or plant cell. Thus, the phenotype of the plant or plant cell is altered. Alternatively, the Zea mays LOX5 gene promoter nucelotide sequence provided herein can be utilized to direct the expression of any of the disease resistance coding sequences provided herein.

A number of promoters can be used in the practice of the invention. The promoters can be selected based on the desired outcome. That is, the nucleic acids can be combined with constitutive, tissue-preferred, or other promoters for expression in plants. Such constitutive promoters include, for example, the core promoter of the Rsyn7 promoter and other constitutive promoters disclosed in WO 99/43838 and U.S. Pat. No. 6,072,050; Scp1 promoter (U.S. patent application Ser. No. 09/028,819), rice actin (McElroy et al. (1990) Plant Cell 2:163–171); ubiquitin (Christensen et al. (1989) Plant Mol. Biol. 12:619–632 and Christensen et al. (1992) Plant Mol. Biol. 18:675–689); pEMU (Last et al. (1991) Theor. Appl. Genet. 81:581–588); MAS (Velten et al. (1984) EMBO J. 3:2723–2730); ALS promoter (U.S. application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) Neth. J. Plant Pathol. 89:245–254; Uknes et al. (1992) Plant Cell 4:645–656; and Van Loon (1985) Plant Mol. Virol. 4:111–116. See also "Inducible Maize Promoters", WO 99/43819, published Sept. 9, 1999, herein incorporated by reference.

Of interest are promoters that are expressed locally at or near the site of pathogen infection. See, for example, Marineau et al. (1987) Plant Mol. Biol. 9:335–342; Matton et al. (1989) Molecular Plant-Microbe Interactions 2:325–331; Somsisch et al. (1986) Proc. Natl. Acad. Sci. USA 83:2427–2430; Somsisch et al. (1988) Mol. Gen. Genet. 2:93–98; and Yang (1996) Proc. Natl. Acad. Sci. USA 93:14972–14977. See also, Chen et al. (1996) Plant J. 10:955–966; Zhang et al. (1994) Proc. Natl. Acad. Sci. USA 91:2507–2511; Warner et al. (1993) Plant J. 3:191–201; Siebertzetal. (1989) Plant Cell 1:961–968; U.S. Pat. No. 5,750,386 (nematode-inducible); and the references cited therein. Of particular interest is the inducible promoter for the maize PRms gene, whose expression is induced by the pathogen Fusarium moniliforme (see, for example, Cordero et al. (1992) Physiol. Mol. Plant Path. 41:189–200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) Ann. Rev. Phytopath. 28:425–449; Duan et al. (1996) Nature Biotechnology 14:494–498); wun1 and wun2, U.S. Pat. No. 5,428,148; win1 and win2 (Stanford et al. (1989) Mol. Gen. Genet. 215:200–208); systemin (McGurl et al. (1992) Science 225:1570–1573); WIP1 (Rohmeier et al. (1993) Plant Mol. Biol. 22:783–792; Eckelkamp et al. (1993) FEBS Letters 323:73–76); MPI gene (Corderok et al. (1994) Plant J. 6(2):141–150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2—2promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88:10421–10425 and McNellis et al. (1998) Plant J. 14(2):247–257) and tetracycline-inducible and tetracycline-repressible promoters (see, for example, Gatz et al. (1991) Mol. Gen. Genet. 227:229–237, and U.S. Pat. Nos. 5,814,618 and 5,789,156), herein incorporated by reference.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810–812); rice actin (McElroy et al. (1990)

*Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Where low level expression is desired, weak promoters will be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

Tissue-preferred promoters can be used to target antipathogenic gene expression within a particular tissue. Tissue-preferred promoters include Yamamoto et al. (1997) *Plant J.* 12(2):255–265; Kawamata et al. (1997) *Plant Cell Physiol.* 38(7):792–803; Hansen et al. (1997) *Mol. Gen. Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol Biol.* 23(6): 1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and cela (cellulose synthase) (see WO 00/11177, herein incorporated by reference). Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

Leaf-specific promoters are known in the art. See, for example, Yamamoto et al. (1997) *Plant J.* 12(2):255–265; Kwon et al. (1994) *Plant Physiol.* 105:357–67; Yamamoto et al. (1994) *Plant Cell Physiol.* 35(5):773–778; Gotor et al. (1993) *Plant J.* 3:509–18; Orozco et al. (1993) *Plant Mol. Biol.* 23(6):1129–1138; and Matsuoka et al. (1993) *Proc. Natl. Acad. Sci. USA* 90(20):9586–9590.

Root-preferred promoters are known and can be selected from the many available from the literature or isolated de novo from various compatible species. See, for example, Hire et al. (1992) *Plant Mol. Biol.* 20(2):207–218 (soybean root-specific glutamine synthetase gene); Keller and Baumgartner (1991) *Plant Cell* 3(10):1051–1061 (root-specific control element in the GRP 1.8 gene of French bean); Sanger et al. (1990) *Plant Mol. Biol.* 14(3):433–443 (root-specific promoter of the mannopine synthase (MAS) gene of *Agrobacterium tumefaciens*); and Miao et al. (1991) *Plant Cell* 3(1): 11–22 (full-length cDNA clone encoding cytosolic glutamine synthetase (GS), which is expressed in roots and root nodules of soybean). See also Bogusz et al. (1990) *Plant Cell* 2(7):633–641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69–76). They concluded that enhancer and tissue-specific DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2) :343–350). The TR1' gene, fused to nptII (neomycin phosphotransferase II) showed similar characteristics. Additional root-preferred promoters include the VfENOD-GRP3 gene promoter (Kuster et al. (1995) *Plant Mol Biol.* 29(4): 759–772); and rolB promoter (Capana et al. (1994) *Plant Mol. Biol.* 25(4):681–691. See also U.S. Pat. Nos. 5,837, 876; 5,750,386; 5,633,363; 5,459,252; 5,401,836; 5,110, 732; and 5,023,179.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. See, for example, Campbell and Gowri (1990) Plant Physiol. 92:1-11 for a discussion of host-preferred codon usage. Methods are available in the art for synthesizing plant-preferred genes. See, for example, U.S. Pat. Nos. 5,380,831, 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* :90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff(1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Sci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334:721–724. Such disclosures are herein incorporated by reference. The above list of selectable marker genes is not meant to be limiting. Any selectable marker gene can be used in the present invention.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774–8778; herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104–126; Clark et al. (1989) *J. Biol. Chem.* 264:17544–17550; Della-Cioppa et al. (1987) *Plant Physiol.* 84:965–968; Romer et al. (1993) *Biochem. Biophys. Res. Commun.* 196:1414–1421; and Shah et al. (1986) *Science* 233:478–481.

Chloroplast targeting sequences are known in the art and include the chloroplast small subunit of ribulose-1,5-bisphosphate carboxylase (Rubisco) (de Castro Silva Filho et al. (1996) *Plant Mol. Biol.* 30:769–780; Schnell et al. (1991) *J. Biol. Chem.* 266(5):3335–3342); 5-(enolpyruvyl) shikimate-3-phosphate synthase (EPSPS) (Archer et al. (1990) *J. Bioenerg. Biomemb.* 22(6):789–810); tryptophan synthase (Zhao et al. (1995) *J. Biol. Chem.* 270(11): 6081–6087); plastocyanin (Lawrence et al. (1997) *J. Biol. Chem.* 272(33):20357–20363); chorismate synthase (Schmidt et al. (1993) *J. Biol. Chem.* 268(36): 27447–27457); and the light harvesting chlorophyll a/b binding protein (LHBP) (Lamppa et al. (1988) *J. Biol. Chem.* 263:14996–14999). See also Von Heijne et al. 1991) *Plant Mol. Biol. Rep.* 9:104–126; Clark et al. (1989) *J. Biol. Chem.* 264:17544–17550; Della-Cioppa et al. (1987) *Plant Physiol.* 84:965–968; Romer et al. (1993) *Biochem. Biophys. Res. Commun.* 196:1414–1421; and Shah et al. (1986) *Science* 233:478–481.

Methods for transformation of chloroplasts are known in the art. See, for example, Svab et al. (1990) *Proc. Natl. Acad. Sci. USA* 87:8526–8530; Svab and Maliga (1993) *Proc. Natl. Acad. Sci. USA* 90:913–917; Svab and Maliga (1993) *EMBO J*. 12:601–606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301–7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Transformation

DNA constructs comprising the LOX nucleotide sequences, or alternatively, DNA constructs comprising the LOX5 *Zea mays* gene promoter of the invention operably linked to a nucleotide sequence of interest can be used to transform any host cell (i.e., prokaryotic cells and eukaryotic cells, such as yeast, insect, plant and mammalian cells).

The methods of the invention involve introducing a nucleotide construct into a host cell. By "introducing" is intended presenting to the cell the nucleotide construct in such a manner that the construct gains access to the interior of a cell. The methods of the invention do not depend on a particular method for introducing a nucleotide construct to a host cell, only that the nucleotide construct gains access to the interior of at least one cell of the host (i.e. plant). Methods for introducing nucleotide constructs into host cell are known in the art including, but not limited to, stable transformation methods, transient transformation methods, and virus-mediated methods.

By "stable transformation" is intended that the nucleotide construct introduced into a host cell integrates into the genome of the cell and is capable of being inherited by progeny thereof. By "transient transformation" is intended that a nucleotide construct introduced into a host cell does not integrate into the genome of the cell.

It is to be understood that the method of transformation/transfection is not critical to the instant invention; various methods of transformation or transfection are currently available. Thus, any method, which provides for effective transformation/transfection may be employed. For example, the nucleotide constructs (e.g., expression constructs) of the invention may be introduced into host cells by contacting cells with a virus or viral nucleic acids. Generally, such methods involve incorporating a nucleotide construct of the invention within a viral DNA or RNA molecule. It is recognized that the LOX protein of the invention may be initially synthesized as part of a viral polyprotein, which later may be processed by proteolysis in vivo or in vitro to produce the desired recombinant protein. Further, it is recognized that the promoter of the invention also encompasses a promoter promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866, 785, 5,589,367 and 5,316,931; herein incorporated by reference.

In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (Townsend et al., U.S. Pat. No. 5,563,055; Zhao et al., U.S. Pat. No. 5,981, 840), direct gene transfer (Paszkowski et al. (1984) *EMBO J* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923–926); and Lec1 transformation (WO 00/28058). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited, and then seeds are harvested to ensure constitutive expression of the desired phenotypic characteristic has been achieved.

The present invention may be used for transformation of any plant species, including, but not limited to, monocots and dicots. Examples of plants of interest include, but are not limited to, corn (*Zea mays*), Brassica sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and muskmelon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

WY; Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived P L promoter and N-gene ribosome binding site (Shimatake et al. (1981) *Nature* 292:128). The inclusion of selection markers in DNA vectors transfected in *E coli*. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) *Gene* 22:229–235); Mosbach et al. (1983) *Nature* 302:543–545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous nucleotide sequences in yeast is well known (Sherman et al. (1982) *Methods in Yeast Genetics*, Cold Spring Harbor Laboratory). Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques, radioimmunoassay, or other standard immunoassay techniques.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See, Schneider (1987) *J. Embryol. Exp. Morphol.* 27:353–365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al.(1983) *J. Virol.* 45:773–781). Additionally, gene sequences to control replication in the host cell may be incorporated into the vector such as those found in bovine papilloma virus type-vectors (Saveria-Campo (1985) *DNA Cloning Vol. II a Practical Approach*, D. M. Glover, Ed., IRL Press, Arlington, Va., pp. 213–238).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art (Kuchler (1997) *Biochemical Methods in Cell Culture and Virology*, Dowden, Hutchinson and Ross, Inc.).

Methods for Modulating Expression of the Antipathogenic Sequences

The present invention further provides a method for modulating (i.e., increasing or decreasing) the concentration or composition of the sequences of the present invention in a plant or part thereof. Increasing or decreasing the concentration and/or the composition (i.e., the ratio of the polypeptides of the present invention) in a plant can effect modulation. The method comprises introducing into a plant cell, a recombinant expression cassette comprising a polynucleotide of the present invention as described above to obtain a transformed plant cell, culturing the transformed plant cell under plant cell growing conditions, and inducing or repressing expression of a polynucleotide of the present invention in the plant for a time sufficient to modulate concentration and/or composition in the plant or plant part.

In some embodiments, the content and/or composition of polypeptides of the present invention in a plant may be modulated by altering, in vivo or in vitro, the promoter of a gene to up- or down-regulate gene expression. Alternately, the nucleotide sequence of the LOX5 gene promoter of the invention (SEQ ID NO:54) could be altered (e.g., mutated) and then utilized to modulate the expression of a coding sequence of interest that is operably linked thereto. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art and discussed briefly, supra.

In general, the concentration of a composition of the invention is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, infra. Induction of expression of a polynucleotide of the present invention can also be controlled by exogenous administration of an effective amount of inducing compound. Inducible promoters and inducing compounds, which activate expression from these promoters, are well known in the art. In various embodiments, the polypeptides of the present invention are modulated in monocots, particularly maize.

It is recognized that with these nucleotide sequences, antisense constructions, complementary to at least a portion of the messenger RNA (mRNA) for the disease resistant sequences of the invention can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

Methods of Use for the Promoter Sequences

The nucleotide sequences for the LOX5 promoter disclosed in the present invention, as well as variants and fragments thereof, are useful in the genetic manipulation of any host (particularly a plant or plant cell) when assembled with a DNA construct such that the promoter sequence is operably linked to a nucleotide sequence encoding a heterologous nucleotide sequence of interest. In this manner, the nucleotide sequences of the promoter of the invention are provided in expression cassettes along with heterologous nucleotide sequences for expression in a host of interest.

The promoter for the LOX5 gene may regulate expression of operably linked nucleotide sequences in an inducible manner. That is, expression of the operably linked nucleotide sequences in a plant cell may be induced in response to a stimulus. By "stimulus" is intended a chemical, which may be applied externally or may accumulate in response to another external stimulus. A stimulus includes, for example, a pathogen, which may, for example, induce expression as a result of invading a plant cell; wounding or other factor such as environmental stresses, including but not limited to, drought, temperature, and salinity. Hence, the promoter sequences when operably linked to a disease resistance sequence can enhance disease resistance in a transformed plant.

Synthetic hybrid promoter regions are known in the art. Such regions comprise upstream promoter elements of one nucleotide sequence operably linked to the promoter element of another nucleotide sequence. In an embodiment of the invention, heterologous gene expression is controlled by a synthetic hybrid promoter comprising the LOX5 promoter sequences of the invention, or a variant or fragment thereof, operably linked to upstream promoter element(s) from a heterologous promoter. Upstream promoter elements that are involved in the plant defense system have been identified and may be used to generate a synthetic promoter. See, for example, Rushton et al. (1998) *Curr. Opin. Plant Biol.* 1:311–315. Alternatively, a synthetic LOX5 promoter sequence may comprise duplications of the upstream promoter elements found within the promoter sequence.

It is recognized that the promoter sequence of the invention may be used with its native coding sequences. A DNA construct comprising the LOX5 promoter operably linked with its native gene may be used to transform any plant of interest to bring about a desired phenotypic change, such as enhanced disease resistance. Where the promoter and its native gene is naturally occurring within the plant, i.e., in maize, transformation of the plant with these operably linked sequences may result in either a change in phenotype, such as enhanced disease resistance resulting either from overexpression of the operably linked sequence or the due to insertion of the operably linked coding sequence within a different region of the chromosome thereby altering the plant's genome.

In another embodiment of the invention, expression cassettes will comprise a transcriptional initiation region comprising the promoter sequences disclosed herein, or variants or fragments thereof, operably linked to the heterologous nucleotide sequence. Thus, the promoter nucleotide sequence and methods disclosed herein are useful in regulating expression of any heterologous nucleotide sequence in a host plant in order to vary the phenotype of a plant.

Various changes in phenotype are of interest including modifying the fatty acid composition in a plant, altering the amino acid content of a plant, and the like. Phenotypes that alter the disease resistance of the plant to various abiotic and biotic stresses including pathogens, wounding, and environment stress are of particular interest. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. application Ser. Nos. 08/838,763, filed Apr. 10, 1997; 08/824,379, filed Mar. 26, 1997; 08/824,382, filed Mar. 26, 1997; and U.S. Pat. No. 5,703,049; herein incorporated by reference. Another example is lysine and/or sulfur rich seed protein encoded by the soybean 2S albumin described in U.S. application Ser. No. 08/618,911, filed Mar. 20, 1996, and the chymotrypsin inhibitor from barley, described in Williamson et al. (1987) *Eur. J Biochem.* 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and PCT/US97/20441, filed Oct. 31, 1997, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497–502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. application Ser. No. 08/484,815, filed Jun. 7, 1995); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

The following examples are offered by way of illustration and not by way of limitation.

EXPERIMENTAL

Example 1
Transformation and Regeneration of Maize Transgenic Plants

Immature maize embryos from greenhouse donor plants are bombarded with a plasmid containing a LOX nucleotide sequence of the invention operably linked to a ubiquitin promoter and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a LOX nucleotide sequence of the invention operably linked to a ubiquitin promoter is made. This plasmid DNA plus plasmid DNA containing a PAT selectable marker is precipitated onto 1.1 $\mu$m (average diameter) tungsten pellets using a $CaCl_2$ precipitation procedure as follows:

100 $\mu$l prepared tungsten particles in water
10 $\mu$l (1 $\mu$g) DNA in Tris EDTA buffer (1 $\mu$g total DNA)
100 $\mu$l 2.5 M $CaCl_2$
10 $\mu$l 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 $\mu$l 100% ethanol is added to the final tungsten particle pellet. For particle gun bombardment, the tungsten/DNA particles are briefly sonicated and 10 $\mu$l spotted onto the center of each macrocarrier and allowed to dry about 2 minutes before bombardment.

Particle Gun Treatment

The sample plates are bombarded at level #4 in particle gun #HE34-1 or #HE34–2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for altered defense response, or altered LOX activity.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 mill Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l Bialaphos (both added after sterilizing the medium and cooling to room temperature).

Plant regeneration medium (288J) comprises 4.3 g/l MS salts (GIBCO 11117-074), 5.0 mill MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l Bialaphos (added after sterilizing the medium and cooling to 60° C.). Hormone-free medium (272V) comprises 4.3 g/l MS salts (GIBCO 11117-074), 5.0 ml/I MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 2
Transformation and Regeneration of Maize Transgenic Plants with an Expression Cassette Comprising a Homologous Promoter and LOX Nucleotide Sequence Immature maize embryos from greenhouse donor plants are bombarded with a plasmid containing a nucleotide sequence of interest operably linked to the *Zea mays* LOX5 transcriptional initiation region (e.g., promoter region) set forth in SEQ ID NO:54 and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a LOX nucleotide sequence of the invention operably linked to the LOX5 transcriptional initiation region (e.g., promoter region) set forth in SEQ ID NO:54 is made. This plasmid DNA plus plasmid DNA containing a PAT selectable marker is precipitated onto 1.1 $\mu$m (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M CaCl$_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34–1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for altered expression of the nucleotide sequence of interest.

Bombardment and Culture Media

Bombardment medium (560Y) comprises 4.0 g/l N6 basal salts (SIGMA C-1416), 1.0 ml/l Eriksson's Vitamin Mix (10000× SIGMA-1511), 0.5 mg/l thiamine HCl, 120.0 g/l sucrose, 1.0 mg/l 2,4-D, and 2.88 g/l L-proline (brought to volume with D-I H$_2$O following adjustment to pH 5.8 with KOH); 2.0 g/l Gelrite (added after bringing to volume with D-I H$_2$O); and 8.5 mg/l silver nitrate (added after sterilizing the medium and cooling to room temperature). Selection medium (560R) comprises 4.0 g/l N6 basal salts (SIGMA C-1416), 1.0 mill Eriksson's Vitamin Mix (1000× SIGMA-1511), 0.5 mg/l thiamine HCl, 30.0 g/l sucrose, and 2.0 mg/l 2,4-D (brought to volume with D-I H$_2$O following adjustment to pH 5.8 with KOH); 3.0 gel Gelrite (added after bringing to volume with D-I H$_2$O); and 0.85 mg/l silver nitrate and 3.0 mg/l Bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H$_2$O) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H$_2$O after adjusting to pH 5.6); 3.0 g/l Gelrite (added after bringing to volume with D-I H$_2$O); and 1.0 mg/l indoleacetic acid and 3.0 mg/l Bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H$_2$O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H$_2$O), sterilized and cooled to 60° C.

Example 3

*Azrobacterium*-Mediated Transformation

For *Agrobacterium*-mediated transformation of maize with LOX nucleotide sequences of the invention the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the DNA constructs of interest to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example 4

Transformation and Regeneration of Sunflower Plants

The intact meristem method is used for transformation of sunflower plants and expression of a LOX sequence of the invention.

Explant Preparation

Seeds are dehulled and surface-sterilized for 20 minutes in a 20% Chlorox™ bleach solution with the addition of two to three drops of Tween 20 per 100 ml of solution, and then rinsed three times with distilled water. Sterilized seeds are imbibed in the dark at 26° C. for 20 hours on filter paper moistened with water. Meristem explants are created by removing cotyledons and root radicle from imbibed seeds, and then culturing overnight at 26° C. in the dark on 374E medium (1× MS salts, Shepards vitamins, 40 mg/l adenine sulfate, 30 g/l sucrose, o.5 mg/l BAP, 0.25 mg/l IAA, 0.1 mg/l IAA, pH 5.6, 8g/l phytagar). Primary leaves are then removed and explants are transferred to 374M medium (374E except 12 g/l phytagar), arranged in a manner suitable for particle gun bombardment, and cultured overnight at 26° C. in the dark.

Preparation of DNA

A plasmid vector comprising a LOX nucleotide sequence operably linked to a ubiquitin promoter is constructed. The plasmid contains a kanamycin selectable marker gene. The transformation is performed as follows.

Transformation

Approximately 18.8 mg of 1.8 μm tungsten particles are suspended in 150 μl absolute ethanol, and sonicated for 2–4 seconds. After sonication, 10 μl of the suspension is dropped on the center of the surface of a macrocarrier. Each plate of meristem explants is bombarded twice with 650 psi rupture discs in the top shelf at 26 mm of Hg helium gun vacuum, using a BioRad helium gun.

The plasmid vector having a DNA construct expressing a LOX polypeptide is introduced into *Agrobacterium* strain EHA 105 (see above) via freeze-thawing as described by Holsters et al. (1978) *Mol. Gen. Genet.* 163:181–187. Actively growing, transformed *Agrobacteria* were maintained in shaking liquid cultures using 60A medium with kanamycin (YEP, 50 mg/l kanamycin: 10 g/l yeast extract, 10 g/l bactopeptone, 5 g/l NaCl, pH 7.0, 50 mg/l kanamycin). On the day before the *Agrobacterium* strain is to be used, new liquid cultures are initiated in 60A with kanamycin from the active maintenance culture. They are cultured with shaking at 26° C. until they reach an optical density (OD vis=600 nm) of about 1.0. When the cultures have established this density, they are centrifuged (6000 rpm, 5 min), the supernatant is discarded, and the pellet of bacteria is resuspended in inoculation medium (12.5 mM 2-(N-morpholino) ethanesulfonic acid, 1 g/l NH4Cl, and 0.3 g/l MgSO4, at pH 5.7), to a final calculated concentration of *Agrobacteria* of 4.0 at OD 600. The particle bombarded explants are inoculated with *Agrobacterium* by first spreading the explants apart on the 374M medium, then placing a droplet of the above suspension directly onto the top of each meristem. The explants are co-cultivated on the medium for 4 days, after which the explants are transferred to 374 C medium (GBA with 1% sucrose and with no BAP, IAA, or GA3, and supplemented with 250 μg/ml cefotaxime). The explants are cultured on this medium for about 2 weeks under 16 hours of daylight, at 26° C.

Recovering Nodes and Plants

Following the 4 days of co-cultivation time on 374M medium, the explants are transferred to 374D (374C medium with 50 mg/l kanamycin) selection medium containing kanamycin. After 2 weeks of selection, explants with associated shoots are transferred to 374C medium and selection resistant shoots are screened using NPTII ELISA. Positive shoots are removed for recovery by in vitro grafting and transformation verified by further NPTII ELISA analysis. Negative shoots are discarded. Explants with smaller shoots which could not be assayed following the 2 weeks on 374D are transferred to 374G (374E with 250 mg/l cefotaxime) for 3–4 days then back to 374C for 2 additional weeks. Assays are then done to identify positive shoots that are too small to sample in the first round and recovery initiated. Recovered positive shoots are grafted to Pioneer sunflower hybrid in vitro-grown sunflower seedling rootstock. The seeds are dehulled and surface-sterilized for 20 minutes in a 20% Chlorox™ bleach solution with two to three drops of Tween20 per 100 ml total volume, and rinsed three times with distilled water. The sterilized seeds are germinated for three days on filter paper moistened with water, then transferred into "48 Medium" (one-half strength MS salts, 0.5% sucrose, 0.3% gelrite, at pH 5.0) and grown at 26° C. at 26 in the dark for 3 days, then incubated at 16 hour day culture conditions. The upper portions of selected seedlings are removed, a vertical slice is made in each hypocotyl, and a transformed shoot is inserted into the vertical slice. The cut area is wrapped with parafilm, and after one-week culture on the medium, the grafted plants are transferred to soil. In the first two weeks they are maintained under high humidity conditions to acclimatize to the greenhouse environment.

Transformed sectors of TO plants are identified by additional NPTII assays of the greenhouse established positive grafted shoots. After assay, non-transformed sectors are trimmed off to promote auxiliary bud development and auxiliary buds from transgenic sectors are recovered so as to establish the best probability to encompass the sector of transformation in germ line cells so that the transformation event is recovered in the next generation. Seed from TO plants are collected, de-hulled, surface sterilized, and germinated on filter paper wetted with water. T1 seedlings are then sampled for NPTII ELISA by removing green cotyledon pieces followed by transfer to seedling growth medium 48P (0.1× MS salts, 0.5% sucrose, pH 5.6, 0.3% gelrite). NPTII positive, actively growing T1 seedlings are transferred at the two-leaf stage to soil for growth in the greenhouse. Seed from the confirmed T1 transgenics is used to grow T2 plants.

T2 seeds are planted in a greenhouse. Positive plants are screened by NPTII assay. Various plant tissues are harvested at 80-day-old stage after planting. The harvested material is put in mini-tubes, frozen and stored at −80° C.

Plants transformed with the plasmid comprising the LOX nucleotide sequences are monitored and scored for an altered defense response, or a modulation in LOX activity.

Example 5

Soybean Embryo Transformation

Soybean embryos are bombarded with a plasmid containing a LOX sequence operably linked to a ubiquitin promoter as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature (London)* 327:70–73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the DNA construct can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1

M), and 50 μl CaCl₂ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference in its entirety.

Although the foregoing invention has been described in some detail by way of illustration and example for purposes of clarity of understanding, it will be obvious that certain changes and modifications may be practiced within the scope of the appended claims.

That which is claimed is:

1. An isolated nucleic acid molecule comprising a nucleotide sequence selected from the group consisting of:
    (a) the nucleotide sequence set forth in SEQ ID NO: 25;
    (b) a nucleotide sequence encoding the amino acid sequence set forth in SEQ ID NO: 26;
    (c) a nucleotide sequence comprising an antisense sequence corresponding to the nucleotide sequence of a) or b);
    (d) a nucleotide sequence having at least 95% sequence identity to SEQ ID NO: 25, wherein said nucleotide sequence encodes a polypeptide having lipoxygenase activity.

2. A DNA construct comprising the nucleic acid molecule of claim 1, wherein said nucleic acid molecule is operably linked to a promoter that drives expression in a host cell.

3. A cell having stably incorporated into its genome at least one DNA construct comprising a nucleotide sequence operably linked to a heterologous promoter that drives expression in said cell, wherein said nucleotide sequence is selected from the group consisting of:
    (a) the nucleotide sequence set forth in SEQ ID NO: 25;
    (b) a nucleotide sequence encoding the amino acid sequence set forth in SEQ ID NO: 26;
    (c) a nucleotide sequence comprising an antisense sequence corresponding to the nucleotide sequence of a) or b);
    (d) a nucleotide sequence having at least 95% sequence identity to SEQ ID NO: 25, wherein said nucleotide sequence encodes a polypeptide having lipoxygenase activity.

4. The cell of claim 3, wherein said cell is a plant cell.

5. A transformed plant having stably incorporated into its genome at least one DNA construct comprising a nucleotide sequence operably linked to a heterologous promoter that drives expression in a plant, wherein said nucleotide sequence is selected from the group consisting of:
    (a) the nucleotide sequence set forth in SEQ ID NO: 25;
    (b) a nucleotide sequence encoding the amino acid sequence set forth in SEQ ID NO: 26;
    (c) a nucleotide sequence comorising an antisense sequence corresponding to the nucleotide sequence of a) or b);
    (d) a nudeotide sequence having at least 95% sequence identity to SEQ ID NO: 25, wherein said nucleotide sequence encodes a polypeptide having lipoxygenase activity.

6. The plant of claim 5, wherein said promoter is a constitutive promoter.

7. The plant of claim 5, wherein said promoter is a tissue-preferred promoter.

8. The plant of claim 5, wherein said promoter is an inducible promoter.

9. The plant of claim 8, wherein said promoter is a pathogen-inducible promoter.

10. The plant of claim 5, wherein said plant is a monocot.

11. The plant of claim 10, wherein said monocot is selected from the group consisting of maize, wheat, rice, barley, sorghum, or rye.

12. The plant of claim 5, wherein said plant is a dicot.

13. A transformed seed of the plant of claim claim 5, wherein the seed comprise the DNA construct.

14. A method for enhancing a plant defense response, said method comprising stably introducing into the genome of a plant at least one DNA construct comprising a nucleotide sequence operably linked to a heterologous promoter that drives expression in a plant, wherein said nucleotide sequence is selected from the group consisting of:

(a) the nucleotide sequence set forth in SEQ ID NO: 25;

(b) a nucleotide sequence encoding the amino acid sequence set forth in SEQ ID NO: 26;

(c) a nucleotide sequence having at least 95% sequence identity to SEQ ID NO: 25, wherein said nucleotide sequence encodes a polypeptide having lipoxygenase activity.

* * * * *

UNITED STATES PATENT AND TRADEMARK OFFICE
CERTIFICATE OF CORRECTION

PATENT NO. : 6,921,847 B2
DATED : July 26, 2005
INVENTOR(S) : Pedro A. Navarro Acevedo et al.

It is certified that error appears in the above-identified patent and that said Letters Patent is hereby corrected as shown below:

<u>Column 277,</u>
Lines 41-42 and 59-60, should read -- sequence having at least 95% sequence identity to the nucleotide sequence of a); --.

<u>Column 278,</u>
Line 41, should read -- (c) a nucleotide sequence comprising an antisense --;
Lines 42 and 43, should read -- sequence having at least 90% sequence identity to the nucleotide sequence of a); --.

Signed and Sealed this

Fourth Day of October, 2005

JON W. DUDAS
*Director of the United States Patent and Trademark Office*